US010851413B2

(12) United States Patent
Ochoa et al.

(10) Patent No.: US 10,851,413 B2
(45) Date of Patent: Dec. 1, 2020

(54) CONSENSUS-BASED ALLELE DETECTION

(71) Applicant: Progenika Biopharma S.A., Derio (ES)

(72) Inventors: Jorge Ochoa, Derio (ES); David Arteta, Derio (ES); Mariá José Illescas, Derio (ES); Monica Lopez, Derio (ES); Marianne Stef, Derio (ES); Diego Tejedor, Derio (ES); Antonio Martìnez, Derio (ES)

(73) Assignee: Progenika Biopharma S.A., Derio (ES)

( * ) Notice: Subject to any disclaimer, the term of this patent is extended or adjusted under 35 U.S.C. 154(b) by 566 days.

(21) Appl. No.: 15/503,338

(22) PCT Filed: Aug. 12, 2015

(86) PCT No.: PCT/EP2015/068601
§ 371 (c)(1),
(2) Date: Feb. 10, 2017

(87) PCT Pub. No.: WO2016/023962
PCT Pub. Date: Feb. 18, 2016

(65) Prior Publication Data

US 2018/0305756 A1 Oct. 25, 2018

(30) Foreign Application Priority Data

Aug. 13, 2014 (GB) .................................. 1414350.7

(51) Int. Cl.
*G16B 30/10* (2019.01)
*C12Q 1/6881* (2018.01)
*C12Q 1/6827* (2018.01)

(52) U.S. Cl.
CPC ......... *C12Q 1/6881* (2013.01); *C12Q 1/6827* (2013.01); *G16B 30/10* (2019.02); *C12Q 2600/156* (2013.01); *C12Q 2600/16* (2013.01); *C12Q 2600/172* (2013.01)

(58) Field of Classification Search
None
See application file for complete search history.

(56) References Cited

FOREIGN PATENT DOCUMENTS

WO WO-2012171990 A1 * 12/2012 .......... C12Q 1/6881

OTHER PUBLICATIONS

Mamanova et al. Target-enrichment strategies for next-generation sequencing Nature Methods vol. 7, pp. 111-118 (Year: 2010).*
Erlich et al. Next-generation sequencing for HLA typing of class I loci BMC Genomics vol. 12, article 42 (Year: 2011).*
Wang et al. High-throughput, high-fidelity HLA genotyping with deep sequencing Proceedings of the National Academy of Sciences, USA vol. 109, pp. 8676-8681 (Year: 2012).*
Perry et al. Evolutionary genetics of the human Rh blood group system Human Genetics vol. 131, pp. 1205-1216 (Year: 2012).*
Avent et al. Next Generation Sequencing: Academic Overkill or High-Resolution Blood Group Genotyping Vox Sanguinis vol. 106 (Supplement 1), p. 37 (Year: 2014).*
Fichou et al. A convenient qualitative and quantitative method to investigate RHD-RHCE hybrid genes Transfusion vol. 53, pp. 2974—(Year: 2013).*
NCBI Reference Sequence NG 007494.1 (Year: 2002).*
NCBI Reference Sequence NG 009208.2 (Year: 2010).*
Okuda et al. The Analysis of Nucleotide Substitutions, Gaps, and Recombination Events between RHD and RHCE Genes through Complete Sequencing Biochemical and Biophysical Research Communications vol. 274, pp. 670-683 (Year: 2000).*
Ewing et al. Base-Calling of Automated Sequencer Traces Using Phred. II. Error Probabilities Genome Research vol. 8, pp. 186-194 (Year: 1998).*
Babraham Bioinformatics (Babraham Bioinformatics [retrieved on Sep. 17, 2019] Retrieved from the Internet: www.bioinformatics.babraham.ac.uk/projects.fastqc/). (Year: 2010).*
Li Aligning sequence reads, clone sequences and assembly contigs with BWA-MEM arXiv:1303.3997v2 [q-bio.GN] (Year: 2013).*
Spellman et al. Advances in the Selection of HLA-Compatble Donors: Refinements in HLA Typing and Matching over the First 20 Years of th National Marrow Donor Program Registry Biology of Blood and Marrow Transplantation vol. 14, pp. 37-44 (Year: 2008).*
Hurley et al. National Marrow Donor Program HLA-Matching Guidelines for Unrelated Marrow Transplants Biology of Blood and Marrow Transplantation vol. 9, pp. 610-615 (Year: 2003).*

(Continued)

*Primary Examiner* — John S Brusca
(74) *Attorney, Agent, or Firm* — Klarquist Sparkman, LLP

(57) ABSTRACT

The present invention provides a method for genotyping alleles in at least one homologous genetic loci set, comprising: (i) providing a DNA-containing sample that includes said at least one homologous genetic loci set; (ii) performing PCR amplification of regions of said homologous genetic loci set using consensus sequence-specific primers, wherein said consensus sequence-specific primers bind to consensus sequences that are common to a plurality of genes within the genetic loci set, thereby generating a pool of amplification products; (iii) sequencing a plurality of said amplification products in order to determine the relative proportion of each nucleotide at each position in a sequencing read; (iv) performing a sequence alignment between the sequencing read results of (iii) and at least one reference sequence, which reference sequence corresponds to one of the genes in said homologous genetic loci set; and (v) performing genotype calling of the allele or alleles in said sample based on the relative proportion of each nucleotide at each of a plurality of discriminant positions in said alignment. Also disclose are related products, kits and systems for performing the method.

19 Claims, 34 Drawing Sheets

Specification includes a Sequence Listing.

(56) References Cited

OTHER PUBLICATIONS

Avent et al. Molecular Analysis of Rh Transcripts and Polypeptides From Individuals Expressing the DVI Variant Phenotype: An RHD Gene Deletion Event Does Not Generate All DVIccEe Phenotypes Blood vol. 89, pp. 1779-1786 (Year: 1997).*

Bentley et al., "High-resolution, high-throughput HLA genotyping by next-generation sequencing," *Tissue Antigens*, vol. 74, pp. 393-403, 2009.

Database GENESEQ, Database Accession No. BBM81249, Oct. 23, 2014, 1 page.

Database GENESEQ, Database Accession No. BBP52112, Dec. 4, 2014, 1 page.

Freeman et al., "Profiling the T-cell receptor beta-chain repertoire by massively parallel sequencing," *Genome Research*, vol. 19, No. 10, pp. 1817-1824, 2009.

Stabentheiner et al, "Overcoming methodical limits of standard RHD genotyping by next-generation sequencing," *Vox Sanguinis*, vol. 100, No. 4, pp. 381-388, 2011.

Database EMBL, Database Accession No. AX022511, Sep. 7, 2000, 1 page.

Database EMBL, Database Accession No. CS559152, May 17, 2007, 1 page.

Database EMBL, Database Accession No. DL475619, Dec. 29, 2008, 1 page.

Database EMBL, Database Accession No. HH191614, Aug. 26, 2010, 1 page.

Database EMBL, Database Accession No. GZ126978, Feb. 26, 2012, 1 page.

Database EMBL, Database Accession No. JB762706, Oct. 18, 2013, 1 page.

Database EMBL, Database Accession No. JD23558, Jan. 25, 2015, 1 page.

Database EMBL, Database Accession No. JD412512, Jan. 25, 2015, 1 page.

Hemker et al., "DAR, a New RhD Variant Involving Exons 4, 5, and 7, Often in Linkage With CeAR, a New Rhce Variant Frequently Found in African Blacks," *Blood*, vol. 94, No. 12, pp. 4337-4342, 1999.

Ringquist et al., "Clustering and Alignment of Polymorphic Sequences for HLA-DRB1 Genotyping," *PLoS ONE*, 8(3):e59835, 2013 (7 pages).

* cited by examiner

Fig 1: Amplification of Exon1

1:100bp ladder
2:Ex01 F3R1(sample 1)
3:Ex01 F3R1(sample 2)
4:Ex02 F1R1
5:Ex02 F1R2
6:Ex02 F2R1
7:Ex02 F2R2

Fig 2: Amplification of Exon 1 (repeat) and exon 2

Fig 3: Amplification of Exon 3

Fig 4: Amplification of Exon 4

Fig 5: Amplification of Exon 5

```
RHD_ex01              ------------------TTGGAGAGAGGGGTGATGCCTGGTGCTGGTGGAACCCCTGCA   42
RHCE_ce_ex01          CAAGCCCTCAAGTAGGTGTTGGAGAGAGGGGTGATGCCTGGTGCTGGTGGAACCCCTGCA   60
RHCE_cE_ex01          CAAGCCCTCAAGTAGGTGTTGGAGAGAGGGGTGATGCCTGGTGCTGGTGGAACCCCTGCA   60
RHCE_Ce_ex01          CAAGCCCTCAAGTAGGTGTTGGAGAGAGGGGTGATGCCTGGTGCTGGTGGAACCCCTGCA   60
RHCE_CE_ex01          CAAGCCCTCAAGTAGGTGTTGGAGAGAGGGGTGATGCCTGGTGCTGGTGGAACCCCTGCA   60
RHCE_consensus_ex01   CAAGCCCTCAAGTAGGTGTTGGAGAGAGGGGTGATGCCTGGTGCTGGTGGAACCCCTGCA   60
                                        ******************************************

RHD_ex01              CAGAGACGGACACAGGATGAGCTCTAAGTACCCGCGGTCTGTCCGGCGCTGCCTGCCCCT   102 (44)
RHCE_ce_ex01          CAGAGACGGACACAGGATGAGCTCTAAGTACCCGCGGTCTGTCCGGCGCTGCCTGCCCCT   120
RHCE_cE_ex01          CAGAGACGGACACAGGATGAGCTCTAAGTACCCGCGGTCTGTCCGGCGCTGCCTGCCCCT   120
RHCE_Ce_ex01          CAGAGACGGACACAGGATGAGCTCTAAGTACCCGCGGTCTGTCCGGCGCTGCCTGCCCCT   120
RHCE_CE_ex01          CAGAGACGGACACAGGATGAGCTCTAAGTACCCGCGGTCTGTCCGGCGCTGCCTGCCCCT   120
RHCE_consensus_ex01   CAGAGACGGACACAGGATGAGCTCTAAGTACCCGCGGTCTGTCCGGCGCTGCCTGCCCCT   120
                      ************************************************************

RHD_ex01              CTGGGCCCTAACACTGGAAGCAGCTCTCATTCTCCTCTTCTATTTTTTTACCCACTATGA   162 (104)
RHCE_ce_ex01          CTGGGCCCTAACACTGGAAGCAGCTCTCATTCTCCTCTTCTATTTTTTTACCCACTATGA   180
RHCE_cE_ex01          CTGGGCCCTAACACTGGAAGCAGCTCTCATTCTCCTCTTCTATTTTTTTACCCACTATGA   180
RHCE_Ce_ex01          CTGCGCCCTAACACTGGAAGCAGCTCTCATTCTCCTCTTCTATTTTTTTACCCACTATGA   180
RHCE_CE_ex01          CTGCGCCCTAACACTGGAAGCAGCTCTCATTCTCCTCTTCTATTTTTTTACCCACTATGA   180
RHCE_consensus_ex01   CTGSGCCCTAACACTGGAAGCAGCTCTCATTCTCCTCTTCTATTTTTTTACCCACTATGA   180
                      *** ********************************************************

RHD_ex01              CGCTTCCTTAGAGGATCAAAAGGGGCTCGTGGCATCCTATCAAGGTGAGAGTTCATTGGA   222 (164)
RHCE_ce_ex01          CGCTTCCTTAGAGGATCAAAAGGGGCTCGTGGCATCCTATCAAGGTGAGAGTTCATTGGA   240
RHCE_cE_ex01          CGCTTCCTTAGAGGATCAAAAGGGGCTCGTGGCATCCTATCAAGGTGAGAGTTCATTGGA   240
RHCE_Ce_ex01          CGCTTCCTTAGAGGATCAAAAGGGGCTCGTGGCATCCTATCAAGGTGAGAGTTCATTGGA   240
RHCE_CE_ex01          CGCTTCCTTAGAGGATCAAAAGGGGCTCGTGGCATCCTATCAAGGTGAGAGTTCATTGGA   240
RHCE_consensus_ex01   CGCTTCCTTAGAGGATCAAAAGGGGCTCGTGGCATCCTATCAAGGTGAGAGTTCATTGGA   240
                      ************************************************************
```

Figure 16A

```
RHD_ex01            AAAGTGGTCACAGGAGCAAATAGCAGGGGCAGGGGCGGGGAGGCCTGTGGTTCTCCAGG    282
RHCE_ce_ex01        ACAGTGGTCACAGGAGCAAATAGCAGGGGCAGGGGCGGGGAGGCCTATGGTTCTCCAGG    300
RHCE_cE_ex01        ACAGTGGTCACAGGAGCAAATAGCAGGGGCAGGGGCGGGGAGGCCTATGGTTCTCCAGG    300
RHCE_Ce_ex01        ACAGTGGTCACAGGAGCAAATAGCAGGGGCAGGGGCGGGGAGGCCTATGGTTCTCCAGG    300
RHCE_CE_ex01        ACAGTGGTCACAGGAGCAAATAGCAGGGGCAGGGGCGGGGAGGCCTATGGTTCTCCAGG    300
RHCE_consensus_ex01 ACAGTGGTCACAGGAGCAAATAGCAGGGGCAGGGGCGGGGAGGCCTATGGTTCTCCAGG    300
                    * ********************************************* ***********

RHD_ex01            GGCACAGAGATGTTCCTTTCTACAAAATCCCAAGGAAAAAGATTCCCCCATC-------    332
RHCE_ce_ex01        GGCACAGAGATGTTCCTTTCTACAAAATCCCGAGGAAAAAGATTCCCCCATCTTCCGTAG    360
RHCE_cE_ex01        GGCACAGAGATGTTCCTTTCTACAAAATCCCGAGGAAAAAGATTCCCCCATCTTCCGTAG    360
RHCE_Ce_ex01        GGCACAGAGATGTTCCTTTCTACAAAATCCCGAGGAAAAAGATTCCCCCATCTTCCGTAG    360
RHCE_CE_ex01        GGCACAGAGATGTTCCTTTCTACAAAATCCCGAGGAAAAAGATTCCCCCATCTTCCGTAG    360
RHCE_consensus_ex01 GGCACAGAGATGTTCCTTTCTACAAAATCCCGAGGAAAAAGATTCCCCCATCTTCCGTAG    360
                    ******************************* ****************** *  *****

RHD_ex01            ---------------------------------    332  (SEQ ID NO: 27)
RHCE_ce_ex01        ATTGCACCGAAATTCAGTCAACAA            384  (SEQ ID NO: 28)
RHCE_cE_ex01        ATTGCACCGAAATTCAGTCAACAA            384  (SEQ ID NO: 29)
RHCE_Ce_ex01        ATTGCACCGAAATTCAGTCAACAA            384  (SEQ ID NO: 30)
RHCE_CE_ex01        ATTGCACCGAAATTCAGTCAACAA            384  (SEQ ID NO: 31)
RHCE_consensus_ex01 ATTGCACCGAAATTCAGTCAACAA            384  (SEQ ID NO: 32)
```

Figure 16B

```
RHD_ex02              TCTTGCATGCCCCTTCCAGCTGCCATTTAGTAAGACTCTAATTTCATACCACCCTAAATC  60
RHCE_ce_ex02          TCTTGCATGCCCCTTCCAGCTGCCATTTAGTAAGACTCTAATTTCATACCACCCTAAATC  60
RHCE_cE_ex02          TCTTGCATGCCCCTTCCAGCTGCCATTTAGTAAGACTCTAATTTCATACCACCCTAAATC  60
RHCE_Ce_ex02          TCTTGCATGCCCCTTCCAGCTGCCATTTAGTAAGACTCTAATTTCATACCACCCTAAATC  60
RHCE_CE_ex02          TCTTGCATGCCCCTTCCAGCTGCCATTTAGTAAGACTCTAATTTCATACCACCCTAAATC  60
RHCE_consensus_ex02   TCTTGCATGCCCCTTCCAGCTGCCATTTAGTAAGACTCTAATTTCATACCACCCTAAATC  60
                      ************************************************************

RHD_ex02              TCGTCTGCTTCCCCCTCGTCCTTCTCGCCATCTCCCCACCGAGCAGTTGGCCAAGATCTG  120 (162)
RHCE_ce_ex02          TCGTCTGCTTCCCCCTCCTCCTTCTCACCATCTCCCCACCGAGCAGTCGGCCAAGATCTG  120
RHCE_cE_ex02          TCGTCTGCTTCCCCCTCCTCCTTCTCACCATCTCCCCACCGAGCAGTCGGCCAAGATCTG  120
RHCE_Ce_ex02          TCGTCTGCTTCCCCCTCCTCCTTCTCGCCATCTCCCCACCGAGCAGTTGGCCAAGATCTG  120
RHCE_CE_ex02          TCGTCTGCTTCCCCCTCCTCCTTCTCGCCATCTCCCCACCGAGCAGTTGGCCAAGATCTG  120
RHCE_consensus_ex02   TCGTCTGCTTCCCCCTCCTCCTTCTCRCCATCTCCCCACCGAGCAGTYGGCCAAGATCTG  120
                      ***************** ******** ******************** ************

RHD_ex02              ACCGTGATGGCGGCCATTGGCTTGGGCTTCCTCACCTCGAGTTTCCGGAGACACAGCTGG  180 (222)
RHCE_ce_ex02          ACCGTGATGGCGGCCCTTGGCTTGGGCTTCCTCACCTCAAATTTCCGGAGACACAGCTGG  180
RHCE_cE_ex02          ACCGTGATGGCGGCCCTTGGCTTGGGCTTCCTCACCTCAAATTTCCGGAGACACAGCTGG  180
RHCE_Ce_ex02          ACCGTGATGGCGGCCATTGGCTTGGGCTTCCTCACCTCGAGTTTCCGGAGACACAGCTGG  180
RHCE_CE_ex02          ACCGTGATGGCGGCCATTGGCTTGGGCTTCCTCACCTCGAGTTTCCGGAGACACAGCTGG  180
RHCE_consensus_ex02   ACCGTGATGGCGGCCMTTGGCTTGGGCTTCCTCACCTCRARTTTCCGGAGACACAGCTGG  180
                      *************** ********************** * *******************

RHD_ex02              AGCAGTGTGGCCTTCAACCTCTTCATGCTGGCGCTTGGTGTGCAGTGGGCAATCCTGCTG  240 (282)
RHCE_ce_ex02          AGCAGTGTGGCCTTCAACCTCTTCATGCTGGCGCTTGGTGTGCAGTGGGCAATCCTGCTG  240
RHCE_cE_ex02          AGCAGTGTGGCCTTCAACCTCTTCATGCTGGCGCTTGGTGTGCAGTGGGCAATCCTGCTG  240
RHCE_Ce_ex02          AGCAGTGTGGCCTTCAACCTCTTCATGCTGGCGCTTGGTGTGCAGTGGGCAATCCTGCTG  240
RHCE_CE_ex02          AGCAGTGTGGCCTTCAACCTCTTCATGCTGGCGCTTGGTGTGCAGTGGGCAATCCTGCTG  240
RHCE_consensus_ex02   AGCAGTGTGGCCTTCAACCTCTTCATGCTGGCGCTTGGTGTGCAGTGGGCAATCCTGCTG  240
                      ************************************************************
```

Figure 17A

```
RHD_ex02             GACGGCTTCCTGAGCCAGTTCCCTTCTGGGAAGGTGGTCATCACACTGTTCAGGTATTGG     300
RHCE_ce_ex02         GACGGCTTCCTGAGCCAGTTCCCTCCTGGGAAGGTGGTCATCACACTGTTCAGGTATTGG     300
RHCE_cE_ex02         GACGGCTTCCTGAGCCAGTTCCCTCCTGGGAAGGTGGTCATCACACTGTTCAGGTATTGG     300
RHCE_Ce_ex02         GACGGCTTCCTGAGCCAGTTCCCTTCTGGGAAGGTGGTCATCACACTGTTCAGGTATTGG     300
RHCE_CE_ex02         GACGGCTTCCTGAGCCAGTTCCCTTCTGGGAAGGTGGTCATCACACTGTTCAGGTATTGG     300
RHCE_consensus_ex02  GACGGCTTCCTGAGCCAGTTCCCTYCTGGGAAGGTGGTCATCACACTGTTCAGGTATTGG     300
                     ************************ ***********************************

RHD_ex02             GATGGTGGCTGGATCACTTCTGGGTCATAGAGGGAATGGACCCCGAAAGGACAGGTTCCA     360
RHCE_ce_ex02         GATGGTGGCTGGATCACTTCTGGGTCATAGAGGGAATGGACCCCGAAAGGACAGGTTCCA     360
RHCE_cE_ex02         GATGGTGGCTGGATCACTTCTGGGTCATAGAGGGAATGGACCCCGAAAGGACAGGTTCCA     360
RHCE_Ce_ex02         GATGGTGGCTGGATCACTTCTGGGTCATAGAGGGAATGGACCCCGAAAGGACAGGTTCCA     360
RHCE_CE_ex02         GATGGTGGCTGGATCACTTCTGGGTCATAGAGGGAATGGACCCCGAAAGGACAGGTTCCA     360
RHCE_consensus_ex02  GATGGTGGCTGGATCACTTCTGGGTCATAGAGGGAATGGACCCCGAAAGGACAGGTTCCA     360
                     ************************************************************

RHD_ex02             GAAGATCTGGGATATTGCCCCCTCTCTGTCTAGCACCAGT    400    (SEQ ID NO: 33)
RHCE_ce_ex02         GAAGATCTGGGATATTGCCCCCTCTCTGTCTAGCACCAGT    400    (SEQ ID NO: 34)
RHCE_cE_ex02         GAAGATCTGGGATATTGCCCCCTCTCTGTCTAGCACCAGT    400    (SEQ ID NO: 35)
RHCE_Ce_ex02         GAAGATCTGGGATATTGCCCCCTCTCTGTCTAGCACCAGT    400    (SEQ ID NO: 36)
RHCE_CE_ex02         GAAGATCTGGGATATTGCCCCCTCTCTGTCTAGCACCAGT    400    (SEQ ID NO: 37)
RHCE_consensus_ex02  GAAGATCTGGGATATTGCCCCCTCTCTGTCTAGCACCAGT    400    (SEQ ID NO: 38)
                     ****************************************
```

Figure 17B

```
RHD_ex03                  ------------TCCCACAGAAAGTAGGTGCCCAACAGTGTTTGTTGAAAGAATGAATGA     48
RHCE_ce_ex03              TTGTCTTCTATTTCCACAGAAAGTAAGGTGCCCAACAGTGTT------------TGTTGA     48
RHCE_cE_ex03              TTGTCTTCTATTTCCACAGAAAGTAAGGTGCCCAACAGTGTT------------TGTTGA     48
RHCE_Ce_ex03              TTGTCTTCTATTTCCACAGAAAGTAAGGTGCCCAACAGTGTT------------TGTTGA     48
RHCE_CE_ex03              TTGTCTTCTATTTCCACAGAAAGTAAGGTGCCCAACAGTGTT------------TGTTGA     48
RHCE_consensus_ex03       TTGTCTTCTATTTCCACAGAAAGTAAGGTGCCCAACAGTGTT------------TGTTGA     48
                                      ***     **   ****************                ***

RHD_ex03                  ATGAATGAATGAATGAATGAATGAGTGAGAGGCATCCTTCCTTCTCAGTCGTCCTGGCTC     108
RHCE_ce_ex03              ATGAATGAATGAATGAATGAATGAGTGAGAGGCATCCTTCCTTCTCAGTCATCCTGGCTC     108
RHCE_cE_ex03              ATGAATGAATGAATGAATGAATGAGTGAGAGGCATCCTTCCTTCTCAGTCATCCTGGCTC     108
RHCE_Ce_ex03              ATGAATGAATGAATGAATGAATGAGTGAGAGGCATCCTTCCTTCTCAGTCATCCTGGCTC     108
RHCE_CE_ex03              ATGAATGAATGAATGAATGAATGAGTGAGAGGCATCCTTCCTTCTCAGTCATCCTGGCTC     108
RHCE_consensus_ex03       ATGAATGAATGAATGAATGAATGAGTGAGAGGCATCCTTCCTTCTCAGTCATCCTGGCTC     108
                          ************************************************** *********

RHD_ex03                  TCCCTCTCTCCCCCAGTATTCGGCTGGCCACCATGAGTGCTTTGTCGGTGCTGATCTCAG     168 (379)
RHCE_ce_ex03              TCCTTCTCACCCCCAGTATTCGGCTGGCCACCATGAGTGCTATGTCGGTGCTGATCTCAG     168
RHCE_cE_ex03              TCCTTCTCACCCCCAGTATTCGGCTGGCCACCATGAGTGCTATGTCGGTGCTGATCTCAG     168
RHCE_Ce_ex03              TCCTTCTCACCCCCAGTATTCGGCTGGCCACCATGAGTGCTATGTCGGTGCTGATCTCAG     168
RHCE_CE_ex03              TCCTTCTCACCCCCAGTATTCGGCTGGCCACCATGAGTGCTATGTCGGTGCTGATCTCAG     168
RHCE_consensus_ex03       TCCTTCTCACCCCCAGTATTCGGCTGGCCACCATGAGTGCTATGTCGGTGCTGATCTCAG     168
                          *** **** ******************************** ******************

RHD_ex03                  TGGATGCTGTCTTGGGGAAGGTCAACTTGGCGCAGTTGGTGGTGATGGTGCTGGTGGAGG     228 (439)
RHCE_ce_ex03              CGGGTGCTGTCTTGGGGAAGGTCAACTTGGCGCAGTTGGTGGTGATGGTGCTGGTGGAGG     228
RHCE_cE_ex03              CGGGTGCTGTCTTGGGGAAGGTCAACTTGGCGCAGTTGGTGGTGATGGTGCTGGTGGAGG     228
RHCE_Ce_ex03              CGGGTGCTGTCTTGGGGAAGGTCAACTTGGCGCAGTTGGTGGTGATGGTGCTGGTGGAGG     228
RHCE_CE_ex03              CGGGTGCTGTCTTGGGGAAGGTCAACTTGGCGCAGTTGGTGGTGATGGTGCTGGTGGAGG     228
RHCE_consensus_ex03       CGGGTGCTGTCTTGGGGAAGGTCAACTTGGCGCAGTTGGTGGTGATGGTGCTGGTGGAGG     228
                           ** ********************************************************
```

Figure 18A

```
RHD_ex03              TGACAGCTTTAGGCAACCTGAGGATGGTCATCAGTAATATCTTCAACGTGAGTCATGGTG     288
RHCE_ce_ex03          TGACAGCTTTAGGCACCCTGAGGATGGTCATCAGTAATATCTTCAACGTGAGTCATGGTG     288
RHCE_cE_ex03          TGACAGCTTTAGGCACCCTGAGGATGGTCATCAGTAATATCTTCAACGTGAGTCATGGTG     288
RHCE_Ce_ex03          TGACAGCTTTAGGCACCCTGAGGATGGTCATCAGTAATATCTTCAACGTGAGTCATGGTG     288
RHCE_CE_ex03          TGACAGCTTTAGGCACCCTGAGGATGGTCATCAGTAATATCTTCAACGTGAGTCATGGTG     288
RHCE_consensus_ex03   TGACAGCTTTAGGCACCCTGAGGATGGTCATCAGTAATATCTTCAACGTGAGTCATGGTG     288
                      *************** ********************************************

RHD_ex03              CTGGGAGGAGGGACCTGGGAGAAAAGGGCCAAAAGCTCCATTTGGTGGGGTTTCCAGGGT     348
RHCE_ce_ex03          CTGGGAGGAGGGACCTGGGAGAAAAGGGCCAAAAGCTCCATTTGGTGGGGCTTCCGGGGT     348
RHCE_cE_ex03          CTGGGAGGAGGGACCTGGGAGAAAAGGGCCAAAAGCTCCATTTGGTGGGGCTTCCGGGGT     348
RHCE_Ce_ex03          CTGGGAGGAGGGACCTGGGAGAAAAGGGCCAAAAGCTCCATTTGGTGGGGCTTCCGGGGT     348
RHCE_CE_ex03          CTGGGAGGAGGGACCTGGGAGAAAAGGGCCAAAAGCTCCATTTGGTGGGGCTTCCGGGGT     348
RHCE_consensus_ex03   CTGGGAGGAGGGACCTGGGAGAAAAGGGCCAAAAGCTCCATTTGGTGGGGCTTCCGGGGT     348
                      ************************************************** **** ****

RHD_ex03              TTTGAAAAATAAAGACAACCTGTAATCCCAGCTACTTGGGAGGTTGAGGAGG        400    (SEQ ID NO: 39)
RHCE_ce_ex03          TTTGAAAAATAAAGACAACCTGTAATCCCAGCTACTTGGGAGGTTGAGGAGG        400    (SEQ ID NO: 40)
RHCE_cE_ex03          TTTGAAAAATAAAGACAACCTGTAATCCCAGCTACTTGGGAGGTTGAGGAGG        400    (SEQ ID NO: 41)
RHCE_Ce_ex03          TTTGAAAAATAAAGACAACCTGTAATCCCAGCTACTTGGGAGGTTGAGGAGG        400    (SEQ ID NO: 42)
RHCE_CE_ex03          TTTGAAAAATAAAGACAACCTGTAATCCCAGCTACTTGGGAGGTTGAGGAGG        400    (SEQ ID NO: 43)
RHCE_consensus_ex03   TTTGAAAAATAAAGACAACCTGTAATCCCAGCTACTTGGGAGGTTGAGGAGG        400    (SEQ ID NO: 44)
                      ****************************************************
```

Figure 18B

```
RHD_ex04             AACACCAGTCTCATGGCTTCAAGTCACACCTCCTAAGTGAAGCTCTGAACTTTCTCCAAG   60
RHCE_ce_ex04         -ACACCAGTCTCGTGGCTTCAAGTCACACCTCCTAAGTGAAGCTCTGAACTTTCTCCAAG   59
RHCE_cE_ex04         -ACACCAGTCTCGTGGCTTCAAGTCACACCTCCTAAGTGAAGCTCTGAACTTTCTCCAAG   59
RHCE_Ce_ex04         -ACACCAGTCTCGTGGCTTCAAGTCACACCTCCTAAGTGAAGCTCTGAACTTTCTCCAAG   59
RHCE_CE_ex04         -ACACCAGTCTCGTGGCTTCAAGTCACACCTCCTAAGTGAAGCTCTGAACTTTCTCCAAG   59
RHCE_consensus_ex04  -ACACCAGTCTCGTGGCTTCAAGTCACACCTCCTAAGTGAAGCTCTGAACTTTCTCCAAG   59
                      *********** ***********************************************

RHD_ex04             GACTATCAGGGCTTGC-CCCGGGCAGAGGATGCCGACACTCACTGCTCTTACTGGGTTTT   119
RHCE_ce_ex04         GACCATCAGGGCTTTCCCCTGGGCAGAGGATGCCGACACTCACTGCTCTTACTGGGTTTT   119
RHCE_cE_ex04         GACCATCAGGGCTTTCCCCTGGGCAGAGGATGCCGACACTCACTGCTCTTACTGGGTTTT   119
RHCE_Ce_ex04         GACCATCAGGGCTTTCCCCTGGGCAGAGGATGCCGACACTCACTGCTCTTACTGGGTTTT   119
RHCE_CE_ex04         GACCATCAGGGCTTTCCCCTGGGCAGAGGATGCCGACACTCACTGCTCTTACTGGGTTTT   119
RHCE_consensus_ex04  GACCATCAGGGCTTTCCCCTGGGCAGAGGATGCCGACACTCACTGCTCTTACTGGGTTTT   119
                     *** ********** * ** ****************************************

RHD_ex04             ATTGCAGACAGACTACCACATGAACATGATGCACATCTACGTGTTCGCAGCCTATTTTGG   179 (539)
RHCE_ce_ex04         ATTGCAGACAGACTACCACATGAACCTGAGGCACTTCTACGTGTTCGCAGCCTATTTTGG   179
RHCE_cE_ex04         ATTGCAGACAGACTACCACATGAACCTGAGGCACTTCTACGTGTTCGCAGCCTATTTTGG   179
RHCE_Ce_ex04         ATTGCAGACAGACTACCACATGAACCTGAGGCACTTCTACGTGTTCGCAGCCTATTTTGG   179
RHCE_CE_ex04         ATTGCAGACAGACTACCACATGAACCTGAGGCACTTCTACGTGTTCGCAGCCTATTTTGG   179
RHCE_consensus_ex04  ATTGCAGACAGACTACCACATGAACCTGAGGCACTTCTACGTGTTCGCAGCCTATTTTGG   179
                     ************************* *** **** *************************

RHD_ex04             GCTGTCTGTGGCCTGGTGCCTGCCAAAGCCTCTACCCGAGGGAACGGAGGATAAAGATCA   239 (599)
RHCE_ce_ex04         GCTGACTGTGGCCTGGTGCCTGCCAAAGCCTCTACCCAAGGGAACGGAGGATAATGATCA   239
RHCE_cE_ex04         GCTGACTGTGGCCTGGTGCCTGCCAAAGCCTCTACCCAAGGGAACGGAGGATAATGATCA   239
RHCE_Ce_ex04         GCTGACTGTGGCCTGGTGCCTGCCAAAGCCTCTACCCAAGGGAACGGAGGATAATGATCA   239
RHCE_CE_ex04         GCTGACTGTGGCCTGGTGCCTGCCAAAGCCTCTACCCAAGGGAACGGAGGATAATGATCA   239
RHCE_consensus_ex04  GCTGACTGTGGCCTGGTGCCTGCCAAAGCCTCTACCCAAGGGAACGGAGGATAATGATCA   239
                     **** ******************************** **************** *****
```

Figure 19A

```
RHD_ex04              GACAGCAACGATACCCAGTTTGTCTGCCATGCTGGGTAAGGACAAGGTGGGGTGAGTGGT    299
RHCE_ce_ex04          GAGAGCAACGATACCCAGTTTGTCTGCCATGCTGGGTAAGGACAAGGTGGGGTGAGTGGT    299
RHCE_cE_ex04          GAGAGCAACGATACCCAGTTTGTCTGCCATGCTGGGTAAGGACAAGGTGGGGTGAGTGGT    299
RHCE_Ce_ex04          GAGAGCAACGATACCCAGTTTGTCTGCCATGCTGGGTAAGGACAAGGTGGGGTGAGTGGT    299
RHCE_CE_ex04          GAGAGCAACGATACCCAGTTTGTCTGCCATGCTGGGTAAGGACAAGGTGGGGTGAGTGGT    299
RHCE_consensus_ex04   GAGAGCAACGATACCCAGTTTGTCTGCCATGCTGGGTAAGGACAAGGTGGGGTGAGTGGT    299
                      ** *********************************************************

RHD_ex04              CTCCTACTTGGGCTGAGCAGAATGGCTCAGAAAAGGCTCTGGCTGAAAAAATCTCCCTCC    359
RHCE_ce_ex04          CTCATACTTGGGCTGAGCAGAATGGCTCAGAAAAGGCTCTGGCTGAAAAAATCTCCCTCC    359
RHCE_cE_ex04          CTCATACTTGGGCTGAGCAGAATGGCTCAGAAAAGGCTCTGGCTGAAAAAATCTCCCTCC    359
RHCE_Ce_ex04          CTCATACTTGGGCTGAGCAGAATGGCTCAGAAAAGGCTCTGGCTGAAAAAATCTCCCTCC    359
RHCE_CE_ex04          CTCATACTTGGGCTGAGCAGAATGGCTCAGAAAAGGCTCTGGCTGAAAAAATCTCCCTCC    359
RHCE_consensus_ex04   CTCATACTTGGGCTGAGCAGAATGGCTCAGAAAAGGCTCTGGCTGAAAAAATCTCCCTCC    359
                      *** ********************************************************

RHD_ex04              TTTACCAAGTTCCCCTGGGTGTCTGAAGCCCTTCCATCATG   400    (SEQ ID NO: 45)
RHCE_ce_ex04          TTTACCAACTTCCCCTGGGTGTCTGAAGCCCTTCCATCATG   400    (SEQ ID NO: 46)
RHCE_cE_ex04          TTTACCAACTTCCCCTGGGTGTCTGAAGCCCTTCCATCATG   400    (SEQ ID NO: 47)
RHCE_Ce_ex04          TTTACCAACTTCCCCTGGGTGTCTGAAGCCCTTCCATCATG   400    (SEQ ID NO: 48)
RHCE_CE_ex04          TTTACCAACTTCCCCTGGGTGTCTGAAGCCCTTCCATCATG   400    (SEQ ID NO: 49)
RHCE_consensus_ex04   TTTACCAACTTCCCCTGGGTGTCTGAAGCCCTTCCATCATG   400    (SEQ ID NO: 50)
                      ******** ********************************
```

Figure 19B

```
RHD_ex05              CTCTAAGTGACAAGGCTGAGACTCTCCAGCCCTAGGATTCTCATCCAAAACCCCTCGAGG    60
RHCE_ce_ex05          CTCTAAGTGACAAGGCTGAGACTCTCCAGCCCTAGGATTCTCATCCAAAACCCCTCGAGG    60
RHCE_cE_ex05          CTCTAAGTGACAAGGCTGAGACTCTCCAGCCCTAGGATTCTCATCCAAAACCCCTCGAGG    60
RHCE_Ce_ex05          CTCTAAGTGACAAGGCTGAGACTCTCCAGCCCTAGGATTCTCATCCAAAACCCCTCGAGG    60
RHCE_CE_ex05          CTCTAAGTGACAAGGCTGAGACTCTCCAGCCCTAGGATTCTCATCCAAAACCCCTCGAGG    60
RHCE_consensus_ex5    CTCTAAGTGACAAGGCTGAGACTCTCCAGCCCTAGGATTCTCATCCAAAACCCCTCGAGG    60
                      ************************************************************

RHD_ex05              CTCAGACCTTTGGAGCAGGAGTGTGATTCTGGCCAACCACCCTCTCTGGCCCCCAGGCGC    120 (638)
RHCE_ce_ex05          CTCAGACCTTTGGAGCAGGAGTGTGATTCTGGCCAACCACCCTCTCTGGCCCCCAGGCGC    120
RHCE_cE_ex05          CTCAGACCTTTGGAGCAGGAGTGTGATTCTGGCCAACCACCCTCTCTGGCCCCCAGGCGC    120
RHCE_Ce_ex05          CTCAGACCTTTGGAGCAGGAGTGTGATTCTGGCCAACCACCCTCTCTGGCCCCCAGGCGC    120
RHCE_CE_ex05          CTCAGACCTTTGGAGCAGGAGTGTGATTCTGGCCAACCACCCTCTCTGGCCCCCAGGCGC    120
RHCE_consensus_ex5    CTCAGACCTTTGGAGCAGGAGTGTGATTCTGGCCAACCACCCTCTCTGGCCCCCAGGCGC    120
                      ************************************************************

RHD_ex05              CCTCTTCTTGTGGATGTTCTGGCCAAGTTTCAACTCTGCTCTGCTGAGAAGTCCAATCGA    180 (698)
RHCE_ce_ex05          CCTCTTCTTGTGGATGTTCTGGCCAAGTGTCAACTCTGCTCTGCTGAGAAGTCCAATCCA    180
RHCE_cE_ex05          CCTCTTCTTGTGGATGTTCTGGCCAAGTGTCAACTCTCCTCTGCTGAGAAGTCCAATCCA    180
RHCE_Ce_ex05          CCTCTTCTTGTGGATGTTCTGGCCAAGTGTCAACTCTGCTCTGCTGAGAAGTCCAATCCA    180
RHCE_CE_ex05          CCTCTTCTTGTGGATGTTCTGGCCAAGTGTCAACTCTCCTCTGCTGAGAAGTCCAATCCA    180
RHCE_consensus_ex5    CCTCTTCTTGTGGATGTTCTGGCCAAGTGTCAACTCTSCTCTGCTGAGAAGTCCAATCCA    180
                      **************************** ******** ******************** *

RHD_ex05              AAGGAAGAATGCCGTGTTCAACACCTACTATGCTGTAGCAGTCAGCGTGGTGACAGCCAT    240 (758)
RHCE_ce_ex05          AAGGAAGAATGCCATGTTCAACACCTACTATGCTCTAGCAGTCAGTGTGGTGACAGCCAT    240
RHCE_cE_ex05          AAGGAAGAATGCCATGTTCAACACCTACTATGCTCTAGCAGTCAGTGTGGTGACAGCCAT    240
RHCE_Ce_ex05          AAGGAAGAATGCCATGTTCAACACCTACTATGCTCTAGCAGTCAGTGTGGTGACAGCCAT    240
RHCE_CE_ex05          AAGGAAGAATGCCATGTTCAACACCTACTATGCTCTAGCAGTCAGTGTGGTGACAGCCAT    240
RHCE_consensus_ex5    AAGGAAGAATGCCATGTTCAACACCTACTATGCTCTAGCAGTCAGTGTGGTGACAGCCAT    240
                      ************* ******************** ********** **************
```

Figure 20A

```
RHD_ex05            CTCAGGGTCATCCTTGGCTCACCCCCAAGGGAAGATCAGCAAGGTGAGCAGGGCGCTGCC    300
RHCE_ce_ex05        CTCAGGGTCATCCTTGGCTCACCCCCAAAGGAAGATCAGCATGGTGAGCAGGGCGCTGCC    300
RHCE_cE_ex05        CTCAGGGTCATCCTTGGCTCACCCCCAAAGGAAGATCAGCATGGTGAGCAGGGCGCTGCC    300
RHCE_Ce_ex05        CTCAGGGTCATCCTTGGCTCACCCCCAAAGGAAGATCAGCATGGTGAGCAGGGCGCTGCC    300
RHCE_CE_ex05        CTCAGGGTCATCCTTGGCTCACCCCCAAAGGAAGATCAGCATGGTGAGCAGGGCGCTGCC    300
RHCE_consensus_ex5  CTCAGGGTCATCCTTGGCTCACCCCCAAAGGAAGATCAGCATGGTGAGCAGGGCGCTGCC    300
                    **************************** ************ ******************

RHD_ex05            CTTGGGCAGCACTTGGGTCTAACAGGACTAGCACACATATTTATGCCCCTCCCCACCCCA    360
RHCE_ce_ex05        CTTGGGCAGCACTTGGGTCTAACAGGACTAGCACACATATTTATGCCCCTCCCCACCCCA    360
RHCE_cE_ex05        CTTGGGCAGCACTTGGGTCTAACAGGACTAGCACACATATTTATGCCCCTCCCCACCCCA    360
RHCE_Ce_ex05        CTTGGGCAGCACTTGGGTCTAACAGGACTAGCACACATATTTATGCCCCTCCCCACCCCA    360
RHCE_CE_ex05        CTTGGGCAGCACTTGGGTCTAACAGGACTAGCACACATATTTATGCCCCTCCCCACCCCA    360
RHCE_consensus_ex5  CTTGGGCAGCACTTGGGTCTAACAGGACTAGCACACATATTTATGCCCCTCCCCACCCCA    360
                    ************************************************************

RHD_ex05            GGGCCAGCGTGGGTTGGGAGAGGGCATGCCGGGTGGTGGAGCTGTGCCTG  410    (SEQ ID NO: 51)
RHCE_ce_ex05        GGGCCAGCGTGGGTTGGGAGAGGGCATGCCGGGTGGTGGA----------  400    (SEQ ID NO: 52)
RHCE_cE_ex05        GGGCCAGCGTGGGTTGGGAGAGGGCATGCCGGGTGGTGGA----------  400    (SEQ ID NO: 53)
RHCE_Ce_ex05        GGGCCAGCGTGGGTTGGGAGAGGGCATGCCGGGTGGTGGA----------  400    (SEQ ID NO: 54)
RHCE_CE_ex05        GGGCCAGCGTGGGTTGGGAGAGGGCATGCCGGGTGGTGGA----------  400    (SEQ ID NO: 55)
RHCE_consensus_ex5  GGGCCAGCGTGGGTTGGGAGAGGGCATGCCGGGTGGTGGA----------  400    (SEQ ID NO: 56)
                    ****************************************
```

Figure 20B

```
RHCE_ce_ex06           GGTGGTTTCAGGATCAGCAAAGCAGGGAGGATGTTACAGGGTTGCCTTGTTCCCAGCGTG    60
RHCE_cE_ex06           GGTGGTTTCAGGATCAGCAAAGCAGGGAGGATGTTACAGGGTTGCCTTGTTCCCAGCGTG    60
RHCE_Ce_ex06           GGTGGTTTCAGGATCAGCAAAGCAGGGAGGATGTTACAGGGTTGCCTTGTTCCCAGCGTG    60
RHCE_CE_ex06           GGTGGTTTCAGGATCAGCAAAGCAGGGAGGATGTTACAGGGTTGCCTTGTTCCCAGCGTG    60
RHCE_consensus_ex06    GGTGGTTTCAGGATCAGCAAAGCAGGGAGGATGTTACAGGGTTGCCTTGTTCCCAGCGTG    60
RHD_ex06               AGTGGTTTCAGGATCAGCAAAGCAGGGAGGATGTTACAGGGTTGCCTTGTTCCCAGCGTG    60
                        ***********************************************************

RHCE_ce_ex06           CTGGTCACTTGCAGCAAGATGGTGTTCTCTCTCTACCTTGCTTCCTTTACCCACACGCTA    120
RHCE_cE_ex06           CTGGTCACTTGCAGCAAGATGGTGTTCTCTCTCTACCTTGCTTCCTTTACCCACACGCTA    120
RHCE_Ce_ex06           CTGGTCACTTGCAGCAAGATGGTGTTCTCTCTCTACCTTGCTTCCTTTACCCACACGCTA    120
RHCE_CE_ex06           CTGGTCACTTGCAGCAAGATGGTGTTCTCTCTCTACCTTGCTTCCTTTACCCACACGCTA    120
RHCE_consensus_ex06    CTGGTCACTTGCAGCAAGATGGTGTTCTCTCTCTACCTTGCTTCCTTTACCCACACGCTA    120
RHD_ex06               CTGGTCACTTGCAGCAAGATGGTGTTCTCTCTCTACCTTGCTTCCTTTACCCACACGCTA    120
                       ************************************************************

RHCE_ce_ex06           TTTCTTTGCAGACTTATGTGCACAGTGCGGTGTTGGCAGGAGGCGTGGCTGTGGGTACCT    180
RHCE_cE_ex06           TTTCTTTGCAGACTTATGTGCACAGTGCGGTGTTGGCAGGAGGCGTGGCTGTGGGTACCT    180
RHCE_Ce_ex06           TTTCTTTGCAGACTTATGTGCACAGTGCGGTGTTGGCAGGAGGCGTGGCTGTGGGTACCT    180
RHCE_CE_ex06           TTTCTTTGCAGACTTATGTGCACAGTGCGGTGTTGGCAGGAGGCGTGGCTGTGGGTACCT    180
RHCE_consensus_ex06    TTTCTTTGCAGACTTATGTGCACAGTGCGGTGTTGGCAGGAGGCGTGGCTGTGGGTACCT    180
RHD_ex06               TTTCTTTGCAGACTTATGTGCACAGTGCGGTGTTGGCAGGAGGCGTGGCTGTGGGTACCT    180
                       ************************************************************

RHCE_ce_ex06           CGTGTCACCTGATCCCTTCTCCGTGGCTTGCCATGGTGCTGGGTCTTGTGGCTGGGCTGA    240
RHCE_cE_ex06           CGTGTCACCTGATCCCTTCTCCGTGGCTTGCCATGGTGCTGGGTCTTGTGGCTGGGCTGA    240
RHCE_Ce_ex06           CGTGTCACCTGATCCCTTCTCCGTGGCTTGCCATGGTGCTGGGTCTTGTGGCTGGGCTGA    240
RHCE_CE_ex06           CGTGTCACCTGATCCCTTCTCCGTGGCTTGCCATGGTGCTGGGTCTTGTGGCTGGGCTGA    240
RHCE_consensus_ex06    CGTGTCACCTGATCCCTTCTCCGTGGCTTGCCATGGTGCTGGGTCTTGTGGCTGGGCTGA    240
RHD_ex06               CGTGTCACCTGATCCCTTCTCCGTGGCTTGCCATGGTGCTGGGTCTTGTGGCTGGGCTGA    240
                       ************************************************************
```

Figure 21A

```
RHCE_ce_ex06          TCTCCATCGGGGGAGCCAAGTGCCTGCCGGTAAGAAACTAGACAACTAATGCTCTCTGCT     300
RHCE_cE_ex06          TCTCCATCGGGGGAGCCAAGTGCCTGCCGGTAAGAAACTAGACAACTAATGCTCTCTGCT     300
RHCE_Ce_ex06          TCTCCATCGGGGGAGCCAAGTGCCTGCCGGTAAGAAACTAGACAACTAATGCTCTCTGCT     300
RHCE_CE_ex06          TCTCCATCGGGGGAGCCAAGTGCCTGCCGGTAAGAAACTAGACAACTAATGCTCTCTGCT     300
RHCE_consensus_ex06   TCTCCATCGGGGGAGCCAAGTGCCTGCCGGTAAGAAACTAGACAACTAATGCTCTCTGCT     300
RHD_ex06              TCTCCGTCGGGGGAGCCAAGTACCTGCCGGTAAGAAACTAGACAACTAACCTCCTCTGCT     300
                      ***** *************** *************************    *******

RHCE_ce_ex06          TTGGCTGAAGGCCAGCAGGACGCTGGGACCTGATGGGCCACTGTGCAGTGCACAGCTGCA     360
RHCE_cE_ex06          TTGGCTGAAGGCCAGCAGGACGCTGGGACCTGATGGGCCACTGTGCAGTGCACAGCTGCA     360
RHCE_Ce_ex06          TTGGCTGAAGGCCAGCAGGACGCTGGGACCTGATGGGCCACTGTGCAGTGCACAGCTGCA     360
RHCE_CE_ex06          TTGGCTGAAGGCCAGCAGGACGCTGGGACCTGATGGGCCACTGTGCAGTGCACAGCTGCA     360
RHCE_consensus_ex06   TTGGCTGAAGGCCAGCAGGACGCTGGGACCTGATGGGCCACTGTGCAGTGCACAGCTGCA     360
RHD_ex06              TTGGCTGAAGGCCAGCAGGACGCTGGGACCTGATGGGCCACTGTGCAGTGCACAGCTGCA     360
                      ************************************************************

RHCE_ce_ex06          TTAGGCAGGTGTTGGTGCATTCTCTTATTGGCTTCAACGC   400    (SEQ ID NO: 88)
RHCE_cE_ex06          TTAGGCAGGTGTTGGTGCATTCTCTTATTGGCTTCAACGC   400    (SEQ ID NO: 89)
RHCE_Ce_ex06          TTAGGCAGGTGTTGGTGCATTCTCTTATTGGCTTCAACGC   400    (SEQ ID NO: 90)
RHCE_CE_ex06          TTAGGCAGGTGTTGGTGCATTCTCTTATTGGCTTCAACGC   400    (SEQ ID NO: 91)
RHCE_consensus_ex06   TTAGGCAGGTGTTGGTGCATTCTCTTATTGGCTTCAACGC   400    (SEQ ID NO: 92)
RHD_ex06              TTAGGCAGGTGTCGGCGCATTCTCTTATTGGCTTCAACGC   400    (SEQ ID NO: 87)
                      ************ ** ************************
```

Figure 21B

```
RHCE_ce_ex07          AGAAGGGCTTCTTTGAGGTGAGCCTTAGTGCCCATCCCCATTTGGTG-GCGCGGATACCA   59
RHCE_cE_ex07          AGAAGGGCTTCTTTGAGGTGAGCCTTAGTGCCCATCCCCATTTGGTG-GCGCGGATACCA   59
RHCE_Ce_ex07          AGAAGGGCTTCTTTGAGGTGAGCCTTAGTGCCCATCCCCATTTGGTG-GCGCGGATACCA   59
RHCE_CE_ex07          AGAAGGGCTTCTTTGAGGTGAGCCTTAGTGCCCATCCCCATTTGGTG-GCGCGGATACCA   59
RHCE_consensus_ex07   AGAAGGGCTTCTTTGAGGTGAGCCTTAGTGCCCATCCCCATTTGGTG-GCGCGGATACCA   59
RHD_ex07              -GAAGGGCTTCTTTGAGGTGAGCCTTAGTGCCCATCCCCCTTTGGTGGCCCCGGATACCA   59
                       ************************************** *******  * *********

RHCE_ce_ex07          AGGGTGTGTGAAAGGGGTGGGTAGGGAATATGGGTCTCACCTGCCAATCTGCTTATAATA   119
RHCE_cE_ex07          AGGGTGTGTGAAAGGGGTGGGTAGGGAATATGGGTCTCACCTGCCAATCTGCTTATAATA   119
RHCE_Ce_ex07          AGGGTGTGTGAAAGGGGTGGGTAGGGAATATGGGTCTCACCTGCCAATCTGCTTATAATA   119
RHCE_CE_ex07          AGGGTGTGTGAAAGGGGTGGGTAGGGAATATGGGTCTCACCTGCCAATCTGCTTATAATA   119
RHCE_consensus_ex07   AGGGTGTGTGAAAGGGGTGGGTAGGGAATATGGGTCTCACCTGCCAATCTGCTTATAATA   119
RHD_ex07              AGGGTGTGTGAAAGGGGTGGGTAGGGAATATGGGTCTCACCTGCCAATCTGCTTATAATA   119
                      ************************************************************

RHCE_ce_ex07          ACACTTGTCCACAGGTGTGTTGTAACCGAGTGCTGGGGATTCACCACATCTCCGTCATGC   179
RHCE_cE_ex07          ACACTTGTCCACAGGTGTGTTGTAACCGAGTGCTGGGGATTCACCACATCTCCGTCATGC   179
RHCE_Ce_ex07          ACACTTGTCCACAGGTGTGTTGTAACCGAGTGCTGGGGATTCACCACATCTCCGTCATGC   179
RHCE_CE_ex07          ACACTTGTCCACAGGTGTGTTGTAACCGAGTGCTGGGGATTCACCACATCTCCGTCATGC   179
RHCE_consensus_ex07   ACACTTGTCCACAGGTGTGTTGTAACCGAGTGCTGGGGATTCACCACATCTCCGTCATGC   179
RHD_ex07              ACACTTGTCCACAGGGGTGTTGTAACCGAGTGCTGGGGATTCCCCACAGCTCCATCATGG   179
                      *************** ************************** ***** **** *****

RHCE_ce_ex07          ACTCCATCTTCAGCTTGCTGGGTCTGCTTGGAGAGATCACCTACATTGTGCTGCTGGTGC   239
RHCE_cE_ex07          ACTCCATCTTCAGCTTGCTGGGTCTGCTTGGAGAGATCACCTACATTGTGCTGCTGGTGC   239
RHCE_Ce_ex07          ACTCCATCTTCAGCTTGCTGGGTCTGCTTGGAGAGATCACCTACATTGTGCTGCTGGTGC   239
RHCE_CE_ex07          ACTCCATCTTCAGCTTGCTGGGTCTGCTTGGAGAGATCACCTACATTGTGCTGCTGGTGC   239
RHCE_consensus_ex07   ACTCCATCTTCAGCTTGCTGGGTCTGCTTGGAGAGATCACCTACATTGTGCTGCTGGTGC   239
RHD_ex07              GCTACAACTTCAGCTTGCTGGGTCTGCTTGGAGAGATCATCTACATTGTGCTGCTGGTGC   239
                       ** ** ******************************** ********************
```

Figure 22A

```
RHCE_ce_ex07          TTCATACTGTCTGGAACGGCAATGGCATGTGGGTCACTGGGCTTACCCCCCATCCCCTTA    299
RHCE_cE_ex07          TTCATACTGTCTGGAACGGCAATGGCATGTGGGTCACTGGGCTTACCCCCCATCCCCTTA    299
RHCE_Ce_ex07          TTCATACTGTCTGGAACGGCAATGGCATGTGGGTCACTGGGCTTACCCCCCATCCCCTTA    299
RHCE_CE_ex07          TTCATACTGTCTGGAACGGCAATGGCATGTGGGTCACTGGGCTTACCCCCCATCCCCTTA    299
RHCE_consensus_ex07   TTCATACTGTCTGGAACGGCAATGGCATGTGGGTCACTGGGCTTACCCCCCATCCCCTTA    299
RHD_ex07              TTGATACCGTCGGAGCCGGCAATGGCATGTGGGTCACTGGGCTTACCCCCCATCCCCTTA    299
                      ** **** *** *   ********************************************

RHCE_ce_ex07          ACACTCCCCTCCAACTCAGGAAGAAATGTGTGCAGAGTCCTTAGCTGGGGCGTGTGCACT    359
RHCE_cE_ex07          ACACTCCCCTCCAACTCAGGAAGAAATGTGTGCAGAGTCCTTAGCTGGGGCGTGTGCACT    359
RHCE_Ce_ex07          ACACTCCCCTCCAACTCAGGAAGAAATGTGTGCAGAGTCCTTAGCTGGGGCGTGTGCACT    359
RHCE_CE_ex07          ACACTCCCCTCCAACTCAGGAAGAAATGTGTGCAGAGTCCTTAGCTGGGGCGTGTGCACT    359
RHCE_consensus_ex07   ACACTCCCCTCCAACTCAGGAAGAAATGTGTGCAGAGTCCTTAGCTGGGGCGTGTGCACT    359
RHD_ex07              ACACTCCCCTCCAACTCAGGAAGAAATGTGTGCAGAGTCCTTAGCTGGGGCGTGTGCACT    359
                      ************************************************************

RHCE_ce_ex07          CGGGGCCAGGTGCTCAGTAGGCTTCGGTGAATATTTGTTGG   400   (SEQ ID NO: 94)
RHCE_cE_ex07          CGGGGCCAGGTGCTCAGTAGGCTTCGGTGAATATTTGTTGG   400   (SEQ ID NO: 95)
RHCE_Ce_ex07          CGGGGCCAGGTGCTCAGTAGGCTTCGGTGAATATTTGTTGG   400   (SEQ ID NO: 96)
RHCE_CE_ex07          CGGGGCCAGGTGCTCAGTAGGCTTCGGTGAATATTTGTTGG   400   (SEQ ID NO: 97)
RHCE_consensus_ex07   CGGGGCCAGGTGCTCAGTAGGCTTCGGTGAATATTTGTTGG   400   (SEQ ID NO: 98)
RHD_ex07              CGGGGCCAGGTGCTCAGTAGGCTTCGGTGAATATTTGTTGG   400   (SEQ ID NO: 93)
                      *****************************************
```

Figure 22B

```
RHCE_ce_ex08          TTGGGAAAATGCCAGGGGAATGTACCAGCCAGGGAGAGGACCCTTGTTTTCCTCATGGCC   60
RHCE_cE_ex08          TTGGGAAAATGCCAGGGGAATGTACCAGCCAGGGAGAGGACCCTTGTTTTCCTCATGGCC   60
RHCE_Ce_ex08          TTGGGAAAATGCCAGGGGAATGTACCAGCCAGGGAGAGGACCCTTGTTTTCCTCATGGCC   60
RHCE_CE_ex08          TTGGGAAAATGCCAGGGGAATGTACCAGCCAGGGAGAGGACCCTTGTTTTCCTCATGGCC   60
RHCE_consensus_ex08   TTGGGAAAATGCCAGGGGAATGTACCAGCCAGGGAGAGGACCCTTGTTTTCCTCATGGCC   60
RHD_ex08              TTGGGAAAATGCCAGGGGAATGTACCAGCCAGGGAGAGGACCCTTGTTTTCCTCATGGCC   60
                      ************************************************************

RHCE_ce_ex08          CTTCCTGGCAATGGCACTACTGACACCGACAGTCCTTTTTGTCCCTGATGACCTCTGCTG   120
RHCE_cE_ex08          CTTCCTGGCAATGGCACTACTGACACCGACAGTCCTTTTTGTCCCTGATGACCTCTGCTG   120
RHCE_Ce_ex08          CTTCCTGGCAATGGCACTACTGACACCGACAGTCCTTTTTGTCCCTGATGACCTCTGCTG   120
RHCE_CE_ex08          CTTCCTGGCAATGGCACTACTGACACCGACAGTCCTTTTTGTCCCTGATGACCTCTGCTG   120
RHCE_consensus_ex08   CTTCCTGGCAATGGCACTACTGACACCGACAGTCCTTTTTGTCCCTGATGACCTCTGCTG   120
RHD_ex08              CTTCCTGGCAATGGCACTACTGACACCGACAGTCCTTTTTGTCCCTGATGACCTCTGCTG   120
                      ************************************************************

RHCE_ce_ex08          CCTGATGCCCAAGTGACCACCTCTGCTTTGTCATTTCTAGGATTGGCTTCCAGGTCCTCC   180
RHCE_cE_ex08          CCTGATGCCCAAGTGACCACCTCTGCTTTGTCATTTCTAGGATTGGCTTCCAGGTCCTCC   180
RHCE_Ce_ex08          CCTGATGCCCAAGTGACCACCTCTGCTTTGTCATTTCTAGGATTGGCTTCCAGGTCCTCC   180
RHCE_CE_ex08          CCTGATGCCCAAGTGACCACCTCTGCTTTGTCATTTCTAGGATTGGCTTCCAGGTCCTCC   180
RHCE_consensus_ex08   CCTGATGCCCAAGTGACCACCTCTGCTTTGTCATTTCTAGGATTGGCTTCCAGGTCCTCC   180
RHD_ex08              CCTGATGCCCAAGTGACCACCTCTGCTTTGTCATTTCTAGGATTGGCTTCCAGGTCCTCC   180
                      ************************************************************

RHCE_ce_ex08          TCAGCATTGGGGAACTCAGCTTGGCCATCGTGATAGCTCTCACGTCTGGTCTCCTGACAG   240
RHCE_cE_ex08          TCAGCATTGGGGAACTCAGCTTGGCCATCGTGATAGCTCTCACGTCTGGTCTCCTGACAG   240
RHCE_Ce_ex08          TCAGCATTGGGGAACTCAGCTTGGCCATCGTGATAGCTCTCACGTCTGGTCTCCTGACAG   240
RHCE_CE_ex08          TCAGCATTGGGGAACTCAGCTTGGCCATCGTGATAGCTCTCACGTCTGGTCTCCTGACAG   240
RHCE_consensus_ex08   TCAGCATTGGGGAACTCAGCTTGGCCATCGTGATAGCTCTCACGTCTGGTCTCCTGACAG   240
RHD_ex08              TCAGCATTGGGGAACTCAGCTTGGCCATCGTGATAGCTCTCACGTCTGGTCTCCTGACAG   240
                      ************************************************************
```

Figure 23A

```
RHCE_ce_ex08          GTCAGTGTGAGGCCACCTTTCTTCCACCATTGCCAGGACACAGCACCCACGTCCAGAGCG     300
RHCE_cE_ex08          GTCAGTGTGAGGCCACCTTTCTTCCACCATTGCCAGGACACAGCACCCACGTCCAGAGCG     300
RHCE_Ce_ex08          GTCAGTGTGAGGCCACCTTTCTTCCACCATTGCCAGGACACAGCACCCACGTCCAGAGCG     300
RHCE_CE_ex08          GTCAGTGTGAGGCCACCTTTCTTCCACCATTGCCAGGACACAGCACCCACGTCCAGAGCG     300
RHCE_consensus_ex08   GTCAGTGTGAGGCCACCTTTCTTCCACCATTGCCAGGACACAGCACCCACGTCCAGAGCG     300
RHD_ex08              GTCAGTGTGAGGCCACCTTTCTTCCACCATTGCCAGGACACAGCACCCACGTCCAGAGCG     300
                      ************************************************************

RHCE_ce_ex08          CACCCTGCCGTGTGGCTGGATGTCTATGTGCCCCATCTCCTTCCCTGAGGATCACATAAT     360
RHCE_cE_ex08          CACCCTGCCGTGTGGCTGGATGTCTATGTGCCCCATCTCCTTCCCTGAGGATCACATAAT     360
RHCE_Ce_ex08          CACCCTGCCGTGTGGCTGGATGTCTATGTGCCCCATCTCCTTCCCTGAGGATCACATAAT     360
RHCE_CE_ex08          CACCCTGCCGTGTGGCTGGATGTCTATGTGCCCCATCTCCTTCCCTGAGGATCACATAAT     360
RHCE_consensus_ex08   CACCCTGCCGTGTGGCTGGATGTCTATGTGCCCCATCTCCTTCCCTGAGGATCACATAAT     360
RHD_ex08              CACCCTGCCGTGTGGCTGGATGTCTATGTGCCCCATCTCCTTCCCTGAGGATCACATAAT     360
                      ************************************************************

RHCE_ce_ex08          TTCAGAATTGGAAAGGTTCTTAGAGGTCACCTGCTGCTAA    400     (SEQ ID NO: 100)
RHCE_cE_ex08          TTCAGAATTGGAAAGGTTCTTAGAGGTCACCTGCTGCTAA    400     (SEQ ID NO: 101)
RHCE_Ce_ex08          TTCAGAATTGGAAAGGTTCTTAGAGGTCACCTGCTGCTAA    400     (SEQ ID NO: 102)
RHCE_CE_ex08          TTCAGAATTGGAAAGGTTCTTAGAGGTCACCTGCTGCTAA    400     (SEQ ID NO: 103)
RHCE_consensus_ex08   TTCAGAATTGGAAAGGTTCTTAGAGGTCACCTGCTGCTAA    400     (SEQ ID NO: 104)
RHD_ex08              TTCAGAATTGGAAAGGTTCTTAGAGGTCACCTGCTGCTAA    400     (SEQ ID NO: 99)
                      ****************************************
```

Figure 23B

```
RHCE_ce_ex09          --GTCCAGGAATGACAGGGCGTCCATTTATTTGTCTTTCAATTGTGGGAGAAAAAGGATT   58
RHCE_cE_ex09          --GTCCAGGAATGACAGGGCGTCCATTTATTTGTCTTTCAATTGTGGGAGAAAAAGGATT   58
RHCE_Ce_ex09          --GTCCAGGAATGACAGGGCGTCCATTTATTTGTCTTTCAATTGTGGGAGAAAAAGGATT   58
RHCE_CE_ex09          --GTCCAGGAATGACAGGGCGTCCATTTATTTGTCTTTCAATTGTGGGAGAAAAAGGATT   58
RHCE_consensus_ex09   --GTCCAGGAATGACAGGGCGTCCATTTATTTGTCTTTCAATTGTGGGAGAAAAAGGATT   58
RHD_ex09              TGGTCCAGGAATGACAGGGCTTCCATTTATTTGTCTTTCAATTGTGGGAGAAAAAGGATT   60
                        ****************** ***************************************

RHCE_ce_ex09          TCTGTTGAGACACTGTCGTTTTGACACACACAATATTTTGATTAATCTTGAGATTAAAAA   118
RHCE_cE_ex09          TCTGTTGAGACACTGTCGTTTTGACACACACAATATTTTGATTAATCTTGAGATTAAAAA   118
RHCE_Ce_ex09          TCTGTTGAGACACTGTCGTTTTGACACACACAATATTTTGATTAATCTTGAGATTAAAAA   118
RHCE_CE_ex09          TCTGTTGAGACACTGTCGTTTTGACACACACAATATTTTGATTAATCTTGAGATTAAAAA   118
RHCE_consensus_ex09   TCTGTTGAGACACTGTCGTTTTGACACACACAATATTTTGATTAATCTTGAGATTAAAAA   118
RHD_ex09              TCTGTTGAGATACTGTCGTTTTGACAC--ACAATATTTCGATTAATCTTGAGATTAAAAA   118
                      ********** ****************  ********* *********************

RHCE_ce_ex09          TCCTGTGCTCCAAATCTTTTAACATTAAATTATGCATTTAAACAGGTTTGCTCCTAAATC   178
RHCE_cE_ex09          TCCTGTGCTCCAAATCTTTTAACATTAAATTATGCATTTAAACAGGTTTGCTCCTAAATC   178
RHCE_Ce_ex09          TCCTGTGCTCCAAATCTTTTAACATTAAATTATGCATTTAAACAGGTTTGCTCCTAAATC   178
RHCE_CE_ex09          TCCTGTGCTCCAAATCTTTTAACATTAAATTATGCATTTAAACAGGTTTGCTCCTAAATC   178
RHCE_consensus_ex09   TCCTGTGCTCCAAATCTTTTAACATTAAATTATGCATTTAAACAGGTTTGCTCCTAAATC   178
RHD_ex09              TCCTGTGCTCCAAATCTTTTAACATTAAATTATGCATTTAAACAGGTTTGCTCCTAAATC   178
                      ************************************************************

RHCE_ce_ex09          TCAAAATATGGAAAGCACCTCATGTGGCTAAATATTTTGATGACCAAGTTTTCTGGAAGG   238
RHCE_cE_ex09          TCAAAATATGGAAAGCACCTCATGTGGCTAAATATTTTGATGACCAAGTTTTCTGGAAGG   238
RHCE_Ce_ex09          TCAAAATATGGAAAGCACCTCATGTGGCTAAATATTTTGATGACCAAGTTTTCTGGAAGG   238
RHCE_CE_ex09          TCAAAATATGGAAAGCACCTCATGTGGCTAAATATTTTGATGACCAAGTTTTCTGGAAGG   238
RHCE_consensus_ex09   TCAAAATATGGAAAGCACCTCATGTGGCTAAATATTTTGATGACCAAGTTTTCTGGAAGG   238
RHD_ex09              TTAAAATATGGAAAGCACCTCATGAGGCTAAATATTTTGATGACCAAGTTTTCTGGAAGG   238
                      * ********************** ***********************************
```

Figure 24A

```
RHCE_ce_ex09          TAAGATTTTTCACCTATTAACGTGATAGATTTTGAGTGCATGAACTTAAAAACATACCTG   298
RHCE_cE_ex09          TAAGATTTTTCACCTATTAACGTGATAGATTTTGAGTGCATGAACTTAAAAACATACCTG   298
RHCE_Ce_ex09          TAAGATTTTTCACCTATTAACGTGATAGATTTTGAGTGCATGAACTTAAAAACATACCTG   298
RHCE_CE_ex09          TAAGATTTTTCACCTATTAACGTGATAGATTTTGAGTGCATGAACTTAAAAACATACCTG   298
RHCE_consensus_ex09   TAAGATTTTTCACCTATTAACGTGATAGATTTTGAGTGCATGAACTTAAAAACATACCTG   298
RHD_ex09              TAAGATTTTTCACCTATTAACGTGATAGATTTTGAGTGCATGAACTTAAAAACATACCTG   298
                      ************************************************************

RHCE_ce_ex09          GGTATATATGTTGACTTGCTGTTTATGAGTAAAACAAAAACAAAAATGGAGTAAGGAGCA   358
RHCE_cE_ex09          GGTATATATGTTGACTTGCTGTTTATGAGTAAAACAAAAACAAAAATGGAGTAAGGAGCA   358
RHCE_Ce_ex09          GGTATATATGTTGACTTGCTGTTTATGAGTAAAACAAAAACAAAAATGGAGTAAGGAGCA   358
RHCE_CE_ex09          GGTATATATGTTGACTTGCTGTTTATGAGTAAAACAAAAACAAAAATGGAGTAAGGAGCA   358
RHCE_consensus_ex09   GGTATATATGTTGACTTGCTGTTTATGAGTAAAACAAAAACAAAAATGGAGTAAGGAGCA   358
RHD_ex09              AGTATATATGTTGACTTGCTGTTTATGAGTAAAACAAAAACAAAAATGGAGTAAGGAGCA   358
                       ***********************************************************

RHCE_ce_ex09          TTGCAGGAGGAACTAGAGGAGAAACAAATCCATGATATGCAT 400    (SEQ ID NO: 106)
RHCE_cE_ex09          TTGCAGGAGGAACTAGAGGAGAAACAAATCCATGATATGCAT 400    (SEQ ID NO: 107)
RHCE_Ce_ex09          TTGCAGGAGGAACTAGAGGAGAAACAAATCCATGATATGCAT 400    (SEQ ID NO: 108)
RHCE_CE_ex09          TTGCAGGAGGAACTAGAGGAGAAACAAATCCATGATATGCAT 400    (SEQ ID NO: 109)
RHCE_consensus_ex09   TTGCAGGAGGAACTAGAGGAGAAACAAATCCATGATATGCAT 400    (SEQ ID NO: 110)
RHD_ex09              TTGCAGGAGGAACTAGAGGAGAAACAAATCCATGATATGCAT 400    (SEQ ID NO: 105)
                      ******************************************
```

Figure 24B

```
RHCE_ce_ex10         TTATCAACAATCCATGTAAAACGTTAGATGAAATAAAACCTATATATCCAAGATCTCTTC   60
RHCE_cE_ex10         TTATCAACAATCCATGTAAAACGTTAGATGAAATAAAACCTATATATCCAAGATCTCTTC   60
RHCE_Ce_ex10         TTATCAACAATCCATGTAAAACGTTAGATGAAATAAAACCTATATATCCAAGATCTCTTC   60
RHCE_CE_ex10         TTATCAACAATCCATGTAAAACGTTAGATGAAATAAAACCTATATATCCAAGATCTCTTC   60
RHCE_consensus_ex10  TTATCAACAATCCATGTAAAACGTTAGATGAAATAAAACCTATATATCCAAGATCTCTTC   60
RHD_ex10             TTATCAACAATCCATGTAAAACGTTAGATGAAATAAAACCTATATATCCAAGATCTCTTC   60
                     ************************************************************

RHCE_ce_ex10         CAATTCAGATTTTATGAAAGAATTTCTAAGGTCTTTGTAATGAGACATTTAGGCTGTTTC   120
RHCE_cE_ex10         CAATTCAGATTTTATGAAAGAATTTCTAAGGTCTTTGTAATGAGACATTTAGGCTGTTTC   120
RHCE_Ce_ex10         CAATTCAGATTTTATGAAAGAATTTCTAAGGTCTTTGTAATGAGACATTTAGGCTGTTTC   120
RHCE_CE_ex10         CAATTCAGATTTTATGAAAGAATTTCTAAGGTCTTTGTAATGAGACATTTAGGCTGTTTC   120
RHCE_consensus_ex10  CAATTCAGATTTTATGAAAGAATTTCTAAGGTCTTTGTAATGAGACATTTAGGCTGTTTC   120
RHD_ex10             CAATTCAGATTTTATGAAAGAATTTCTAAGGTCTTTGTAATGAGACATTTAGGCTGTTTC   120
                     ************************************************************

RHCE_ce_ex10         AAGAGATCAAGCCAAAATCAGTATGTGGGTTCATCTGCAATAAAAATGTTTGTTTTGCTT   180
RHCE_cE_ex10         AAGAGATCAAGCCAAAATCAGTATGTGGGTTCATCTGCAATAAAAATGTTTGTTTTGCTT   180
RHCE_Ce_ex10         AAGAGATCAAGCCAAAATCAGTATGTGGGTTCATCTGCAATAAAAATGTTTGTTTTGCTT   180
RHCE_CE_ex10         AAGAGATCAAGCCAAAATCAGTATGTGGGTTCATCTGCAATAAAAATGTTTGTTTTGCTT   180
RHCE_consensus_ex10  AAGAGATCAAGCCAAAATCAGTATGTGGGTTCATCTGCAATAAAAATGTTTGTTTTGCTT   180
RHD_ex10             AAGAGATCAAGCCAAAATCAGTATGTGGGTTCATCTGCAATAAAAATGTTTGTTTTGCTT   180
                     ************************************************************

RHCE_ce_ex10         TTACAGTTTCCTCATTTGGCTGTTGGATTTTAAGCAAAAGCATCCAAGAAAAACAAGGCC   240
RHCE_cE_ex10         TTACAGTTTCCTCATTTGGCTGTTGGATTTTAAGCAAAAGCATCCAAGAAAAACAAGGCC   240
RHCE_Ce_ex10         TTACAGTTTCCTCATTTGGCTGTTGGATTTTAAGCAAAAGCATCCAAGAAAAACAAGGCC   240
RHCE_CE_ex10         TTACAGTTTCCTCATTTGGCTGTTGGATTTTAAGCAAAAGCATCCAAGAAAAACAAGGCC   240
RHCE_consensus_ex10  TTACAGTTTCCTCATTTGGCTGTTGGATTTTAAGCAAAAGCATCCAAGAAAAACAAGGCC   240
RHD_ex10             TTACAGTTTCCTCATTTGGCTGTTGGATTTTAAGCAAAAGCATCCAAGAAAAACAAGGCC   240
                     ************************************************************
```

Figure 25A

```
RHCE_ce_ex10          TGTTCAAAAACAAGACAACTTCCTCTCACTGTTGCCTGCATTTGTACGTGAGAAACGCTC   300
RHCE_cE_ex10          TGTTCAAAAACAAGACAACTTCCTCTCACTGTTGCCTGCATTTGTACGTGAGAAACGCTC   300
RHCE_Ce_ex10          TGTTCAAAAACAAGACAACTTCCTCTCACTGTTGCCTGCATTTGTACGTGAGAAACGCTC   300
RHCE_CE_ex10          TGTTCAAAAACAAGACAACTTCCTCTCACTGTTGCCTGCATTTGTACGTGAGAAACGCTC   300
RHCE_consensus_ex10   TGTTCAAAAACAAGACAACTTCCTCTCACTGTTGCCTGCATTTGTACGTGAGAAACGCTC   300
RHD_ex10              TGTTCAAAAACAAGACAACTTCCTCTCACTGTTGCCTGCATTTGTACGTGAGAAACGCTC   300
                      ************************************************************

RHCE_ce_ex10          ATGACAGCAAAGTCTCCTTATGTATAATGAAACAAGGTCAGAGACAGATTTGATATTAAA   360
RHCE_cE_ex10          ATGACAGCAAAGTCTCCTTATGTATAATGAAACAAGGTCAGAGACAGATTTGATATTAAA   360
RHCE_Ce_ex10          ATGACAGCAAAGTCTCCTTATGTATAATGAAACAAGGTCAGAGACAGATTTGATATTAAA   360
RHCE_CE_ex10          ATGACAGCAAAGTCTCCTTATGTATAATGAAACAAGGTCAGAGACAGATTTGATATTAAA   360
RHCE_consensus_ex10   ATGACAGCAAAGTCTCCTTATGTATAATGAAACAAGGTCAGAGACAGATTTGATATTAAA   360
RHD_ex10              ATGACAGCAAAGTCTCCAATGTTCGCGCAGGCACTGGAGTCAGAGAAAATGGAGTTGAAT   360
                      *****************     *            **    *** * * * **  * **

RHCE_ce_ex10          AAATTAAAGACTAAAAACTTAGTTTAAGAGTCAATTTAAT   400   (SEQ ID NO: 112)
RHCE_cE_ex10          AAATTAAAGACTAAAAACTTAGTTTAAGAGTCAATTTAAT   400   (SEQ ID NO: 113)
RHCE_Ce_ex10          AAATTAAAGACTAAAAACTTAGTTTAAGAGTCAATTTAAT   400   (SEQ ID NO: 114)
RHCE_CE_ex10          AAATTAAAGACTAAAAACTTAGTTTAAGAGTCAATTTAAT   400   (SEQ ID NO: 115)
RHCE_consensus_ex10   AAATTAAAGACTAAAAACTTAGTTTAAGAGTCAATTTAAT   400   (SEQ ID NO: 116)
RHD_ex10              CCTTTCTCTGCCACTCTTTGAGGAGAATCTCACCATTTAT   400   (SEQ ID NO: 111)
                         **     * *     * **   **        ** **
```

Figure 25B

```
RHCE_ce_in2     CTGTTTTGAGTCCCTTCAGGGGAGGGGCCTATCTTATTCAACGTTGTTCTTTGTTTTCCT    60
RHCE_cE_in2     CTGTTTTGAGTCCCTTCAGGGGAGGGGCCTATCTTATTCAACGTTGTTCTTTGTTTTCCT    60
RHCE_Ce_in2     CTGTTTTGAGTCCCTTCAGGGGAGGGGCCTATCTTATTCAACGTTGTTCTTTGTTTTCCT    60
RHCE_CE_in2     CTGTTTTGAGTCCCTTCAGGGGAGGGGCCTATCTTATTCAACGTTGTTCTTTGTTTTCCT    60
RHD_in2         CTGTTTTGAGTCCCTTCAGGGGAGGGGCCTATCTTATTCAACGTTGTTGTTTGTTTTCCT    60
                ************************************************ ***********

RHCE_ce_in2     CACATACTGATAACTTAGCAAATGGCTATTGGAACAAAAATGAAAATAAACGGAACCCTG    120
RHCE_cE_in2     CACATACTGATAACTTAGCAAATGGCTATTGGAACAAAAATGAAAATAAACGGAACCCTG    120
RHCE_Ce_in2     CACATACTGATAACTTAGCAAATGGCTATTGGAACAAAAATGAAAATAAACGGAACCCTG    120
RHCE_CE_in2     CACATACTGATAACTTAGCAAATGGCTATTGGAACAAAAATGAAAATAAACGGAACCCTG    120
RHD_in2         CACATACTGATAACTTAGCAAATGGCTATTGGAGCAAAAATGAAAATAAACGGAACTCTG    120
                ********************************* ********************** ***

RHCE_ce_in2     AAGTGGGATGTTTTAAATTTTTATTTATTTTTTTAGAGACAGGGTCTTGCTCTGTTGCCC    180
RHCE_cE_in2     AAGTGGGATGTTTTAAATTTTTATTTATTTTTTTAGAGACAGGGTCTTGCTCTGTTGCCC    180
RHCE_Ce_in2     AAGTGGGATGTTTTAAATTTTTATTTATTTTTTTAGAGACAGGGTCTTGCTCTGTTGCCC    180
RHCE_CE_in2     AAGTGGGATGTTTTAAATTTTTATTTATTTTTTTAGAGACAGGGTCTTGCTCTGTTGCCC    180
RHD_in2         AAGTGGGATGTTTTAAAATTTTATT---TTTTTTAGAGACAGGGTCTTGCTCTGTTGCCC    177
                **************** *******    ********************************

RHCE_ce_in2     AGTCTGGAGTGCAGTGGTACAATCATAGCTCA----------------------------    212
RHCE_cE_in2     AGTCTGGAGTGCAGTGGTACAATCATAGCTCA----------------------------    212
RHCE_Ce_in2     AGTCTGGAGTGCAGTGGTACAATCATAGCTCATTGCTATAGCTTAAGGACTCACCTGGCA    240
RHCE_CE_in2     AGTCTGGAGTGCAGTGGTACAATCATAGCTCATTGCTATAGCTTAAGGACTCACCTGGCA    240
RHD_in2         AGTCTGGAGTGCAGTGGTACAATCATAGCTCA----------------------------    209
                ********************************

RHCE_ce_in2     ------------------------------------------------------------    212
RHCE_cE_in2     ------------------------------------------------------------    212
RHCE_Ce_in2     GCAACACCAAACCAGGGCCACCACCATTTGAAATCCCCCAGGGTGCCCTTTGTCACTTCC    300
RHCE_CE_in2     GCAACACCAAACCAGGGCCACCACCATTTGAAATCCCCCAGGGTGCCCTTTGTCACTTCC    300
RHD_in2         ------------------------------------------------------------    209
```

Figure 26A

```
RHCE_ce_in2   ---------------------TTGCAGCCTCTGCCTCCTGGGCTCAAGTGATCCTCCCAC   251
RHCE_cE_in2   ----------------------CTGCAGCCTCTGCCTCCTGGGCTCAAGTGATCCTCCCAC   251
RHCE_Ce_in2   CAGTGGTACAATCATAGCTCACTGCAGCCTCTGCCTCCTGGGCTCAAGTGATCCTCCCAC   360
RHCE_CE_in2   CAGTGGTACAATCATAGCTCACTGCAGCCTCTGCCTCCTGGGCTCAAGTGATCCTCCCAC   360
RHD_in2       ---------------------TTGCAGCCTGTGCCTCCTGGGCTCAAGTGATCCTCCCAC   248
                                     *************************************

RHCE_ce_in2   CTCAGCCTCCTGAGTTAAATTTTTTTACAGACGCCTGCTACCATGCCCGGCTAATTT   308   (SEQ ID NO: 118)
RHCE_cE_in2   CTCAGCCTCCTGAGTTAAATTTTTTTACAGACGCCTGCTACCATGCCCGGCTAATTT   308   (SEQ ID NO: 119)
RHCE_Ce_in2   CTCAGCCTCCTGAGTTAAATTTTTTTACAGACGCCTGCTACCATGCCCGGCTAATTT   417   (SEQ ID NO: 120)
RHCE_CE_in2   CTCAGCCTCCTGAGTTAAATTTTTTTACAGACGCCTGCTACCATGCCCGGCTAATTT   417   (SEQ ID NO: 121)
RHD_in2       CTCAGCCTCCTGAGTTAAATTTTTTTACAGGCGCCTGCTACCATGCCCTGCTAATTT   305   (SEQ ID NO: 117)
              ****************************** ***************** ********
```

Figure 26B

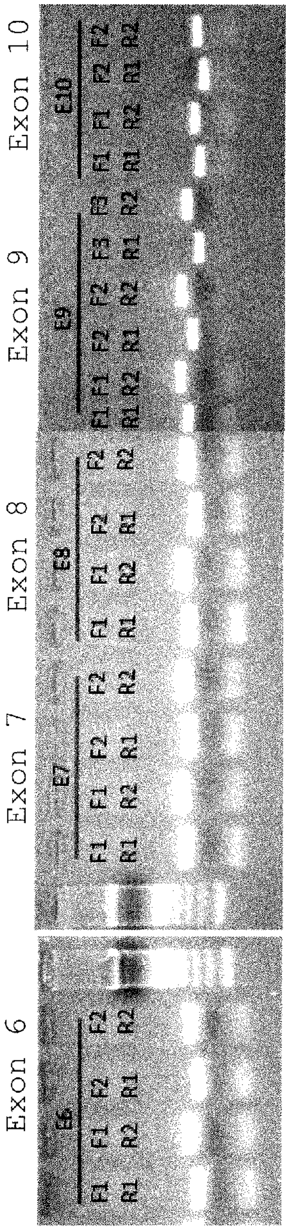
Figure 27. Amplification of Exons 6 through 10

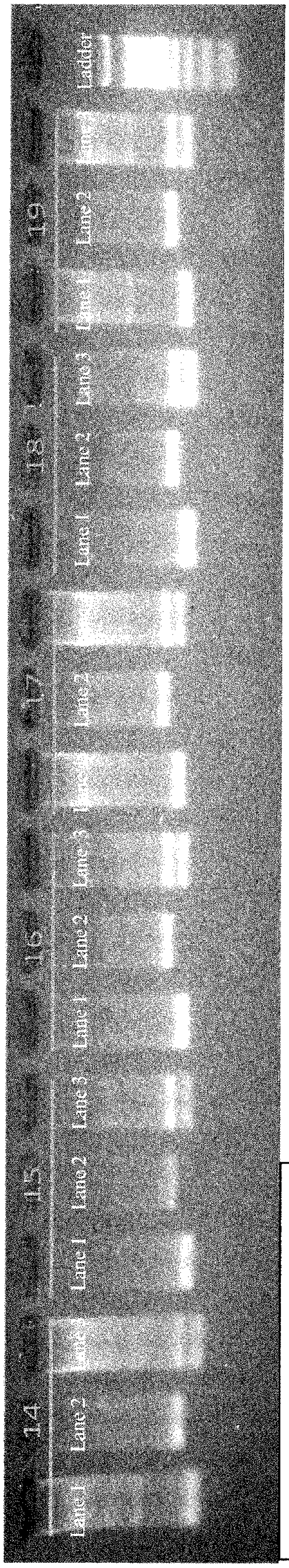
Primer combinations for Intron 2
Reaction 14: F3R6
Reaction 15: F2R3
Reaction 16: F1R3
Reaction 17: F1R4
Reaction 18: F3R8
Reaction 19: F2R4
Genotypes
Lane 1: D/cc
Lane 2: dd/CC
Lane 3: DD/CC
Figure 28. Amplification of Intron 2

CONSENSUS-BASED ALLELE DETECTION

CROSS REFERENCE TO RELATED APPLICATIONS

This is the § 371 U.S. National Stage of International Application No. PCT/EP2015/068601, filed Aug. 12, 2015, which was published in English under PCT Article 21(2), which in turn claims the benefit of GB Application No. 1414350.7, filed Aug. 13, 2014, which is incorporated by reference herein in its entirety.

FIELD OF THE INVENTION

The invention relates to methods for next-generation-sequencing-based detection of alleles in highly homologous genetic loci, for example RHD/RHCE. The invention also relates to products, in particular, consensus sequence-specific primers and kits for use in such methods.

BACKGROUND TO THE INVENTION

DNA sequencing by the Sanger dideoxy method is based on a single detection event at each position of a usually homogeneous pool of DNA molecules. From this event, a qualitative presence/absence call is made for each one of four nucleotides (A, C, G, T) at each position in the DNA segment. Thus, Sanger sequencing is not a quantitative technique.

DNA sequencing by next-generation methods, on the other hand, is based on multiple detection events at each position, each event corresponding to a single DNA molecule in the pool. From the multiplicity of events, the relative abundance of each of the four nucleotides at each position in the DNA segment can be calculated. Thus, next-generation sequencing allows for a quantitative measurement of particular sequences in a heterogeneous pool of DNA molecules.

DNA sequencing is the gold standard in the molecular diagnosis of genetic diseases and in the detection of allelic variants of clinical relevance, such as those encoding human leukocyte, red cell and platelet antigens. A challenge to accurate DNA sequencing is presented by highly homologous genes, such as the human leukocyte antigen (HLA) system, the red cell antigen-encoding RHD-RHCE, or GYPA-GYPB-GYPE sets.

Discrimination among homologous genes is commonly achieved through the use of primers designed to bind to gene-specific sequences. In some genetic regions, however, there are no gene-specific sequences to avail, or they are located too far apart to allow for the development of standard amplification assays. These facts pose a significant challenge to sequencing in general, and to next-generation sequencing in particular, given the length limitations to which readable DNA segments are subject.

Accordingly, there remains a need for further methods for amplification of highly homologous genetic loci and reliable sequencing and/or allele detection thereof. It is an object of the present invention to address these and other needs.

SUMMARY OF THE INVENTION

The present inventors have demonstrated amplification of highly homologous genetic loci using consensus-sequence-specific primers, as described herein, followed by sequence alignment with reference sequences to resolve the highly homologous genetic loci and allele detection using next-generation sequencing (NGS). The present invention therefore provides a way to enable sequencing of regions with widely-separated or without gene-specific sequences through the use of primers that bind to consensus sequences within the set of homologous genes. Since the number of consensus positions is usually larger than the number of gene-specific positions, this also facilitates primer design and meeting the segment length requirements. A challenge present by the use of primers that bind to consensus sequences is a loss of specificity, as a result of the simultaneous amplification of all genes within the set. However, the present inventors have found that the challenge presented by the aforementioned loss of specificity can largely be overcome by exploiting the quantitative nature of next-generation sequencing and the existing knowledge about gene- and allele-specific sequences. Specifically, the alleles present in a sample for each of the genes in a high-homology set can be determined from (1) the particular sequences detected at each polymorphic position, (2) their relative proportion, and (3) their combination throughout the genetic segment. While (1) and (3) are shared with Sanger sequencing, (2) is unique to next-generation sequencing. The examples described herein demonstrate reliable genotype and bloodtype calling for a range of samples based on multiplex next-generation sequencing followed by data analysis.

Accordingly, in a first aspect the present invention provides a method for genotyping alleles in at least one homologous genetic loci set, comprising:

(i) providing a DNA-containing sample that includes said at least one homologous genetic loci set;

(ii) performing PCR amplification of regions of said homologous genetic loci set using consensus sequence-specific primers, wherein said consensus sequence-specific primers bind to consensus sequences that are common to a plurality of genes within the genetic loci set, thereby generating a pool of amplification products;

(iii) sequencing a plurality of said amplification products in order to determine the relative proportion of each nucleotide at each position in a sequencing read;

(iv) performing a sequence alignment between the sequencing read results of (iii) and at least one reference sequence, which reference sequence corresponds to one of the genes in said homologous genetic loci set; and (v) performing genotype calling of the allele or alleles in said sample based on the relative proportion of each nucleotide at each of a plurality of discriminant positions in said alignment.

In some cases in accordance with this and other aspects of the present invention the homologous genetic loci set comprises a first gene and a second gene which exhibit a high degree of sequence identity, e.g. as a result of an ancestral gene duplication event. In certain cases the first gene has at least 90%, at least 95% or at least 97% nucleotide sequence identity with the second gene. Particular examples of homologous genetic loci sets include the RHD-RHCE genes, the human leukocyte antigen (HLA) system genes; and the glycophorin-encoding genes GypA-GypB-GypE. In some cases, the homologous genetic loci set comprises the human RHD gene of SEQ ID NO: 25 and the human RHCE gene of SEQ ID NO: 26 (or one of the RHCE haplotypes ce, Ce, cE or CE, respectively).

In cases where the homologous genetic loci set comprises the RHD gene and the RHCE gene, the at least one reference sequence may comprise:

(i) at least one exon or intron of the RHD gene of SEQ ID NO: 25 or the reverse complement thereof;

(ii) at least one exon or intron of the RHCE gene of SEQ ID NO: 26 or of one of the RHCE haplotypes ce, Ce, cE or CE, respectively or the reverse complement thereof;

(iii) at least one of the RHD exon 1 sequence as shown in SEQ ID NO: 27, the RHCE exon 1 sequences as shown in SEQ ID NOs: 28-31, being RHCE haplotypes ce, Ce, cE or CE, respectively, and/or the RHCE exon 1 consensus sequence as shown in SEQ ID NO: 32 or the reverse complement thereof;

(iv) at least one of the RHD exon 2 sequence as shown in SEQ ID NO: 33, the RHCE exon 2 sequences as shown in SEQ ID NOs: 34-37, being RHCE haplotypes ce, Ce, cE or CE, respectively, and/or the RHCE exon 2 consensus sequence as shown in SEQ ID NO: 38 or the reverse complement thereof;

(v) at least one of the RHD exon 3 sequence as shown in SEQ ID NO: 39, the RHCE exon 3 sequences as shown in SEQ ID NOs: 40-43, being RHCE haplotypes ce, Ce, cE or CE, respectively, and/or the RHCE exon 3 consensus sequence as shown in SEQ ID NO: 44 or the reverse complement thereof;

(vi) at least one of the RHD exon 4 sequence as shown in SEQ ID NO: 45, the RHCE exon 4 sequences as shown in SEQ ID NOs: 46-49, being RHCE haplotypes ce, Ce, cE or CE, respectively, and/or the RHCE exon 4 consensus sequence as shown in SEQ ID NO: 50 or the reverse complement thereof;

(vii) at least one of the RHD exon 5 sequence as shown in SEQ ID NO: 51, the RHCE exon 5 sequences as shown in SEQ ID NOs: 52-55, being RHCE haplotypes ce, Ce, cE or CE, respectively, and/or the RHCE exon 5 consensus sequence as shown in SEQ ID NO: 56 or the reverse complement thereof;

(viii) at least one of the RHD exon 6 sequence as shown in SEQ ID NO: 87, the RHCE exon 6 sequences as shown in SEQ ID NOs: 88-91, being RHCE haplotypes ce, Ce, cE or CE, respectively, and/or the RHCE exon 6 consensus sequence as shown in SEQ ID NO: 92 or the reverse complement thereof;

(ix) at least one of the RHD exon 7 sequence as shown in SEQ ID NO: 93, the RHCE exon 7 sequences as shown in SEQ ID NOs: 94-97, being RHCE haplotypes ce, Ce, cE or CE, respectively, and/or the RHCE exon 7 consensus sequence as shown in SEQ ID NO: 98 or the reverse complement thereof;

(x) at least one of the RHD exon 8 sequence as shown in SEQ ID NO: 99, the RHCE exon 8 sequences as shown in SEQ ID NOs: 100-103, being RHCE haplotypes ce, Ce, cE or CE, respectively, and/or the RHCE exon 8 consensus sequence as shown in SEQ ID NO: 104 or the reverse complement thereof;

(xi) at least one of the RHD exon 9 sequence as shown in SEQ ID NO: 105, the RHCE exon 9 sequences as shown in SEQ ID NOs: 106-109, being RHCE haplotypes ce, Ce, cE or CE, respectively, and/or the RHCE exon 9 consensus sequence as shown in SEQ ID NO: 110 or the reverse complement thereof;

(xii) at least one of the RHD exon 10 sequence as shown in SEQ ID NO: 111, the RHCE exon 10 sequences as shown in SEQ ID NOs: 112-115, being RHCE haplotypes ce, Ce, cE or CE, respectively, and/or the RHCE exon 10 consensus sequence as shown in SEQ ID NO: 116 or the reverse complement thereof; and/or (xiii) at least one of the RHD intron 2 sequence as shown in SEQ ID NO: 117, the RHCE intron 2 sequences as shown in SEQ ID NOs: 118-121, being RHCE haplotypes ce, Ce, cE or CE, respectively, or the reverse complement thereof.

The reference sequence may include at least 5, 10, 20, 30, 40, 50, 60, 70, 80, 90 or 100 nucleotides upstream and/or downstream of said exon or intron. In some cases the reference sequence comprises only the exon sequence portion indicated in bold FIGS. 16-20 and 21-26, respectively. In other cases the reference sequence includes some (e.g. 25%, 50% or 75%) of or all of the upstream and/or downstream flanking intronic sequence indicated in non-bold of FIGS. 16-20 and 21-26, respectively.

In certain cases in accordance with this and other aspects of the present invention the said at least one reference sequence comprises at least two reference sequences, including: (i) at least one exon or intron of the RHD gene of SEQ ID NO: 25 or the reverse complement thereof (e.g. one of SEQ ID NOS: 27, 33, 39, 45, 51, 87, 93, 99, 105, 111 or 117); and (ii) a least one exon or intron of an RHCE gene sequence, such as of SEQ ID NO: 26, (e.g. one of SEQ ID NOS: 28-32, 34-38, 40-44, 46-50, 52-56, 88-92, 94-98, 100-104, 106-110, 112-116, or 118-121) or the reverse complement thereof.

In certain cases in accordance with this and other aspects of the present invention the plurality of discriminant positions in said alignment are selected from the positions set forth in Table 2, Table 11 and Table 13. The identity of the bases that may be detected at each of said discriminant positions is also indicated in Table 2, Table 11 and Table 13, as are the corresponding genotypes. For example, position 48 of exon 1 is polymorphic G/C.

The present inventors have found that particular consensus-sequence primers as defined herein are able to amplify both RHD and RHCE gene segments (e.g. exon 1 of RHD and of RHCE) and find use in the methods of the present invention.

Accordingly, in certain cases of the method of the first aspect of the invention each of said consensus sequence-specific primers comprises or consists of a nucleotide sequence selected from the group consisting of:

| | | |
|---|---|---|
| RHex01 F1 | TCCCTCAAGCCCTCAAGTAG | (SEQ ID NO: 3) |
| RHex01 F2 | TGTTGGAGAGAGGGGTGATG | (SEQ ID NO: 4) |
| RHex01 F3 | CTGCACAGAGACGGACACAG | (SEQ ID NO: 5) |
| RHex01 R1 | CCCTGCTATTTGCTCCTGTG | (SEQ ID NO: 6) |
| RHex01 R2 | AAAGGAACATCTGTGCCCCT | (SEQ ID NO: 7) |
| RHex02 F1 | CCCTTCCAGCTGCCATTTAG | (SEQ ID NO: 8) |
| RHex02 F2 | AAATCTCGTCTGCTTCCCCC | (SEQ ID NO: 9) |
| RHex02 R1 | AAGTGATCCAGCCACCATCC | (SEQ ID NO: 10) |
| RHex02 R2 | GTCCATTCCCTCTATGACCC | (SEQ ID NO: 11) |

-continued

| | | |
|---|---|---|
| RHex03 F1 | AGGTGCCCAACAGTGTTTGT | (SEQ ID NO: 12) |
| RHex03 F2 | TGAGTGAGAGGCATCCTTCC | (SEQ ID NO: 13) |
| RHex03 R1 | TTTGGCCCTTTTCTCCCAGG | (SEQ ID NO: 14) |
| RHDex03 R2 | GAAACCCCACCAAATGGAGC | (SEQ ID NO: 15) |
| RHCEex03 R3 | GAAGCCCCACCAAATGGAGC | (SEQ ID NO: 16) |
| RHex04 F1 | GGCTTCAAGTCACACCTCCT | (SEQ ID NO: 17) |
| RHex04 F2 | CAGAGGATGCCGACACTCAC | (SEQ ID NO: 18) |
| RHex04 R1 | CCATTCTGCTCAGCCCAAGT | (SEQ ID NO: 19) |
| RHex04 R2 | CAGCCAGAGCCTTTTCTGAG | (SEQ ID NO: 20) |
| RHex05 F1 | CAGCCCTAGGATTCTCATCC | (SEQ ID NO: 21) |
| RHex05 F2 | AGCAGGAGTGTGATTCTGGC | (SEQ ID NO: 22) |
| RHex05 R1 | CTGTTAGACCCAAGTGCTGC | (SEQ ID NO: 23) |
| RHex05 R2 | TGGGGAGGGGCATAAATATG | (SEQ ID NO: 24) |
| RHex06 F1 | GGTCACTTGCAGCAAGATGG | (SEQ ID NO: 59) |
| RHex06 F2 | ACCTTGCTTCCTTTACCCAC | (SEQ ID NO: 60) |
| RHex06 R1 | TGGCCTTCAGCCAAAGCAGA | (SEQ ID NO: 61) |
| RHex06 R2 | CTAATGCAGCTGTGCACTGC | (SEQ ID NO: 62) |
| RHex07 F1 | TGTGTGAAAGGGGTGGGTAG | (SEQ ID NO: 63) |
| RHex07 F2 | GTCTCACCTGCCAATCTGCT | (SEQ ID NO: 64) |
| RHex07 R1 | GTTGGAGGGGAGTGTTAAGG | (SEQ ID NO: 65) |
| RHex07 R2 | CCAGCTAAGGACTCTGCACA | (SEQ ID NO: 66) |
| RHex08 F1 | ATGGCACTACTGACACCGAC | (SEQ ID NO: 67) |
| RHex08 F2 | TTGTCCCTGATGACCTCTGC | (SEQ ID NO: 68) |
| RHex08 R1 | TGTCCTGGCAATGGTGGAAG | (SEQ ID NO: 69) |
| RHex08 R2 | GCACATAGACATCCAGCCAC | (SEQ ID NO: 70) |
| RHex09 F1 | AGCTGGTCCAGGAATGACAG | (SEQ ID NO: 71) |
| RHex09 F2 | GTGGGAGAAAAAGGATTTCTGTTGAGA | (SEQ ID NO: 72) |
| RHex09 F3 | TCTTGAGATTAAAAATCCTGTGCTCCA | (SEQ ID NO: 73) |
| RHex09 R1 | AGTTCATGCACTCAAAATCTATCACGT | (SEQ ID NO: 74) |
| RHex09 R2 | CCTGCAATGCTCCTTACTCC | (SEQ ID NO: 75) |
| RHex10 F1 | GGCTGTTTCAAGAGATCAAGCC | (SEQ ID NO: 76) |
| RHex10 F2 | TCAGTATGTGGGTTCATCTGCA | (SEQ ID NO: 77) |
| RHex10 R1 | AGGCAACAGTGAGAGGAAGTTG | (SEQ ID NO: 78) |
| RHex10 R2 | TGCTGTCATGAGCGTTTCTCAC | (SEQ ID NO: 79) |
| RHin2 F1 | CTTGTGCCACTTGACTTGGGACTG | (SEQ ID NO: 80) |
| RHin2 F2 | CTGTTTTGAGTCCCTTCAGGGGAG | (SEQ ID NO: 81) |
| RHin2 F3 | CTCACATACTGATAACTTAGCAAATGGC | (SEQ ID NO: 82) |
| RHin2 R1 | GATCACTTGAGCCCAGGAGGC | (SEQ ID NO: 83) |
| RHin2 R2 | TTAACTCAGGAGGCTGAGGTGG | (SEQ ID NO: 84) |
| RHin2 R3 | CTGAGGTGGGAGGATCACTTGAG | (SEQ ID NO: 85) |
| RHCEin2 R4 | AAATTAGCCGGGCATGGTAGCAG | (SEQ ID NO: 86) |

or a variant of one of said sequences 3-24 and 59-86 having not more than one, two or three nucleotide changes by substitution, addition or deletion. Variants of the primers of SEQ ID NOs: 3-24 and 59-86 may, in particular, comprise additional nucleotides at the 5' and/or 3' end, which extend the primer sequence to include contiguous sequence neighbouring the portion of the RHD and RHCE genomic sequence that the said primer of one of SEQ ID NOs: 3-24 and 59-86 hybridises to. Additionally or alternatively, a variant primer may be truncated at the 5' and/or 3' end, e.g. to be 1, 2, or 3 nucleotides shorter in length.

In some cases in accordance with the method of this and other aspects of the present invention, one or more of the consensus sequence-specific primers may further comprise a tag or adaptor. For example, the primer may comprise a next generation sequencing tag or adaptor, e.g., at its 5' end. In certain cases one or more of the consensus sequence-specific primers comprises a next generation sequencing tag with the sequence ACACTCTTTCCCTACACGACGCTCTTC-CGATCT (SEQ ID NO: 1). The tag of SEQ ID NO: 1 may be at the 5' end of a forward primer such as a forward primer of one or more of SEQ ID NOs: 3-5, 8-9, 12-13, 17-18, 21-22, 59-60, 63-64, 67-68, 71-73, 76-77, and 80-82. Alternatively or additionally, one or more of the consensus sequence-specific primers may comprise a next generation sequencing tag with the sequence GTGACTGGAGTTCA-GACGTGTGCTCTTCCGATCT (SEQ ID NO: 2). The tag of SEQ ID NO: 2 may be at the 5' end of a reverse primer such as a reverse primer of one or more of SEQ ID NOs: 6-7, 10-11, 14-16, 19-20, 23-24, 61-62, 65-66, 69-70, 74-75, 78-79, and 83-86.

In other cases in accordance with the method of this and other aspects of the present invention, one or more of the consensus sequence-specific primers may further comprise a tag and/or adaptor. For example, the primer may comprise a next generation sequencing tag or adaptor, e.g., at its 5' end. In certain cases one or more of the consensus sequence-specific primers comprises a next generation sequencing tag with the sequence ACACTCTTTCCCTACCTGTAAAACGACGGCCAGT (SEQ ID NO: 57). The tag of SEQ ID NO: 1 or 57 may be at the 5' end of a forward primer such as a forward primer of one or more of SEQ ID NOs: 3-5, 8-9, 12-13, 17-18, 21-22, 59-60, 63-64, 67-68, 71-73, 76-77, and 80-82. Alternatively or additionally, one or more of the consensus sequence-specific primers may comprise a next generation sequencing tag with the sequence GGTTGCTCGCCAGGAAACAGCTATGACC (SEQ ID NO: 58). The tag of SEQ ID NO: 2 or 58 may be at the 5' end of a reverse primer such as a reverse primer of one or more of SEQ ID NOs: 6-7, 10-11, 14-16, 19-20, 23-24, 61-62, 65-66, 69-70, 74-75, 78-79, and 83-86.

In some cases in accordance with the method of this and other aspects of the present invention, the method comprises sequencing each of exons 1, 2, 3, 4 and 5 of the RHD gene and each of exons 1, 2, 3, 4 and 5 of the RHCE gene. Alternatively or additionally, in accordance with the method of this and other aspects of the present invention, the method may comprise sequencing each of exons 6, 7, 8, 9 and 10 and intron 2 of the RHD gene and each of exons 6, 7, 8, 9 and 10 and intron 2 of the RHCE gene.

In some cases in accordance with the method of this and other aspects of the present invention, the method comprises classifying the sample in terms of its RHD/RHCE genotype. In certain cases the genotype is selected from the group consisting of:

(a) CE(exons 1-2)-DD(exons 3-9)-CE(exon 10);
(b) DDCcEe;
(c) DdCCee;
(d) ddCcEe;
(e) DdCcee(exons 1-2)-ddCcee(exons 3-9)-DD(exon 10);
(f) ddCcee;
(g) DDCcEe;
(h) DdccEe;
(i) ddccee;
(j) DDCCee;
(k) DdCcee;
(l) ddCCee;
(m) DDccEE; and
(n) D?ccEe.

In some cases the genotype is other than any one of genotypes (a) to (n). The classification of the sample as being of one or said genotypes is typically made based on the relative proportion of each nucleotide at each of said plurality of discriminant positions in said alignment. Preferably, the classification of the genotype of the sample is made based on criteria set forth in Tables 2, 6, 8, 13, 15, 17, 19, 21, 23, 25, 27, 29, 30 and/or 31.

In some cases in accordance with the method of this and other aspects of the present invention, the method further comprises determining the blood type of the sample based on the genotype. In certain cases the blood type of the sample is selected from the group consisting of:

(i) RHD+, Cw type;
(ii) RHD+, CcEe;
(iii) wDt3, Cce;
(iv) RHD*DIIIa-het;
(v) Ce, RHD+;
(vi) DAR-hem;
(vii) r's;
(viii) Ce, RHD+;
(ix) rr;
(x) R1R1;
(xi) R1r;
(xii) r'r';
(xiii) R2R2;
(xiv) Pseudogen/-; and
(xv) DVI type 1/-

In some cases in accordance with the method of this and other aspects of the present invention, the sample is classified as having a blood type allele selected from the group consisting of: RHD*r'$^S$; RHD*r'$^S$-like; RHD*r'$^S$ Type 1; RHD*r'$^S$ Type 2; RHD*DIIIa; RHD*DIIIa IVS3+3100G; RHD*DIII_FN; RHD*DIVa-2; RHD*DIVa; RHD*DIII-type4; RHD*DIII-type6; RHD*DIII-type7; RHD*DIII-type8; RHCE*ce$^S$; RHCE*ce$^S$1006T; RHCE*ce$^S$1006C; RHCE*ce733G; RHCE*ce48C, 733G, 1025T; RHCE*ce48C, 697G, 733G; RHCE*ce340T, 733G; and RHCE*ce48C, 733G, 748A, based on the genotype of the sample at one or more polymorphic positions in the RHD gene and/or RHCE gene.

In some cases in accordance with the method of this and other aspects of the present invention, the method comprises obtaining the number of reads covering the reference bases and the number of reads covering alternate bases after alignment for use in said genotype calling.

In some cases in accordance with the method of this and other aspects of the present invention, the method comprises defining a cut-off for the proportion of reads covering the reference bases versus the reads covering the alternate bases for variant calling.

In some cases in accordance with the method of this and other aspects of the present invention, the method comprises obtaining the number of reads covering reference forward bases, number of reads covering reference reverse bases, number of reads covering alternate forward bases and number of reads covering alternate reverse bases for use in genotype calling.

In some cases in accordance with the method of this and other aspects of the present invention, the method further comprises computing a mapping quality score for each sequence alignment and/or an overall mapping quality score for a plurality of said sequence alignments. In certain cases the mapping quality score for each sequence alignment and/or said overall mapping quality score for said plurality of sequence alignments is required to be at least 15, 16, 17, 18, 19, 20, 21, 22, 23, 24, 25, 26, 27, 28, 29 or at least 30 Phred Score units in order for said genotype calling to be considered reliable.

In some cases in accordance with the method of this and other aspects of the present invention, a pre-process step is performed prior to said sequence alignment in order to improve alignment quality. In certain cases the pre-process step comprises excluding sequence reads shorter than 10, 20, 30, 40, 50, 60, 70 or shorter than 76 nucleotides. In certain cases the pre-process step includes trimming sequence reads, for example removing 1, 2, 3, 4 or 5 nucleotides from the 5' and/or 3' end of each sequencing read.

In some cases in accordance with the method of this and other aspects of the present invention, the method further comprises performing a quality control step to evaluate quality of the sequencing reads prior to performing said sequence alignment, and wherein evaluating the quality of each forward and/or each reverse sequencing read comprises determining one or more parameters selected from the group consisting of: Per base sequence quality, Per sequence quality score, Per base sequence content, Per base GC content, Per sequence GC content, Per base N content, Sequence Length Distribution, Sequence Duplication Level, Overrepresented sequences, and Kmer Content.

In some cases in accordance with the method of this and other aspects of the present invention, the or each sequence alignment is performed using an algorithm such as the Burrows-Wheeler Aligner exact match (BWA MEM).

In some cases in accordance with the method of this and other aspects of the present invention, the method further comprises evaluating one or more of said sequence alignments to determine at least one parameter selected from the group consisting of: coverage, variant frequency, genotype average quality call, mapping quality, and calling quality. In certain cases the minimum coverage threshold is set at 10×, 15×, 20×, 25× or 30×. In certain cases the minimum variant frequency to call an alternative genotype is 2%, 5%, 10%, 15%, 20% or 30%. In certain cases the genotype average quality call is at least 18, 19, 20, 21, 22, 23, 24, 25, 26, 27, 28, 29, 30, 31, 32, 33, 34 or 35 Phred Score units. In certain cases the mapping quality is at least 15, 16, 17, 18, 19, 20, 21, 22, 23, 24, 25, 26, 27, 28, 29 or 30 Phred Score units. In certain cases the calling quality is at least 15, 16, 17, 18, 19, 20, 21, 22, 23, 24, 25, 26, 27, 28, 29 or 30 Phred Score units.

In some cases in accordance with the method of this and other aspects of the present invention, cut-off criteria may be set such that in order to define a homozygous call, a minimum of 50%, 60%, 70%, 80%, 90%, 95% or 99% of reads must support the called allele. Alternatively or additionally, cut-off criteria may be set such that in order to define a heterozygous call, between 30% and 70%, between 35% and 65%, between 40% and 60%, or between 45% and 55% of reads must support the alternative allele. Alternatively or additionally, cut-off criteria may be set such that in order to define a hemizygous call, between 15% and 45%, between 20% and 40%, between 20% and 35%, or between 25% and 35% of reads must support the called allele.

In some cases in accordance with the method of this and other aspects of the present invention, coverage is evaluated independently for forward and for reverse strand alignment, and wherein the forward-to-reverse coverage ratio is between 0.6 and 1.4, between 0.7 and 1.3, between 0.8 and 1.2, or between 0.85 and 1.15.

In accordance with this and other aspects of the present invention, the sample is preferably obtained or has been previously obtained from a human subject. In some cases the subject is undergoing, or is a candidate for, blood transfusion or bone marrow transplantation. In some cases the subject has sickle cell disease (SCD) or Thalassemia major. In some cases the subject has non-Caucasian ancestry. In some cases, the subject has African ancestry.

In accordance with this and other aspects of the present invention, the sample may be any suitable biological sample from which it is possible to obtain nucleic acid, particularly genomic DNA, for use in a PCR reaction. Suitable samples include any material of bodily origin (liquid, solid or aspirate) such as blood, hair, cheek cells and skin cells.

In accordance with this and other aspects of the present invention, the sample may be subjected to one or more treatments to extract a nucleic acid prior to or as part of said amplification by PCR.

In accordance with this and other aspects of the present invention, the method may further comprise carrying out serological analysis on a blood sample that has been obtained from the subject. This may be particularly useful to corroborate or clarify a phenotype prediction made. Combining the genotype-based prediction of blood type with a serological-based prediction may be useful, e.g., to improve accuracy or to resolve ambiguous results. However, it is also specifically contemplated herein that the method of this and other aspects of the present invention may not comprise carrying out serological analysis. Removing the need to carry out serological analysis provides considerable savings in terms of time, cost and/or resources.

In a second aspect the present invention provides a plurality of primers for PCR amplification of one or more segments of the RHD gene and of the RHCE gene, wherein the nucleotide sequence of each primer of said plurality comprises or consists of a nucleotide sequence selected from the group consisting of:

| | | |
|---|---|---|
| RHex01 F1 | TCCCTCAAGCCCTCAAGTAG | (SEQ ID NO: 3) |
| RHex01 F2 | TGTTGGAGAGAGGGGTGATG | (SEQ ID NO: 4) |
| RHex01 F3 | CTGCACAGAGACGGACACAG | (SEQ ID NO: 5) |
| RHex01 R1 | CCCTGCTATTTGCTCCTGTG | (SEQ ID NO: 6) |
| RHex01 R2 | AAAGGAACATCTGTGCCCCT | (SEQ ID NO: 7) |
| RHex02 F1 | CCCTTCCAGCTGCCATTTAG | (SEQ ID NO: 8) |
| RHex02 F2 | AAATCTCGTCTGCTTCCCCC | (SEQ ID NO: 9) |
| RHex02 R1 | AAGTGATCCAGCCACCATCC | (SEQ ID NO: 10) |
| RHex02 R2 | GTCCATTCCCTCTATGACCC | (SEQ ID NO: 11) |
| RHex03 F1 | AGGTGCCCAACAGTGTTTGT | (SEQ ID NO: 12) |
| RHex03 F2 | TGAGTGAGAGGCATCCTTCC | (SEQ ID NO: 13) |
| RHex03 R1 | TTTGGCCCTTTTCTCCCAGG | (SEQ ID NO: 14) |
| RHDex03 R2 | GAAACCCCACCAAATGGAGC | (SEQ ID NO: 15) |
| RHCEex03 R3 | GAAGCCCCACCAAATGGAGC | (SEQ ID NO: 16) |
| RHex04 F1 | GGCTTCAAGTCACACCTCCT | (SEQ ID NO: 17) |
| RHex04 F2 | CAGAGGATGCCGACACTCAC | (SEQ ID NO: 18) |
| RHex04 R1 | CCATTCTGCTCAGCCCAAGT | (SEQ ID NO: 19) |
| RHex04 R2 | CAGCCAGAGCCTTTTCTGAG | (SEQ ID NO: 20) |
| RHex05 F1 | CAGCCCTAGGATTCTCATCC | (SEQ ID NO: 21) |
| RHex05 F2 | AGCAGGAGTGTGATTCTGGC | (SEQ ID NO: 22) |

-continued

| | | |
|---|---|---|
| RHex05 R1 | CTGTTAGACCCAAGTGCTGC | (SEQ ID NO: 23) |
| RHex05 R2 | TGGGGAGGGGCATAAATATG | (SEQ ID NO: 24) |
| RHex06 F1 | GGTCACTTGCAGCAAGATGG | (SEQ ID NO: 59) |
| RHex06 F2 | ACCTTGCTTCCTTTACCCAC | (SEQ ID NO: 60) |
| RHex06 R1 | TGGCCTTCAGCCAAAGCAGA | (SEQ ID NO: 61) |
| RHex06 R2 | CTAATGCAGCTGTGCACTGC | (SEQ ID NO: 62) |
| RHex07 F1 | TGTGTGAAAGGGGTGGGTAG | (SEQ ID NO: 63) |
| RHex07 F2 | GTCTCACCTGCCAATCTGCT | (SEQ ID NO: 64) |
| RHex07 R1 | GTTGGAGGGGAGTGTTAAGG | (SEQ ID NO: 65) |
| RHex07 R2 | CCAGCTAAGGACTCTGCACA | (SEQ ID NO: 66) |
| RHex08 F1 | ATGGCACTACTGACACCGAC | (SEQ ID NO: 67) |
| RHex08 F2 | TTGTCCCTGATGACCTCTGC | (SEQ ID NO: 68) |
| RHex08 R1 | TGTCCTGGCAATGGTGGAAG | (SEQ ID NO: 69) |
| RHex08 R2 | GCACATAGACATCCAGCCAC | (SEQ ID NO: 70) |
| RHex09 F1 | AGCTGGTCCAGGAATGACAG | (SEQ ID NO: 71) |
| RHex09 F2 | GTGGGAGAAAAAGGATTTCTGTTGAGA | (SEQ ID NO: 72) |
| RHex09 F3 | TCTTGAGATTAAAAATCCTGTGCTCCA | (SEQ ID NO: 73) |
| RHex09 R1 | AGTTCATGCACTCAAAATCTATCACGT | (SEQ ID NO: 74) |
| RHex09 R2 | CCTGCAATGCTCCTTACTCC | (SEQ ID NO: 75) |
| RHex10 F1 | GGCTGTTTCAAGAGATCAAGCC | (SEQ ID NO: 76) |
| RHex10 F2 | TCAGTATGTGGGTTCATCTGCA | (SEQ ID NO: 77) |
| RHex10 R1 | AGGCAACAGTGAGAGGAAGTTG | (SEQ ID NO: 78) |
| RHex10 R2 | TGCTGTCATGAGCGTTTCTCAC | (SEQ ID NO: 79) |
| RHin2 F1 | CTTGTGCCACTTGACTTGGGACTG | (SEQ ID NO: 80) |
| RHin2 F2 | CTGTTTTGAGTCCCTTCAGGGGAG | (SEQ ID NO: 81) |
| RHin2 F3 | CTCACATACTGATAACTTAGCAAATGGC | (SEQ ID NO: 82) |
| RHin2 R1 | GATCACTTGAGCCCAGGAGGC | (SEQ ID NO: 83) |
| RHin2 R2 | TTAACTCAGGAGGCTGAGGTGG | (SEQ ID NO: 84) |
| RHin2 R3 | CTGAGGTGGGAGGATCACTTGAG | (SEQ ID NO: 85) |
| RHCEin2 R4 | AAATTAGCCGGGCATGGTAGCAG | (SEQ ID NO: 86) |

or is a variant of one of said sequences 3-24 and 59-86 having not more than one, two or three nucleotide changes by substitution, addition or deletion. In some cases the primers may be as defined in accordance with the first aspect of the invention.

Variants of the primers of SEQ ID NOs: 3-24 and 59-86 may, in particular, comprise additional nucleotides at the 5' and/or 3' end, which extend the primer sequence to include contiguous sequence neighbouring the portion of the RHD and RHCE genomic sequence that the said primer of one of SEQ ID NOs: 3-24 and 59-86 hybridises to. Additionally or alternatively, a variant primer may be truncated at the 5' and/or 3' end, e.g. to be 1, 2, or 3 nucleotides shorter in length.

In some cases in accordance with the plurality of primers of the second aspect of the invention, one or more of the consensus sequence-specific primers may further comprise a tag or adaptor. For example, the primer may comprise a next generation sequencing tag or adaptor, e.g., at its 5' end. In certain cases one or more of the consensus sequence-specific primers comprises a next generation sequencing tag with the sequence ACACTCTTTCCCTACACGACGCTCTTC-CGATCT (SEQ ID NO: 1). The tag of SEQ ID NO: 1 may be at the 5' end of a forward primer such as a forward primer of one or more of SEQ ID NOs: 3-5, 8-9, 12-13, 17-18, 21-22, 59-60, 63-64, 67-68, 71-73, 76-77, and 80-82. Alternatively or additionally, one or more of the consensus sequence-specific primers may comprise a next generation sequencing tag with the sequence GTGACTGGAGTTCA-GACGTGTGCTCTTCCGATCT (SEQ ID NO: 2). The tag of SEQ ID NO: 2 may be at the 5' end of a reverse primer such as a reverse primer of one or more of SEQ ID NOs: 6-7, 10-11, 14-16, 19-20, 23-24, 61-62, 65-66, 69-70, 74-75, 78-79, and 83-86.

In some cases, following the addition of the next-generation sequencing tag, adapters can be added. These adapters are added by using a forward primer sequence that comprises the next generation sequence tag as well as an adapter sequence, such as AATGATACGGCGACCACCGAGATC-TACACTCTTTCCCTACACGACGCTCTTCCGATCT (SEQ ID NO: 122) and/or a reverse primer sequence CAAGCAGAAGACGGCATACGAGATXXXXXXXXGT-GACTGGAGTTCAGACGTGTGCTCTTC (SEQ ID NO: 123) which contains an 8-nucleotide barcode added for patient identification (noted as XXXXXXXX in SEQ ID NO: 123).

Sequencing primers include those for forward sequencing ACACTCTTTCCCTACACGACGCTCTTCCGATCT (SEQ ID NO: 124), reverse sequencing GTGACTGGAGT-TCAGACGTGTGCTCTTCCGATCT (SEQ ID NO: 125), and index sequencing AGATCGGAAGAGCACACGTCT-GAACTCCAGTCAC (SEQ ID NO: 126).

In other cases in accordance with the plurality of primers of the second aspect of the invention, one or more of the consensus sequence-specific primers may further comprise a tag or adaptor. For example, the primer may comprise a next generation sequencing tag or adaptor, e.g., at its 5' end. In certain cases one or more of the consensus sequence-specific primers comprises a next generation sequencing tag with the sequence TGTAAAACGACGGCCAGT (SEQ ID NO: 57). The tag of SEQ ID NO: 57 may be at the 5' end of a forward primer such as a forward primer of one or more of SEQ ID NOs: 3-5, 8-9, 12-13, 17-18, 21-22, 59-60, 63-64, 67-68, 71-73, 76-77 and 80-82.

Alternatively or additionally, one or more of the consensus sequence-specific primers may comprise a next generation sequencing tag with the sequence CAGGAAACAGCTATGACC (SEQ ID NO: 58). The tag of SEQ ID NO: 58 may be at the 5' end of a reverse primer such as a reverse primer of one or more of SEQ ID NOs: 6-7, 10-11, 14-16, 19-20, 23-24, 61-62, 65-66, 69-70, 74-75, 78-79 and 83-86. Following the addition of the next-generation sequencing tag, adapters are added using a forward primer sequence AATGATACGGCGACCACCGAGATCTACACTCTTTCCCTACCTGTAAAACGACGGCCAGT (SEQ ID NO: 127) and a reverse primer CAAGCAGAAGACGGCATACGAGATXXXXXXXXGGTTGCTCGCCAGGAAACAGCTATGACC (SEQ ID NO: 128) which contains an 8-nucleotide barcode added for patient identification (noted as XXXXXXXX in SEQ ID NO: 128).

Sequencing primers include those for forward sequencing ACACTCTTTCCCTACCTGTAAAACGACGGCCAGT (SEQ ID NO: 129), reverse sequencing GGTTGCTCGCCAGGAAACAGCTATGACC (SEQ ID NO: 130), and index sequencing GGTCATAGCTGTTTCCTGGCGAGCAACC (SEQ ID NO: 131).

In some cases the plurality of primers comprises at least one forward primer and at least one reverse primer. In particular cases the plurality of primers comprises at least one primer pair selected from the group consisting of:

(i) an exon 1 forward primer selected from SEQ ID NOs: 3-5, and an exon 1 reverse primer selected from SEQ ID NOs: 6 and 7;

(ii) an exon 2 forward primer selected from SEQ ID NOs: 8 and 9, and an exon 2 reverse primer selected from SEQ ID NOs: 10 and 11;

(iii) an exon 3 forward primer selected from SEQ ID NOs: 12 and 13, and an exon 3 reverse primer selected from SEQ ID NOs: 14-16;

(iv) an exon 4 forward primer selected from SEQ ID NOs: 17 and 18, and an exon 4 reverse primer selected from SEQ ID NOs: 19 and 20;

(v) an exon 5 forward primer selected from SEQ ID NOs: 21 and 22, and an exon 5 reverse primer selected from SEQ ID NOs: 23 and 24. In particular cases the primer pair is other than the forward primer of SEQ ID NO: 5 in combination with the reverse primer of SEQ ID NO: 6;

(vi) an exon 6 forward primer selected from SEQ ID NOs: 59 and 60, and an exon 6 reverse primer selected from SEQ ID NOs: 61 and 62;

(vii) an exon 7 forward primer selected from SEQ ID NOs: 63 and 64, and an exon 7 reverse primer selected from SEQ ID NOs: 65 and 66;

(viii) an exon 8 forward primer selected from SEQ ID NOs: 67 and 68, and an exon 8 reverse primer selected from SEQ ID NOs: 69 and 70;

(ix) an exon 9 forward primer selected from SEQ ID NOs: 71-73, and an exon 9 reverse primer selected from SEQ ID NOs: 74 and 75;

(x) an exon 10 forward primer selected from SEQ ID NOs: 76 and 77, and an exon 10 reverse primer selected from SEQ ID NOs: 78 and 79;

(xi) an intron 2 forward primer selected from SEQ ID NOs: 80-82, and an intron 2 reverse primer selected from SEQ ID NOs: 83-86;

In some cases in accordance with the plurality of primers of the second aspect of the invention, at least one of the primers further comprises a next generation sequencing tag and/or further comprises a detectable label (e.g. a fluorescent label), a biotinylated nucleotide, or a locked nucleic acid (LNA) portion. In particular, the primers may, in some cases, be other than a fragment of a naturally occurring nucleotide sequence. As will be apparent to the skilled person, primers having one or more non-natural bases (e.g. a base analogue d5SICS and dNaM) and/or a modified backbone (e.g. 2'-O-methyl-substituted RNA, locked nucleic acid (LNA), BNA (Bridged Nucleic Acid) or morpholino nucleic acid) are structurally distinct from fragments of naturally occurring nucleotide sequence.

The primers of the second aspect of the invention may be DNA or RNA. Preferably, the primers are DNA primers.

The primers of the second aspect of the invention find particular use in accordance with the methods of the invention.

In a third aspect the present invention provides a kit for assessing a subject's blood type, said kit comprising: a plurality of primers of the second aspect of the invention;

optionally, one or more PCR amplification reagents and/or one or more next generation sequencing reagents.

In a fourth aspect the present invention provides a system for use in determining a subject's blood type, the system comprising:

a kit of the third aspect of the invention; and at least one detector arranged to detect a signal from a detectably labelled amplicon produced by PCR amplification carried out on DNA obtained from said subject;

at least one controller in communication with the at least one detector, the controller being programmed with computer-readable instructions to transform said signal into a predicted nucleotide sequence. Typically the system is in the form of a next generation sequencing platform, wherein the detector is arranged to detect signal from a fluorescently labelled reversible terminator attached to dNTPs as they are added to a growing polynucleotide ("sequencing by synthesis").

In some cases in accordance with the fourth aspect of the invention, the controller is programmed with computer-readable instructions to prepare an alignment between said predicted nucleotide sequence and a reference sequence for an RHD gene and/or a reference sequence for an RHCE gene.

In some cases in accordance with the fourth aspect of the invention, the controller is programmed with computer-readable instructions to determine the genotype of said sample based on the relative proportion of each nucleotide at each of a plurality of discriminant positions in said alignment.

In some cases in accordance with the fourth aspect of the invention, the controller is programmed with computer-readable instructions to transform the genotype of said sample into predicted blood type haplotypes, and optionally, to transform said predicted blood type haplotypes into a predicted blood type phenotype.

In a fifth aspect, the present invention provides use of a plurality of primers of the second aspect of the invention in the preparation of a sequencing library.

In a sixth aspect, the present invention provides use of a plurality of primers of the second aspect of the invention, a kit of the third aspect of the invention or a system of the fourth aspect of the invention in a method of sequencing. In some cases the use is in a method of next generation sequencing, such as sequencing by synthesis or Illumina® sequencing.

In a seventh aspect, the present invention provides use of a plurality of primers of the second aspect of the invention, a kit of the third aspect of the invention or a system of the fourth aspect of the invention in a method of the first aspect of the invention.

In an eighth aspect, the present invention provides method of blood matching, the method comprising:

carrying out the method of the first aspect of the invention on a recipient sample from a recipient subject in need of donor blood and on a donor sample from a potential donor subject;

comparing the blood type alleles present in the recipient sample with those present in the donor subject and thereby determining the compatibility of the recipient subject to receive blood from the potential donor subject.

In some cases, the method in accordance with the eighth aspect of the invention may be carried out for a plurality of recipient subjects and a plurality of potential donor subjects, e.g., to assist screening compatibility of a blood donor/blood transfusion service.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

DESCRIPTION OF THE FIGURES

FIG. 16A-B shows a sequence alignment of exon 1 (in bold), as well as upstream and downstream intronic positions (non-bold), for RHD (SEQ ID NO: 27), RHCE gene alleles RHCE*ce (SEQ ID NO: 28), RHCE*cE (SEQ ID NO: 29), RHCE*Ce (SEQ ID NO: 30), and RHCE*CE (SEQ ID NO: 31), and the consensus sequence for RHCE (SEQ ID NO: 32). Identical nucleotides are indicated with an asterisk. Gaps are indicated with a dash. Numbers at the end of rows indicate, for the last nucleotide in said row, its position in the alignment as well as its exonic position (in parenthesis).

FIG. 17A-B shows a sequence alignment of exon 2 (in bold), as well as upstream and downstream intronic positions (non-bold), for RHD (SEQ ID NO: 33), RHCE gene alleles RHCE*ce (SEQ ID NO: 34), RHCE*cE (SEQ ID NO: 35), RHCE*Ce (SEQ ID NO: 36), and RHCE*CE (SEQ ID NO: 37), and the consensus sequence for RHCE (SEQ ID NO: 38). Identical nucleotides are indicated with an asterisk. Gaps are indicated with a dash. Numbers at the end of rows indicate, for the last nucleotide in said row, its position in the alignment as well as its exonic position (in parenthesis).

FIG. 18A-B shows a sequence alignment of exon 3 (in bold), as well as upstream and downstream intronic positions (non-bold), for RHD (SEQ ID NO: 39), RHCE gene alleles RHCE*ce (SEQ ID NO: 40), RHCE*cE (SEQ ID NO: 41), RHCE*Ce (SEQ ID NO: 42), and RHCE*CE (SEQ ID NO: 43), and the consensus sequence for RHCE (SEQ ID NO: 44). Identical nucleotides are indicated with an asterisk. Gaps are indicated with a dash. Numbers at the end of rows indicate, for the last nucleotide in said row, its position in the alignment as well as its exonic position (in parenthesis).

FIG. 19A-B shows a sequence alignment of exon 4 (in bold), as well as upstream and downstream intronic positions (non-bold), for RHD (SEQ ID NO: 45), RHCE gene alleles RHCE*ce (SEQ ID NO: 46), RHCE*cE (SEQ ID NO: 47), RHCE*Ce (SEQ ID NO: 48), and RHCE*CE (SEQ ID NO: 49), and the consensus sequence for RHCE (SEQ ID NO: 50). Identical nucleotides are indicated with an asterisk. Gaps are indicated with a dash. Numbers at the end of rows indicate, for the last nucleotide in said row, its position in the alignment as well as its exonic position (in parenthesis).

FIG. 20A-B shows a sequence alignment of exon 5 (in bold), as well as upstream and downstream intronic positions (non-bold), for RHD (SEQ ID NO: 51), RHCE gene alleles RHCE*ce (SEQ ID NO: 52), RHCE*cE (SEQ ID NO: 53), RHCE*Ce (SEQ ID NO: 54), and RHCE*CE (SEQ ID NO: 55), and the consensus sequence for RHCE (SEQ ID NO: 56). Identical nucleotides are indicated with an asterisk. Gaps are indicated with a dash. Numbers at the end of rows indicate, for the last nucleotide in said row, its position in the alignment as well as its exonic position (in parenthesis).

FIG. 21A-B shows a sequence alignment of exon 6 (in bold), as well as upstream and downstream intronic positions (non-bold), for RHD (SEQ ID NO: 87), RHCE gene alleles RHCE*ce (SEQ ID NO: 88), RHCE*cE (SEQ ID NO: 89), RHCE*Ce (SEQ ID NO: 90), and RHCE*CE (SEQ ID NO: 91), and the consensus sequence for RHCE (SEQ ID NO: 92). Identical nucleotides are indicated with an asterisk. Gaps are indicated with a dash. Numbers at the end of rows indicate, for the last nucleotide in said row, its position in the alignment as well as its exonic position (in parenthesis).

FIG. 22A-B shows a sequence alignment of exon 7 (in bold), as well as upstream and downstream intronic positions (non-bold), for RHD (SEQ ID NO: 93), RHCE gene alleles RHCE*ce (SEQ ID NO: 94), RHCE*cE (SEQ ID NO: 95), RHCE*Ce (SEQ ID NO: 96), and RHCE*CE (SEQ ID NO: 97), and the consensus sequence for RHCE (SEQ ID NO: 98). Identical nucleotides are indicated with an asterisk. Gaps are indicated with a dash. Numbers at the end of rows indicate, for the last nucleotide in said row, its position in the alignment as well as its exonic position (in parenthesis).

FIG. 23A-B shows a sequence alignment of exon 8 (in bold), as well as upstream and downstream intronic positions (non-bold), for RHD (SEQ ID NO: 99), RHCE gene alleles RHCE*ce (SEQ ID NO: 100), RHCE*cE (SEQ ID NO: 101), RHCE*Ce (SEQ ID NO: 102), and RHCE*CE (SEQ ID NO: 103), and the consensus sequence for RHCE (SEQ ID NO: 104). Identical nucleotides are indicated with an asterisk. Gaps are indicated with a dash.

Figure 1:
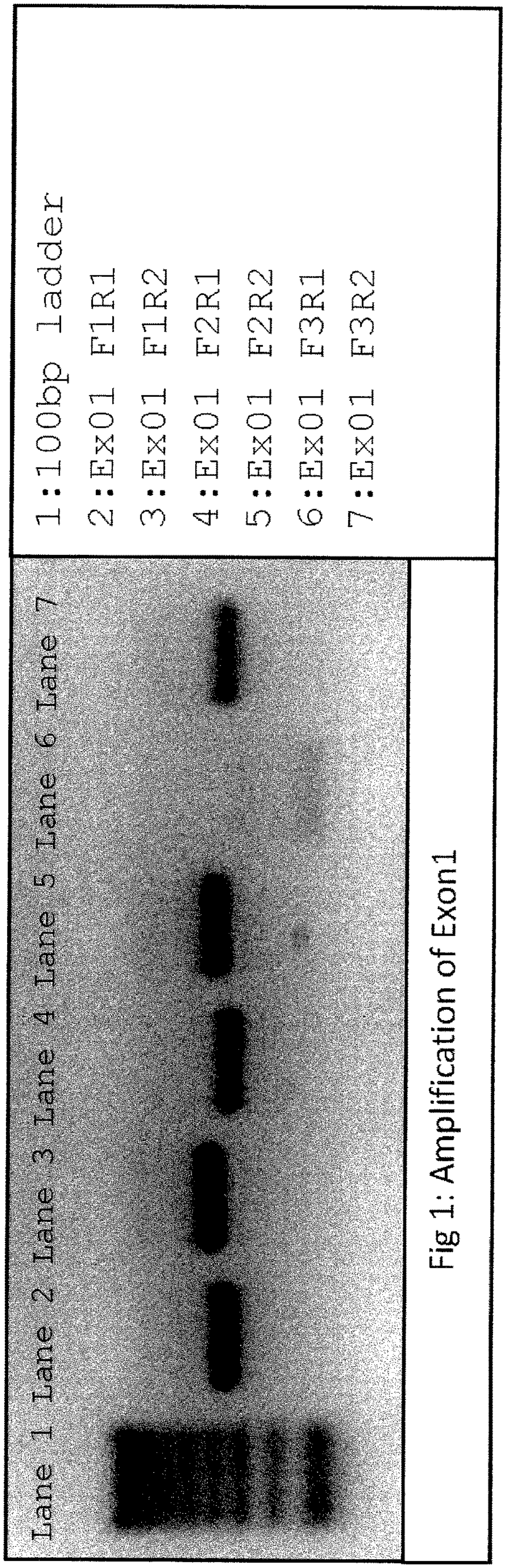
FIG. 1 shows an agarose gel image demonstrating PCR amplification products of exon 1 primers. Lane 1—100 bp ladder; lane 2—Ex01 F1R1; lane 3—Ex01 F1R2; lane 4—Ex01 F2R1; lane 5—Ex01 F2R2; lane 6—Ex01 F3R1; lane 7—Ex01 F3R2. All primer combinations other than Ex01 F3R1 of lane 6 showed successful exon 1 amplification.

Numbers at the end of rows indicate, for the last nucleotide in said row, its position in the alignment as well as its exonic position (in parenthesis).

FIG. 24A-B shows a sequence alignment of exon 9 (in bold), as well as upstream and downstream intronic positions (non-bold), for RHD (SEQ ID NO: 105), RHCE gene alleles RHCE*ce (SEQ ID NO: 106), RHCE*cE (SEQ ID NO: 107), RHCE*Ce (SEQ ID NO: 108), and RHCE*CE (SEQ ID NO: 109), and the consensus sequence for RHCE (SEQ ID NO: 110). Identical nucleotides are indicated with an asterisk. Gaps are indicated with a dash. Numbers at the end of rows indicate, for the last nucleotide in said row, its position in the alignment as well as its exonic position (in parenthesis).

FIG. 25A-B shows a sequence alignment of exon 10 (in bold), as well as upstream and downstream intronic positions (non-bold), for RHD (SEQ ID NO: 111), RHCE gene alleles RHCE*ce (SEQ ID NO: 112), RHCE*cE (SEQ ID NO: 113), RHCE*Ce (SEQ ID NO: 114), and RHCE*CE (SEQ ID NO: 115), and the consensus sequence for RHCE (SEQ ID NO: 116). Identical nucleotides are indicated with an asterisk. Gaps are indicated with a dash.

Numbers at the end of rows indicate, for the last nucleotide in said row, its position in the alignment as well as its exonic position (in parenthesis).

FIG. 26A-B shows a sequence alignment of the 109 base pair insert (in bold) as well as upstream and downstream intronic positions (non-bold) in intron 2, for RHD (SEQ ID NO: 117), RHCE gene alleles RHCE*ce (SEQ ID NO: 118), RHCE*cE (SEQ ID NO: 119), RHCE*Ce (SEQ ID NO: 120), and RHCE*CE (SEQ ID NO: 121). Identical nucleotides are indicated with an asterisk. Gaps are indicated with a dash. Numbers at the end of rows indicate, for the last nucleotide in said row, its position in the alignment.

FIG. 27 shows an agarose gel image demonstrating PCR amplification products of exons 6 to 10 with different primer combinations. All primer combinations showed successful amplification.

FIG. 28 shows an agarose gel image demonstrating PCR amplification products of intron 2 with different primer combinations. All primer combinations showed successful amplification.

The Sequence Listing is submitted as an ASCII text file in the form of the file named Sequence_Listing.txt, which was created on Feb. 10, 2017, and is 226,919 bytes, which is incorporated by reference herein.

DETAILED DESCRIPTION OF THE INVENTION

The present invention finds use in the determination alleles in highly homologous gene sets, such as the clinically relevant RHD and RHCE genes that encode blood antigens. The invention provides a method for genotyping alleles in at least one homologous genetic loci set, comprising:

(i) providing a DNA-containing sample that includes said at least one homologous genetic loci set;

(ii) performing PCR amplification of regions of said homologous genetic loci set using consensus sequence-specific primers, wherein said consensus sequence-specific primers bind to consensus sequences that are common to a plurality of genes within the genetic loci set, thereby generating a pool of amplification products;

(iii) sequencing a plurality of said amplification products in order to determine the relative proportion of each nucleotide at each position in a sequencing read;

(iv) performing a sequence alignment between the sequencing read results of (iii) and at least one reference sequence, which reference sequence corresponds to one of the genes in said homologous genetic loci set; and (v) performing genotype calling of the allele or alleles in said sample based on the relative proportion of each nucleotide at each of a plurality of discriminant positions in said alignment.

Advantageously, the method of the present invention may further comprise genotyping a sample obtained from a human subject at one or more positions in intron 7 of the RHD gene and/or in intron 7 of the RHCE gene. Blood typing by making use of intron 7 polymorphisms is described in WO2012/171990, the entire contents of which is expressly incorporated herein by reference. Blood typing by making use of a combination of polymorphisms in the RHD gene and/or the RHCE gene are described in US2012/0172239 and EP2471949, the entire contents of which are both expressly incorporated herein by reference.

The Rh blood group D antigen is encoded by the RHD gene, which comprises 10 exons. The complete RHD gene sequence is available at NCBI Reference Sequence: No. NG_007494.1, GI:171184448, (SEQ ID NO: 25), the entire contents of which is incorporated herein by reference. The RHD gene exons 1-5 and 6-10, and intron 2 have the sequences set forth in bold in FIGS. 16-20 and 21-26.

The Rh blood group C antigen is encoded by the RHCE gene, which comprises 10 exons. The complete RHCE gene sequence is available at NCBI Reference Sequence: NG_009208.2, GI:301336136, (SEQ ID NO: 26), the entire contents of which is incorporated herein by reference. An updated RHCE gene sequence is available at: NG_009208.3. The RHCE gene alleles RHCE*ce, RHCE*Ce, RHCE*cE, and RHCE*CE have the exon nucleotide sequences set forth in FIGS. 16-20 and 21-26 (exons 1-5 and 6-10, and intron 2, respectively). The RHCE consensus sequences of exons 1-5 and 6-10 are also shown in FIGS. 16-20 and 21-26, respectively.

The term "sample" as used herein is intended to encompass any material (solid, liquid or aspirate) obtained directly or indirectly from a subject, such as a human subject, in which the genetic loci set of interest is found. In particular, the term "sample" includes any biological fluid such as blood, plasma, urine, saliva, cerebrospinal fluid and interstitial fluid, any solid matter, such as tissue, bone and hair, any cell or cell extract, any derived cell line, such as an immortalised tumour cell line and stem cell line, an extract of any of the preceding sample types, such as fixed or paraffin-embedded tissue. In certain preferred embodiments, the sample is an extract of human genomic DNA, optionally amplified and/or purified.

As used herein, the term "genotyping" is intended to encompass any method for determining the identity of the nucleotide at a particular position such as a polymorphic position at a specified locus. Thus, genotyping includes identifying one or both alleles of a particular gene. Genotyping may employ any of a variety of techniques, including but not limited to, allele-specific hybridisation, allele-specific PCR, sequencing of all or part of a gene. Preferably, genotyping is carried out in accordance with the method of the first aspect of the invention.

Unless specified otherwise, all nucleic acid sequences, such as primer sequences, are set forth herein in the direct 5' to 3'. Thus, for example, the primer sequence TCCCTCAAGCCCTCAAGTAG (SEQ ID NO: 3) may equally be written as 5'-TCCCTCAAGCCCTCAAGTAG-3' (SEQ ID NO: 3).

As described herein, certain blood type alleles are less common and a typically referred to as "variants" (e.g. RHD*$r'^{S}$). Variant blood type alleles are in some cases referred to herein simply as "blood type variants".

EXAMPLES

Examples

For the following examples, two genes related to the human Rh blood group system were chosen: the RHD and RHCE genes. These genes, which are arranged in tandem, are structural paralogs resulting from a duplication of a common gene ancestor. Both genes are very similar (identical in 97% of their sequence), each containing 10 exons and spanning approximately 75 kb. These genes encode the highly polymorphic and antigenic RhD and RhCE proteins, which differ by more than 30 amino acids. RHD encodes the D antigen and RHCE encodes the antithetical C and c, and E and e antigens, in several combinations (ce, cE, Ce, or CE). There exist tens of additional Rh system antigens besides theses five principal ones.

The C and c antigens are codominant and encoded by alleles (alternative forms) of the RHCE gene. Thus, if both alleles are present (one on each chromosome) both antigens are expressed on the red blood cell. The E and e antigens also are codominant and encoded by alleles of the RHCE gene. However, most D negative individuals are due to deletion of the RHD gene (although there are exceptions, including non-expression due to point mutations, indels, or rearrangements with RHCE). The C and c antigens differ by four amino acids: one encoded by exon 1 and three encoded by exon 2. Additionally, the C antigen differs from c and D due to a 109 base pair insertion in intron 2. The E and e antigens differ by one amino acid encoded by exon 5. Additionally, exon 2 is shared between RHD and RHCE in the case of RHCE*Ce and RHCE*CE alleles. Exon 8 and 10 are shared between RHD and all the RHCE alleles. In fact, transfer of exons between RHD and RHCE, creating hybrid genes, is known to occur in both directions.

Throughout the text, antigens are referred to as D, C, c, E, and e. The two mentioned genes are referred to as RHD and RHCE. Alleles of the RHCE gene are designated as RHCE*ce, RHCE*Ce, RHCE*cE, and RHCE*CE. The proteins are referred to as RhD and RhCE or, if designated according to the specific antigens they bear, as Rhce, RhCe, RhcE, or RhCE.

Example 1—Amplification of Homologous Loci Using Consensus Sequence-Specific Primers Primers suitable for next generation sequencing (NGS) and specific for consensus sequence between RHD and RHCE genes were designed for exons 1 through 5, and tested for correct product amplifications of both genes using different primer combinations, both in uniplex and in multiplex reactions. Amplifications were tested in eight different samples, including rare Rh blood group types:

TABLE 1

| Blood type of samples | |
|---|---|
| Sample | Blood type |
| Sample 1 | RHD+, Cw type |
| Sample 2 | RHD+, CcEe |
| Sample 3 | wDt3, Cce |
| Sample 4 | RHD*DIIIa-het |
| Sample 5 | Ce, RHD+ |
| Sample 6 | DAR-hem |
| Sample 7 | r's |
| Sample 8 | Ce, RHD+ |

All primers consisted of a NGS tag portion in their 5' end and a sequence-specific portion. In this example, used tags were:

for forward primers: ACACTCTTTCCCTACACGACGCTCTTCCGATCT (SEQ ID NO: 1)

for reverse primers: GTGACTGGAGTTCAGACGTGTGCTCTTCCGATCT (SEQ ID NO: 2)

Consensus Sequence-Specific Portions were:

| | | SEQ ID NO: |
|---|---|---|
| RH Exon 1 Forward primers | | |
| RHex01 F1 | TCCCTCAAGCCCTCAAGTAG | 3 |
| RHex01 F2 | TGTTGGAGAGAGGGGTGATG | 4 |
| RHex01 F3 | CTGCACAGAGACGGACACAG | 5 |
| Reverse primers | | |
| RHex01 R1 | CCCTGCTATTTGCTCCTGTG | 6 |
| RHex01 R2 | AAAGGAACATCTGTGCCCCT | 7 |
| RH Exon 2 Forward primers | | |
| RHex02 F1 | CCCTTCCAGCTGCCATTTAG | 8 |
| RHex02 F2 | AAATCTCGTCTGCTTCCCCC | 9 |
| Reverse primers | | |
| RHex02 R1 | AAGTGATCCAGCCACCATCC | 10 |
| RHex02 R2 | GTCCATTCCCTCTATGACCC | 11 |
| RH Exon 3 Forward primers | | |
| RHex03 F1 | AGGTGCCCAACAGTGTTTGT | 12 |
| RHex03 F2 | TGAGTGAGAGGCATCCTTCC | 13 |
| Reverse primers | | |
| RHex03 R1 | TTTGGCCCTTTTCTCCCAGG | 14 |
| RHDex03 R2 | GAAACCCCACCAAATGGAGC | 15 |
| RHCEex03 R3 | GAAGCCCCACCAAATGGAGC | 16 |
| RH Exon 4 Forward primers | | |
| RHex04 F1 | GGCTTCAAGTCACACCTCCT | 17 |
| RHex04 F2 | CAGAGGATGCCGACACTCAC | 18 |
| Reverse primers | | |
| RHex04 R1 | CCATTCTGCTCAGCCCAAGT | 19 |
| RHex04 R2 | CAGCCAGAGCCTTTTCTGAG | 20 |

-continued

| | | SEQ ID NO: |
|---|---|---|
| RH Exon 5 Forward primers | | |
| RHex05 F1 | CAGCCCTAGGATTCTCATCC | 21 |
| RHex05 F2 | AGCAGGAGTGTGATTCTGGC | 22 |
| Reverse primers | | |
| RHex05 R1 | CTGTTAGACCCAAGTGCTGC | 23 |
| RHex05 R2 | TGGGGAGGGGCATAAATATG | 24 |

PCR were performed in 10 μL reactions using the following conditions:

| | |
|---|---|
| Kapa HotStart ReadyMix (2X) | 5.0 μL |
| template DNA (20 ng/uL) | 1.4 μL |
| Fwd primer (10 ng/uL) | 1.2 μL |
| Rev primer (10 ng/uL) | 1.2 μL |
| dH2O | 1.2 μL |

| | | |
|---|---|---|
| 95° C. | 3 min | |
| 95° C. | 15 sec | 38 cycles |
| 60° C. | 15 sec | |
| 72° C. | 30 sec | |
| 4° C. | infinity | |

Figure 2:
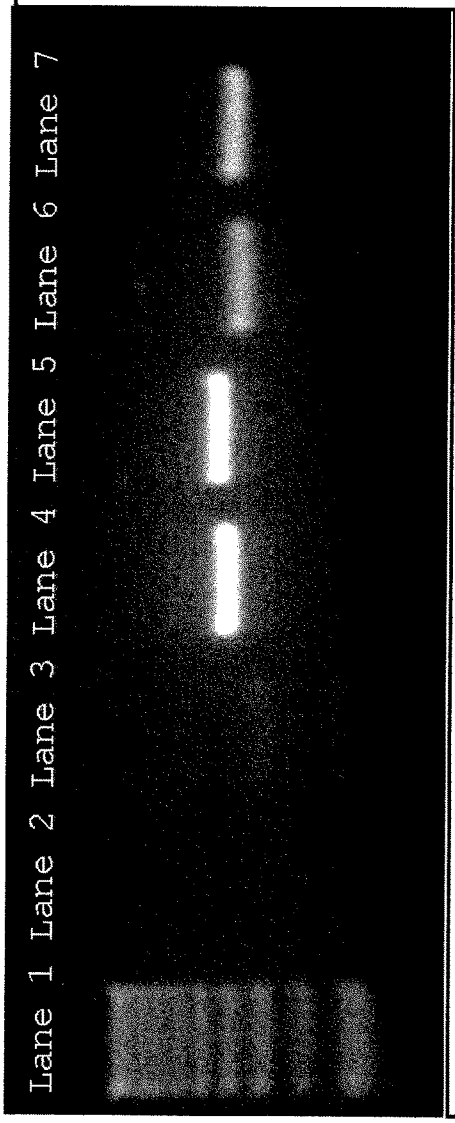
FIG. 2 shows an agarose gel image demonstrating PCR amplification products of exon 1 primers (repeat) and exon 2 primers. Lane 1—100 bp ladder; lane 2—Ex01 F3R1 (sample 1); lane 3—Ex01 F3R1 (sample 2); lane 4—Ex02 F1R1; lane 5—Ex02 F1R2; lane 6—Ex02 F2R1; lane 7—Ex02 F2R2. All primer combinations other than the repeat runs of Ex01 F3R1 of lanes 2 and 3 showed successful amplification.
Figure 3:
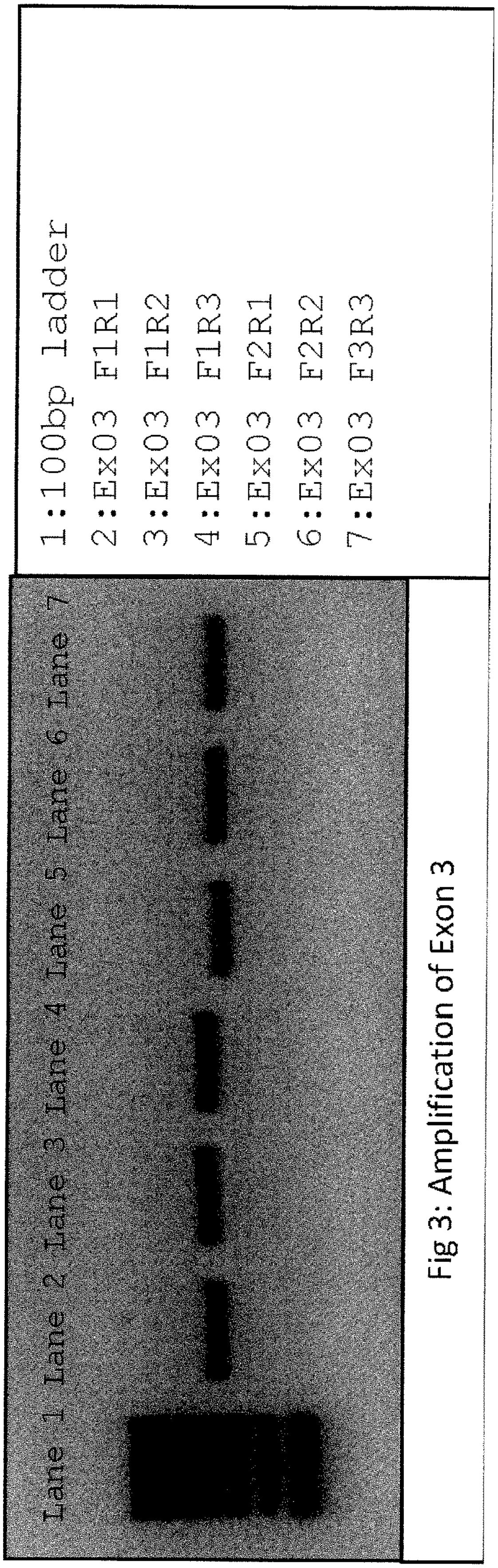
FIG. 3 shows an agarose gel image demonstrating PCR amplification products of exon 3 primers. Lane 1—100 bp ladder; lane 2—Ex03 F1R1; lane 3—Ex03 F1R2; lane 4—Ex03 F1R3; lane 5—Ex03 F2R1; lane 6—Ex03 F2R2; lane 7—Ex03 F3R3. All primer combinations showed successful exon 3 amplification.
Figure 4:
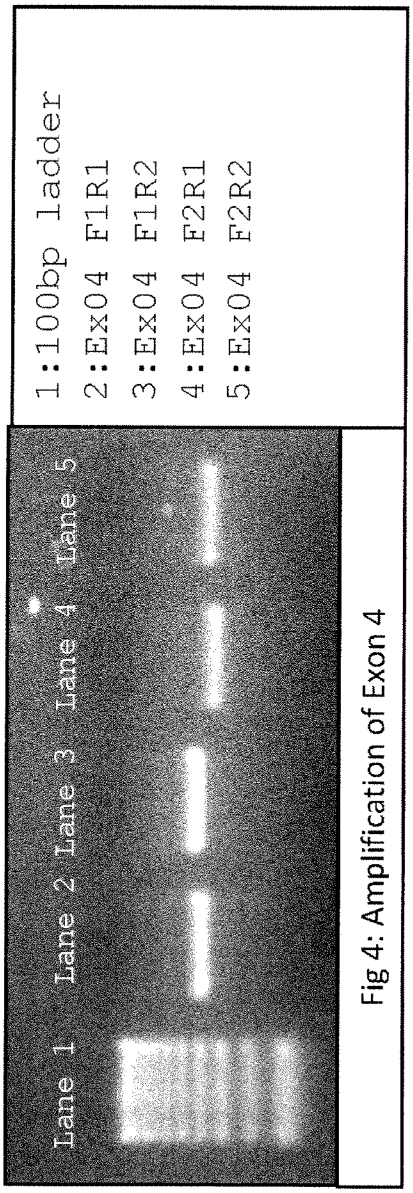
FIG. 4 shows an agarose gel image demonstrating PCR amplification products of exon 4 primers. Lane 1—100 bp ladder; lane 2—Ex04 F1R1; lane 3—Ex04 F1R2; lane 4—Ex04 F2R1; lane 5—Ex04 F2R2. All primer combinations showed successful exon 4 amplification.
Figure 5:
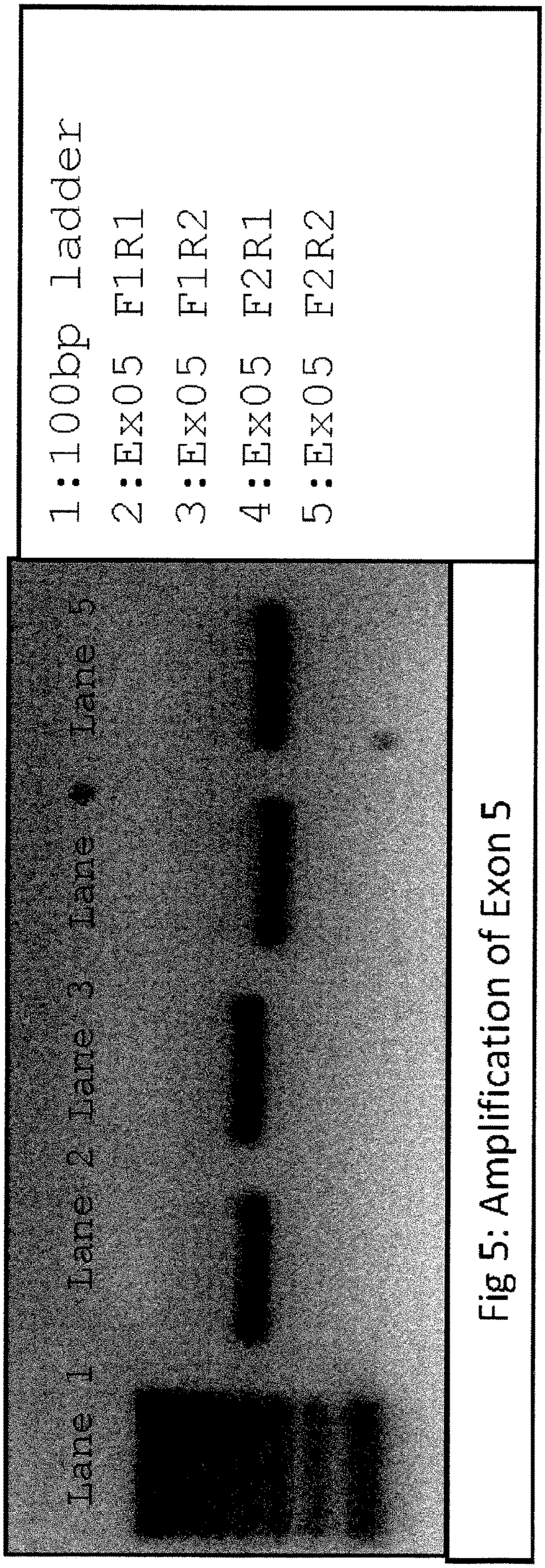
FIG. 5 shows an agarose gel image demonstrating PCR amplification products of exon 5 primers. Lane 1—100 bp ladder; lane 2—Ex05 F1R1; lane 3—Ex05 F1R2; lane 4—Ex05 F2R1; lane 5—Ex05 F2R2. All primer combinations showed successful exon 5 amplification.

PCR products were run on agarose gels in order to confirm amplifications (FIGS. 1-5). Except for one primer combination for Exon 1 (RHex01 F3 and RHex01 R1), all other primer combinations showed successful amplifications.

Example 2—Identification of Amplified Products from Example 1

This example shows that amplification products using different primer combinations shown in example 1 correspond indeed to both genes (RHD and RHCE). In other words, homologous regions of both genes were amplified at the same time by the consensus sequence-specific primers.

Figure 6:
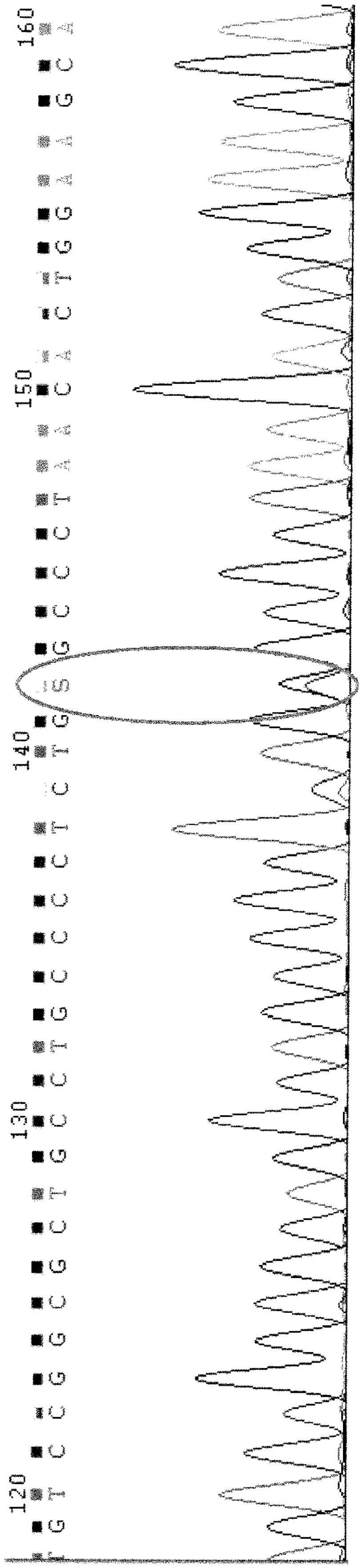
FIG. 6 shows an electropherogram illustrating detection of heterozygote allele at position 48 of exon 1 (see double peak, circled) discriminating between RHD and the C allele of RHCE in a sample with the genotype DDCCee. The sample sequence reads: TGTCCGGCGCTGCCTGCCCCTCTGSGCCCTAACACTGGAAGCA (SEQ ID NO: 132).
Figure 7:
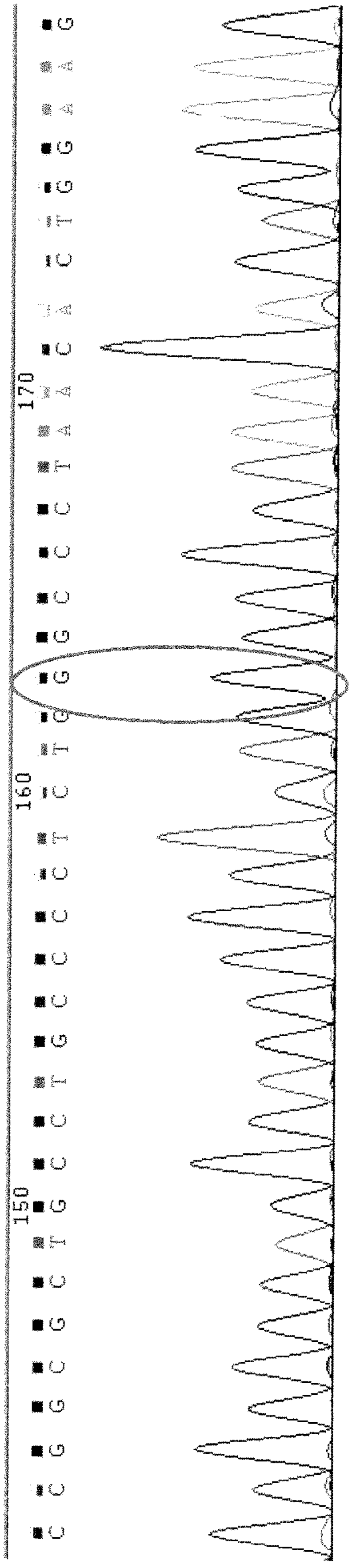
FIG. 7 shows an electropherogram illustrating detection of homozygote position 48 of exon 1 of RHCE (see circled G peak) in a sample with the genotype ddccee. The sample sequence reads: CCGGCGCTGCCTGCCCCTCTGGGCCCTAACACTGGAAG (SEQ ID NO: 133).
Figure 8:
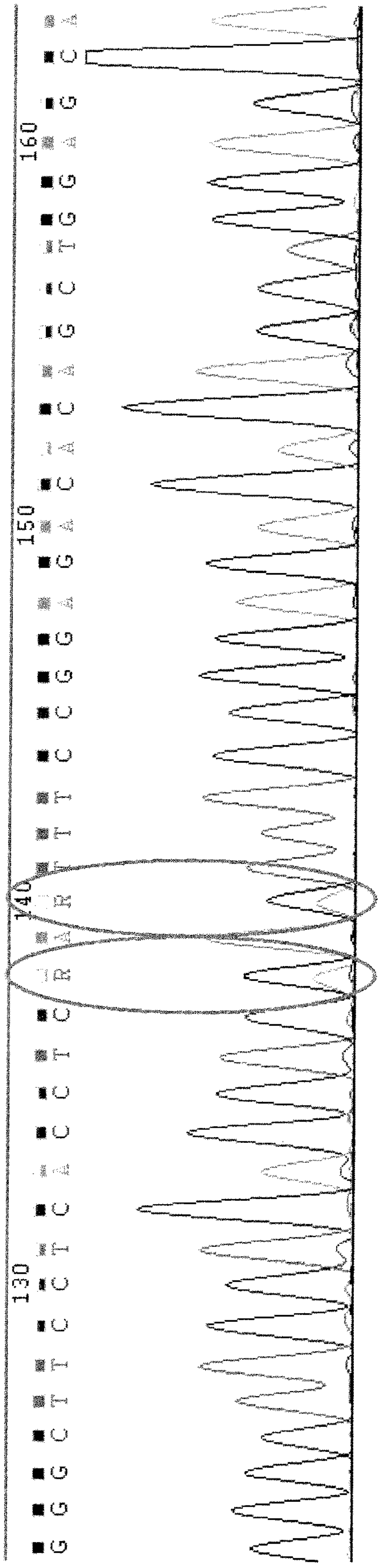
FIG. 8 shows an electropherogram illustrating detection of heterozygote positions 201 and 203 of exon 2 (see circled peaks) discriminating between RHD and the c allele of RHCE in a sample with the genotype DDCCee. The sample sequence reads: GGGCTTCCTCACCTCRARTTTCCGGAGACACAGCTGGAGCA (SEQ ID NO: 134).
Figure 9:
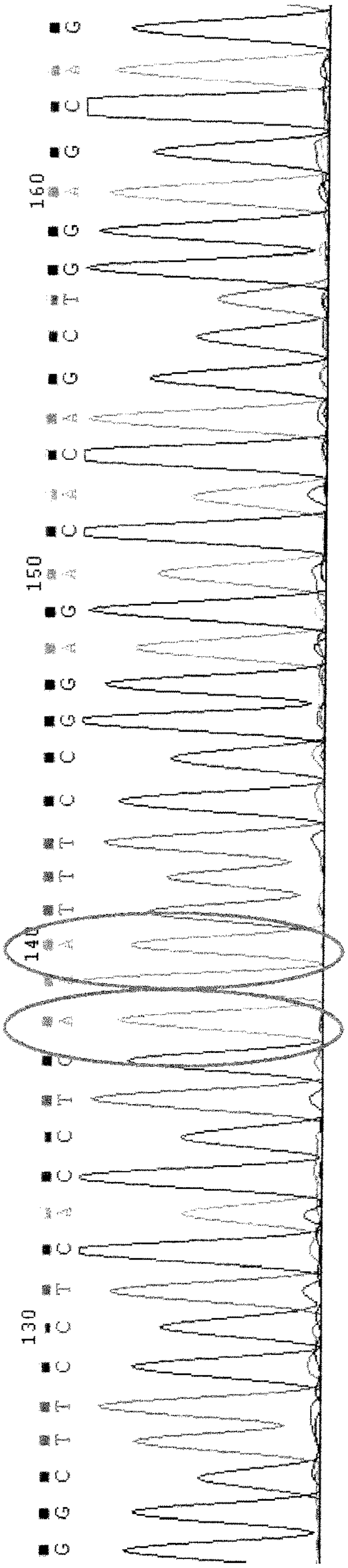
FIG. 9 shows an electropherogram illustrating detection of homozygote positions 201 and 203 of exon 2 of RHCE (see circled peaks) in a sample with the genotype ddccee. The sample sequence reads: GGCTTCCTCACCTCAAATTTCCGGAGACACAGCTGGAGC AG (SEQ ID NO: 135)
Figure 10:
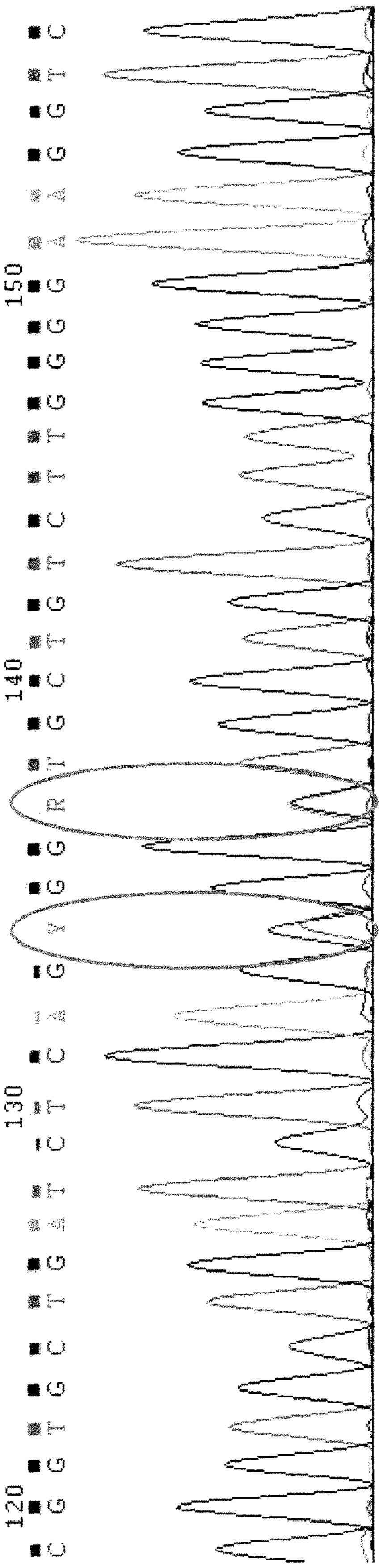
FIG. 10 shows an electropherogram illustrating detection of heterozygote positions 380 and 383 in exon 3 (see circled peaks) discriminating between RHD and RHCE in a sample with the genotype DDCCee. The sample sequence reads: CGGTGCTGATCTC AGYGGRTGCTGTCTTGGGGAAGGTC (SEQ ID NO: 136).
Figure 11:
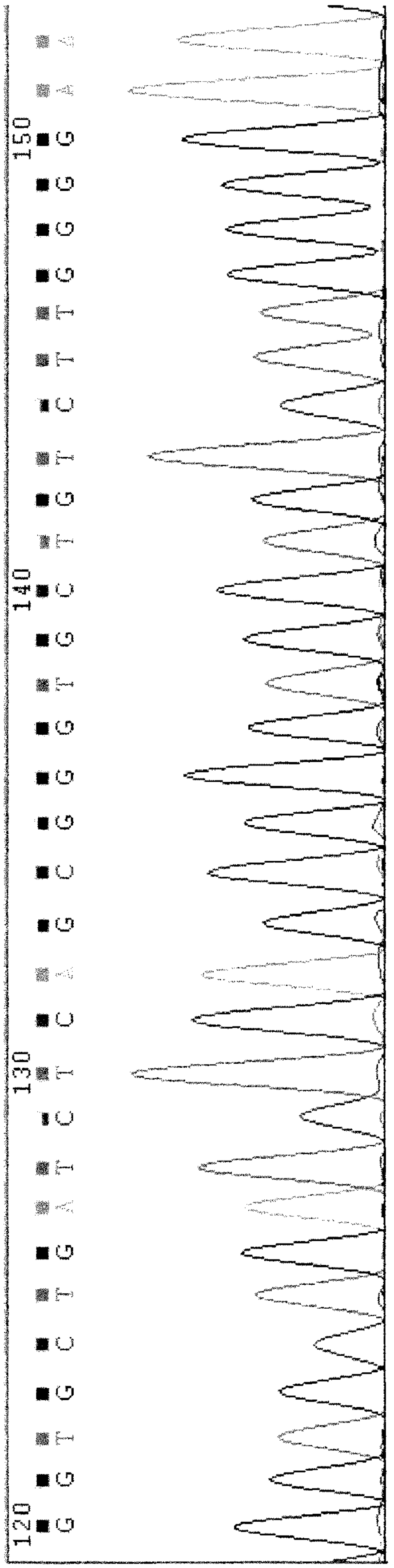
FIG. 11 shows an electropherogram illustrating detection of homozygote positions 380 and 383 of exon 3 of RHCE (see circled peaks) in a sample with the genotype ddccee. The sample sequence reads: GGTGCTGATCTCAGCGGGTGCTGTCTTGGGGAA (SEQ ID NO: 137).
Figure 12:
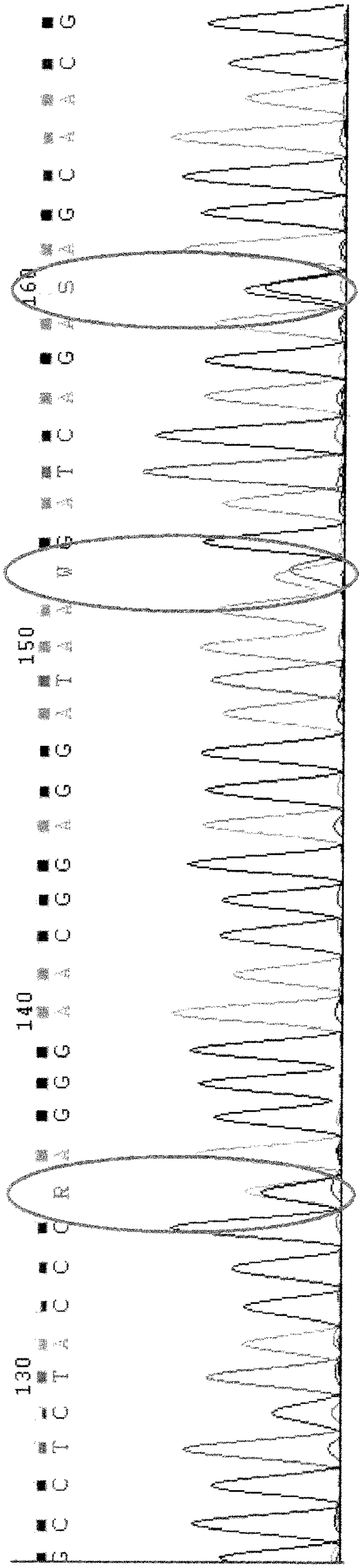
FIG. 12 shows an electropherogram illustrating detection of heterozygote positions 577, 594, and 602 of exon 4 (see circled peaks) discriminating between RHD and RHCE in a sample with the genotype DDCCee. The sample sequence reads: GCCTCTACCCRAGGGAACGGAGGATAAWGATCAGASAGCAACG (SEQ ID NO: 138).
Figure 13:
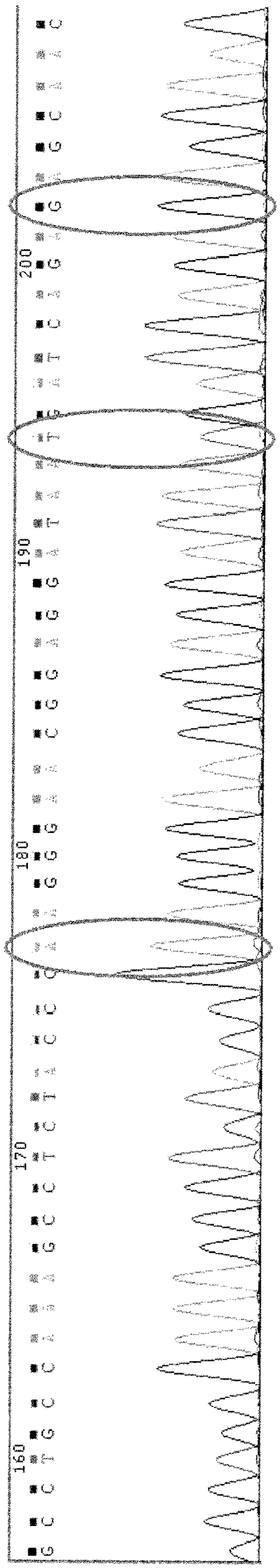
FIG. 13 shows an electropherogram illustrating detection of homozygote positions 577, 594, and 602 of exon 4 of RHCE (see circled peaks) in a sample with the genotype ddccee. The sample sequence reads: GCCTGCCAAAGCCTCTACCCAAGGGAACGGAGGATAAT GATCAGAGAGCAAC (SEQ ID NO: 139).
Figure 14:
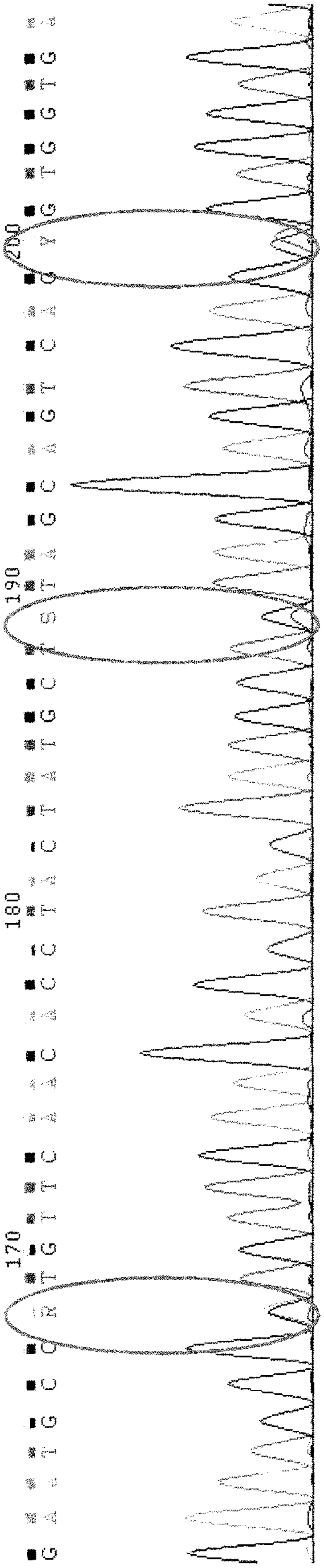
FIG. 14 shows an electropherogram illustrating detection of heterozygote position 712, 733, 744 of exon 5 (see circled peaks) discriminating between RHD and RHCE in a sample with the genotype DDCCee. The sample sequence reads: GAATGCCRTGTT CAACACCTACTATGCTSTAGCAGTCAGYGTGGTGA (SEQ ID NO: 140).
Figure 15:
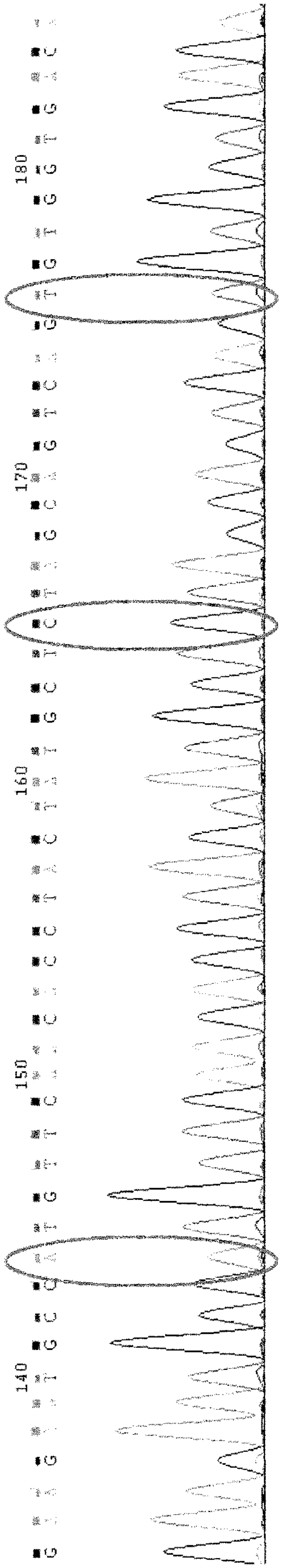
FIG. 15 shows an electropherogram illustrating detection of homozygote positions 712, 733, 744 of exon 5 of RHCE (see circled peaks) in a sample with the genotype ddccee. The sample sequence reads: GAAGAATGCCATGTTCAACACCTACTATGCTCTAGCAGT CAGTGTGGTGACA (SEQ ID NO: 141).

Amplification products were purified and Sanger sequenced in an ABI PRISM® 3730XL Genetic Analyzer according to standard procedures. Samples had been fully characterized previously for their Rh blood group phenotype and genotype. Thus, for each exon, discriminating positions between both genes were successfully identified. Table 2 shows said positions for two samples (genotypes DDCCee and ddccee). If both genes had been amplified by the same primer set, electropherograms for said samples should show double peaks (heterozygotes) at said positions (FIGS. 6-15).

TABLE 2

| Polymorphic positions | | | | |
|---|---|---|---|---|
| Exon | Genotype | | Discriminating position | Bases to be detected |
| 1 | DD | CCee | 48 | G, C |
| | dd | ccee | | G |
| 2 | DD | CCee | 150 | T, C |
| | | | 178 | A, C |

TABLE 2-continued

| Polymorphic positions | | | | |
|---|---|---|---|---|
| Exon | Genotype | | Discriminating position | Bases to be detected |
| | | | 201 | G, A |
| | | | 203 | G, A |
| | | | 307 | T, C |
| | dd | ccee | 150 | C |
| | | | 178 | C |
| | | | 201 | A |
| | | | 203 | A |
| | | | 307 | C |
| 3 | DD | CCee | 361 | T, A |
| | | | 380 | T, C |
| | | | 383 | A, G |
| | | | 455 | A, C |
| | dd | ccee | 361 | A |
| | | | 380 | C |
| | | | 383 | G |
| | | | 455 | C |
| 4 | DD | CCee | 505 | G, T |
| | | | 509 | T, A |
| | | | 514 | A, T |
| | | | 544 | A, G |
| | | | 577 | T, A |
| | | | 594 | G, C |
| | | | 602 | G, T |
| | dd | ccee | 505 | C |
| | | | 509 | G |
| | | | 514 | T |
| | | | 544 | A |
| | | | 577 | A |
| | | | 594 | T |
| | | | 602 | G |
| 5 | DD | CCee | 667 | T, G |
| | | | 676 | G |
| | | | 697 | G, C |
| | | | 712 | G, A |
| | | | 733 | G, C |
| | | | 744 | C, T |
| | | | 787 | G, A |
| | | | 800 | A, T |
| | dd | ccee | 667 | G |
| | | | 676 | G |
| | | | 697 | C |
| | | | 712 | A |
| | | | 733 | C |
| | | | 744 | T |
| | | | 787 | A |
| | | | 800 | T |

In all cases, electropherograms showed double peaks at the corresponding discriminating positions, indicating homologous regions of both genes had been simultaneously amplified and sequenced (FIGS. 6-15).

Example 3—in Silico Analysis of RHD/RHCE Sequencing Reads

Simulated sequence reads from theoretical exon sequences of the RHD and RHCE genes that would be generated by the above presented primers were created using ART (art_Illumina Q version). Illumina pair-end reads were created with the following parameters: length=200 nucleotides, coverage=40 reads, mean fragment size=230 nucleotides, mean size deviation=10. Default settings were used for insertion and deletion rates: first-read insertion rate=0.00009, deletion rate=0.00011, second-read insertion rate=0.00015, second-read deletion rate=0.00023. Files were generated in the standard raw data format of NGS technologies (.fastq format) that included quality values for each pair-end read created.

Sequences were aligned to the RHD gene (RefSeq Gene NG_007494.1; SEQ ID NO: 25) and RHCE (RefSeq Gene NGG_009208.2; SEQ ID NO: 26), the latter bearing mutations corresponding to a ce haplotype. Alignment was performed using Burrows-Wheeler Aligner software with seed length=45 nucleotides and two mismatches in the seed. Alignment files were generated in BAM format, which were then indexed using SAMTools software. Three different software programs were then used to extract RHD and RHCE variants: SAMTools, Shore and VarScan. Coverage and mapping quality for all exons were evaluated. IGV software was used for visualization of alignments of both genes against a reference that included both genes.

Results are summarized in Table 3 below:

TABLE 3

| Summary of results, by exon | |
|---|---|
| Exon | Alignment summary |
| 1 | Reads generated from RHD aligned with its reference exclusively.<br>Approximately 5% of reads generated from RHCE variants aligned with RHD with mapping quality close to 0. |
| 2 | Reads generated from RHD aligned with its reference exclusively.<br>At this exon, allele C of RHCE has an identical sequence to RHD and these reads were aligned to RHD than RHCE. Final coverage detected for RHCE in this exon was unbalanced with RHD.<br>Reads corresponding to allele c aligned with RHCE reference exclusively. |
| 3 | Reads generated from RHD aligned with its reference exclusively.<br>Reads generated from RHCE variants aligned with RHCE reference exclusively. |
| 4 | Reads generated from RHD aligned with its reference exclusively.<br>Reads generated from RHCE variants aligned with RHCE reference exclusively. |
| 5 | Reads generated from RHD aligned with its reference exclusively.<br>Reads generated from RHCE variants aligned with RHCE reference exclusively. |
| 6 | Reads generated from RHD aligned with its reference almost exclusively, except for 5% that aligned with RHCE with a mapping quality close to 0.<br>Reads generated from RHCE aligned with RHCE reference almost exclusively, except for 6.5% of RHCE reads that aligned with RHD reference with a mapping quality close to 0. |
| 7 | Reads generated from RHD aligned with its reference exclusively.<br>Reads generated from RHCE variants aligned with RHCE reference exclusively. |
| 8 | Reads generated from RHD and RHCE (C, c, E, and e combinations) aligned indiscriminately with both genes with a low mapping quality value. |
| 9 | Reads generated from RHD aligned with its reference exclusively.<br>Reads generated from RHCE variants aligned with RHCE reference exclusively. |
| 10 | Reads generated from RHD and RHCE (C, c, E, and e combinations) aligned indiscriminately with both genes but with a low mapping quality value. |

CONCLUSION

Variants were correctly aligned and successfully assigned to the corresponding RHD or RHCE genes using standard parameters known in the art. Only a very low proportion of the reads was assigned to the incorrect gene, as in the case of exons 1 and 6. In all cases, this was detected by low mapping quality values, and bore no effect in the correct determination of sequences from both genes. Furthermore, reads with low quality values can easily be filtered out of the analysis to render them moot. Similarly, unresolved assignments were produced for reads from exons 8, 10, and some reads (those for the allele identical to RHD) from exon 2. These exons do not show enough discriminating positions between both genes, and this was again correctly detected by the analysis, showing low mapping quality values or unbalanced coverage, alerting of the situation. Again, filtering out reads with low quality values would prevent any undetected wrong assignment of sequence.

Example 4—NGS of Exons 1 Through 5 of the RHD and RHCE Genes of Known-Genotype Samples Consensus Sequence-Specific Primers Libraries were generated and NGS performed, using consensus sequence-specific primers for exons 1 through 5 in a multiplex reaction, for ten reference samples of known genotype in order to evaluate the correctness of the genotyping method. These samples had been characterized previously and presented the following genotypes:

TABLE 4

Genotypes of Samples A-J:

| Sample | Genotype |
|---|---|
| Sample A | CE (exons 1-2)-DD (exons 3-9)-CE (exon 10) |
| Sample B | DDCcEe |
| Sample C | DdCCee |
| Sample D | ddCcEe |
| Sample E | DdCcee (exons 1-2)-ddCcee (exons 3-9)-DD (exon 10) |
| Sample F | ddCcee |
| Sample G | DDCcEe |
| Sample H | DdccEe |
| Sample I | Ddccee |
| Sample J | DDCCee |

Multiplex sequencing reactions were performed in two step PCRs (PCR1 and PCR2), following standard procedures. Conditions for PCR1 were:

| Primer Mix (1 uM) |
|---|
| RHex01-F1-OHBCM0620-RHex01-R2-OHBCM0634 |
| RHex02-F2-OHBCM0624-RHex02-R1-OHBCM0635 |
| RHex03-F2-OHBCM0628-RHex03-R1-OHBCM0640 |
| RHex04-F1-OHBCM0629-RHex04-R1-OHBCM0643 |
| RHex05-F1-OHBCM0631-RHex05-R1-OHBCM0645 |

| Reagent | Vol per sample (ul) |
|---|---|
| Multiplex Mix | 7.5 |
| Primer Mix | 4 |
| H20 | 0.5 |
| DNA template (20 ng/ul) | 3 |

| Cycling | | |
|---|---|---|
| 95° C. | 15 min | |
| 95° C. | 45 sec | 23 cycles |
| 61° C. | 60 sec | |
| 72° C. | 90 sec | |
| 72° C. | 10 min | |

Conditions for PCR2 were the same as for PCR1, substituting the primers for an equimolar mixture of each reverse primer (containing Agilent indexes for NGS sequencing) and OHBCM0657, and cycling 15 instead of 23 times.

Libraries so created were then purified using AMPure® XP beads, quantified using Qubit® 2.0, and run using MiSeq v.2 reagents, all as per manufacturer instructions.

Data Analysis

FastQC software was used to determine basic statistics on the quality of each sample read (forward and reverse), including Per base sequence quality, Per sequence quality scores, Per base sequence content, Per base GC content, Per sequence GC content, Per base N content, Sequence Length Distribution, Sequence Duplication Levels, Overrepresented sequences and Kmer Content.

Trimmomatic software was used to remove reads with less than 76 nucleotides. Reads were trimmed by 2 bp at their 3' end with Fastx-trimmer tool from FASTX-toolkit software.

Sequences were aligned using Burrows-Wheeler Aligner Maximal exact match (BWA MEM) algorithm from BWA software against a reference file (multiple sequences in a fasta format) that included only the reference sequences of the five exons plus 50 bps upstream and downstream of said exons. Results are presented for an alignment against a reference of gene RHD (NG007494.1; SEQ ID NO: 25) (exons 1-5; SEQ ID NOS: 27, 33, 39, 45 and 51, respectively) and a consensus sequence for 4 alleles (RHCE*ce, RHCE*Ce, RHCE*cE, and RHCE*CE) of gene RHCE (NG009208.2) (exons 1-5; SEQ ID NOS: 32, 38, 44, 50 and 56, respectively). Alignment files were generated in BAM format including information such as bitwise flag, alignment position, mapping quality, extended CIGAR string and query quality. In this example of analysis, the alignment results were sorted using Picard Tools software and indexed using SAMTools software. The sorted-indexed bam file was parsed to generate an alignment summary for each position including alignment and base-pair information at each chromosomal position such as bitwise flag, mapping quality, query quality, chromosome name, coordinate, reference base, alternate base, number of reads covering the site, read bases, base qualities and mapping qualities, forming a pileup formatted file using SAMTools software.

VarScan software was used to parse the pileup formatted file, obtain genotypes at each sequence position and extract RHD and RHCE variants. In this step, SNPs and INDELs are detected using available parameters in the software. In this case, minimum coverage was set at 15×, minimum variant frequency to call an alternative genotype above 5%, and genotype average quality call of 30 Phred Score units.

The pileup file resulting from alignment was also parsed to evaluate base calling, coverage and mapping quality at each nucleotide position in the reference sequence. Standard alignment values such as coverage in forward strand, coverage in reverse strand, total coverage and mapping quality were recorded and interpreted.

A selection method was designed where cutoff criteria were set, as follows. To define homozygous calls, a minimum of 70% of reads must have supported the called allele. To define heterozygous calls, between 30 and 70% of total reads must have supported the alternative allele. In addition to this, the mapping quality and calling quality should have been above 20 Phred Score units. When coverage is evaluated independently for forward or reverse strand alignment, reads supporting the call also had to convey to defined criteria, such as having a forward-to-reverse coverage ratio of between 0.7 and 1.35.

Expected and observed results can be seen in Tables 5-8 (see below).

Example 5—Amplification of Homologous Loci Using Consensus Sequence-Specific Primers Primers suitable for next generation sequencing (NGS) and specific for consensus sequence between RHD and RHCE genes were designed for exons 6 through 10 and intron 2, and tested for correct product amplifications of both genes using different primer combinations in uniplex reactions.

Amplifications were tested with one sample:

TABLE 9

| Blood type of samples | |
|---|---|
| Sample | Genotype |
| Sample 1 | D/cc |

Consensus sequence-specific portions were:

| | | |
|---|---|---|
| RHex06 F1 | GGTCACTTGCAGCAAGATGG | (SEQ ID NO: 59) |
| RHex06 F2 | ACCTTGCTTCCTTTACCCAC | (SEQ ID NO: 60) |
| RHex06 R1 | TGGCCTTCAGCCAAAGCAGA | (SEQ ID NO: 61) |
| RHex06 R2 | CTAATGCAGCTGTGCACTGC | (SEQ ID NO: 62) |
| RHex07 F1 | TGTGTGAAAGGGGTGGGTAG | (SEQ ID NO: 63) |
| RHex07 F2 | GTCTCACCTGCCAATCTGCT | (SEQ ID NO: 64) |
| RHex07 R1 | GTTGGAGGGGAGTGTTAAGG | (SEQ ID NO: 65) |
| RHex07 R2 | CCAGCTAAGGACTCTGCACA | (SEQ ID NO: 66) |
| RHex08 F1 | ATGGCACTACTGACACCGAC | (SEQ ID NO: 67) |
| RHex08 F2 | TTGTCCCTGATGACCTCTGC | (SEQ ID NO: 68) |
| RHex08 R1 | TGTCCTGGCAATGGTGGAAG | (SEQ ID NO: 69) |
| RHex08 R2 | GCACATAGACATCCAGCCAC | (SEQ ID NO: 70) |
| RHex09 F1 | AGCTGGTCCAGGAATGACAG | (SEQ ID NO: 71) |
| RHex09 F2 | GTGGGAGAAAAAGGATTTCTGTTGAGA | (SEQ ID NO: 72) |
| RHex09 F3 | TCTTGAGATTAAAAATCCTGTGCTCCA | (SEQ ID NO: 73) |
| RHex09 R1 | AGTTCATGCACTCAAAATCTATCACGT | (SEQ ID NO: 74) |
| RHex09 R2 | CCTGCAATGCTCCTTACTCC | (SEQ ID NO: 75) |
| RHex10 F1 | GGCTGTTTCAAGAGATCAAGCC | (SEQ ID NO: 76) |
| RHex10 F2 | TCAGTATGTGGGTTCATCTGCA | (SEQ ID NO: 77) |
| RHex10 R1 | AGGCAACAGTGAGAGGAAGTTG | (SEQ ID NO: 78) |
| RHex10 R2 | TGCTGTCATGAGCGTTTCTCAC | (SEQ ID NO: 79) |
| RHin2 F1 | CTTGTGCCACTTGACTTGGGACTG | (SEQ ID NO: 80) |
| RHin2 F2 | CTGTTTTGAGTCCCTTCAGGGGAG | (SEQ ID NO: 81) |
| RHin2 F3 | CTCACATACTGATAACTTAGCAAATGGC | (SEQ ID NO: 82) |
| RHin2 R1 | GATCACTTGAGCCCAGGAGGC | (SEQ ID NO: 83) |
| RHin2 R2 | TTAACTCAGGAGGCTGAGGTGG | (SEQ ID NO: 84) |
| RHin2 R3 | CTGAGGTGGGAGGATCACTTGAG | (SEQ ID NO: 85) |
| RHCEin2 R4 | AAATTAGCCGGGCATGGTAGCAG | (SEQ ID NO: 86) |

PCR were performed in 15 μL reactions using the following conditions:

| | |
|---|---|
| Qiagen Multiplex kit (2X) | 7.5 μL |
| Template DNA (20 ng/uL) | 3.5 μL |
| Primer mix | 1.0 μL |
| dH2O | 3.0 μL |

| | | |
|---|---|---|
| 95° C. | 15 min | |
| 95° C. | 45 sec | 23 cycles |
| 60° C. | 64 sec | |
| 72° C. | 90 sec | |
| 72° C. | 10 min | |
| 4° C. | infinity | |

PCR products for Sample 1 were run on agarose gels in order to confirm amplifications (FIG. 27-28).

Example 6—NGS of Exons 1 Through 10 of the RHD and RHCE Genes of Known-Genotype Samples Consensus Sequence-Specific Primers Libraries were generated and NGS performed, using consensus sequence-specific primers for exons 1 through 10 and intron 2 in two multiplex reactions, for seven reference samples of known genotype in order to evaluate the correctness of the genotyping method. These samples had been characterized previously and presented the following genotypes:

TABLE 10

| Blood type of samples | |
|---|---|
| Sample | Genotype |
| Sample 1 | ddccee |
| Sample 2 | DDCCee |
| Sample 3 | DdCcee |
| Sample 4 | ddCCee |
| Sample 5 | DDccEE |
| Sample 6 | ddccee |
| Sample 7 | DccEe |

TABLE 11

| Polymorphic positions | | | | | |
|---|---|---|---|---|---|
| | | Expected bases by genotype | | | |
| Exon | Position | D | Ce | cE | ce |
| 1 | i01+18 | A | C | C | C |
| 2 | c.150 | T | T | C | C |
| | c.178 | A | A | C | C |
| | c.201 | G | G | A | A |
| | c.203 | G | G | A | A |
| | c.307 | T | T | C | C |
| 3 | i02−13 | C | T | T | T |
| | i02−8 | T | A | A | A |
| | c.361 | T | A | A | A |
| | c.380 | T | C | C | C |
| | c.383 | A | G | G | G |
| | c.455 | A | C | C | C |
| 4 | i03−48 | deletion | T | T | T |
| | c.505 | A | C | C | C |
| | c.509 | T | G | G | G |
| | c.513 | A | T | T | T |
| | c.544 | T | A | A | A |
| | c.577 | G | A | A | A |
| | c.594 | A | T | T | T |
| | c.602 | C | G | G | G |
| 5 | c.667 | T | G | G | G |
| | c.676 | G | G | C | G |
| | c.697 | G | C | C | C |
| | c.712 | G | A | A | A |
| | c.733 | G | C | C | C |
| | c.744 | C | T | T | T |
| | c.787 | G | A | A | A |
| | c.800 | A | T | T | T |
| 6 | c.916 | G | A | A | A |
| | c.932 | A | G | G | G |
| | i06+21 | C | T | T | T |
| | i06+22 | C | G | G | G |
| | i06+23 | T | C | C | C |
| | i06+24 | C | T | T | T |
| 7 | c.941 | G | T | T | T |
| | c.968 | C | A | A | A |
| | c.974 | G | T | T | T |
| | c.979 | A | G | G | G |
| | c.985 | G | C | C | C |
| | c.986 | G | A | A | A |
| | c.989 | A | C | C | C |
| | c.992 | A | T | T | T |
| | c.1025 | T | C | C | C |
| | c.1048 | G | C | C | C |
| | c.1053 | C | T | T | T |
| | c.1057 | G | T | T | T |
| | c.1059 | A | G | G | G |
| | c.1060 | G | A | A | A |
| | c.1061 | C | A | A | A |
| 9 | i08−75 | deletion | C | C | C |
| | i08−74 | deletion | A | A | A |
| | i08−67 | C | T | T | T |
| | c.1170 | T | C | C | C |
| | c.1193 | A | T | T | T |
| | i09+62 | A | G | G | G |
| Intron 2 | | Absent | Present | Absent | Absent |

Multiplexes were prepared with the following combinations of primers:

| | Multiplex mix A | | Multiplex mix B | |
|---|---|---|---|---|
| Region | FW | RV | FW | RV |
| Exon 1 | F3 | R1 | F2 | R2 |
| Exon 2 | F2 | R2 | F1 | R1 |
| Exon 3 | F3 | R1 | F2 | R3 |
| Exon 4 | F1 | R1 | F2 | R2 |
| Exon 5 | F2 | R1 | F1 | R2 |
| Exon 6 | F2 | R2 | F1 | R1 |
| Exon 7 | F1 | R1 | F2 | R2 |

-continued

| | Multiplex mix A | | Multiplex mix B | |
|---|---|---|---|---|
| Region | FW | RV | FW | RV |
| Exon 8 | F1 | R1 | F2 | R2 |
| Exon 9 | F3 | R2 | F1 | R1 |
| Exon 10 | F1 | R1 | F2 | R2 |
| Intron 2 | F3 | R8 | F2 | R3 |

Multiplex sequencing reactions were performed in two step PCRs (PCR1 and PCR2), following standard procedures. Conditions for PCR1 were:

| Reagent | Vol per sample (ul) |
|---|---|
| Qiagen Multiplex Mix | 7.5 |
| Primer Mix | 1 |
| H20 | 3 |
| DNA template (20 ng/ul) | 3.5 |

| Cycling | | |
|---|---|---|
| 95° C. | 15 min | |
| 95° C. | 45 sec | 23 cycles |
| 61° C. | 60 sec | |
| 72° C. | 90 sec | |
| 72° C. | 10 min | |

Conditions for PCR2 were the same as for PCR1, substituting the primers for an equimolar mixture of each reverse primer (containing Agilent indexes for NGS sequencing) and a forward primer, and cycling 10 instead of 23 times.

Libraries so created were then purified using SequalPrep normalization plate, quantified using Qubit® 2.0, and run using MiSeq v.3 reagents, all as per manufacturer instructions.

Data Analysis

FastQC software was used to determine basic statistics on the quality of each sample read (forward and reverse), including Per base sequence quality, Per sequence quality scores, Per base sequence content, Per base GC content, Per sequence GC content, Per base N content, Sequence Length Distribution, Sequence Duplication Levels, Overrepresented sequences and Kmer Content.

Trimmomatic software was used to remove reads with less than 76 nucleotides. Reads were trimmed by 2 bp at their 3' end with Fastx-trimmer tool from FASTX-toolkit software.

Sequences were aligned using Burrows-Wheeler Aligner Maximal exact match (BWA MEM) algorithm from BWA software against a reference file (multiple sequences in a fasta format) that included only the reference sequences of the five exons plus 50 bps upstream and downstream of said exons. Results are presented for an alignment against a reference of gene RHD (NG007494.1; SEQ ID NO: 25) (exons 1-10 and intron 2; SEQ ID NOS: 27, 33, 39, 45, 51, 87, 93, 99, 105, 111, and 117, respectively) and sequence of gene RHCE (NG009208.2) (exons 1-10 and intron 2; SEQ ID NOS: 28, 34, 40, 46,52, 88, 94, 100, 106, 112, and 120, respectively). Alignment files were generated in BAM format including information such as bitwise flag, alignment position, mapping quality, extended CIGAR string and query quality. In this example of analysis, the alignment results were sorted using Picard Tools software and indexed using SAMTools software. The sorted-indexed bam file was parsed to generate an alignment summary for each position including alignment and base-pair information at each chromosomal position such as bitwise flag, mapping quality, query quality, chromosome name, coordinate, reference base, alternate base, number of reads covering the site, read bases, base qualities and mapping qualities, forming a pileup formatted file using SAMTools software.

VarScan software was used to parse the pileup formatted file, obtain genotypes at each sequence position and extract RHD and RHCE variants. In this step, SNPs and INDELs are detected using available parameters in the software. In this case, minimum coverage was set at 15×, minimum variant frequency to call an alternative genotype above 5%, and genotype average quality call of 30 Phred Score units.

The pileup file resulting from alignment was also parsed to evaluate base calling, coverage and mapping quality at each nucleotide position in the reference sequence. Standard alignment values such as coverage in forward strand, coverage in reverse strand, total coverage and mapping quality were recorded and interpreted.

A selection method was designed where cutoff criteria were set, as follows. To define homozygous calls, a minimum of 70% of reads must have supported the called allele. To define heterozygous calls, between 30 and 70% of total reads must have supported the alternative allele. In addition to this, the mapping quality and calling quality should have been above 20 Phred Score units. When coverage is evaluated independently for forward or reverse strand alignment, reads supporting the call also had to convey to defined criteria, such as having a forward-to-reverse coverage ratio of between 0.7 and 1.35. Expected and observed results can be seen in Tables 14-21 and 31.

Example 7—NGS of Exons 1 Through 10 of the RHD and RHCE Genes of Known-Genotype Samples Consensus Sequence-Specific Primers Libraries were generated and NGS performed, using consensus sequence-specific primers for exons 1 through 10 and intron 2 in two multiplex reactions, for six reference samples of known genotype in order to evaluate the correctness of the genotyping method. These samples had been characterized previously and presented the following genotypes:

TABLE 12

| Blood type of samples | |
|---|---|
| Sample | Genotype |
| Sample 1 | DDCCee |
| Sample 2 | ddccee |
| Sample 3 | ddCcee |
| Sample 4 | ddCcEe |
| Sample 5 | DCcee |
| Sample 6 | ddccee |

TABLE 13

| Polymorphic positions | | | | | |
|---|---|---|---|---|---|
| | | Expected bases by genotype | | | |
| Exon | Position | D | Ce | cE | ce |
| 1 | i01+18 | A | C | C | C |
| 2 | c.150 | T | T | C | C |
| | c.178 | A | A | C | C |
| | c.201 | G | G | A | A |
| | c.203 | G | G | A | A |
| | c.307 | T | T | C | C |
| 3 | i02-13 | C | T | T | T |
| | i02-8 | T | A | A | A |
| | c.361 | T | A | A | A |
| | c.380 | T | C | C | C |
| | c.383 | A | G | G | G |
| | c.455 | A | C | C | C |
| 4 | i03-48 | deletion | T | T | T |
| | c.505 | A | C | C | C |
| | c.509 | T | G | G | G |
| | c.513 | A | T | T | T |
| | c.544 | T | A | A | A |
| | c.577 | G | A | A | A |
| | c.594 | A | T | T | T |
| | c.602 | C | G | G | G |
| 5 | c.667 | T | G | G | G |
| | c.676 | G | G | C | G |
| | c.697 | G | C | C | C |
| | c.712 | G | A | A | A |
| | c.733 | G | C | C | C |
| | c.744 | C | T | T | T |
| | c.787 | G | A | A | A |
| | c.800 | A | T | T | T |
| 6 | c.916 | G | A | A | A |
| | c.932 | A | G | G | G |
| | i06+21 | C | T | T | T |
| | i06+22 | C | G | G | G |
| | i06+23 | T | C | C | C |
| | i06+24 | C | T | T | T |
| 7 | c.941 | G | T | T | T |
| | c.968 | C | A | A | A |
| | c.974 | G | T | T | T |
| | c.979 | A | G | G | G |
| | c.985 | G | C | C | C |
| | c.986 | G | A | A | A |
| | c.989 | A | C | C | C |
| | c.992 | A | T | T | T |
| | c.1025 | T | C | C | C |
| | c.1048 | G | C | C | C |
| | c.1053 | C | T | T | T |
| | c.1057 | G | T | T | T |
| | c.1059 | A | G | G | G |
| | c.1060 | G | A | A | A |
| | c.1061 | C | A | A | A |
| 9 | i08-75 | deletion | C | C | C |
| | i08-74 | deletion | A | A | A |
| | i08-67 | C | T | T | T |
| | c.1170 | T | C | C | C |
| | c.1193 | A | T | T | T |
| | i09+62 | A | G | G | G |
| Intron 2 | | Absent | Present | Absent | Absent |

Multiplexes were prepared with the following combinations of primers:

| | Multiplex mix A | | Multiplex mix B | |
|---|---|---|---|---|
| Region | FW | RV | FW | RV |
| Exon 1 | F3 | R1 | F2 | R2 |
| Exon 2 | F2 | R2 | F1 | R1 |
| Exon 3 | F3 | R1 | F2 | R3 |
| Exon 4 | F1 | R1 | F2 | R2 |
| Exon 5 | F2 | R1 | F1 | R2 |
| Exon 6 | F2 | R2 | F1 | R1 |
| Exon 7 | F1 | R1 | F2 | R2 |
| Exon 8 | F1 | R1 | F2 | R2 |
| Exon 9 | F3 | R2 | F1 | R1 |
| Exon 10 | F1 | R1 | F2 | R2 |
| Intron 2 | F3 | R8 | F2 | R3 |

Multiplex sequencing reactions were performed in two step PCRs (PCR1 and PCR2), following standard procedures. Conditions for PCR1 were:

| Reagent | Vol per sample (ul) |
|---|---|
| Qiagen Multiplex Mix | 7.5 |
| Primer Mix | 1 |
| H20 | 3 |
| DNA template (20 ng/ul) | 3.5 |

| Cycling | | |
|---|---|---|
| 95° C. | 15 min | |
| 95° C. | 45 sec | 23 cycles |
| 61° C. | 60 sec | |
| 72° C. | 90 sec | |
| 72° C. | 10 min | |

Conditions for PCR2 were the same as for PCR1, substituting the primers for an equimolar mixture of each reverse primer (containing Agilent indexes for NGS sequencing) and a forward primer, and cycling 10 instead of 23 times.

Libraries so created were then purified using SequalPrep normalization plate, quantified using Qubit® 2.0, and run using MiSeq v.3 reagents, all as per manufacturer instructions.

Data Analysis

FastQC software was used to determine basic statistics on the quality of each sample read (forward and reverse), including Per base sequence quality, Per sequence quality scores, Per base sequence content, Per base GC content, Per sequence GC content, Per base N content, Sequence Length Distribution, Sequence Duplication Levels, Overrepresented sequences and Kmer Content.

Trimmomatic software was used to remove reads with less than 76 nucleotides. Reads were trimmed by 2 bp at their 3' end with Fastx-trimmer tool from FASTX-toolkit software.

Sequences were aligned using Burrows-Wheeler Aligner Maximal exact match (BWA MEM) algorithm from BWA software against a reference file (multiple sequences in a fasta format) that included only the reference sequences of the five exons plus 50 bps upstream and downstream of said exons. Results are presented for an alignment against a reference of gene RHD (NG007494.1; SEQ ID NO: 25) (exons 1-10 and intron 2; SEQ ID NOS: 27, 33, 39, 45, 51, 87, 93, 99, 105, 111, and 117, respectively) and sequence of gene RHCE (NG009208.2) (exons 1-10 and intron 2; SEQ ID NOS: 28, 34, 40, 46, 52, 88, 94, 100, 106, 112, and 120, respectively). Alignment files were generated in BAM format including information such as bitwise flag, alignment position, mapping quality, extended CIGAR string and query quality. In this example of analysis, the alignment results were sorted using Picard Tools software and indexed using SAMTools software. The sorted-indexed bam file was parsed to generate an alignment summary for each position including alignment and base-pair information at each chromosomal position such as bitwise flag, mapping quality, query quality, chromosome name, coordinate, reference base, alternate base, number of reads covering the site, read bases, base qualities and mapping qualities, forming a pileup formatted file using SAMTools software.

VarScan software was used to parse the pileup formatted file, obtain genotypes at each sequence position and extract RHD and RHCE variants. In this step, SNPs and INDELs are detected using available parameters in the software. In this case, minimum coverage was set at 15×, minimum variant frequency to call an alternative genotype above 5%, and genotype average quality call of 30 Phred Score units.

The pileup file resulting from alignment was also parsed to evaluate base calling, coverage and mapping quality at each nucleotide position in the reference sequence. Standard alignment values such as coverage in forward strand, coverage in reverse strand, total coverage and mapping quality were recorded and interpreted.

A selection method was designed where cutoff criteria were set, as follows. To define homozygous calls, a minimum of 70% of reads must have supported the called allele. To define heterozygous calls, between 30 and 70% of total reads must have supported the alternative allele. In addition to this, the mapping quality and calling quality should have been above 20 Phred Score units. When coverage is evaluated independently for forward or reverse strand alignment, reads supporting the call also had to convey to defined criteria, such as having a forward-to-reverse coverage ratio of between 0.7 and 1.35.

Expected and observed results can be seen in Tables 22-29 and 31.

In three examples (4, 6 and 7), several combinations of SEQ ID NOs: 3-24 and 59-86 were evaluated to test the accuracy of the detection of alleles in the highly homologous genes RHD and RHCE through next-generation sequencing. The regions amplified by the method bear discriminating nucleotide positions between RHD, RHCE*Ce, RHCE*CE, RHCE*ce and RHCE*cE. These positions were then analyzed to determine whether they permit a calculation of the proportion of alleles present in each gene, and, thus, the determination of the correct genotype of a sample. Discriminating positions occur in exons 1, 2, 3, 4, 5, 6, 7, and 9. Additionally, a region in intron 2 that presents a 109 base pair insert was also evaluated in the determination of the RHCE Big C genotyping. In the examples, the method was also tested to see if it is capable of rendering all the bases contained in the coding regions, as well as the insert in intron 2 which is useful for blood typing.

In Tables 14 to 31, the reference base and detected base appear in the column "Mutation in reference to coding region". For example, in Table 14, for which the reference sequence is the RHD gene, the reference sequence has a T at position c.150 in exon 2, while the detected variant (the mutation in reference to coding region) is a C (noted by the ">" symbol). The values reported for every position are calculated by dividing the number of reads supporting the variant within the total number of reads. In Tables 5 to 8, the format changes slightly to report the aforementioned calculation as a percentage. Mutations for each RHCE allele and RHD are summarized under the column "Polymorphic sites" only for coding region positions. These positions are considered stable to discriminate between the RHD, RHCE*Ce, RHCE*CE, RHCE*ce and RHCE*cE.

The expected allele ratio is calculated on the basis of the existence of none, one or two RHD alleles and none, one or two RHCE alleles. For example, on Table 14, the sample with the genotype "ddccee" has no RHD gene and two alleles of genotype little c and little e for RHCE. When the NGS sequences of this sample are mapped to the reference RHD, the positions with a different variant than the reference will be detected. For this sample, all expected variants (Table 15) when aligning to RHD are 100% from the RHCE gene because RHD is deleted. On the other hand, when aligning to the RHCE reference (Tables 18 and 19), there are no expected variants because the sample's sequence is identical to the reference sequence. In the case of intron 2, the ratios are calculated based on the number of reads that aligned to the reference sequence within the sum of reads that aligned to RHCE and RHD.

In Example 4, a total of 24 discriminating nucleotide positions between RHD and RHCE were evaluated for exons 1 through 5 of the RH genes for each sample and reference sequence. In said example, the sum of the nucleotide positions (24 per sample) for all samples evaluated (7) using two reference sequences amounts to 336. The concordance between observed and expected allele ratios for the total of nucleotide positions evaluated for the combination of primers used in Example 4 is 100%.

In Examples 6 and 7, a total of 50 discriminating nucleotide positions between RHD and RHCE were evaluated for exons 1 through 10 of the RH genes for primer mix A and 52 for primer mix B. In said examples, the sum of the nucleotide positions (50 for primer mix A and 52 for primer mix B per sample) for all samples evaluated (13) using two reference sequences amounts to 1300 for primer mix A and 1352 for primer mix B. The concordance between observed and expected allele ratios for the combination of primers used in Examples 6 and 7 is 96% for primer mix A and 90% for primer mix B.

The conclusion, thus, is that, through the data analysis of three examples, it was confirmed that the regions sequenced by the method cover the entire coding regions of the ten exons and the 109 base pair insert in intron 2 of the RH genes (RHD and RHCE), allowing blood typing of the group. The application of consensus sequence-specific primers permits the homogeneous amplification of the two genes and, in this regard, makes it a quantitative method which allows the genotype prediction.

Accuracy of this genotype prediction may be reduced in samples with large sequence rearrangements, but even then, the lowest expected accuracy of the invention is 90%. These examples show that through the use of combinations of SEQ ID NO: 3-24 and 59-86, homologous genes can be simultaneously genotyped.

The examples demonstrate that the method allows the simultaneous sequencing of genes RHD and RHCE and the correct genotyping of variant positions to assign the proportion or allele ratio of each gene. In this regard, the method overcomes limitations of serological testing and Sanger sequencing in blood typing. Additionally, the method is high-throughput which is advantageous in the clinical setting for blood typing massive amounts of samples.

TABLE 5

| | | | | | | | RHCE Obtained results based on analysis | | | | | | |
|---|---|---|---|---|---|---|---|---|---|---|---|---|---|
| Polymorphic sites | | | | | | | CE (exon 1)-DD (exons 2-9)-CE | | DdCcee (exons 1-2)-ddCcee (exons 3-9)- | | | | |
| ce | cE | Ce | CE | D | Ex | Exonic position | (exon 10) | ddCcEe | DD (exon 10) | ddCcee | DDCcEe | ddccee | DDCCee |
| C | C | T | T | T | 2 | 150 | T 99% | C 51% T 48% | C 34% T 65% | C 52% T 47% | C 25% T 74% | C 99% | T 99% |
| C | C | A | A | A | | 178 | A 99% | A 48% C 51% | C 34% A 65% | A 47% C 52% | C 25% A 74% | C 99% | A 99% |
| A | A | G | G | G | | 201 | G 99% | A 50% G 49% | A 35% G 66% | A 51% G 49% | A 25% G 74% | A 99% | G 99% |
| A | A | G | G | G | | 203 | G 99% | A 50% G 49% | A 33% G 65% | A 50% G 49% | A 25% G 74% | A 99% | G 99% |
| C | C | T | T | T | | 307 | T 99% | C 51% T 49% | C 34% T 65% | C 50% T 49% | C 25% T 74% | C 99% | T 99% |
| A | A | A | A | T | 3 | 361 | T 99% | No calls for variants (no variant detected) | No calls for variants (no variant detected) | No calls for variants (no variant detected) | T 48% | No calls for variants (no variant detected) | T 49% |
| C | C | C | C | T | | 380 | T 99% | | | | T 48% | | T 49% |
| G | G | G | G | A | | 383 | A 99% | | | | A 48% | | A 49% |
| C | C | C | C | A | | 455 | A 99% | | | | A 48% | | A 49% |
| C | C | C | C | A | 4 | 505 | A 99% | | | | A 52% | | A 52% |
| G | G | G | G | T | | 509 | T 99% | | | | T 52% | | T 52% |
| T | T | T | T | A | | 514 | A 99% | | | | A 53% | | A 52% |
| A | A | A | A | T | | 544 | T 99% | | | | T 53% | | T 52% |
| A | A | A | A | G | | 577 | G 99% | | | | G 53% | | G 52% |
| T | T | T | T | A | | 594 | A 99% | | | | A 52% | | A 51% |
| G | G | G | G | C | | 602 | C 99% | | | | C 53% | | C 52% |
| G | G | G | G | T | 5 | 667 | T 99% | | | | T 50% | | T 51% |
| G | C | G | C | G | | 676 | G 100% | C 50% G 50% | G 99% | G 99% | C 25% G 74% | G 99% | G 99% |
| C | C | C | C | G | | 697 | G 99% | No calls for variants (no variant detected) | No calls for variants (no variant detected) | No calls for variants (no variant detected) | G 50% | No calls for variants (no variant detected) | G 51% |
| A | A | A | A | G | | 712 | G 99% | | | | G 50% | | G 52% |
| C | C | C | C | G | | 733 | G 99% | | | | G 50% | | G 51% |
| T | T | T | T | C | | 744 | C 99% | | | | C 50% | | C 51% |
| A | A | A | A | G | | 787 | G 99% | | | | G 52% | | G 53% |
| T | T | T | T | A | | 800 | A 99% | | | | A 50% | | A 51% |

TABLE 6

RHCE
Expected results based on known genotypes

| Polymorphic sites ce | cE | Ce | CE | D | Ex | Exonic position | CE (exon 1)-DD (exons 2-9)-CE (exon 10) | ddCcEe | DdCcee (exons 1-2)-ddCcee (exons 3-9)-DD (exon 10) | ddCcee | DDCcEe | ddccee | DDCCee |
|---|---|---|---|---|---|---|---|---|---|---|---|---|---|
| C | C | T | T | T | 2 | 150 | T 100% | C 50% T 50% | C 33.3% T 66.6% | C 50% T 50% | C 25% T 75% | C 100% | T 100% |
| C | C | A | A | A | | 178 | A 100% | C 50% A 50% | C 33.3% A 66.6% | A 50% C 50% | C 25% A 75% | C 100% | A 100% |
| A | A | G | G | G | | 201 | G 100% | A 50% G 50% | A 33.3% G 66.6% | A 50% G 50% | A 25% G 75% | A 100% | G 100% |
| A | A | G | G | G | | 203 | G 100% | A 50% G 50% | A 33.3% G 66.6% | A 50% G 50% | A 25% G 75% | A 100% | G 100% |
| C | C | T | T | T | | 307 | T 100% | C 50% T 50% | C 33.3% T 66.6% | C 50% T 50% | C 25% T 75% | C 100% | T 100% |
| A | A | A | A | T | 3 | 361 | T 100% | RHD | RHD | RHD | T 50% | RHD | T 50% |
| C | C | C | C | T | | 380 | T 100% | deleted, | deleted, | deleted, | T 50% | deleted, | T 50% |
| G | G | G | G | A | | 383 | A 100% | no calls | no calls | no calls | A 50% | no calls | A 50% |
| C | C | C | C | A | | 455 | A 100% | expected | expected | expected | A 50% | expected | A 50% |
| C | C | C | C | A | 4 | 505 | A 100% | | | | A 50% | | A 50% |
| G | G | G | G | T | | 509 | T 100% | | | | T 50% | | T 50% |
| T | T | T | T | A | | 514 | A 100% | | | | A 50% | | A 50% |
| A | A | A | A | T | | 544 | T 100% | | | | T 50% | | T 50% |
| A | A | A | A | G | | 577 | G 100% | | | | G 50% | | G 50% |
| T | T | T | T | A | | 594 | A 100% | | | | A 50% | | A 50% |
| G | G | G | G | C | | 602 | C 100% | | | | C 50% | | C 50% |
| G | G | G | G | T | 5 | 667 | T 100% | | | | T 50% | | T 50% |
| G | C | G | C | G | | 676 | G 100% | C 50% G 50% | G 100% | G 100% | C 25% G 75% | G 100% | G 100% |
| C | C | C | C | G | | 697 | G 100% | RHD | RHD | RHD | G 50% | RHD | G 50% |
| A | A | A | A | G | | 712 | G 100% | deleted, | deleted, | deleted, | G 50% | deleted, | G 50% |
| C | C | C | C | G | | 733 | G 100% | no calls | no calls | no calls | G 50% | no calls | G 50% |
| T | T | T | T | C | | 744 | C 100% | expected | expected | expected | C 50% | expected | C 50% |
| A | A | A | A | G | | 787 | G 100% | | | | G 50% | | G 50% |
| T | T | T | T | A | | 800 | A 100% | | | | A 50% | | A 50% |

TABLE 7

RHD
Obtained results based on analysis

| Polymorphic sites ce | cE | Ce | CE | D | Exon | Exonic position | CE (exon 1)-DD (exons 2-9)-CE (exon 10) | ddCcEe | DdCcee (exons 1-2)-ddCcee (exons 3-9)-DD (exon 10) | ddCcee | DDCcEe | ddccee | DDCCee |
|---|---|---|---|---|---|---|---|---|---|---|---|---|---|
| C | C | T | T | T | 2 | 150 | No calls for | C 51% | C 34% | C 52% | C 25% | C 99% | No calls for |
| C | C | A | A | A | | 178 | variants (no | C 51% | C 34% | C 51% | C 24% | C 99% | variants (no |
| A | A | G | G | G | | 201 | variant | A 50% | A 33% | A 50% | A 24% | A 99% | variant |
| A | A | G | G | G | | 203 | detected) | A 50% | A 33% | A 50% | A 24% | A 99% | detected) |
| C | C | T | T | T | | 307 | | C 50% | C 34% | C 50% | C 24% | C 99% | |
| A | A | A | A | T | 3 | 361 | | A 99% | A 99% | A 99% | A 51% | A 99% | A 49% |
| C | C | C | C | T | | 380 | | C 99% | C 99% | C 99% | C 51% | C 99% | C 50% |
| G | G | G | G | A | | 383 | | G 99% | G 99% | G 99% | G 51% | G 99% | G 50% |
| C | C | C | C | A | | 455 | | C 99% | C 99% | C 99% | C 51% | C 99% | C 49% |
| C | C | C | C | A | 4 | 505 | | C 99% | C 99% | C 99% | C 46% | C 99% | C 47% |
| G | G | G | G | T | | 509 | | G 99% | G 99% | G 99% | G 46% | G 99% | G 47% |
| T | T | T | T | A | | 514 | | T 99% | T 99% | T 99% | T 46% | T 99% | T 47% |
| A | A | A | A | T | | 544 | | A 99% | A 99% | A 99% | A 46% | A 99% | A 47% |
| A | A | A | A | G | | 577 | | A 99% | A 99% | A 99% | A 46% | A 99% | A 47% |
| T | T | T | T | A | | 594 | | T 99% | T 99% | T 99% | T 46% | T 99% | T 47% |
| G | G | G | G | C | | 602 | | G 99% | G 99% | G 99% | G 46% | G 99% | G 47% |
| T | T | T | T | G | 5 | 667 | | G 99% | G 99% | G 99% | G 49% | G 99% | G 48% |
| G | C | G | C | G | | 676 | | C 49% | No call | No call | C 25% | No call | No call |
| C | C | C | C | G | | 697 | | C 99% | C 99% | C 99% | C 49% | C 99% | C 48% |
| A | A | A | A | G | | 712 | | A 99% | A 99% | A 99% | A 49% | A 99% | A 47% |
| C | C | C | C | G | | 733 | | C 99% | C 99% | C 99% | C 49% | C 99% | C 48% |
| T | T | T | T | C | | 744 | | T 99% | T 99% | T 99% | T 49% | T 99% | T 48% |
| A | A | A | A | G | | 787 | | A 99% | A 99% | A 99% | A 47% | A 99% | A 46% |
| T | T | T | T | A | | 800 | | T 99% | T 99% | T 99% | T 48% | T 99% | T 47% |

TABLE 8

RHD
Expected results based on known genotype

| Polymorphic sites | | | | | | Exonic | CE (exon 1)-DD (exons 2-9)-CE | | DdCcee (exons 1-2)-ddCcee (exons 3-9)- | | | | |
|---|---|---|---|---|---|---|---|---|---|---|---|---|---|
| ce | cE | Ce | CE | D | Exon | position | (exon 10) | ddCcEe | DD (exon 10) | ddCcee | DDCcEe | ddccee | DDCCee |
| C | C | T | T | T | 2 | 150 | RHCE deleted, | C 50% | C 33.3% | C 50% | C 25% | C 100% | No calls |
| C | C | A | A | A | | 178 | no calls | C 50% | C 33.3% | C 50% | C 25% | C 100% | expected |
| A | A | G | G | G | | 201 | expected | A 50% | A 33.3% | A 50% | A 25% | A 100% | |
| A | A | G | G | G | | 203 | | A 50% | A 33.3% | A 50% | A 25% | A 100% | |
| C | C | T | T | T | | 307 | | C 50% | C 33.3% | C 50% | C 25% | C 100% | |
| A | A | A | A | T | 3 | 361 | | A 100% | A 100% | A 100% | A 50% | A 100% | A 50% |
| C | C | C | C | T | | 380 | | C 100% | C 100% | C 100% | C 50% | C 100% | C 50% |
| G | G | G | G | A | | 383 | | G 100% | G 100% | G 100% | G 50% | G 100% | G 50% |
| C | C | C | C | A | | 455 | | C 100% | C 100% | C 100% | C 50% | C 100% | C 50% |
| C | C | C | C | A | 4 | 505 | | C 100% | C 100% | C 100% | C 50% | C 100% | C 50% |
| G | G | G | G | T | | 509 | | G 100% | G 100% | G 100% | G 50% | G 100% | G 50% |
| T | T | T | T | A | | 514 | | T 100% | T 100% | T 100% | T 50% | T 100% | T 50% |
| A | A | A | A | T | | 544 | | A 100% | A 100% | A 100% | A 50% | A 100% | A 50% |
| A | A | A | A | G | | 577 | | A 100% | A 100% | A 100% | A 50% | A 100% | A 50% |
| T | T | T | T | A | | 594 | | T 100% | T 100% | T 100% | T 50% | T 100% | T 50% |
| G | G | G | G | C | | 602 | | G 100% | G 100% | G 100% | G 50% | G 100% | G 50% |
| T | T | T | T | G | 5 | 667 | | T 100% | T 100% | T 100% | T 50% | T 100% | T 50% |
| G | C | G | C | G | | 676 | | C 50% | No calls expected | No calls expected | C 25% | No calls expected | No calls expected |
| C | C | C | C | G | | 697 | | C 100% | C 100% | C 100% | C 50% | C 100% | C 50% |
| A | A | A | A | G | | 712 | | A 100% | A 100% | A 100% | A 50% | A 100% | A 50% |
| C | C | C | C | G | | 733 | | C 100% | C 100% | C 100% | C 50% | C 100% | C 50% |
| T | T | T | T | C | | 744 | | T 100% | T 100% | T 100% | T 50% | T 100% | T 50% |
| A | A | A | A | G | | 787 | | A 100% | A 100% | A 100% | A 50% | A 100% | A 50% |
| T | T | T | T | A | | 800 | | T 100% | T 100% | T 100% | T 50% | T 100% | T 50% |

TABLE 14

Observed genotypes against reference sequence RHD (SEQ NO: 25) using the combination of primers of mix A.

| | Mutation in reference | Genotypes | | | | | | |
|---|---|---|---|---|---|---|---|---|
| Exon | to coding region | ddccee | DDCCee | DdCcee | ddCCee | DDccEE | ddccee | D?ccEe |
| 1 | c.148 + 18A > C | 1.00 | 0.48 | 0.64 | 1.00 | 0.48 | 0.65 | 0.66 |
| 2 | c.150T > C | 1.00 | 0.00 | 0.35 | 0.00 | 0.57 | 0.75 | 0.70 |
| | c.178A > C | 1.00 | 0.00 | 0.35 | 0.00 | 0.56 | 0.73 | 0.69 |
| | c.201G > A | 1.00 | 0.00 | 0.32 | 0.00 | 0.54 | 0.72 | 0.68 |
| | c.203G > A | 1.00 | 0.00 | 0.32 | 0.00 | 0.53 | 0.72 | 0.67 |
| | c.307T > C | 1.00 | 0.00 | 0.32 | 0.00 | 0.54 | 0.73 | 0.68 |
| 3 | c.335 − 13C > T | 1.00 | 0.45 | 0.55 | 1.00 | 0.43 | 0.61 | 0.60 |
| | c.336 − 8T > A | 1.00 | 0.44 | 0.54 | 1.00 | 0.43 | 0.61 | 0.59 |
| | c.361T > A | 1.00 | 0.46 | 0.57 | 1.00 | 0.46 | 0.63 | 0.61 |
| | c.380T > C | 1.00 | 0.47 | 0.56 | 1.00 | 0.46 | 0.63 | 0.61 |
| | c.383A > G | 1.00 | 0.47 | 0.57 | 1.00 | 0.46 | 0.64 | 0.62 |
| | c.455A > C | 1.00 | 0.47 | 0.57 | 1.00 | 0.46 | 0.63 | 0.62 |
| 4 | c.487 − 48insT | 1.00 | 0.50 | 0.65 | 1.00 | 0.51 | 0.73 | 1.00 |
| | c.505A > C | 1.00 | 0.51 | 0.66 | 1.00 | 0.52 | 0.74 | 1.00 |
| | c.509T > G | 1.00 | 0.50 | 0.65 | 1.00 | 0.51 | 0.73 | 1.00 |
| | c.514A > T | 1.00 | 0.51 | 0.66 | 1.00 | 0.51 | 0.74 | 1.00 |
| | c.544T > A | 1.00 | 0.51 | 0.66 | 1.00 | 0.52 | 0.74 | 1.00 |
| | c.577G > A | 1.00 | 0.50 | 0.65 | 1.00 | 0.52 | 0.73 | 1.00 |
| | c.594A > T | 1.00 | 0.51 | 0.65 | 1.00 | 0.52 | 0.74 | 1.00 |
| | c.602C > G | 1.00 | 0.51 | 0.65 | 1.00 | 0.52 | 0.74 | 1.00 |
| 5 | c.667T > G | 1.00 | 0.50 | 0.67 | 1.00 | 0.49 | 1.00 | 1.00 |
| | c.676G > C | 0.00 | 0.00 | 0.00 | 0.00 | 0.49 | 0.00 | 0.65 |
| | c.697G > C | 1.00 | 0.50 | 0.67 | 1.00 | 0.49 | 0.65 | 1.00 |
| | c.712G > A | 1.00 | 0.50 | 0.67 | 1.00 | 0.49 | 0.65 | 1.00 |
| | c.733G > C | 1.00 | 0.50 | 0.67 | 1.00 | 0.49 | 0.65 | 1.00 |
| | c.744C > T | 1.00 | 0.50 | 0.67 | 1.00 | 0.49 | 0.65 | 1.00 |
| | c.787G > A | 1.00 | 0.49 | 0.67 | 1.00 | 0.49 | 0.65 | 1.00 |
| | c.800A > T | 1.00 | 0.50 | 0.67 | 1.00 | 0.49 | 0.65 | 1.00 |
| 6 | c.916G > A | 1.00 | 0.50 | 0.67 | 1.00 | 0.50 | 0.67 | 0.66 |
| | c.932A > G | 1.00 | 0.50 | 0.67 | 1.00 | 0.50 | 0.67 | 0.67 |
| | c.939 + 21C > T | 1.00 | 0.50 | 0.67 | 1.00 | 0.49 | 0.67 | 0.66 |
| | c.939 + 22C > G | 1.00 | 0.50 | 0.67 | 1.00 | 0.49 | 0.67 | 0.66 |
| | c.939 + 23T > C | 0.99 | 0.51 | 0.67 | 0.99 | 0.50 | 0.67 | 0.66 |
| | c.939 + 24C > T | 1.00 | 0.50 | 0.67 | 0.99 | 0.49 | 0.67 | 0.66 |

TABLE 14-continued

Observed genotypes against reference sequence RHD (SEQ NO: 25) using the combination of primers of mix A.

| Exon | Mutation in reference to coding region | ddccee | DDCCee | DdCcee | ddCCee | DDccEE | ddccee | D?ccEe |
|---|---|---|---|---|---|---|---|---|
| | | Genotypes | | | | | | |
| 7 | c.941G > T | 1.00 | 0.50 | 0.62 | 1.00 | 0.50 | 0.64 | 0.65 |
| | c.968C > A | 1.00 | 0.50 | 0.61 | 1.00 | 0.49 | 0.63 | 0.64 |
| | c.974G > T | 1.00 | 0.50 | 0.62 | 1.00 | 0.49 | 0.63 | 0.64 |
| | c.979A > G | 1.00 | 0.50 | 0.62 | 1.00 | 0.50 | 0.64 | 0.64 |
| | c.985G > C | 1.00 | 0.50 | 0.62 | 1.00 | 0.50 | 0.64 | 0.65 |
| | c.985G > A | 1.00 | 0.50 | 0.62 | 1.00 | 0.50 | 0.63 | 0.64 |
| | c.989A > C | 1.00 | 0.50 | 0.62 | 1.00 | 0.49 | 0.63 | 0.64 |
| | c.992A > T | 1.00 | 0.50 | 0.62 | 1.00 | 0.49 | 0.63 | 0.64 |
| | c.1025T > C | 1.00 | 0.50 | 0.62 | 1.00 | 0.50 | 0.64 | 0.65 |
| | c.1048G > C | 1.00 | 0.50 | 0.62 | 1.00 | 0.50 | 0.64 | 0.64 |
| | c.1053C > T | 1.00 | 0.50 | 0.62 | 1.00 | 0.50 | 0.63 | 0.64 |
| | c.1057G > T | 0.99 | 0.49 | 0.61 | 0.99 | 0.49 | 0.63 | 0.64 |
| | c.1059A > G | 0.99 | 0.50 | 0.62 | 1.00 | 0.50 | 0.63 | 0.64 |
| | c.1060G > A | 1.00 | 0.50 | 0.62 | 1.00 | 0.49 | 0.63 | 0.64 |
| 9 | c.1061C > A | 1.00 | 0.50 | 0.62 | 1.00 | 0.50 | 0.64 | 0.65 |
| | c.1170T > C | 1.00 | 0.51 | 0.65 | 1.00 | 0.46 | 0.36 | 0.67 |
| | c.1193A > T | 1.00 | 0.52 | 0.66 | 1.00 | 0.47 | 0.37 | 0.68 |
| | c.1227 + 62A > G | 1.00 | 0.50 | 0.65 | 1.00 | 0.46 | 0.36 | 0.67 |

TABLE 15

Expected genotypes based on genotype, reference sequence RHD (SEQ NO: 25) using the combination of primers of mix A.

| Exon | Mutation in reference to coding region | ddccee | DDCCee | DdCcee | ddCCee | DDccEE | ddccee | D?ccEe |
|---|---|---|---|---|---|---|---|---|
| | | Genotypes | | | | | | |
| 1 | c.148 + 18A > C | 1.00 | 0.50 | 0.67 | 1.00 | 0.50 | 0.67 | 0.67 |
| 2 | c.150T > C | 1.00 | 0.00 | 0.33 | 0.00 | 0.50 | 0.67 | 0.67 |
| | c.178A > C | 1.00 | 0.00 | 0.33 | 0.00 | 0.50 | 0.67 | 0.67 |
| | c.201G > A | 1.00 | 0.00 | 0.33 | 0.00 | 0.50 | 0.67 | 0.67 |
| | c.203G > A | 1.00 | 0.00 | 0.33 | 0.00 | 0.50 | 0.67 | 0.67 |
| | c.307T > C | 1.00 | 0.00 | 0.33 | 0.00 | 0.50 | 0.67 | 0.67 |
| 3 | c.336 − 13C > T | 1.00 | 0.50 | 0.67 | 1.00 | 0.50 | 0.67 | 0.67 |
| | c.336 − 8T > A | 1.00 | 0.50 | 0.67 | 1.00 | 0.50 | 0.67 | 0.67 |
| | c.361T > A | 1.00 | 0.50 | 0.67 | 1.00 | 0.50 | 0.67 | 0.67 |
| | c.380T > C | 1.00 | 0.50 | 0.67 | 1.00 | 0.50 | 0.67 | 0.67 |
| | c.383A > G | 1.00 | 0.50 | 0.67 | 1.00 | 0.50 | 0.67 | 0.67 |
| | c.455A > C | 1.00 | 0.50 | 0.67 | 1.00 | 0.50 | 0.67 | 0.67 |
| 4 | c.487 − 48insT | 1.00 | 0.50 | 0.67 | 1.00 | 0.50 | 0.67 | 0.67 |
| | c.505A > C | 1.00 | 0.50 | 0.67 | 1.00 | 0.50 | 0.67 | 1.00 |
| | c.509T > G | 1.00 | 0.50 | 0.67 | 1.00 | 0.50 | 0.67 | 1.00 |
| | c.514A > T | 1.00 | 0.50 | 0.67 | 1.00 | 0.50 | 0.67 | 1.00 |
| | c.544T > A | 1.00 | 0.50 | 0.67 | 1.00 | 0.50 | 0.67 | 1.00 |
| | c.577G > A | 1.00 | 0.50 | 0.67 | 1.00 | 0.50 | 0.67 | 1.00 |
| | c.594A > T | 1.00 | 0.50 | 0.67 | 1.00 | 0.50 | 0.67 | 1.00 |
| | c.602C > G | 1.00 | 0.50 | 0.67 | 1.00 | 0.50 | 0.67 | 1.00 |
| 5 | c.667T > G | 1.00 | 0.50 | 0.67 | 1.00 | 0.50 | 1.00 | 1.00 |
| | c.676G > C | 0.00 | 0.00 | 0.00 | 0.00 | 0.50 | 0.00 | 0.67 |
| | c.697G > C | 1.00 | 0.50 | 0.67 | 1.00 | 0.50 | 0.67 | 1.00 |
| | c.712G > A | 1.00 | 0.50 | 0.67 | 1.00 | 0.50 | 0.67 | 1.00 |
| | c.733G > C | 1.00 | 0.50 | 0.67 | 1.00 | 0.50 | 0.67 | 1.00 |
| | c.744C > T | 1.00 | 0.50 | 0.67 | 1.00 | 0.50 | 0.67 | 1.00 |
| | c.787G > A | 1.00 | 0.50 | 0.67 | 1.00 | 0.50 | 0.67 | 1.00 |
| | c.800A > T | 1.00 | 0.50 | 0.67 | 1.00 | 0.50 | 0.67 | 1.00 |
| 6 | c.916G > A | 1.00 | 0.50 | 0.67 | 1.00 | 0.50 | 0.67 | 0.67 |
| | c.932A > G | 1.00 | 0.50 | 0.67 | 1.00 | 0.50 | 0.67 | 0.67 |
| | c.939 + 21C > T | 1.00 | 0.50 | 0.67 | 1.00 | 0.50 | 0.67 | 0.67 |
| | c.939 + 22C > G | 1.00 | 0.50 | 0.67 | 1.00 | 0.50 | 0.67 | 0.67 |
| | c.939 + 23T > C | 1.00 | 0.50 | 0.67 | 1.00 | 0.50 | 0.67 | 0.67 |
| | c.939 + 24C > T | 1.00 | 0.50 | 0.67 | 1.00 | 0.50 | 0.67 | 0.67 |
| 7 | c.941G > T | 1.00 | 0.50 | 0.67 | 1.00 | 0.50 | 0.67 | 0.67 |
| | c.968C > A | 1.00 | 0.50 | 0.67 | 1.00 | 0.50 | 0.67 | 0.67 |
| | c.974G > T | 1.00 | 0.50 | 0.67 | 1.00 | 0.50 | 0.67 | 0.67 |
| | c.979A > G | 1.00 | 0.50 | 0.67 | 1.00 | 0.50 | 0.67 | 0.67 |
| | c.985G > C | 1.00 | 0.50 | 0.67 | 1.00 | 0.50 | 0.67 | 0.67 |
| | c.986G > A | 1.00 | 0.50 | 0.67 | 1.00 | 0.50 | 0.67 | 0.67 |
| | c.989A > C | 1.00 | 0.50 | 0.67 | 1.00 | 0.50 | 0.67 | 0.67 |
| | c.992A > T | 1.00 | 0.50 | 0.67 | 1.00 | 0.50 | 0.67 | 0.67 |

TABLE 15-continued

Expected genotypes based on genotype, reference sequence RHD (SEQ NO: 25) using the combination of primers of mix A.

| Exon | Mutation in reference to coding region | Genotypes ddccee | DDCCee | DdCcee | ddCCee | DDccEE | ddccee | D?ccEe |
|---|---|---|---|---|---|---|---|---|
| | c.1025T > C | 1.00 | 0.50 | 0.67 | 1.00 | 0.50 | 0.67 | 0.67 |
| | c.1048G > C | 1.00 | 0.50 | 0.67 | 1.00 | 0.50 | 0.67 | 0.67 |
| | c.1053C > T | 1.00 | 0.50 | 0.67 | 1.00 | 0.50 | 0.67 | 0.67 |
| | c.1057G > T | 1.00 | 0.50 | 0.67 | 1.00 | 0.50 | 0.67 | 0.67 |
| | c.1059A > G | 1.00 | 0.50 | 0.67 | 1.00 | 0.50 | 0.67 | 0.67 |
| | c.1060G > A | 1.00 | 0.50 | 0.67 | 1.00 | 0.50 | 0.67 | 0.67 |
| 9 | c.1061C > A | 1.00 | 0.50 | 0.67 | 1.00 | 0.50 | 0.67 | 0.67 |
| | c.1170T > C | 1.00 | 0.50 | 0.67 | 1.00 | 0.50 | 0.67 | 0.67 |
| | c.1193A > T | 1.00 | 0.50 | 0.67 | 1.00 | 0.50 | 0.67 | 0.67 |
| | c.1227 + 62A > G | 1.00 | 0.50 | 0.67 | 1.00 | 0.50 | 0.67 | 0.67 |

TABLE 16

Observed genotypes against reference sequence RHD (SEQ NO: 25) using the combination of primers of mix B.

| Exon | Mutation in reference to coding region | Genotypes ddccee | DDCCee | DdCcee | ddCCee | DDccEE | ddccee | D?ccEe |
|---|---|---|---|---|---|---|---|---|
| 1 | c.148 + 18A > C | 1 | 0.48 | 0.65 | 1 | 0.52 | 0.64 | 0.65 |
| 2 | c.150T > C | 1 | 0 | 0.33 | 0 | 0.53 | 0.68 | 0.71 |
| | c.178A > C | 1 | 0 | 0.33 | 0 | 0.53 | 0.69 | 0.71 |
| | c.201G > A | 1 | 0 | 0.33 | 0 | 0.53 | 0.68 | 0.7 |
| | c.203G > A | 1 | 0 | 0.32 | 0 | 0.53 | 0.68 | 0.7 |
| | c.307T > C | 1 | 0 | 0.33 | 0 | 0.53 | 0.68 | 0.7 |
| 3 | c.336 − 13C > T | 1 | 0.51 | 0.64 | 1 | 0.56 | 0.67 | 0.66 |
| | c.336 − 8T > A | 1 | 0.51 | 0.64 | 1 | 0.56 | 0.67 | 0.66 |
| | c.361T > A | 1 | 0.51 | 0.64 | 1 | 0.56 | 0.67 | 0.66 |
| | c.380T > C | 1 | 0.51 | 0.64 | 1 | 0.56 | 0.68 | 0.66 |
| | c.383A > G | 1 | 0.51 | 0.64 | 1 | 0.56 | 0.68 | 0.66 |
| | c.455A > C | 1 | 0.51 | 0.65 | 1 | 0.56 | 0.67 | 0.66 |
| 4 | c.505A > C | 1 | 0.5 | 0.65 | 1 | 0.49 | 0.71 | 1 |
| | c.509T > G | 1 | 0.5 | 0.65 | 1 | 0.49 | 0.71 | 1 |
| | c.514A > T | 1 | 0.5 | 0.65 | 1 | 0.49 | 0.71 | 1 |
| | c.544T > A | 1 | 0.5 | 0.65 | 1 | 0.49 | 0.71 | 1 |
| | c.577G > A | 1 | 0.5 | 0.65 | 1 | 0.49 | 0.71 | 1 |
| | c.594A > T | 1 | 0.51 | 0.65 | 1 | 0.49 | 0.72 | 1 |
| | c.602C > G | 1 | 0.5 | 0.66 | 1 | 0.49 | 0.71 | 1 |
| 5 | c.667T > G | 1 | 0.55 | 0.76 | 1 | 0.68 | 1 | 1 |
| | c.676G > C | 0 | 0 | 0 | 0 | 0.67 | 0 | 0.66 |
| | c.697G > C | 1 | 0.55 | 0.76 | 1 | 0.67 | 0.75 | 1 |
| | c.712G > A | 1 | 0.55 | 0.76 | 1 | 0.67 | 0.75 | 1 |
| | c.733G > C | 1 | 0.55 | 0.76 | 1 | 0.68 | 0.76 | 1 |
| | c.744C > T | 1 | 0.55 | 0.76 | 1 | 0.68 | 0.75 | 1 |
| | c.787G > A | 1 | 0.51 | 0.73 | 1 | 0.65 | 0.72 | 1 |
| | c.800A > T | 1 | 0.54 | 0.76 | 1 | 0.68 | 0.75 | 1 |
| 6 | c.916G > A | 1 | 0.52 | 0.64 | 1 | 0.5 | 0.64 | 0.67 |
| | c.932A > G | 1 | 0.51 | 0.64 | 1 | 0.5 | 0.64 | 0.67 |
| | c.939 + 21C > T | 0.99 | 0.5 | 0.63 | 1 | 0.49 | 0.63 | 0.66 |
| | c.939 + 22C > G | 0.99 | 0.49 | 0.62 | 1 | 0.48 | 0.63 | 0.65 |
| | c.939 + 23T > C | 0.97 | 0.5 | 0.62 | 0.98 | 0.49 | 0.63 | 0.66 |
| | c.939 + 24C > T | 0.99 | 0.49 | 0.62 | 0.99 | 0.48 | 0.62 | 0.65 |
| 7 | c.941G > T | 1 | 0.48 | 0.63 | 1 | 0.49 | 0.62 | 0.66 |
| | c.968C > A | 1 | 0.48 | 0.63 | 1 | 0.49 | 0.62 | 0.66 |
| | c.974G > T | 1 | 0.48 | 0.63 | 1 | 0.48 | 0.62 | 0.66 |
| | c.979A > G | 1 | 0.48 | 0.63 | 1 | 0.49 | 0.62 | 0.66 |
| | c.985G > C | 1 | 0.48 | 0.63 | 1 | 0.49 | 0.62 | 0.66 |
| | c.986G > A | 1 | 0.48 | 0.63 | 1 | 0.48 | 0.62 | 0.66 |
| | c.989A > C | 1 | 0.48 | 0.63 | 1 | 0.49 | 0.62 | 0.66 |
| | c.992A > T | 1 | 0.48 | 0.63 | 1 | 0.48 | 0.62 | 0.66 |
| | c.1025T > C | 1 | 0.48 | 0.63 | 1 | 0.49 | 0.62 | 0.66 |
| | c.1048G > C | 1 | 0.48 | 0.63 | 1 | 0.48 | 0.62 | 0.66 |
| | c.1053C > T | 1 | 0.48 | 0.63 | 1 | 0.49 | 0.62 | 0.66 |
| | c.1057G > T | 0.99 | 0.48 | 0.62 | 1 | 0.48 | 0.62 | 0.65 |
| | c.1059A > G | 1 | 0.48 | 0.63 | 1 | 0.49 | 0.62 | 0.66 |
| | c.1060G > A | 1 | 0.48 | 0.62 | 1 | 0.48 | 0.61 | 0.65 |

TABLE 16-continued

Observed genotypes against reference sequence RHD (SEQ NO: 25) using the combination of primers of mix B.

| Exon | Mutation in reference to coding region | Genotypes ddccee | DDCCee | DdCcee | ddCCee | DDccEE | ddccee | D?ccEe |
|---|---|---|---|---|---|---|---|---|
| 9 | c.1061C > A | 1 | 0.48 | 0.63 | 1 | 0.48 | 0.62 | 0.65 |
| | c.1154 − 81_1154 − 80insAC | 0.98 | 0.50 | 0.64 | 0.98 | 0.49 | 0.34 | 0.67 |
| | c.1154 − 67C > T | 1 | 0.51 | 0.66 | 1 | 0.5 | 0.35 | 0.68 |
| | c.1170T > C | 1 | 0.51 | 0.65 | 1 | 0.5 | 0.35 | 0.67 |
| | c.1193A > T | 1 | 0.51 | 0.66 | 1 | 0.51 | 0.35 | 0.68 |

TABLE 17

Expected genotypes based on genotypes, reference sequence RHD (SEQ NO: 25) using the combination of primers of mix B.

| Exon | Mutation in reference to coding region | Genotypes ddccee | DDCCee | DdCcee | ddCCee | DDccEE | ddccee | D?ccEe |
|---|---|---|---|---|---|---|---|---|
| 1 | c.148 + 18A > C | 1 | 0.5 | 0.67 | 1 | 0.5 | 0.67 | 0.67 |
| 2 | c.150T > C | 1 | 0 | 0.33 | 0 | 0.5 | 0.67 | 0.67 |
| | c.178A > C | 1 | 0 | 0.33 | 0 | 0.5 | 0.67 | 0.67 |
| | c.201G > A | 1 | 0 | 0.33 | 0 | 0.5 | 0.67 | 0.67 |
| | c.203G > A | 1 | 0 | 0.33 | 0 | 0.5 | 0.67 | 0.67 |
| | c.307T > C | 1 | 0 | 0.33 | 0 | 0.5 | 0.67 | 0.67 |
| 3 | c.336 − 13C > T | 1 | 0.5 | 0.67 | 1 | 0.5 | 0.67 | 0.67 |
| | c.336 − 8T > A | 1 | 0.5 | 0.67 | 1 | 0.5 | 0.67 | 0.67 |
| | c.361T > A | 1 | 0.5 | 0.67 | 1 | 0.5 | 0.67 | 0.67 |
| | c.380T > C | 1 | 0.5 | 0.67 | 1 | 0.5 | 0.67 | 0.67 |
| | c.383A > G | 1 | 0.5 | 0.67 | 1 | 0.5 | 0.67 | 0.67 |
| | c.455A > C | 1 | 0.5 | 0.67 | 1 | 0.5 | 0.67 | 0.67 |
| 4 | c.505A > C | 1 | 0.5 | 0.67 | 1 | 0.5 | 0.67 | 1.00 |
| | c.509T > G | 1 | 0.5 | 0.67 | 1 | 0.5 | 0.67 | 1.00 |
| | c.514A > T | 1 | 0.5 | 0.67 | 1 | 0.5 | 0.67 | 1.00 |
| | c.544T > A | 1 | 0.5 | 0.67 | 1 | 0.5 | 0.67 | 1.00 |
| | c.577G > A | 1 | 0.5 | 0.67 | 1 | 0.5 | 0.67 | 1.00 |
| | c.594A > T | 1 | 0.5 | 0.67 | 1 | 0.5 | 0.67 | 1.00 |
| | c.602C > G | 1 | 0.5 | 0.67 | 1 | 0.5 | 0.67 | 1.00 |
| 5 | c.667T > G | 1 | 0.5 | 0.67 | 1 | 0.5 | 1 | 1.00 |
| | c.676G > C | 0 | 0 | 0 | 0 | 0.5 | 0 | 0.67 |
| | c.697G > C | 1 | 0.5 | 0.67 | 1 | 0.5 | 0.67 | 1.00 |
| | c.712G > A | 1 | 0.5 | 0.67 | 1 | 0.5 | 0.67 | 1.00 |
| | c.733G > C | 1 | 0.5 | 0.67 | 1 | 0.5 | 0.67 | 1.00 |
| | c.744C > T | 1 | 0.5 | 0.67 | 1 | 0.5 | 0.67 | 1.00 |
| | c.787G > A | 1 | 0.5 | 0.67 | 1 | 0.5 | 0.67 | 1.00 |
| | c.800A > T | 1 | 0.5 | 0.67 | 1 | 0.5 | 0.67 | 1.00 |
| 6 | c.916G > A | 1 | 0.5 | 0.67 | 1 | 0.5 | 0.67 | 0.67 |
| | c.932A > G | 1 | 0.5 | 0.67 | 1 | 0.5 | 0.67 | 0.67 |
| | c.939 + 21C > T | 1 | 0.5 | 0.67 | 1 | 0.5 | 0.67 | 0.67 |
| | c.939 + 22C > G | 1 | 0.5 | 0.67 | 1 | 0.5 | 0.67 | 0.67 |
| | c.939 + 23T > C | 1 | 0.5 | 0.67 | 1 | 0.5 | 0.67 | 0.67 |
| | c.939 + 24C > T | 1 | 0.5 | 0.67 | 1 | 0.5 | 0.67 | 0.67 |
| 7 | c.941G > T | 1 | 0.5 | 0.67 | 1 | 0.5 | 0.67 | 0.67 |
| | c.968C > A | 1 | 0.5 | 0.67 | 1 | 0.5 | 0.67 | 0.67 |
| | c.974G > T | 1 | 0.5 | 0.67 | 1 | 0.5 | 0.67 | 0.67 |
| | c.979A > G | 1 | 0.5 | 0.67 | 1 | 0.5 | 0.67 | 0.67 |
| | c.985G > C | 1 | 0.5 | 0.67 | 1 | 0.5 | 0.67 | 0.67 |
| | c.986G > A | 1 | 0.5 | 0.67 | 1 | 0.5 | 0.67 | 0.67 |
| | c.989A > C | 1 | 0.5 | 0.67 | 1 | 0.5 | 0.67 | 0.67 |
| | c.992A > T | 1 | 0.5 | 0.67 | 1 | 0.5 | 0.67 | 0.67 |
| | c.1025T > C | 1 | 0.5 | 0.67 | 1 | 0.5 | 0.67 | 0.67 |
| | c.1048G > C | 1 | 0.5 | 0.67 | 1 | 0.5 | 0.67 | 0.67 |
| | c.1053C > T | 1 | 0.5 | 0.67 | 1 | 0.5 | 0.67 | 0.67 |
| | c.1057G > T | 1 | 0.5 | 0.67 | 1 | 0.5 | 0.67 | 0.67 |
| | c.1059A > G | 1 | 0.5 | 0.67 | 1 | 0.5 | 0.67 | 0.67 |
| | c.1060G > A | 1 | 0.5 | 0.67 | 1 | 0.5 | 0.67 | 0.67 |
| 9 | c.1061C > A | 1 | 0.5 | 0.67 | 1 | 0.5 | 0.67 | 0.67 |
| | c.1154 − 81_1154 − 80insAC | 1 | 0.5 | 0.67 | 1 | 0.5 | 0.67 | 0.67 |
| | c.1154 − 67C > T | 1 | 0.5 | 0.67 | 1 | 0.5 | 0.67 | 0.67 |
| | c.1170T > C | 1 | 0.5 | 0.67 | 1 | 0.5 | 0.67 | 0.67 |
| | c.1193A > T | 1 | 0.5 | 0.67 | 1 | 0.5 | 0.67 | 0.67 |

TABLE 18

Observed genotypes against reference sequence RHCE (SEQ NO: 26) using the combination of primers of mix A.

| Exon | Mutation in reference to coding region | Genotypes ddccee | DDCCee | DdCcee | ddCCee | DDccEE | ddccee | D?ccEe |
|---|---|---|---|---|---|---|---|---|
| 1 | c.148 + 18C > A | 0.00 | 0.53 | 0.36 | 0.00 | 0.52 | 0.35 | 0.34 |
| 2 | c.150C > T | 0.00 | 1.00 | 0.67 | 1.00 | 0.45 | 0.27 | 0.32 |
| | c.178C > A | 0.00 | 1.00 | 0.67 | 1.00 | 0.45 | 0.28 | 0.32 |
| | c.201A > G | 0.00 | 1.00 | 0.68 | 1.00 | 0.46 | 0.28 | 0.32 |
| | c.203A > G | 0.00 | 1.00 | 0.68 | 1.00 | 0.46 | 0.28 | 0.32 |
| | c.307C > T | 0.00 | 1.00 | 0.68 | 1.00 | 0.46 | 0.27 | 0.32 |
| 3 | c.336 − 13T > C | 0.00 | 0.54 | 0.44 | 0.00 | 0.55 | 0.37 | 0.39 |
| | c.336 − 8A > T | 0.00 | 0.53 | 0.44 | 0.00 | 0.55 | 0.37 | 0.39 |
| | c.361A > T | 0.00 | 0.53 | 0.44 | 0.00 | 0.54 | 0.37 | 0.39 |
| | c.380C > T | 0.00 | 0.53 | 0.43 | 0.00 | 0.54 | 0.36 | 0.39 |
| | c.383G > A | 0.00 | 0.53 | 0.43 | 0.00 | 0.54 | 0.36 | 0.38 |
| | c.455C > A | 0.00 | 0.53 | 0.43 | 0.00 | 0.54 | 0.36 | 0.38 |
| 4 | c.487 − 48delT | 0.00 | 0.49 | 0.34 | 0.00 | 0.49 | 0.27 | 0.00 |
| | c.505C > A | 0.00 | 0.49 | 0.34 | 0.00 | 0.48 | 0.25 | 0.00 |
| | c.509G > T | 0.00 | 0.50 | 0.35 | 0.00 | 0.49 | 0.27 | 0.00 |
| | c.514T > A | 0.00 | 0.49 | 0.34 | 0.00 | 0.48 | 0.26 | 0.00 |
| | c.544A > T | 0.00 | 0.49 | 0.35 | 0.00 | 0.48 | 0.26 | 0.00 |
| | c.577A > G | 0.00 | 0.50 | 0.35 | 0.00 | 0.48 | 0.26 | 0.00 |
| | c.594T > A | 0.00 | 0.48 | 0.34 | 0.00 | 0.47 | 0.23 | 0.00 |
| | c.602G > C | 0.00 | 0.49 | 0.34 | 0.00 | 0.48 | 0.24 | 0.00 |
| 5 | c.667G > T | 0.00 | 0.50 | 0.33 | 0.00 | 0.51 | 0.00 | 0.00 |
| | c.676G > C | 0.00 | 0.00 | 0.00 | 0.00 | 0.49 | 0.00 | 0.65 |
| | c.697C > G | 0.00 | 0.50 | 0.33 | 0.00 | 0.51 | 0.35 | 0.00 |
| | c.712A > G | 0.00 | 0.50 | 0.33 | 0.00 | 0.51 | 0.35 | 0.00 |
| | c.733C > G | 0.00 | 0.50 | 0.33 | 0.00 | 0.51 | 0.35 | 0.00 |
| | c.744T > C | 0.00 | 0.50 | 0.33 | 0.00 | 0.51 | 0.35 | 0.00 |
| | c.787A > G | 0.00 | 0.52 | 0.34 | 0.00 | 0.52 | 0.36 | 0.00 |
| | c.800T > A | 0.00 | 0.51 | 0.33 | 0.00 | 0.51 | 0.35 | 0.00 |
| 6 | c.916A > G | 0.00 | 0.50 | 0.33 | 0.00 | 0.51 | 0.33 | 0.34 |
| | c.932G > A | 0.00 | 0.50 | 0.33 | 0.00 | 0.51 | 0.33 | 0.34 |
| | c.939 + 21T > C | 0.00 | 0.49 | 0.33 | 0.00 | 0.50 | 0.33 | 0.33 |
| | c.939 + 22G > C | 0.00 | 0.49 | 0.33 | 0.00 | 0.50 | 0.33 | 0.33 |
| | c.939 + 23C > T | 0.00 | 0.48 | 0.32 | 0.00 | 0.50 | 0.32 | 0.33 |
| | c.939 + 24T > C | 0.00 | 0.50 | 0.33 | 0.00 | 0.51 | 0.33 | 0.34 |
| 7 | c.941T > G | 0.00 | 0.50 | 0.38 | 0.00 | 0.50 | 0.36 | 0.35 |
| | c.968A > C | 0.00 | 0.50 | 0.38 | 0.00 | 0.50 | 0.36 | 0.36 |
| | c.974T > G | 0.00 | 0.50 | 0.38 | 0.00 | 0.50 | 0.37 | 0.36 |
| | c.979G > A | 0.00 | 0.50 | 0.38 | 0.00 | 0.50 | 0.36 | 0.36 |
| | c.985C > G | 0.00 | 0.50 | 0.38 | 0.00 | 0.50 | 0.36 | 0.36 |
| | c.986A > G | 0.00 | 0.50 | 0.38 | 0.00 | 0.50 | 0.36 | 0.36 |
| | c.989C > A | 0.00 | 0.50 | 0.38 | 0.00 | 0.50 | 0.36 | 0.36 |
| | c.992T > A | 0.00 | 0.50 | 0.38 | 0.00 | 0.50 | 0.36 | 0.36 |
| | c.1025C > T | 0.00 | 0.50 | 0.38 | 0.00 | 0.50 | 0.36 | 0.35 |
| | c.1048C > G | 0.00 | 0.50 | 0.38 | 0.00 | 0.50 | 0.36 | 0.36 |
| | c.1053T > C | 0.00 | 0.50 | 0.38 | 0.00 | 0.50 | 0.36 | 0.36 |
| | c.1057T > G | 0.00 | 0.50 | 0.38 | 0.00 | 0.50 | 0.36 | 0.35 |
| | c.1059G > A | 0.00 | 0.49 | 0.37 | 0.00 | 0.49 | 0.36 | 0.35 |
| | c.1060A > G | 0.00 | 0.51 | 0.38 | 0.00 | 0.51 | 0.37 | 0.36 |
| 9 | c.1061A > C | 0.00 | 0.50 | 0.38 | 0.00 | 0.51 | 0.37 | 0.36 |
| | c.1170C > T | 0.00 | 0.49 | 0.35 | 0.00 | 0.54 | 0.64 | 0.33 |
| | c.1193T > A | 0.00 | 0.49 | 0.35 | 0.00 | 0.54 | 0.64 | 0.33 |
| | c.1227 + 62G > A | 0.00 | 0.49 | 0.35 | 0.00 | 0.54 | 0.64 | 0.33 |

TABLE 19

Expected genotypes based on genotype, reference sequence RHCE (SEQ NO: 26) using the combination of primers of mix A.

| Exon | Mutation in reference to coding region | Genotypes ddccee | DDCCee | DdCcee | ddCCee | DDccEE | ddccee | D?ccEe |
|---|---|---|---|---|---|---|---|---|
| 1 | c.148 + 18C > A | 0.00 | 0.50 | 0.33 | 0.00 | 0.50 | 0.33 | 0.33 |
| 2 | c.150C > T | 0.00 | 1.00 | 0.67 | 1.00 | 0.50 | 0.33 | 0.33 |
| | c.178C > A | 0.00 | 1.00 | 0.67 | 1.00 | 0.50 | 0.33 | 0.33 |
| | c.201A > G | 0.00 | 1.00 | 0.67 | 1.00 | 0.50 | 0.33 | 0.33 |
| | c.203A > G | 0.00 | 1.00 | 0.67 | 1.00 | 0.50 | 0.33 | 0.33 |
| | c.307C > T | 0.00 | 1.00 | 0.67 | 1.00 | 0.50 | 0.33 | 0.33 |
| 3 | c.336 − 13T > C | 0.00 | 0.50 | 0.33 | 0.00 | 0.50 | 0.33 | 0.33 |
| | c.336 − 8A > T | 0.00 | 0.50 | 0.33 | 0.00 | 0.50 | 0.33 | 0.33 |

TABLE 19-continued

Expected genotypes based on genotype, reference sequence RHCE (SEQ NO: 26) using the combination of primers of mix A.

| Exon | Mutation in reference to coding region | Genotypes ddccee | DDCCee | DdCcee | ddCCee | DDccEE | ddccee | D?ccEe |
|---|---|---|---|---|---|---|---|---|
| | c.361A > T | 0.00 | 0.50 | 0.33 | 0.00 | 0.50 | 0.33 | 0.33 |
| | c.380C > T | 0.00 | 0.50 | 0.33 | 0.00 | 0.50 | 0.33 | 0.33 |
| | c.383G > A | 0.00 | 0.50 | 0.33 | 0.00 | 0.50 | 0.33 | 0.33 |
| | c.455C > A | 0.00 | 0.50 | 0.33 | 0.00 | 0.50 | 0.33 | 0.33 |
| 4 | c.487 − 48delT | 0.00 | 0.50 | 0.33 | 0.00 | 0.50 | 0.33 | 0.33 |
| | c.505C > A | 0.00 | 0.50 | 0.33 | 0.00 | 0.50 | 0.33 | 0.00 |
| | c.509G > T | 0.00 | 0.50 | 0.33 | 0.00 | 0.50 | 0.33 | 0.00 |
| | c.514T > A | 0.00 | 0.50 | 0.33 | 0.00 | 0.50 | 0.33 | 0.00 |
| | c.544A > T | 0.00 | 0.50 | 0.33 | 0.00 | 0.50 | 0.33 | 0.00 |
| | c.577A > G | 0.00 | 0.50 | 0.33 | 0.00 | 0.50 | 0.33 | 0.00 |
| | c.594T > A | 0.00 | 0.50 | 0.33 | 0.00 | 0.50 | 0.33 | 0.00 |
| | c.602G > C | 0.00 | 0.50 | 0.33 | 0.00 | 0.50 | 0.33 | 0.00 |
| 5 | c.667G > T | 0.00 | 0.50 | 0.33 | 0.00 | 0.50 | 0.00 | 0.00 |
| | c.676G > C | 0.00 | 0.00 | 0.00 | 0.00 | 0.50 | 0.00 | 0.67 |
| | c.697C > G | 0.00 | 0.50 | 0.33 | 0.00 | 0.50 | 0.33 | 0.00 |
| | c.712A > G | 0.00 | 0.50 | 0.33 | 0.00 | 0.50 | 0.33 | 0.00 |
| | c.733C > G | 0.00 | 0.50 | 0.33 | 0.00 | 0.50 | 0.33 | 0.00 |
| | c.744T > C | 0.00 | 0.50 | 0.33 | 0.00 | 0.50 | 0.33 | 0.00 |
| | c.787A > G | 0.00 | 0.50 | 0.33 | 0.00 | 0.50 | 0.33 | 0.00 |
| | c.800T > A | 0.00 | 0.50 | 0.33 | 0.00 | 0.50 | 0.33 | 0.00 |
| 6 | c.916A > G | 0.00 | 0.50 | 0.33 | 0.00 | 0.50 | 0.33 | 0.33 |
| | c.932G > A | 0.00 | 0.50 | 0.33 | 0.00 | 0.50 | 0.33 | 0.33 |
| | c.939 + 21T > C | 0.00 | 0.50 | 0.33 | 0.00 | 0.50 | 0.33 | 0.33 |
| | c.939 + 22G > C | 0.00 | 0.50 | 0.33 | 0.00 | 0.50 | 0.33 | 0.33 |
| | c.939 + 23C > T | 0.00 | 0.50 | 0.33 | 0.00 | 0.50 | 0.33 | 0.33 |
| | c.939 + 24T > C | 0.00 | 0.50 | 0.33 | 0.00 | 0.50 | 0.33 | 0.33 |
| 7 | c.941T > G | 0.00 | 0.50 | 0.33 | 0.00 | 0.50 | 0.33 | 0.33 |
| | c.968A > C | 0.00 | 0.50 | 0.33 | 0.00 | 0.50 | 0.33 | 0.33 |
| | c.974T > G | 0.00 | 0.50 | 0.33 | 0.00 | 0.50 | 0.33 | 0.33 |
| | c.979G > A | 0.00 | 0.50 | 0.33 | 0.00 | 0.50 | 0.33 | 0.33 |
| | c.985C > G | 0.00 | 0.50 | 0.33 | 0.00 | 0.50 | 0.33 | 0.33 |
| | c.986A > G | 0.00 | 0.50 | 0.33 | 0.00 | 0.50 | 0.33 | 0.33 |
| | c.989C > A | 0.00 | 0.50 | 0.33 | 0.00 | 0.50 | 0.33 | 0.33 |
| | c.992T > A | 0.00 | 0.50 | 0.33 | 0.00 | 0.50 | 0.33 | 0.33 |
| | c.1025C > T | 0.00 | 0.50 | 0.33 | 0.00 | 0.50 | 0.33 | 0.33 |
| | c.1048C > G | 0.00 | 0.50 | 0.33 | 0.00 | 0.50 | 0.33 | 0.33 |
| | c.1053T > C | 0.00 | 0.50 | 0.33 | 0.00 | 0.50 | 0.33 | 0.33 |
| | c.1057T > G | 0.00 | 0.50 | 0.33 | 0.00 | 0.50 | 0.33 | 0.33 |
| | c.1059G > A | 0.00 | 0.50 | 0.33 | 0.00 | 0.50 | 0.33 | 0.33 |
| | c.1060A > G | 0.00 | 0.50 | 0.33 | 0.00 | 0.50 | 0.33 | 0.33 |
| 9 | c.1061A > C | 0.00 | 0.50 | 0.33 | 0.00 | 0.50 | 0.33 | 0.33 |
| | c.1170C > T | 0.00 | 0.50 | 0.33 | 0.00 | 0.50 | 0.67 | 0.33 |
| | c.1193T > A | 0.00 | 0.50 | 0.33 | 0.00 | 0.50 | 0.67 | 0.33 |
| | c.1227 + 62G > A | 0.00 | 0.50 | 0.33 | 0.00 | 0.50 | 0.67 | 0.33 |

TABLE 20

Observed genotypes against reference sequence RHCE (SEQ NO: 26) using the combination of primers of mix B.

| Exon | Mutation in reference to coding region | Genotypes ddccee | DDCCee | DdCcee | ddCCee | DDccEE | ddccee | D?ccEe |
|---|---|---|---|---|---|---|---|---|
| 1 | c.148 + 18C > A | 0.00 | 0.52 | 0.34 | 0.00 | 0.48 | 0.36 | 0.35 |
| 2 | c.150C > T | 0.00 | 1.00 | 0.67 | 1.00 | 0.47 | 0.32 | 0.29 |
| | c.178C > A | 0.00 | 1.00 | 0.67 | 1.00 | 0.47 | 0.31 | 0.29 |
| | c.201A > G | 0.00 | 1.00 | 0.67 | 1.00 | 0.47 | 0.32 | 0.30 |
| | c.203A > G | 0.00 | 1.00 | 0.68 | 1.00 | 0.47 | 0.32 | 0.30 |
| | c.307C > T | 0.00 | 1.00 | 0.67 | 1.00 | 0.47 | 0.32 | 0.30 |
| 3 | c.336 − 13T > C | 0.00 | 0.50 | 0.36 | 0.00 | 0.45 | 0.33 | 0.35 |
| | c.336 − 8A > T | 0.00 | 0.50 | 0.36 | 0.00 | 0.45 | 0.33 | 0.34 |
| | c.361A > T | 0.00 | 0.50 | 0.36 | 0.00 | 0.44 | 0.33 | 0.35 |
| | c.380C > T | 0.00 | 0.50 | 0.36 | 0.00 | 0.44 | 0.33 | 0.34 |
| | c.383G > A | 0.00 | 0.50 | 0.36 | 0.00 | 0.44 | 0.32 | 0.34 |
| | c.455C > A | 0.00 | 0.50 | 0.36 | 0.00 | 0.44 | 0.33 | 0.34 |
| 4 | c.505C > A | 0.00 | 0.50 | 0.35 | 0.00 | 0.51 | 0.28 | 0.00 |
| | c.509G > T | 0.00 | 0.50 | 0.35 | 0.00 | 0.51 | 0.29 | 0.00 |
| | c.514T > A | 0.00 | 0.50 | 0.35 | 0.00 | 0.51 | 0.29 | 0.00 |
| | c.544A > T | 0.00 | 0.50 | 0.35 | 0.00 | 0.51 | 0.29 | 0.00 |

TABLE 20-continued

Observed genotypes against reference sequence RHCE (SEQ NO: 26) using the combination of primers of mix B.

| Exon | Mutation in reference to coding region | Genotypes | | | | | | |
|---|---|---|---|---|---|---|---|---|
| | | ddccee | DDCCee | DdCcee | ddCCee | DDccEE | ddccee | D?ccEe |
| | c.577A > G | 0.00 | 0.50 | 0.35 | 0.00 | 0.51 | 0.29 | 0.00 |
| | c.594T > A | 0.00 | 0.49 | 0.35 | 0.00 | 0.51 | 0.28 | 0.00 |
| | c.602G > C | 0.00 | 0.49 | 0.34 | 0.00 | 0.51 | 0.29 | 0.00 |
| 5 | c.667G > T | 0.00 | 0.45 | 0.24 | 0.00 | 0.32 | 0.00 | 0.00 |
| | c.675G > C | 0.00 | 0.00 | 0.00 | 0.00 | 0.67 | 0.00 | 0.66 |
| | c.697C > G | 0.00 | 0.45 | 0.24 | 0.00 | 0.33 | 0.25 | 0.00 |
| | c.712A > G | 0.00 | 0.45 | 0.24 | 0.00 | 0.33 | 0.25 | 0.00 |
| | c.733C > G | 0.00 | 0.45 | 0.24 | 0.00 | 0.32 | 0.24 | 0.00 |
| | c.744T > C | 0.00 | 0.45 | 0.24 | 0.00 | 0.32 | 0.25 | 0.00 |
| | c.787A > G | 0.00 | 0.49 | 0.27 | 0.00 | 0.35 | 0.28 | 0.00 |
| | c.800T > A | 0.00 | 0.46 | 0.24 | 0.00 | 0.32 | 0.24 | 0.00 |
| 6 | c.916A > G | 0.00 | 0.48 | 0.36 | 0.00 | 0.50 | 0.36 | 0.33 |
| | c.932G > A | 0.00 | 0.49 | 0.36 | 0.00 | 0.50 | 0.36 | 0.33 |
| | c.939 + 21T > C | 0.00 | 0.46 | 0.34 | 0.00 | 0.48 | 0.34 | 0.31 |
| | c.939 + 22G > C | 0.00 | 0.47 | 0.35 | 0.00 | 0.49 | 0.35 | 0.32 |
| | c.939 + 23C > T | 0.00 | 0.46 | 0.34 | 0.00 | 0.47 | 0.34 | 0.31 |
| | c.939 + 24T > C | 0.00 | 0.47 | 0.35 | 0.00 | 0.49 | 0.35 | 0.32 |
| 7 | c.941T > G | 0.00 | 0.52 | 0.37 | 0.00 | 0.51 | 0.38 | 0.34 |
| | c.968A > C | 0.00 | 0.52 | 0.37 | 0.00 | 0.51 | 0.38 | 0.34 |
| | c.974T > G | 0.00 | 0.52 | 0.37 | 0.00 | 0.52 | 0.38 | 0.34 |
| | c.979G > A | 0.00 | 0.52 | 0.37 | 0.00 | 0.51 | 0.38 | 0.34 |
| | c.985C > G | 0.00 | 0.52 | 0.37 | 0.00 | 0.51 | 0.38 | 0.34 |
| | c.986A > G | 0.00 | 0.52 | 0.37 | 0.00 | 0.52 | 0.38 | 0.34 |
| | c.989C > A | 0.00 | 0.52 | 0.37 | 0.00 | 0.51 | 0.38 | 0.34 |
| | c.992T > A | 0.00 | 0.52 | 0.37 | 0.00 | 0.52 | 0.38 | 0.34 |
| | c.1025C > T | 0.00 | 0.52 | 0.37 | 0.00 | 0.51 | 0.38 | 0.34 |
| | c.1048C > G | 0.00 | 0.52 | 0.37 | 0.00 | 0.52 | 0.38 | 0.34 |
| | c.1053T > C | 0.00 | 0.52 | 0.37 | 0.00 | 0.51 | 0.38 | 0.34 |
| | c.1057T > G | 0.00 | 0.52 | 0.37 | 0.00 | 0.51 | 0.38 | 0.34 |
| | c.1059G > A | 0.00 | 0.51 | 0.37 | 0.00 | 0.51 | 0.37 | 0.34 |
| | c.1060A > G | 0.00 | 0.52 | 0.37 | 0.00 | 0.51 | 0.38 | 0.35 |
| 9 | c.1061A > C | 0.00 | 0.52 | 0.37 | 0.00 | 0.51 | 0.38 | 0.34 |
| | c.1154 − 82_1154 − 81delAC | 0.00 | 0.49 | 0.34 | 0.00 | 0.50 | 0.65 | 0.32 |
| | c.1154 − 67T > C | 0.00 | 0.49 | 0.34 | 0.00 | 0.50 | 0.65 | 0.32 |
| | c.1170C > T | 0.00 | 0.49 | 0.35 | 0.00 | 0.50 | 0.65 | 0.33 |
| | c.1193T > A | 0.00 | 0.49 | 0.34 | 0.00 | 0.49 | 0.65 | 0.32 |

TABLE 21

Expected genotypes based on genotypes, reference sequence RHCE (SEQ NO: 26) using the combination of primers of mix B.

| Exon | Mutation in reference to coding region | Genotypes | | | | | | |
|---|---|---|---|---|---|---|---|---|
| | | ddccee | DDCCee | DdCcee | ddCCee | DDccEE | ddccee | D?ccEe |
| 1 | c.148 + 18C > A | 0.00 | 0.50 | 0.33 | 0.00 | 0.50 | 0.33 | 0.33 |
| 2 | c.150C > T | 0.00 | 1.00 | 0.67 | 1.00 | 0.50 | 0.33 | 0.33 |
| | c.178C > A | 0.00 | 1.00 | 0.67 | 1.00 | 0.50 | 0.33 | 0.33 |
| | c.201A > G | 0.00 | 1.00 | 0.67 | 1.00 | 0.50 | 0.33 | 0.33 |
| | c.203A > G | 0.00 | 1.00 | 0.67 | 1.00 | 0.50 | 0.33 | 0.33 |
| | c.307C > T | 0.00 | 1.00 | 0.67 | 1.00 | 0.50 | 0.33 | 0.33 |
| 3 | c.336 − 13T > C | 0.00 | 0.50 | 0.33 | 0.00 | 0.50 | 0.33 | 0.33 |
| | c.336 − 8A > T | 0.00 | 0.50 | 0.33 | 0.00 | 0.50 | 0.33 | 0.33 |
| | c.361A > T | 0.00 | 0.50 | 0.33 | 0.00 | 0.50 | 0.33 | 0.33 |
| | c.380C > T | 0.00 | 0.50 | 0.33 | 0.00 | 0.50 | 0.33 | 0.33 |
| | c.383G > A | 0.00 | 0.50 | 0.33 | 0.00 | 0.50 | 0.33 | 0.33 |
| | c.455C > A | 0.00 | 0.50 | 0.33 | 0.00 | 0.50 | 0.33 | 0.33 |
| 4 | c.505C > A | 0.00 | 0.50 | 0.33 | 0.00 | 0.50 | 0.33 | 0.00 |
| | c.509G > T | 0.00 | 0.50 | 0.33 | 0.00 | 0.50 | 0.33 | 0.00 |
| | c.514T > A | 0.00 | 0.50 | 0.33 | 0.00 | 0.50 | 0.33 | 0.00 |
| | c.544A > T | 0.00 | 0.50 | 0.33 | 0.00 | 0.50 | 0.33 | 0.00 |
| | c.577A > G | 0.00 | 0.50 | 0.33 | 0.00 | 0.50 | 0.33 | 0.00 |
| | c.594T > A | 0.00 | 0.50 | 0.33 | 0.00 | 0.50 | 0.33 | 0.00 |
| | c.602G > C | 0.00 | 0.50 | 0.33 | 0.00 | 0.50 | 0.33 | 0.00 |
| 5 | c.667G > T | 0.00 | 0.50 | 0.33 | 0.00 | 0.50 | 0.00 | 0.00 |
| | c.676G > C | 0.00 | 0.00 | 0.00 | 0.00 | 0.50 | 0.00 | 0.67 |
| | c.697C > G | 0.00 | 0.50 | 0.33 | 0.00 | 0.50 | 0.33 | 0.00 |
| | c.712A > G | 0.00 | 0.50 | 0.33 | 0.00 | 0.50 | 0.33 | 0.00 |

TABLE 21-continued

Expected genotypes based on genotypes, reference sequence RHCE (SEQ NO: 26) using the combination of primers of mix B.

| Exon | Mutation in reference to coding region | Genotypes ddccee | DDCCee | DdCcee | ddCCee | DDccEE | ddccee | D?ccEe |
|---|---|---|---|---|---|---|---|---|
| | c.733C > G | 0.00 | 0.50 | 0.33 | 0.00 | 0.50 | 0.33 | 0.00 |
| | c.744T > C | 0.00 | 0.50 | 0.33 | 0.00 | 0.50 | 0.33 | 0.00 |
| | c.787A > G | 0.00 | 0.50 | 0.33 | 0.00 | 0.50 | 0.33 | 0.00 |
| | c.800T > A | 0.00 | 0.50 | 0.33 | 0.00 | 0.50 | 0.33 | 0.00 |
| 6 | c.916A > G | 0.00 | 0.50 | 0.33 | 0.00 | 0.50 | 0.33 | 0.33 |
| | c.932G > A | 0.00 | 0.50 | 0.33 | 0.00 | 0.50 | 0.33 | 0.33 |
| | c.939 + 21T > C | 0.00 | 0.50 | 0.33 | 0.00 | 0.50 | 0.33 | 0.33 |
| | c.939 + 22G > C | 0.00 | 0.50 | 0.33 | 0.00 | 0.50 | 0.33 | 0.33 |
| | c.939 + 23C > T | 0.00 | 0.50 | 0.33 | 0.00 | 0.50 | 0.33 | 0.33 |
| | c.939 + 24T > C | 0.00 | 0.50 | 0.33 | 0.00 | 0.50 | 0.33 | 0.33 |
| 7 | c.941T > G | 0.00 | 0.50 | 0.33 | 0.00 | 0.50 | 0.33 | 0.33 |
| | c.968A > C | 0.00 | 0.50 | 0.33 | 0.00 | 0.50 | 0.33 | 0.33 |
| | c.974T > G | 0.00 | 0.50 | 0.33 | 0.00 | 0.50 | 0.33 | 0.33 |
| | c.979G > A | 0.00 | 0.50 | 0.33 | 0.00 | 0.50 | 0.33 | 0.33 |
| | c.985C > G | 0.00 | 0.50 | 0.33 | 0.00 | 0.50 | 0.33 | 0.33 |
| | c.986A > G | 0.00 | 0.50 | 0.33 | 0.00 | 0.50 | 0.33 | 0.33 |
| | c.989C > A | 0.00 | 0.50 | 0.33 | 0.00 | 0.50 | 0.33 | 0.33 |
| | c.992T > A | 0.00 | 0.50 | 0.33 | 0.00 | 0.50 | 0.33 | 0.33 |
| | c.1025C > T | 0.00 | 0.50 | 0.33 | 0.00 | 0.50 | 0.33 | 0.33 |
| | c.1048C > G | 0.00 | 0.50 | 0.33 | 0.00 | 0.50 | 0.33 | 0.33 |
| | c.1053T > C | 0.00 | 0.50 | 0.33 | 0.00 | 0.50 | 0.33 | 0.33 |
| | c.1057T > G | 0.00 | 0.50 | 0.33 | 0.00 | 0.50 | 0.33 | 0.33 |
| | c.1059G > A | 0.00 | 0.50 | 0.33 | 0.00 | 0.50 | 0.33 | 0.33 |
| | c.1060A > G | 0.00 | 0.50 | 0.33 | 0.00 | 0.50 | 0.33 | 0.33 |
| 9 | c.1061A > C | 0.00 | 0.50 | 0.33 | 0.00 | 0.50 | 0.33 | 0.33 |
| | c.1154 − 82_1154 − 81delAC | 0.00 | 0.50 | 0.33 | 0.00 | 0.50 | 0.67 | 0.33 |
| | c.1154 − 67T > C | 0.00 | 0.50 | 0.33 | 0.00 | 0.50 | 0.67 | 0.33 |
| | c.1170C > T | 0.00 | 0.50 | 0.33 | 0.00 | 0.50 | 0.67 | 0.33 |
| | c.1193T > A | 0.00 | 0.50 | 0.33 | 0.00 | 0.50 | 0.67 | 0.33 |

TABLE 22

Observed genotypes against reference sequence RHD (SEQ NO: 25) using the combination of primers of mix A.

| Exon | Mutation in reference to coding region | Genotypes DDCCee | ddCcEe | ddCcee | ddccee | ddccee | Dccee |
|---|---|---|---|---|---|---|---|
| 1 | c.148 + 18A > C | 0.49 | 1.00 | 1.00 | 1.00 | 1.00 | 0.46 |
| 2 | c.150T > C | 0.00 | 0.51 | 0.51 | 1.00 | 1.00 | 0.28 |
| | c.178A > C | 0.00 | 0.51 | 0.52 | 1.00 | 1.00 | 0.28 |
| | c.201G > A | 0.00 | 0.51 | 0.51 | 1.00 | 1.00 | 0.28 |
| | c.203G > A | 0.00 | 0.50 | 0.50 | 1.00 | 1.00 | 0.27 |
| | c.307T > C | 0.00 | 0.51 | 0.51 | 1.00 | 1.00 | 0.28 |
| 3 | c.336 − 13C > T | 0.55 | 1.00 | 1.00 | 1.00 | 1.00 | 0.52 |
| | c.336 − 8T > A | 0.55 | 1.00 | 1.00 | 1.00 | 1.00 | 0.52 |
| | c.361T > A | 0.54 | 1.00 | 1.00 | 1.00 | 1.00 | 0.52 |
| | c.380T > C | 0.55 | 1.00 | 1.00 | 1.00 | 1.00 | 0.52 |
| | c.383A > G | 0.56 | 1.00 | 1.00 | 1.00 | 1.00 | 0.53 |
| | c.455A > C | 0.55 | 1.00 | 1.00 | 1.00 | 1.00 | 0.52 |
| 4 | c.487 − 48_487 − 47insT | 0.51 | 1.00 | 1.00 | 1.00 | 1.00 | 0.49 |
| | c.505A > C | 0.51 | 1.00 | 1.00 | 1.00 | 1.00 | 0.50 |
| | c.509T > G | 0.50 | 1.00 | 1.00 | 1.00 | 1.00 | 0.48 |
| | c.514A > T | 0.51 | 1.00 | 1.00 | 1.00 | 1.00 | 0.49 |
| | c.544T > A | 0.51 | 1.00 | 1.00 | 1.00 | 1.00 | 0.49 |
| | c.577G > A | 0.49 | 1.00 | 1.00 | 1.00 | 1.00 | 0.48 |
| | c.594A > T | 0.53 | 1.00 | 1.00 | 1.00 | 1.00 | 0.51 |
| | c.602C > G | 0.50 | 1.00 | 1.00 | 1.00 | 1.00 | 0.49 |
| 5 | c.667T > G | 0.45 | 1.00 | 1.00 | 1.00 | 1.00 | 0.47 |
| | c.676G > C | 0.00 | 0.50 | 0.00 | 0.00 | 0.00 | 0.00 |
| | c.697G > C | 0.45 | 1.00 | 1.00 | 1.00 | 1.00 | 0.47 |
| | c.712G > A | 0.45 | 1.00 | 1.00 | 1.00 | 1.00 | 0.46 |
| | c.733G > C | 0.45 | 1.00 | 1.00 | 1.00 | 1.00 | 0.47 |
| | c.744C > T | 0.45 | 1.00 | 1.00 | 1.00 | 1.00 | 0.47 |
| | c.787G > A | 0.42 | 1.00 | 1.00 | 1.00 | 1.00 | 0.43 |
| | c.800A > T | 0.44 | 1.00 | 1.00 | 1.00 | 1.00 | 0.46 |

TABLE 22-continued

Observed genotypes against reference sequence RHD (SEQ NO: 25) using the combination of primers of mix A.

| Exon | Mutation in reference to coding region | Genotypes DDCCee | ddCcEe | ddCcee | ddccee | ddccee | Dccee |
|---|---|---|---|---|---|---|---|
| 6 | c.916G > A | 0.48 | 1.00 | 1.00 | 1.00 | 1.00 | 0.49 |
| | c.932A > G | 0.48 | 1.00 | 1.00 | 1.00 | 1.00 | 0.49 |
| | c.939 + 21C > T | 0.47 | 0.99 | 0.99 | 0.99 | 0.99 | 0.48 |
| | c.939 + 22C > G | 0.45 | 0.98 | 0.97 | 0.98 | 0.98 | 0.47 |
| | c.939 + 23T > C | 0.47 | 0.94 | 0.94 | 0.95 | 0.94 | 0.49 |
| | c.939 + 24C > T | 0.45 | 0.97 | 0.97 | 0.97 | 0.98 | 0.45 |
| 7 | c.941G > T | 0.44 | 1.00 | 1.00 | 1.00 | 1.00 | 0.43 |
| | c.968C > A | 0.45 | 1.00 | 1.00 | 1.00 | 1.00 | 0.43 |
| | c.974G > T | 0.44 | 1.00 | 1.00 | 1.00 | 1.00 | 0.43 |
| | c.979A > G | 0.45 | 1.00 | 1.00 | 1.00 | 1.00 | 0.43 |
| | c.985G > C | 0.44 | 1.00 | 1.00 | 1.00 | 1.00 | 0.43 |
| | c.986G > A | 0.44 | 1.00 | 1.00 | 1.00 | 1.00 | 0.43 |
| | c.989A > C | 0.44 | 1.00 | 1.00 | 1.00 | 1.00 | 0.43 |
| | c.992A > T | 0.45 | 1.00 | 1.00 | 1.00 | 1.00 | 0.43 |
| | c.1025T > C | 0.45 | 1.00 | 1.00 | 1.00 | 1.00 | 0.43 |
| | c.1048G > C | 0.44 | 1.00 | 1.00 | 1.00 | 1.00 | 0.43 |
| | c.1053C > T | 0.44 | 1.00 | 1.00 | 1.00 | 1.00 | 0.43 |
| | c.1057G > T | 0.44 | 0.99 | 0.99 | 0.99 | 0.99 | 0.42 |
| | c.1059A > G | 0.46 | 0.99 | 0.99 | 0.99 | 0.99 | 0.45 |
| | c.1060G > A | 0.42 | 1.00 | 1.00 | 1.00 | 1.00 | 0.41 |
| 9 | c.1061C > A | 0.43 | 0.99 | 1.00 | 1.00 | 1.00 | 0.42 |
| | c.1170T > C | 0.50 | 1.00 | 1.00 | 1.00 | 1.00 | 0.50 |
| | c.1193A > T | 0.51 | 1.00 | 1.00 | 1.00 | 1.00 | 0.51 |
| | c.1227 + 62A > G | 0.51 | 1.00 | 1.00 | 1.00 | 1.00 | 0.50 |

TABLE 23

Expected genotypes based on genotype, reference sequence RHD (SEQ NO: 25) using the combination of primers of mix A.

| Exon | Mutation in reference to coding region | Genotypes DDCCee | ddCcEe | ddCcee | ddccee | ddccee | Dccee |
|---|---|---|---|---|---|---|---|
| 1 | c.148 + 18A > C | 0.50 | 1.00 | 1.00 | 1.00 | 1.00 | 0.67 |
| 2 | c.150T > C | 0.00 | 0.50 | 0.50 | 1.00 | 1.00 | 0.33 |
| | c.178A > C | 0.00 | 0.50 | 0.50 | 1.00 | 1.00 | 0.33 |
| | c.201G > A | 0.00 | 0.50 | 0.50 | 1.00 | 1.00 | 0.33 |
| | c.203G > A | 0.00 | 0.50 | 0.50 | 1.00 | 1.00 | 0.33 |
| | c.307T > C | 0.00 | 0.50 | 0.50 | 1.00 | 1.00 | 0.33 |
| 3 | c.336 − 13C > T | 0.50 | 1.00 | 1.00 | 1.00 | 1.00 | 0.67 |
| | c.336 − 8T > A | 0.50 | 1.00 | 1.00 | 1.00 | 1.00 | 0.67 |
| | c.361T > A | 0.50 | 1.00 | 1.00 | 1.00 | 1.00 | 0.67 |
| | c.380T > C | 0.50 | 1.00 | 1.00 | 1.00 | 1.00 | 0.67 |
| | c.383A > G | 0.50 | 1.00 | 1.00 | 1.00 | 1.00 | 0.67 |
| | c.455A > C | 0.50 | 1.00 | 1.00 | 1.00 | 1.00 | 0.67 |
| 4 | c.487 − 48_487 − 47insT | 0.50 | 1.00 | 1.00 | 1.00 | 1.00 | 0.67 |
| | c.505A > C | 0.50 | 1.00 | 1.00 | 1.00 | 1.00 | 0.67 |
| | c.509T > G | 0.50 | 1.00 | 1.00 | 1.00 | 1.00 | 0.67 |
| | c.514A > T | 0.50 | 1.00 | 1.00 | 1.00 | 1.00 | 0.67 |
| | c.544T > A | 0.50 | 1.00 | 1.00 | 1.00 | 1.00 | 0.67 |
| | c.577G > A | 0.50 | 1.00 | 1.00 | 1.00 | 1.00 | 0.67 |
| | c.594A > T | 0.50 | 1.00 | 1.00 | 1.00 | 1.00 | 0.67 |
| | c.602C > G | 0.50 | 1.00 | 1.00 | 1.00 | 1.00 | 0.67 |
| 5 | c.667T > G | 0.50 | 1.00 | 1.00 | 1.00 | 1.00 | 0.67 |
| | c.676G > C | 0.00 | 0.50 | 0.00 | 0.00 | 0.00 | 0.00 |
| | c.697G > C | 0.50 | 1.00 | 1.00 | 1.00 | 1.00 | 0.67 |
| | c.712G > A | 0.50 | 1.00 | 1.00 | 1.00 | 1.00 | 0.67 |
| | c.733G > C | 0.50 | 1.00 | 1.00 | 1.00 | 1.00 | 0.67 |
| | c.744C > T | 0.50 | 1.00 | 1.00 | 1.00 | 1.00 | 0.67 |
| | c.787G > A | 0.50 | 1.00 | 1.00 | 1.00 | 1.00 | 0.67 |
| | c.800A > T | 0.50 | 1.00 | 1.00 | 1.00 | 1.00 | 0.67 |
| 6 | c.916G > A | 0.50 | 1.00 | 1.00 | 1.00 | 1.00 | 0.67 |
| | c.932A > G | 0.50 | 1.00 | 1.00 | 1.00 | 1.00 | 0.67 |
| | c.939 + 21C > T | 0.50 | 1.00 | 1.00 | 1.00 | 1.00 | 0.67 |
| | c.939 + 22C > G | 0.50 | 1.00 | 1.00 | 1.00 | 1.00 | 0.67 |
| | c.939 + 23T > C | 0.50 | 1.00 | 1.00 | 1.00 | 1.00 | 0.67 |
| | c.939 + 24C > T | 0.50 | 1.00 | 1.00 | 1.00 | 1.00 | 0.67 |

TABLE 23-continued

Expected genotypes based on genotype, reference sequence RHD (SEQ NO: 25) using the combination of primers of mix A.

| Exon | Mutation in reference to coding region | Genotypes DDCCee | ddCcEe | ddCcee | ddccee | ddccee | Dccee |
|---|---|---|---|---|---|---|---|
| 7 | c.941G > T | 0.50 | 1.00 | 1.00 | 1.00 | 1.00 | 0.67 |
| | c.968C > A | 0.50 | 1.00 | 1.00 | 1.00 | 1.00 | 0.67 |
| | c.974G > T | 0.50 | 1.00 | 1.00 | 1.00 | 1.00 | 0.67 |
| | c.979A > G | 0.50 | 1.00 | 1.00 | 1.00 | 1.00 | 0.67 |
| | c.985G > C | 0.50 | 1.00 | 1.00 | 1.00 | 1.00 | 0.67 |
| | c.986G > A | 0.50 | 1.00 | 1.00 | 1.00 | 1.00 | 0.67 |
| | c.989A > C | 0.50 | 1.00 | 1.00 | 1.00 | 1.00 | 0.67 |
| | c.992A > T | 0.50 | 1.00 | 1.00 | 1.00 | 1.00 | 0.67 |
| | c.1025T > C | 0.50 | 1.00 | 1.00 | 1.00 | 1.00 | 0.67 |
| | c.1048G > C | 0.50 | 1.00 | 1.00 | 1.00 | 1.00 | 0.67 |
| | c.1053C > T | 0.50 | 1.00 | 1.00 | 1.00 | 1.00 | 0.67 |
| | c.1057G > T | 0.50 | 1.00 | 1.00 | 1.00 | 1.00 | 0.67 |
| | c.1059A > G | 0.50 | 1.00 | 1.00 | 1.00 | 1.00 | 0.67 |
| | c.1060G > A | 0.50 | 1.00 | 1.00 | 1.00 | 1.00 | 0.67 |
| 9 | c.1061C > A | 0.50 | 1.00 | 1.00 | 1.00 | 1.00 | 0.67 |
| | c.1170T > C | 0.50 | 1.00 | 1.00 | 1.00 | 1.00 | 0.67 |
| | c.1193A > T | 0.50 | 1.00 | 1.00 | 1.00 | 1.00 | 0.67 |
| | c.1227 + 62A > G | 0.50 | 1.00 | 1.00 | 1.00 | 1.00 | 0.67 |

TABLE 24

Observed genotypes against reference sequence RHD (SEQ NO: 25) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| 1 | c.148 + 18A > C | 0.51 | 1.00 | 1.00 | 0.99 | 0.99 | 0.49 |
| 2 | c.150T > C | 0.00 | 0.51 | 0.52 | 1.00 | 1.00 | 0.28 |
| | c.178A > C | 0.00 | 0.52 | 0.53 | 1.00 | 1.00 | 0.29 |
| | c.201G > A | 0.00 | 0.50 | 0.51 | 1.00 | 1.00 | 0.27 |
| | c.203G > A | 0.00 | 0.49 | 0.50 | 1.00 | 1.00 | 0.26 |
| | c.307T > C | 0.00 | 0.48 | 0.47 | 0.99 | 1.00 | 0.25 |
| 3 | c.336 − 13C > T | 0.63 | 1.00 | 1.00 | 1.00 | 1.00 | 0.66 |
| | c.336 − 8T > A | 0.64 | 1.00 | 1.00 | 1.00 | 1.00 | 0.67 |
| | c.361T > A | 0.62 | 1.00 | 1.00 | 1.00 | 1.00 | 0.66 |
| | c.380T > C | 0.64 | 1.00 | 1.00 | 1.00 | 1.00 | 0.67 |
| | c.383A > G | 0.64 | 1.00 | 1.00 | 1.00 | 1.00 | 0.67 |
| | c.455A > C | 0.62 | 1.00 | 1.00 | 1.00 | 1.00 | 0.66 |
| 4 | c.505A > C | 0.50 | 1.00 | 1.00 | 1.00 | 1.00 | 0.50 |
| | c.509T > G | 0.50 | 1.00 | 1.00 | 1.00 | 1.00 | 0.49 |
| | c.514A > T | 0.50 | 1.00 | 1.00 | 1.00 | 1.00 | 0.50 |
| | c.544T > A | 0.50 | 1.00 | 1.00 | 1.00 | 1.00 | 0.50 |
| | c.577G > A | 0.49 | 1.00 | 1.00 | 1.00 | 1.00 | 0.49 |
| | c.594A > T | 0.51 | 1.00 | 1.00 | 1.00 | 1.00 | 0.50 |
| | c.602C > G | 0.50 | 1.00 | 1.00 | 1.00 | 1.00 | 0.50 |
| 5 | c.667T > G | 0.48 | 1.00 | 1.00 | 1.00 | 1.00 | 0.59 |
| | c.676G > C | 0.00 | 0.49 | 0.00 | 0.00 | 0.00 | 0.00 |
| | c.697G > C | 0.49 | 1.00 | 1.00 | 1.00 | 1.00 | 0.60 |
| | c.712G > A | 0.49 | 1.00 | 1.00 | 1.00 | 1.00 | 0.59 |
| | c.733G > C | 0.50 | 1.00 | 1.00 | 1.00 | 1.00 | 0.61 |
| | c.744C > T | 0.50 | 1.00 | 1.00 | 1.00 | 1.00 | 0.61 |
| | c.787G > A | 0.41 | 1.00 | 1.00 | 1.00 | 1.00 | 0.52 |
| | c.800A > T | 0.48 | 1.00 | 1.00 | 1.00 | 1.00 | 0.59 |
| 6 | c.916G > A | 0.49 | 1.00 | 1.00 | 1.00 | 1.00 | 0.50 |
| | c.932A > G | 0.51 | 1.00 | 1.00 | 1.00 | 1.00 | 0.51 |
| | c.939 + 21C > T | 0.41 | 0.99 | 0.98 | 0.99 | 0.99 | 0.42 |
| | c.939 + 22C > G | 0.38 | 0.98 | 0.97 | 0.97 | 0.97 | 0.39 |
| | c.939 + 23T > C | 0.43 | 0.94 | 0.93 | 0.91 | 0.92 | 0.44 |
| | c.939 + 24C > T | 0.38 | 0.98 | 0.98 | 0.97 | 0.97 | 0.41 |
| 7 | c.941G > T | 0.45 | 1.00 | 1.00 | 1.00 | 1.00 | 0.45 |
| | c.968C > A | 0.45 | 1.00 | 1.00 | 1.00 | 1.00 | 0.45 |
| | c.974G > T | 0.45 | 1.00 | 1.00 | 1.00 | 1.00 | 0.44 |
| | c.979A > G | 0.45 | 1.00 | 1.00 | 1.00 | 1.00 | 0.45 |
| | c.985G > C | 0.45 | 1.00 | 1.00 | 1.00 | 1.00 | 0.45 |
| | c.986G > A | 0.46 | 1.00 | 1.00 | 1.00 | 1.00 | 0.45 |
| | c.989A > C | 0.45 | 1.00 | 1.00 | 1.00 | 1.00 | 0.44 |
| | c.992A > T | 0.45 | 1.00 | 1.00 | 1.00 | 1.00 | 0.44 |
| | c.1025T > C | 0.45 | 1.00 | 1.00 | 1.00 | 1.00 | 0.45 |

TABLE 24-continued

Observed genotypes against reference sequence RHD (SEQ NO: 25) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| | c.1048G > C | 0.45 | 1.00 | 1.00 | 1.00 | 1.00 | 0.45 |
| | c.1053C > T | 0.45 | 1.00 | 1.00 | 1.00 | 1.00 | 0.46 |
| | c.1057G > T | 0.44 | 0.99 | 0.99 | 0.99 | 0.99 | 0.44 |
| | c.1059A > G | 0.46 | 0.99 | 0.99 | 0.99 | 1.00 | 0.45 |
| | c.1060G > A | 0.44 | 1.00 | 1.00 | 1.00 | 1.00 | 0.44 |
| 9 | c.1061C > A | 0.45 | 1.00 | 1.00 | 1.00 | 1.00 | 0.45 |
| | c.1154 − 81_1154 − 80insAC | 0.47 | 0.98 | 0.98 | 0.98 | 0.98 | 0.48 |
| | c.1154 − 67C > T | 0.48 | 1.00 | 1.00 | 1.00 | 1.00 | 0.49 |
| | c.1170T > C | 0.47 | 1.00 | 1.00 | 1.00 | 1.00 | 0.47 |
| | c.1193A > T | 0.50 | 1.00 | 1.00 | 1.00 | 1.00 | 0.51 |

TABLE 25

Expected genotypes based on genotypes, reference sequence RHD (SEQ NO: 25) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| 1 | c.148 + 18A > C | 0.50 | 1.00 | 1.00 | 1.00 | 1.00 | 0.67 |
| 2 | c.150T > C | 0.00 | 0.50 | 0.50 | 1.00 | 1.00 | 0.33 |
| | c.178A > C | 0.00 | 0.50 | 0.50 | 1.00 | 1.00 | 0.33 |
| | c.201G > A | 0.00 | 0.50 | 0.50 | 1.00 | 1.00 | 0.33 |
| | c.203G > A | 0.00 | 0.50 | 0.50 | 1.00 | 1.00 | 0.33 |
| | c.307T > C | 0.00 | 0.50 | 0.50 | 1.00 | 1.00 | 0.33 |
| 3 | c.336 − 13C > T | 0.50 | 1.00 | 1.00 | 1.00 | 1.00 | 0.67 |
| | c.336 − 8T > A | 0.50 | 1.00 | 1.00 | 1.00 | 1.00 | 0.67 |
| | c.361T > A | 0.50 | 1.00 | 1.00 | 1.00 | 1.00 | 0.67 |
| | c.380T > C | 0.50 | 1.00 | 1.00 | 1.00 | 1.00 | 0.67 |
| | c.383A > G | 0.50 | 1.00 | 1.00 | 1.00 | 1.00 | 0.67 |
| | c.455A > C | 0.50 | 1.00 | 1.00 | 1.00 | 1.00 | 0.67 |
| 4 | c.505A > C | 0.50 | 1.00 | 1.00 | 1.00 | 1.00 | 0.67 |
| | c.509T > G | 0.50 | 1.00 | 1.00 | 1.00 | 1.00 | 0.67 |
| | c.514A > T | 0.50 | 1.00 | 1.00 | 1.00 | 1.00 | 0.67 |
| | c.544T > A | 0.50 | 1.00 | 1.00 | 1.00 | 1.00 | 0.67 |
| | c.577G > A | 0.50 | 1.00 | 1.00 | 1.00 | 1.00 | 0.67 |
| | c.594A > T | 0.50 | 1.00 | 1.00 | 1.00 | 1.00 | 0.67 |
| | c.602C > G | 0.50 | 1.00 | 1.00 | 1.00 | 1.00 | 0.67 |
| 5 | c.667T > G | 0.50 | 1.00 | 1.00 | 1.00 | 1.00 | 0.67 |
| | c.676G > C | 0.00 | 0.50 | 0.00 | 0.00 | 0.00 | 0.00 |
| | c.697G > C | 0.50 | 1.00 | 1.00 | 1.00 | 1.00 | 0.67 |
| | c.712G > A | 0.50 | 1.00 | 1.00 | 1.00 | 1.00 | 0.67 |
| | c.733G > C | 0.50 | 1.00 | 1.00 | 1.00 | 1.00 | 0.67 |
| | c.744C > T | 0.50 | 1.00 | 1.00 | 1.00 | 1.00 | 0.67 |
| | c.787G > A | 0.50 | 1.00 | 1.00 | 1.00 | 1.00 | 0.67 |
| | c.800A > T | 0.50 | 1.00 | 1.00 | 1.00 | 1.00 | 0.67 |
| 6 | c.916G > A | 0.50 | 1.00 | 1.00 | 1.00 | 1.00 | 0.67 |
| | c.932A > G | 0.50 | 1.00 | 1.00 | 1.00 | 1.00 | 0.67 |
| | c.939 + 21C > T | 0.50 | 1.00 | 1.00 | 1.00 | 1.00 | 0.67 |
| | c.939 + 22C > G | 0.50 | 1.00 | 1.00 | 1.00 | 1.00 | 0.67 |
| | c.939 + 23T > C | 0.50 | 1.00 | 1.00 | 1.00 | 1.00 | 0.67 |
| | c.939 + 24C > T | 0.50 | 1.00 | 1.00 | 1.00 | 1.00 | 0.67 |
| 7 | c.941G > T | 0.50 | 1.00 | 1.00 | 1.00 | 1.00 | 0.67 |
| | c.968C > A | 0.50 | 1.00 | 1.00 | 1.00 | 1.00 | 0.67 |
| | c.974G > T | 0.50 | 1.00 | 1.00 | 1.00 | 1.00 | 0.67 |
| | c.979A > G | 0.50 | 1.00 | 1.00 | 1.00 | 1.00 | 0.67 |
| | c.985G > C | 0.50 | 1.00 | 1.00 | 1.00 | 1.00 | 0.67 |
| | c.986G > A | 0.50 | 1.00 | 1.00 | 1.00 | 1.00 | 0.67 |
| | c.989A > C | 0.50 | 1.00 | 1.00 | 1.00 | 1.00 | 0.67 |
| | c.992A > T | 0.50 | 1.00 | 1.00 | 1.00 | 1.00 | 0.67 |
| | c.1025T > C | 0.50 | 1.00 | 1.00 | 1.00 | 1.00 | 0.67 |
| | c.1048G > C | 0.50 | 1.00 | 1.00 | 1.00 | 1.00 | 0.67 |
| | c.1053C > T | 0.50 | 1.00 | 1.00 | 1.00 | 1.00 | 0.67 |
| | c.1057G > T | 0.50 | 1.00 | 1.00 | 1.00 | 1.00 | 0.67 |
| | c.1059A > G | 0.50 | 1.00 | 1.00 | 1.00 | 1.00 | 0.67 |
| | c.1060G > A | 0.50 | 1.00 | 1.00 | 1.00 | 1.00 | 0.67 |

TABLE 25-continued

| Expected genotypes based on genotypes, reference sequence RHD (SEQ NO: 25) using the combination of primers of mix B. | | | | | | | |
|---|---|---|---|---|---|---|---|
| | Mutation in reference | Genotypes | | | | | |
| Exon | to coding region | DDCCee | ddCcEe | ddCcee | ddccee | ddccee | Dccee |
| 9 | c.1061C > A | 0.50 | 1.00 | 1.00 | 1.00 | 1.00 | 0.67 |
| | c.1154 − 81_1154 − 80insAC | 0.50 | 1.00 | 1.00 | 1.00 | 1.00 | 0.67 |
| | c.1154 − 67C > T | 0.50 | 1.00 | 1.00 | 1.00 | 1.00 | 0.67 |
| | c.1170T > C | 0.50 | 1.00 | 1.00 | 1.00 | 1.00 | 0.67 |
| | c.1193A > T | 0.50 | 1.00 | 1.00 | 1.00 | 1.00 | 0.67 |

TABLE 26

| Observed genotypes against reference sequence RHCE (SEQ NO: 26) using the combination of primers of mix A. | | | | | | | |
|---|---|---|---|---|---|---|---|
| | Mutation in reference | Genotypes | | | | | |
| Exon | to coding region | DDCCee | ddCcEe | ddCcee | ddccee | ddccee | Dccee |
| 1 | c.148 + 18C > A | 0.51 | 0.00 | 0.00 | 0.00 | 0.00 | 0.54 |
| 2 | c.150C > T | 1.00 | 0.49 | 0.49 | 0.00 | 0.00 | 0.72 |
| | c.178C > A | 1.00 | 0.49 | 0.48 | 0.00 | 0.00 | 0.72 |
| | c.201A > G | 1.00 | 0.49 | 0.49 | 0.00 | 0.00 | 0.72 |
| | c.203A > G | 1.00 | 0.50 | 0.50 | 0.00 | 0.00 | 0.73 |
| | c.307C > T | 1.00 | 0.48 | 0.48 | 0.00 | 0.00 | 0.71 |
| 3 | c.336 − 13T > C | 0.45 | 0.00 | 0.00 | 0.00 | 0.00 | 0.48 |
| | c.336 − 8A > T | 0.45 | 0.00 | 0.00 | 0.00 | 0.00 | 0.48 |
| | c.361A > T | 0.46 | 0.00 | 0.00 | 0.00 | 0.00 | 0.48 |
| | c.380C > T | 0.45 | 0.00 | 0.00 | 0.00 | 0.00 | 0.48 |
| | c.383G > A | 0.43 | 0.00 | 0.00 | 0.00 | 0.00 | 0.47 |
| | c.455C > A | 0.44 | 0.00 | 0.00 | 0.00 | 0.00 | 0.48 |
| 4 | c.487 − 48delT | 0.49 | 0.00 | 0.00 | 0.00 | 0.00 | 0.51 |
| | c.505C > A | 0.49 | 0.00 | 0.00 | 0.00 | 0.00 | 0.50 |
| | c.509G > T | 0.50 | 0.00 | 0.00 | 0.00 | 0.00 | 0.52 |
| | c.514T > A | 0.49 | 0.00 | 0.00 | 0.00 | 0.00 | 0.51 |
| | c.544A > T | 0.49 | 0.00 | 0.00 | 0.00 | 0.00 | 0.51 |
| | c.577A > G | 0.51 | 0.00 | 0.00 | 0.00 | 0.00 | 0.51 |
| | c.594T > A | 0.47 | 0.00 | 0.00 | 0.00 | 0.00 | 0.48 |
| | c.602G > C | 0.50 | 0.00 | 0.00 | 0.00 | 0.00 | 0.51 |
| 5 | c.667G > T | 0.55 | 0.00 | 0.00 | 0.00 | 0.00 | 0.53 |
| | c.676G > C | 0.00 | 0.50 | 0.00 | 0.00 | 0.00 | 0.00 |
| | c.697C > G | 0.55 | 0.00 | 0.00 | 0.00 | 0.00 | 0.53 |
| | c.712A > G | 0.55 | 0.00 | 0.00 | 0.00 | 0.00 | 0.54 |
| | c.733C > G | 0.55 | 0.00 | 0.00 | 0.00 | 0.00 | 0.53 |
| | c.744T > C | 0.55 | 0.00 | 0.00 | 0.00 | 0.00 | 0.53 |
| | c.787A > G | 0.58 | 0.00 | 0.00 | 0.00 | 0.00 | 0.57 |
| | c.800T > A | 0.56 | 0.00 | 0.00 | 0.00 | 0.00 | 0.54 |
| 6 | c.916A > G | 0.52 | 0.00 | 0.00 | 0.00 | 0.00 | 0.51 |
| | c.932G > A | 0.51 | 0.00 | 0.00 | 0.00 | 0.00 | 0.51 |
| | c.939 + 21T > C | 0.49 | 0.00 | 0.00 | 0.00 | 0.00 | 0.48 |
| | c.939 + 22G > C | 0.51 | 0.00 | 0.00 | 0.00 | 0.00 | 0.49 |
| | c.939 + 23C > T | 0.47 | 0.00 | 0.00 | 0.00 | 0.00 | 0.46 |
| | c.939 + 24T > C | 0.52 | 0.00 | 0.00 | 0.00 | 0.00 | 0.51 |
| 7 | c.941T > G | 0.55 | 0.00 | 0.00 | 0.00 | 0.00 | 0.57 |
| | c.968A > C | 0.55 | 0.00 | 0.00 | 0.00 | 0.00 | 0.57 |
| | c.974T > G | 0.56 | 0.00 | 0.00 | 0.00 | 0.00 | 0.57 |
| | c.979G > A | 0.55 | 0.00 | 0.00 | 0.00 | 0.00 | 0.57 |
| | c.985C > G | 0.56 | 0.00 | 0.00 | 0.00 | 0.00 | 0.57 |
| | c.986A > G | 0.56 | 0.00 | 0.00 | 0.00 | 0.00 | 0.57 |
| | c.989C > A | 0.56 | 0.00 | 0.00 | 0.00 | 0.00 | 0.57 |
| | c.992T > A | 0.55 | 0.00 | 0.00 | 0.00 | 0.00 | 0.57 |
| | c.1025C > T | 0.55 | 0.00 | 0.00 | 0.00 | 0.00 | 0.57 |
| | c.1048C > G | 0.55 | 0.00 | 0.00 | 0.00 | 0.00 | 0.57 |
| | c.1053T > C | 0.55 | 0.00 | 0.00 | 0.00 | 0.00 | 0.57 |
| | c.1057T > G | 0.55 | 0.00 | 0.00 | 0.00 | 0.00 | 0.56 |
| | c.1059G > A | 0.52 | 0.00 | 0.00 | 0.00 | 0.00 | 0.54 |
| | c.1060A > G | 0.56 | 0.00 | 0.00 | 0.00 | 0.00 | 0.58 |
| 9 | c.1061A > C | 0.56 | 0.00 | 0.00 | 0.00 | 0.00 | 0.57 |
| | c.1170C > T | 0.50 | 0.00 | 0.00 | 0.00 | 0.00 | 0.50 |
| | c.1193T > A | 0.49 | 0.00 | 0.00 | 0.00 | 0.00 | 0.49 |
| | c.1227 + 62G > A | 0.49 | 0.00 | 0.00 | 0.00 | 0.00 | 0.50 |

TABLE 27

Expected genotypes based on genotype, reference sequence RHCE (SEQ NO: 26) using the combination of primers of mix A.

| Exon | Mutation in reference to coding region | Genotypes DDCCee | ddCcEe | ddCcee | ddccee | ddccee | Dccee |
|---|---|---|---|---|---|---|---|
| 1 | c.148 + 18C > A | 0.50 | 0.00 | 0.00 | 0.00 | 0.00 | 0.50 |
| 2 | c.150C > T | 1.00 | 0.50 | 0.50 | 0.00 | 0.00 | 0.50 |
| | c.178C > A | 1.00 | 0.50 | 0.50 | 0.00 | 0.00 | 0.50 |
| | c.201A > G | 1.00 | 0.50 | 0.50 | 0.00 | 0.00 | 0.50 |
| | c.203A > G | 1.00 | 0.50 | 0.50 | 0.00 | 0.00 | 0.50 |
| | c.307C > T | 1.00 | 0.50 | 0.50 | 0.00 | 0.00 | 0.50 |
| 3 | c.336 − 13T > C | 0.50 | 0.00 | 0.00 | 0.00 | 0.00 | 0.50 |
| | c.336 − 8A > T | 0.50 | 0.00 | 0.00 | 0.00 | 0.00 | 0.50 |
| | c.361A > T | 0.50 | 0.00 | 0.00 | 0.00 | 0.00 | 0.50 |
| | c.380C > T | 0.50 | 0.00 | 0.00 | 0.00 | 0.00 | 0.50 |
| | c.383G > A | 0.50 | 0.00 | 0.00 | 0.00 | 0.00 | 0.50 |
| | c.455C > A | 0.50 | 0.00 | 0.00 | 0.00 | 0.00 | 0.50 |
| 4 | c.487 − 48delT | 0.50 | 0.00 | 0.00 | 0.00 | 0.00 | 0.50 |
| | c.505C > A | 0.50 | 0.00 | 0.00 | 0.00 | 0.00 | 0.50 |
| | c.509G > T | 0.50 | 0.00 | 0.00 | 0.00 | 0.00 | 0.50 |
| | c.514T > A | 0.50 | 0.00 | 0.00 | 0.00 | 0.00 | 0.50 |
| | c.544A > T | 0.50 | 0.00 | 0.00 | 0.00 | 0.00 | 0.50 |
| | c.577A > G | 0.50 | 0.00 | 0.00 | 0.00 | 0.00 | 0.50 |
| | c.594T > A | 0.50 | 0.00 | 0.00 | 0.00 | 0.00 | 0.50 |
| | c.602G > C | 0.50 | 0.00 | 0.00 | 0.00 | 0.00 | 0.50 |
| 5 | c.667G > T | 0.50 | 0.00 | 0.00 | 0.00 | 0.00 | 0.50 |
| | c.676G > C | 0.00 | 0.50 | 0.00 | 0.00 | 0.00 | 0.00 |
| | c.697C > G | 0.50 | 0.00 | 0.00 | 0.00 | 0.00 | 0.50 |
| | c.712A > G | 0.50 | 0.00 | 0.00 | 0.00 | 0.00 | 0.50 |
| | c.733C > G | 0.50 | 0.00 | 0.00 | 0.00 | 0.00 | 0.50 |
| | c.744T > C | 0.50 | 0.00 | 0.00 | 0.00 | 0.00 | 0.50 |
| | c.787A > G | 0.50 | 0.00 | 0.00 | 0.00 | 0.00 | 0.50 |
| | c.800T > A | 0.50 | 0.00 | 0.00 | 0.00 | 0.00 | 0.50 |
| 6 | c.916A > G | 0.50 | 0.00 | 0.00 | 0.00 | 0.00 | 0.50 |
| | c.932G > A | 0.50 | 0.00 | 0.00 | 0.00 | 0.00 | 0.50 |
| | c.939 + 21T > C | 0.50 | 0.00 | 0.00 | 0.00 | 0.00 | 0.50 |
| | c.939 + 22G > C | 0.50 | 0.00 | 0.00 | 0.00 | 0.00 | 0.50 |
| | c.939 + 23C > T | 0.50 | 0.00 | 0.00 | 0.00 | 0.00 | 0.50 |
| | c.939 + 24T > C | 0.50 | 0.00 | 0.00 | 0.00 | 0.00 | 0.50 |
| 7 | c.941T > G | 0.50 | 0.00 | 0.00 | 0.00 | 0.00 | 0.50 |
| | c.968A > C | 0.50 | 0.00 | 0.00 | 0.00 | 0.00 | 0.50 |
| | c.974T > G | 0.50 | 0.00 | 0.00 | 0.00 | 0.00 | 0.50 |
| | c.979G > A | 0.50 | 0.00 | 0.00 | 0.00 | 0.00 | 0.50 |
| | c.985C > G | 0.50 | 0.00 | 0.00 | 0.00 | 0.00 | 0.50 |
| | c.986A > G | 0.50 | 0.00 | 0.00 | 0.00 | 0.00 | 0.50 |
| | c.989C > A | 0.50 | 0.00 | 0.00 | 0.00 | 0.00 | 0.50 |
| | c.992T > A | 0.50 | 0.00 | 0.00 | 0.00 | 0.00 | 0.50 |
| | c.1025C > T | 0.50 | 0.00 | 0.00 | 0.00 | 0.00 | 0.50 |
| | c.1048C > G | 0.50 | 0.00 | 0.00 | 0.00 | 0.00 | 0.50 |
| | c.1053T > C | 0.50 | 0.00 | 0.00 | 0.00 | 0.00 | 0.50 |
| | c.1057T > G | 0.50 | 0.00 | 0.00 | 0.00 | 0.00 | 0.50 |
| | c.1059G > A | 0.50 | 0.00 | 0.00 | 0.00 | 0.00 | 0.50 |
| | c.1060A > G | 0.50 | 0.00 | 0.00 | 0.00 | 0.00 | 0.50 |
| 9 | c.1061A > C | 0.50 | 0.00 | 0.00 | 0.00 | 0.00 | 0.50 |
| | c.1170C > T | 0.50 | 0.00 | 0.00 | 0.00 | 0.00 | 0.50 |
| | c.1193T > A | 0.50 | 0.00 | 0.00 | 0.00 | 0.00 | 0.50 |
| | c.1227 + 62G > A | 0.50 | 0.00 | 0.00 | 0.00 | 0.00 | 0.50 |

TABLE 28

Observed genotypes against reference sequence RHCE (SEQ NO: 26) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| 1 | c.148 + 18C > A | 0.49 | 0.00 | 0.00 | 0.00 | 0.00 | 0.50 |
| 2 | c.150C > T | 1.00 | 0.49 | 0.48 | 0.00 | 0.00 | 0.72 |
| | c.178C > A | 1.00 | 0.48 | 0.47 | 0.00 | 0.00 | 0.71 |
| | c.201A > G | 1.00 | 0.50 | 0.48 | 0.00 | 0.00 | 0.73 |
| | c.203A > G | 1.00 | 0.51 | 0.50 | 0.00 | 0.00 | 0.74 |
| | c.307C > T | 0.99 | 0.50 | 0.50 | 0.00 | 0.00 | 0.72 |
| 3 | c.336 − 13T > C | 0.37 | 0 | 0 | 0.00 | 0.00 | 0.34 |
| | c.336 − 8A > T | 0.36 | 0 | 0 | 0.00 | 0.00 | 0.33 |

TABLE 28-continued

Observed genotypes against reference sequence RHCE (SEQ NO: 26) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| | c.361A > T | 0.37 | 0 | 0 | 0.00 | 0.00 | 0.34 |
| | c.380C > T | 0.36 | 0 | 0 | 0.00 | 0.00 | 0.33 |
| | c.383G > A | 0.36 | 0 | 0 | 0.00 | 0.00 | 0.33 |
| | c.455C > A | 0.38 | 0 | 0 | 0.00 | 0.00 | 0.34 |
| 4 | c.505C > A | 0.50 | 0 | 0 | 0.00 | 0.00 | 0.50 |
| | c.509G > T | 0.50 | 0 | 0 | 0.00 | 0.00 | 0.51 |
| | c.514T > A | 0.50 | 0 | 0 | 0.00 | 0.00 | 0.50 |
| | c.544A > T | 0.50 | 0 | 0 | 0.00 | 0.00 | 0.50 |
| | c.577A > G | 0.51 | 0 | 0 | 0.00 | 0.00 | 0.51 |
| | c.594T > A | 0.49 | 0 | 0 | 0.00 | 0.00 | 0.50 |
| | c.602G > C | 0.50 | 0 | 0 | 0.00 | 0.00 | 0.50 |
| 5 | c.667G > T | 0.52 | 0 | 0 | 0.00 | 0.00 | 0.41 |
| | c.676G > C | 0.00 | 0.49 | 0 | 0.00 | 0.00 | 0.00 |
| | c.697C > G | 0.51 | 0 | 0 | 0 | 0 | 0.40 |
| | c.712A > G | 0.51 | 0 | 0 | 0 | 0 | 0.41 |
| | c.733C > G | 0.50 | 0 | 0 | 0 | 0 | 0.39 |
| | c.744T > C | 0.50 | 0 | 0 | 0 | 0 | 0.39 |
| | c.787A > G | 0.57 | 0 | 0 | 0 | 0 | 0.47 |
| | c.800T > A | 0.51 | 0 | 0 | 0 | 0 | 0.39 |
| 6 | c.916A > G | 0.51 | 0 | 0 | 0 | 0 | 0.50 |
| | c.932G > A | 0.49 | 0 | 0 | 0 | 0 | 0.49 |
| | c.939 + 21T > C | 0.39 | 0 | 0 | 0 | 0 | 0.40 |
| | c.939 + 22G > C | 0.43 | 0 | 0 | 0 | 0 | 0.44 |
| | c.939 + 23C > T | 0.36 | 0 | 0 | 0 | 0 | 0.37 |
| | c.939 + 24T > C | 0.42 | 0 | 0 | 0 | 0 | 0.42 |
| 7 | c.941T > G | 0.54 | 0 | 0 | 0 | 0 | 0.55 |
| | c.968A > C | 0.55 | 0 | 0 | 0 | 0 | 0.55 |
| | c.974T > G | 0.55 | 0 | 0 | 0 | 0 | 0.56 |
| | c.979G > A | 0.54 | 0 | 0 | 0 | 0 | 0.55 |
| | c.985C > G | 0.55 | 0 | 0 | 0 | 0 | 0.55 |
| | c.986A > G | 0.54 | 0 | 0 | 0 | 0 | 0.55 |
| | c.989C > A | 0.55 | 0 | 0 | 0 | 0 | 0.56 |
| | c.992T > A | 0.55 | 0 | 0 | 0 | 0 | 0.56 |
| | c.1025C > T | 0.55 | 0 | 0 | 0 | 0 | 0.55 |
| | c.1048C > G | 0.55 | 0 | 0 | 0 | 0 | 0.55 |
| | c.1053T > C | 0.55 | 0 | 0 | 0 | 0 | 0.54 |
| | c.1057T > G | 0.55 | 0 | 0 | 0 | 0 | 0.55 |
| | c.1059G > A | 0.53 | 0 | 0 | 0 | 0 | 0.53 |
| | c.1060A > G | 0.55 | 0 | 0 | 0 | 0 | 0.55 |
| 9 | c.1061A > C | 0.55 | 0 | 0 | 0 | 0 | 0.55 |
| | c.1154 − 82_1154 − 81delAC | 0.52 | 0 | 0 | 0 | 0 | 0.51 |
| | c.1154 − 67T > C | 0.52 | 0 | 0 | 0 | 0 | 0.51 |
| | c.1170C > T | 0.53 | 0 | 0 | 0 | 0 | 0.53 |
| | c.1193T > A | 0.50 | 0 | 0 | 0 | 0 | 0.50 |

TABLE 29

Expected genotypes based on genotypes, reference sequence RHCE (SEQ NO: 26) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| 1 | c.148 + 18C > A | 0.50 | 0.00 | 0.00 | 0.00 | 0.00 | 0.50 |
| 2 | c.150C > T | 1.00 | 0.50 | 0.50 | 0.00 | 0.00 | 0.50 |
| | c.178C > A | 1.00 | 0.50 | 0.50 | 0.00 | 0.00 | 0.50 |
| | c.201A > G | 1.00 | 0.50 | 0.50 | 0.00 | 0.00 | 0.50 |
| | c.203A > G | 1.00 | 0.50 | 0.50 | 0.00 | 0.00 | 0.50 |
| | c.307C > T | 1.00 | 0.50 | 0.50 | 0.00 | 0.00 | 0.50 |
| 3 | c.336 − 13T > C | 0.50 | 0.00 | 0.00 | 0.00 | 0.00 | 0.50 |
| | c.336 − 8A > T | 0.50 | 0.00 | 0.00 | 0.00 | 0.00 | 0.50 |
| | c.361A > T | 0.50 | 0.00 | 0.00 | 0.00 | 0.00 | 0.50 |
| | c.380C > T | 0.50 | 0.00 | 0.00 | 0.00 | 0.00 | 0.50 |
| | c.383G > A | 0.50 | 0.00 | 0.00 | 0.00 | 0.00 | 0.50 |
| | c.455C > A | 0.50 | 0.00 | 0.00 | 0.00 | 0.00 | 0.50 |
| 4 | c.505C > A | 0.50 | 0.00 | 0.00 | 0.00 | 0.00 | 0.50 |
| | c.509G > T | 0.50 | 0.00 | 0.00 | 0.00 | 0.00 | 0.50 |
| | c.514T > A | 0.50 | 0.00 | 0.00 | 0.00 | 0.00 | 0.50 |

TABLE 29-continued

Expected genotypes based on genotypes, reference sequence RHCE (SEQ NO: 26) using the combination of primers of mix B.

| Exon | Mutation in reference to coding region | Genotypes DDCCee | ddCcEe | ddCcee | ddccee | ddccee | Dccee |
|---|---|---|---|---|---|---|---|
| | c.544A > T | 0.50 | 0.00 | 0.00 | 0.00 | 0.00 | 0.50 |
| | c.577A > G | 0.50 | 0.00 | 0.00 | 0.00 | 0.00 | 0.50 |
| | c.594T > A | 0.50 | 0.00 | 0.00 | 0.00 | 0.00 | 0.50 |
| | c.602G > C | 0.50 | 0.00 | 0.00 | 0.00 | 0.00 | 0.50 |
| 5 | c.667G > T | 0.50 | 0.00 | 0.00 | 0.00 | 0.00 | 0.50 |
| | c.676G > C | 0.00 | 0.50 | 0.00 | 0.00 | 0.00 | 0.00 |
| | c.697C > G | 0.50 | 0.00 | 0.00 | 0.00 | 0.00 | 0.50 |
| | c.712A > G | 0.50 | 0.00 | 0.00 | 0.00 | 0.00 | 0.50 |
| | c.733C > G | 0.50 | 0.00 | 0.00 | 0.00 | 0.00 | 0.50 |
| | c.744T > C | 0.50 | 0.00 | 0.00 | 0.00 | 0.00 | 0.50 |
| | c.787A > G | 0.50 | 0.00 | 0.00 | 0.00 | 0.00 | 0.50 |
| | c.800T > A | 0.50 | 0.00 | 0.00 | 0.00 | 0.00 | 0.50 |
| 6 | c.916A > G | 0.50 | 0.00 | 0.00 | 0.00 | 0.00 | 0.50 |
| | c.932G > A | 0.50 | 0.00 | 0.00 | 0.00 | 0.00 | 0.50 |
| | c.939 + 21T > C | 0.50 | 0.00 | 0.00 | 0.00 | 0.00 | 0.50 |
| | c.939 + 22G > C | 0.50 | 0.00 | 0.00 | 0.00 | 0.00 | 0.50 |
| | c.939 + 23C > T | 0.50 | 0.00 | 0.00 | 0.00 | 0.00 | 0.50 |
| | c.939 + 24T > C | 0.50 | 0.00 | 0.00 | 0.00 | 0.00 | 0.50 |
| 7 | c.941T > G | 0.50 | 0.00 | 0.00 | 0.00 | 0.00 | 0.50 |
| | c.968A > C | 0.50 | 0.00 | 0.00 | 0.00 | 0.00 | 0.50 |
| | c.974T > G | 0.50 | 0.00 | 0.00 | 0.00 | 0.00 | 0.50 |
| | c.979G > A | 0.50 | 0.00 | 0.00 | 0.00 | 0.00 | 0.50 |
| | c.985C > G | 0.50 | 0.00 | 0.00 | 0.00 | 0.00 | 0.50 |
| | c.986A > G | 0.50 | 0.00 | 0.00 | 0.00 | 0.00 | 0.50 |
| | c.989C > A | 0.50 | 0.00 | 0.00 | 0.00 | 0.00 | 0.50 |
| | c.992T > A | 0.50 | 0.00 | 0.00 | 0.00 | 0.00 | 0.50 |
| | c.1025C > T | 0.50 | 0.00 | 0.00 | 0.00 | 0.00 | 0.50 |
| | c.1048C > G | 0.50 | 0.00 | 0.00 | 0.00 | 0.00 | 0.50 |
| | c.1053T > C | 0.50 | 0.00 | 0.00 | 0.00 | 0.00 | 0.50 |
| | c.1057T > G | 0.50 | 0.00 | 0.00 | 0.00 | 0.00 | 0.50 |
| | c.1059G > A | 0.50 | 0.00 | 0.00 | 0.00 | 0.00 | 0.50 |
| | c.1060A > G | 0.50 | 0.00 | 0.00 | 0.00 | 0.00 | 0.50 |
| 9 | c.1061A > C | 0.50 | 0.00 | 0.00 | 0.00 | 0.00 | 0.50 |
| | c.1154 − 82_1154 − 81delAC | 0.50 | 0.00 | 0.00 | 0.00 | 0.00 | 0.50 |
| | c.1154 − 67T > C | 0.50 | 0.00 | 0.00 | 0.00 | 0.00 | 0.50 |
| | c.1170C > T | 0.50 | 0.00 | 0.00 | 0.00 | 0.00 | 0.50 |
| | c.1193T > A | 0.50 | 0.00 | 0.00 | 0.00 | 0.00 | 0.50 |

TABLE 30

Observed and expected genotypes for intron 2 against reference sequences RHD (SEQ ID NO: 117) and RHCE (SEQ ID NO: 120)

| Primer mix | Genotype | Observed RHCEin2 | Observed RHDin2 | Expected RHCEin2 | Expected RHDin2 |
|---|---|---|---|---|---|
| A | ddccee | 0.00 | 1.00 | 0.00 | 1.00 |
| | DDCCee | 0.44 | 0.56 | 0.50 | 0.50 |
| | DdCcee | 0.29 | 0.71 | 0.33 | 0.67 |
| | ddCCee | 1.00 | 0.00 | 1.00 | 0.00 |
| | DDccEE | 0.00 | 1.00 | 0.00 | 1.00 |
| | ddccee | 0.00 | 1.00 | 0.00 | 1.00 |
| | D?ccEe | 0.00 | 1.00 | 0.00 | 1.00 |
| B | ddccee | 0.00 | 1.00 | 0.00 | 1.00 |
| | DDCCee | 0.29 | 0.71 | 0.50 | 0.50 |
| | DdCcee | 0.23 | 0.77 | 0.33 | 0.67 |
| | ddCCee | 1.00 | 0.00 | 1.00 | 0.00 |
| | DDccEE | 0.00 | 1.00 | 0.00 | 1.00 |
| | ddccee | 0.00 | 1.00 | 0.00 | 1.00 |
| | D?ccEe | 0.00 | 1.00 | 0.00 | 1.00 |

TABLE 31

Observed and expected genotypes for intron 2 against reference sequences RHD (SEQ ID NO: 117) and RHCE (SEQ ID NO: 120)

| Primer mix | Genotype | Observed RHCEin2 | Observed RHDin2 | Expected RHCEin2 | Expected RHDin2 |
|---|---|---|---|---|---|
| A | DDCCee | 0.42 | 0.58 | 0.5 | 0.5 |
| | ddccee | 0.00 | 1.00 | 0 | 1 |
| | DdCcee | 0.19 | 0.81 | 0.33 | 0.67 |
| | ddCcee | 0.31 | 0.69 | 0.25 | 0.75 |
| | ddCcEe | 0.29 | 0.71 | 0.25 | 0.75 |
| | ddccee | 0.00 | 1.00 | 0 | 1 |
| B | DDCCee | 0.25 | 0.75 | 0.5 | 0.5 |
| | ddccee | 0.00 | 1.00 | 0 | 1 |
| | DdCcee | 0.12 | 0.88 | 0.33 | 0.67 |
| | ddCcee | 0.31 | 0.69 | 0.25 | 0.75 |
| | ddCcEe | 0.32 | 0.68 | 0.25 | 0.75 |
| | ddccee | 0.00 | 1.00 | 0 | 1 |

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

The invention claimed is:

1. A method for genotyping alleles in at least one homologous genetic set, comprising:

(i) providing a DNA-containing sample from a subject that includes at least one homologous genetic loci set, wherein said homologous genetic loci set comprises red cell antigen-encoding RHD gene and RHCE gene;

(ii) performing PCR amplification of regions of said homologous genetic loci set using consensus sequence-specific primers, wherein said consensus sequence-specific primers bind to consensus sequences that are common to the RHD gene and RHCE gene and wherein the consensus sequence-specific primers comprise at least one forward consensus sequence-specific primer and one reverse consensus sequence-specific primer, thereby generating a pool of RHD and RHCE amplification products;

(iii) sequencing a plurality of said RHD and RHCE amplification products in order to determine the relative proportion of each nucleotide at each position;

(iv) performing a sequence alignment between the sequencing read results of (iii) and at least one reference sequence, with said reference sequence corresponding to one of the genes in said RHD and RHCE homologous genetic loci set; and (v) performing genotype calling of the allele or alleles in said sample based on the relative proportion of each nucleotide at each of a plurality of discriminant positions in said alignment.

2. The method according to claim 1, wherein said sequencing said plurality of said amplification products comprises Next Generation Sequencing or Sanger Sequencing.

3. The method according to claim 1, wherein the homologous genetic loci set comprises a first gene and a second gene, and wherein the first gene has at least 90%, at least 95% or at least 97% nucleotide sequence identity with the second gene.

4. The method according to claim 1, wherein said at least one reference sequence comprises:

(i) at least one exon or intron of the RHD gene of SEQ ID NO: 25 or the reverse complement thereof;

(ii) at least one exon or intron of the RHCE gene of SEQ ID NO: 26 or of one of the RHCE alleles RHCE*ce, RHCE*Ce, RHCE*cE or RHCE*CE, respectively or the reverse complement thereof;

(iii) at least one of the RHD exon 1 sequence as shown in SEQ ID NO: 27, the RHCE exon 1 sequences as shown in SEQ ID NOs: 28-31, being RHCE alleles RHCE*ce, RHCE*Ce, RHCE*cE or RHCE*CE, respectively, and/or the RHCE exon 1 consensus sequence as shown in SEQ ID NO: 32 or the reverse complement thereof;

(iv) at least one of the RHD exon 2 sequence as shown in SEQ ID NO: 33, the RHCE exon 2 sequences as shown in SEQ ID NOs: 34-37, being RHCE alleles RHCE*ce, RHCE*Ce, RHCE*cE or RHCE*CE, respectively, and/or the RHCE exon 2 consensus sequence as shown in SEQ ID NO: 38 or the reverse complement thereof;

(v) at least one of the RHD exon 3 sequence as shown in SEQ ID NO: 39, the RHCE exon 3 sequences as shown in SEQ ID NOs: 40-43, being RHCE alleles RHCE*ce, RHCE*Ce, RHCE*cE or RHCE*CE, respectively, and/or the RHCE exon 3 consensus sequence as shown in SEQ ID NO: 44 or the reverse complement thereof;

(vi) at least one of the RHD exon 4 sequence as shown in SEQ ID NO: 45, the RHCE exon 4 sequences as shown in SEQ ID NOs: 46-49, being RHCE alleles RHCE*ce, RHCE*Ce, RHCE*cE or RHCE* CE, respectively, and/or the RHCE exon 4 consensus sequence as shown in SEQ ID NO: 50 or the reverse complement thereof;

(vii) at least one of the RHD exon 5 sequence as shown in SEQ ID NO: 51, the RHCE exon 5 sequences as shown in SEQ ID NOs: 52-55, being RHCE alleles RHCE*ce, RHCE*Ce, RHCE*cE or RHCE*CE, respectively, and/or the RHCE exon 5 consensus sequence as shown in SEQ ID NO: 56 or the reverse complement thereof;

(viii) at least one of the RHD exon 6 sequence as shown in SEQ ID NO: 87, the RHCE exon 6 sequences as shown in SEQ ID NOs: 88-91, being RHCE alleles RHCE*ce, RHCE*Ce, RHCE*cE or RHCE*CE, respectively, and/or the RHCE exon 6 consensus sequence as shown in SEQ ID NO: 90 or the reverse complement thereof;

(ix) at least one of the RHD exon 7 sequence as shown in SEQ ID NO: 93, the RHCE exon 7 sequences as shown in SEQ ID NOs: 94-97, being RHCE alleles RHCE*ce, RHCE*Ce, RHCE*cE or RHCE*CE, respectively, and/or the RHCE exon 7 consensus sequence as shown in SEQ ID NO: 98 or the reverse complement thereof;

(x) at least one of the RHD exon 8 sequence as shown in SEQ ID NO: 99, the RHCE exon 8 sequences as shown in SEQ ID NOs: 100-103, being RHCE alleles RHCE*ce, RHCE*Ce, RHCE*cE or RHCE*CE, respectively, and/or the RHCE exon 8 consensus sequence as shown in SEQ ID NO: 104 or the reverse complement thereof;

(xi) at least one of the RHD exon 9 sequence as shown in SEQ ID NO: 105, the RHCE exon 9 sequences as shown in SEQ ID NOs: 106-109, being RHCE alleles RHCE*ce, RHCE*Ce, RHCE*cE or RHCE*CE, respectively, and/or the RHCE exon 9 consensus sequence as shown in SEQ ID NO: 110 or the reverse complement thereof;

(xii) at least one of the RHD exon 10 sequence as shown in SEQ ID NO: 111, the RHCE exon 10 sequences as shown in SEQ ID NOs: 112-115, being RHCE alleles RHCE*ce, RHCE*Ce, RHCE*cE or RHCE*CE, respectively, and/or the RHCE exon 10 consensus sequence as shown in SEQ ID NO: 116 or the reverse complement thereof; and/or (xiii) at least one of the RHD intron 2 sequence as shown in SEQ ID NO: 117, the RHCE intron 2 sequences as shown in SEQ ID NOs: 118-121, being RHCE haplotypes RHCE*ce, RHCE*Ce, RHCE*cE or RHCE*CE, respectively, or the reverse complement thereof.

5. The method according to claim 4, wherein the said at least one reference sequence comprises at least two reference sequences, including:

(i) at least one exon or intron of the RHD gene of SEQ ID NO: 25 or the reverse complement thereof, comprising an RHD exon sequence selected from any one of SEQ ID NOS:

27, 33, 39, 45, 51, 87, 93, 99, 105, 111 and 117; and (ii) a least one exon or intron of an RHCE gene sequence of SEQ ID NO: 26, comprising an RHCE exon sequence selected from any one of SEQ ID NOS: 28-32, 34-38, 40-44, 46-50, 52-56, 88-92, 94-98, 100-104, 106-110, 112-116, and 118-121 or the reverse complement thereof.

6. The method according to claim 4, wherein said plurality of discriminant positions in said alignment are selected from the following positions:

c.48, IVS1+18, c.150, c.178, c.201, c.203, c.307, IVS2-8, c.361, c.380, c.383, c.455, c.505, c.509, c.544, c.577, c.594, c.602, c.667, c.676, c.697, c.712, c.733, c.744, c.787, c.800, c.916, c.932, IVS6+21, IVS6+22, IVS6+23, IVS6+24, c.941, c.968, c.974, c.979, c.985, c.986, c.989, c.992, c.1025, c.1048, c.1053, c.1057, c.1059, c.1060, c.1061, IVS8-67, c.1170, c.1193, and IVS9+62.

7. The method according to claim 4, wherein the method comprises sequencing each of exons 1, 2, 3, 4, 5, 6, 7, 8, 9 and 10 of the RHD gene and each of exons 1, 2, 3, 4, 5, 6, 7, 8, 9 and 10 of the RHCE gene.

8. The method according to claim 4, wherein the method further comprises determining the blood type of the sample based on the genotype.

9. The method according to claim 1, wherein the method comprises obtaining the number of reads covering reference forward bases, number of reads covering reference reverse bases, number of reads covering alternate forward bases and number of reads covering alternate reverse bases for use in genotype calling.

10. The method according to claim 1, wherein the method further comprises computing a mapping quality score for each sequence alignment and/or an overall mapping quality score for a plurality of said sequence alignments, where said mapping quality score for each sequence alignment and/or said overall mapping quality score for said plurality of sequence alignments is required to be at least 15 Phred Score units in order for said genotype calling to be considered reliable.

11. The method according to claim 1, wherein a pre-process step is performed prior to said sequence alignment in order to improve alignment quality, said pre-process step comprising excluding sequence reads shorter than 10 nucleotides in length or trimming sequence reads.

12. The method according to claim 1, wherein the method further comprises performing a quality control step to evaluate quality of the sequencing reads prior to performing said sequence alignment, and wherein evaluating the quality of each forward and/or each reverse sequencing read comprises determining one or more parameters selected from the group consisting of: Per base sequence quality, Per sequence quality score, Per base sequence content, Per base GC content, Per sequence GC content, Per base N content, Sequence Length Distribution, Sequence Duplication Level, Overrepresented sequences, and Kmer Content.

13. The method according to claim 1, wherein said sequence alignment is performed using the algorithm Burrows-Wheeler Aligner exact match (BWA MEM).

14. The method according to claim 1, wherein the method further comprises evaluating one or more of said sequence alignments to determine at least one parameter selected from the group consisting of: coverage, variant frequency, genotype average quality call, mapping quality, and calling quality.

15. The method according to claim 1, wherein cutoff criteria are set such that in order to define a homozygous call, a minimum of 50% of reads must support the called allele.

16. The method according to claim 1, wherein cutoff criteria are set such that in order to define a heterozygous call, between 30% and 70% of reads must support the alternative allele.

17. The method according to claim 1, wherein cutoff criteria are set such that in order to define a hemizygous call, between 15% and 45% of reads must support the called allele.

18. The method according to claim 1, wherein coverage is evaluated independently for forward and for reverse strand alignment, and wherein the forward-to-reverse coverage ratio is between 0.6 and 1.4.

19. The method according to claim 1, wherein the homologous genetic loci set comprises the RHD gene and the RHCE gene, and wherein said consensus sequence-specific primers comprise at least one forward consensus sequence-specific primer and one reverse consensus sequence-specific primer selected from the group consisting of: SEQ ID NOs: 3-24 and 59-86.

* * * * *

SEQUENCE LISTING

```
<160> NUMBER OF SEQ ID NOS: 141

<210> SEQ ID NO 1
<211> LENGTH: 33
<212> TYPE: DNA
<213> ORGANISM: Artificial sequence
<220> FEATURE:
<223> OTHER INFORMATION: Synthetic sequence: Next generation sequencing
      tag

<400> SEQUENCE: 1

acactctttc cctacacgac gctcttccga tct                                 33


<210> SEQ ID NO 2
<211> LENGTH: 34
<212> TYPE: DNA
<213> ORGANISM: Artificial sequence
<220> FEATURE:
<223> OTHER INFORMATION: Synthetic sequence: Next generation sequencing
      tag

<400> SEQUENCE: 2

gtgactggag ttcagacgtg tgctcttccg atct                                34


<210> SEQ ID NO 3
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 3

tccctcaagc cctcaagtag                                                20


<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 4

tgttggagag aggggtgatg                                                20


<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 5

ctgcacagag acggacacag                                                20


<210> SEQ ID NO 6
<211> LENGTH: 20
<212> TYPE: DNA
<213> ORGANISM: Artificial sequence
```

<220> FEATURE:
<223> OTHER INFORMATION: Synthetic sequence: Consensus sequence - specific primer

<400> SEQUENCE: 6
ccctgctatt tgctcctgtg 20

<210> SEQ ID NO 7
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 7
aaaggaacat ctgtgcccct 20

<210> SEQ ID NO 8
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 8
cccttccagc tgccatttag 20

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 9
aaatctcgtc tgcttccccc 20

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 10
aagtgatcca gccaccatcc 20

<210> SEQ ID NO 11
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 11
gtccattccc tctatgaccc 20

<210> SEQ ID NO 12
<211> LENGTH: 20
<212> TYPE: DNA
<213> ORGANISM: Artificial sequence
<220> FEATURE:

<223> OTHER INFORMATION: Synthetic sequence: Consensus sequence - specific primer

<400> SEQUENCE: 12
aggtgcccaa cagtgtttgt 20

<210> SEQ ID NO 13
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 13
tgagtgagag gcatccttcc 20

<210> SEQ ID NO 14
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 14
tttggccctt ttctcccagg 20

<210> SEQ ID NO 15
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 15
gaaaccccac caaatggagc 20

<210> SEQ ID NO 16
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 16
gaagccccac caaatggagc 20

<210> SEQ ID NO 17
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 17
ggcttcaagt cacacctcct 20

<210> SEQ ID NO 18
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 18
cagaggatgc cgacactcac 20

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 19
ccattctgct cagcccaagt 20

<210> SEQ ID NO 20
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 20
cagccagagc cttttctgag 20

<210> SEQ ID NO 21
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 21
cagccctagg attctcatcc 20

<210> SEQ ID NO 22
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 22
agcaggagtg tgattctggc 20

<210> SEQ ID NO 23
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 23
ctgttagacc caagtgctgc 20

<210> SEQ ID NO 24
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 24
tggggagggg cataaatatg                                                   20

<210> SEQ ID NO 25
<211> LENGTH: 64956
<212> TYPE: DNA
<213> ORGANISM: Homo sapiens

<400> SEQUENCE: 25

| | | | | | |
|---|---|---|---|---|---|
| gacaccccag | ccacgccaag | ccgggaagtc | cccgcctcct | ggagctgaac | ccgcccctct | 60 |
| cccagaggtg | gagctgcggg | gggcgggaac | aggcacggag | aaaataaaca | agactaaaaa | 120 |
| gtcctgagta | gcgctgtgtg | gccgcaaacc | tgaacccacc | ttttgcacca | cgcgggaccc | 180 |
| ggcacgcttc | ctgccaccca | cccctgagag | ggctgcgcgg | ccgacccagt | actagaaaa | 240 |
| cactcgtcac | ctcaatcaag | acgggtacga | aggccaacgg | acgccttcct | ttagaacgct | 300 |
| cagcacacag | agcaacttct | cacgcctact | ctcaaatggc | gtactccaaa | ctagcactcc | 360 |
| cgacgtccag | ctgtgaaccc | agagcggcgg | aaagcccctg | aacccagcgc | ccgggcatgc | 420 |
| gcagacgcgt | tgttgtggtg | ggcgtggctc | cctccggacc | cggcgccccg | ccctccgccc | 480 |
| cgtgtccgca | tgcgcgactg | agccgcgggg | gtggtactgc | tgcatccggg | tgtctgaaga | 540 |
| tccgatgaaa | taacatatgc | aaaatgattg | ggtccgtgat | tggcattcca | gaaatggtag | 600 |
| ctgttattca | gccaacaaat | atttattgag | cacctactat | ggacttccct | ggtgctgagg | 660 |
| atacaacagc | aaccacagca | gtcaaaagtc | cctgtcttca | tgttgctcag | attctcatag | 720 |
| gggaaagcaa | ataatgaaca | aatacacggc | cgggcgcagt | ggctcacgcc | tgtaatccca | 780 |
| gtactttgcg | aggccaaggt | gggcaagtca | cctgaggtca | ggagttcgag | accagactag | 840 |
| ccaacgtggt | gaaaccctgt | cactactaaa | aatacaaaaa | ttagcgcggt | gtggtggctc | 900 |
| atgcctgtag | tcccagctac | ttgggaggct | gaggaaggag | aatcgcttga | acctaaaagg | 960 |
| cagaagttgc | aatgagccaa | gatcgtgcca | ctgcattcca | gcctgggtga | cagagtactc | 1020 |
| cgtctaaaaa | aaaaacctaa | atacacaagt | aaaaatatag | acctcgtcag | atgctagtaa | 1080 |
| gtgctgtgaa | ggaaactaaa | aggggaacac | aaggaaccct | tgtcaagggg | agaagaaagg | 1140 |
| ggagttgatg | ctgtcctttt | aaatagggca | gtcagaggcc | gggcacagtg | gttcacacct | 1200 |
| ataatcccag | cactttggga | ggttgaggtg | ggtggatcac | ttgaggtcag | gagttcaaga | 1260 |
| ccagcctggc | caacctggtg | aaatcctgtc | tctactaaaa | aaacaaaaac | tagccgggtg | 1320 |
| tggtatcacg | cgcctataat | cccagctact | cgggaggctg | aggcgggaga | atcacttgaa | 1380 |
| cctgggaggt | ggaggttgca | gtgagccgag | attgtgccat | tgcagtccag | cctaggcaac | 1440 |
| aagagcaaaa | cttcatctca | aaaaaaaaaa | aaaaatagg | gcagtcaggg | aaaactttcc | 1500 |
| tgagaagggg | atggtggagg | atccagggag | gtgaggtggg | gagcaagcca | gtacagttgt | 1560 |
| tccttgactt | tcgatggggt | tatgtcctga | taaagccatg | gtaagtagga | aatattgtaa | 1620 |
| gtcaaaaatg | catttaatac | atctaaccta | cggaacatca | tagcttagtc | tcacctacct | 1680 |
| taaacatgct | tagaacactt | acattagcct | acagttgggc | aaaatcctct | aacacaaagc | 1740 |
| ctattttatg | ataaagtatt | gaatatctca | tgtaatgtac | tgagtactgt | acggaaagtg | 1800 |
| aaagacggag | tggtgggatg | ggaactctaa | gcgcggcttc | cactgcatgt | gtgttgcttt | 1860 |
| cgcgccatca | taaagttgaa | aagcgttaag | tcaaaccatc | gtacgtcgga | ggccatctgt | 1920 |
| atctggtagg | aggagtgttt | cagacagaga | gaacagcagg | tgcacagagt | gcttttttcc | 1980 |

-continued

```
cagcatttta ttatgaaaaa tttcaaacat ctaccaaaaa aagttgaaag acttgtacag   2040
tgaaaagcca tacatctcac agctagaatc aacaattaac attttactgt atttggtttt   2100
tgacttatct atcctagatc ccttgtgctt tctgtagcag gtgacctgcc ttgaagattt   2160
aaagacagaa tatcaggaaa tgtagtcaga aaatggggcc ttttataaga gtcagagggg   2220
aagagcaaaa cctctgcttt tgacaaatct gttgggagag gccaactgca gggatacctc   2280
ccttttttaa tgaaagcatt tctgttctgc gaggagcggg atcctcttgt caagcagtca   2340
gtccctgctg cttccttact ggggcaggat caggacgcac agggatttgg agtgccttgg   2400
aaccaaccac cacccacgcc gtttgccagc tggtaaacat gcccatcagg tccgggggtt   2460
ggcattgcct ggacatcttt agtgttcatc ttgctgacat ctggtgccct cgggcaggta   2520
ggtgcagttg gctgcctggt ttacagagct tgtactgggc ccaggttagc agaggtcaca   2580
tccatttatc ccactgcgca gaggagttcc ttctcaggaa acccagttta taagaagtac   2640
tgactgccag aaatagagca gaaatgagaa ccaggaggca attgtgagag gaatggagac   2700
ttctgacctc tggggattgg ggtaccctcc cccttaattg ctgttggggt agcagagggc   2760
ttagaagccc atgttcctag acttttagaa ttggaagaag acttagaagt aatctaggct   2820
gggggtcccc aacccccagg ctgtggcccg ttaggaacct gaccgcacag catgagggat   2880
aggccagcga gcactaccgc ctgagctccg cctcctgtca gatcagcagc ggcattagat   2940
tctcataggg gcacaaaccc tattgggaac cgcgcatgag agggatctag gttgcgtgct   3000
ccttaggaga atctaactaa tgcctgatga tctgaggtgg aacagtttca tccccaaacc   3060
atccctccaa cctcaccccg gtccatggaa aaattgtctt ttacaaaacc cgtccctggt   3120
gccaaaaagc ttggggaccc ctgatctagg ctacagttaa gtggtcaaac acccaggtcc   3180
tgaagttagg ctgcctgggt ttaaatccca gctctactgc ttactagccc tgtgaccttg   3240
agcaagtcac ttagtttttc tgtgcctcag ttcactcatt tgtaataaat cctaatagta   3300
cccatcccag tgtcatgaac taagttcata tatgtaaagt acttagaatg gtgcctagca   3360
agtacttaat aacagttagc tctgaaaatg tataaagcaa aattaaccaa tgttttagtg   3420
gtttgcagcc aactttttc tatgcgtgtg ctaacatatt attttataag agtgggaata   3480
tattgtacat gctgttatat aacttgcttt ttcactaaac agtctatcct ctgtgtcagt   3540
tttgataaaa gcgttttcct cttgcttttc ctgcatatgt tcagaaccat catattggta   3600
gcaagtttca tgtcctgtag ttttcttaac caaccccctg ctagtggaca tttaggttag   3660
tctcagtttt ttccttctgt aaataaagct gcactgagca agaagtgact gatgccaagt   3720
gactagatga ccttaggtat gacctctctg ggtcttggtt tcttggtcta aaaacaaaat   3780
gacaggattc gactgggtga ttaaaatctc ctctgatcta cataggaatt gttttcaaga   3840
catttctgca ttcctctagt gacagggtgc tcactacctc atgagtattt cagtggacaa   3900
ctgtaatggt caataaagta tccactttcc acctccctgc agctcctggc cctggcttta   3960
ttctctgggg ctccacacat tcagtttaca ctcagtggcc agtggctggg accattgtag   4020
aaaataagga aactccaatt ccttccttct tttcttcctc tttcatctct tcctccctct   4080
ctacatccct ctctctcttc cttccttcct cgacacttac catgtaccag accttctgcc   4140
aggcacatgg atgggagcac aggggaagtt ggctgcaggg ttagaactaa gtcccaagcc   4200
ccctaaagct catgccaggg gactggactg tccagtactg agggatgggg atgctgaggc   4260
tggtggcctt cctcaaatgc actgtagtgc cccaggcaga gtcctgggct gccctgtgag   4320
gaggtgacca gaggtagagc aacttcaccc taaggctgga tcaggatccc ctccaggttt   4380
```

-continued

```
ttactagagc caaacccaca tctcctttct cttctgccac ccccccttaa aatgcttaga   4440
aacacataga tttaaataca aattcaaatg taagtaattt caactgtgta actatgagga   4500
gtcagttcta cgtgggtcct atctgtatcc tccccagggc tcagctccat tctttgcttt   4560
cattcattct cattcaatac attgttgtta agagctcact gggtgccctc tctgtcatgt   4620
agtaaggttt taaaaagaaa gcctcttctg agcttcagtt tccttattca taaaatagga   4680
gtattgatcc attccttgct tttcttacaa ggatatgctg aagatgactg aagtacagag   4740
taaagaagga ttatgtttgg gtgtcaaagg aatagaatgc cctctttcaa actgagcaca   4800
gcaggaacct gtaacaggaa cacagcaact tgttgaatga atgacaatat tggaaaacat   4860
acatttcctc ccctccccat catagtccct ctgcttccgt gttaactcca tagagaggcc   4920
agcacaacca gccttgcagc ctgagataag gcctttggcg ggtgtctccc ctatcgctcc   4980
ctcaagccct caagtaggtg ttggagagag gggtgatgcc tggtgctggt ggaacccctg   5040
cacagagacg gacacaggat gagctctaag tacccgcggt ctgtccggcg ctgcctgccc   5100
ctctgggccc taacactgga agcagctctc attctcctct tctatttttt tacccactat   5160
gacgcttcct tagaggatca aaaggggctc gtggcatcct atcaaggtga gagttcattg   5220
gaaaagtggt cacaggagca aatagcaggg gcaggggcgg gggaggcctg tggttctcca   5280
ggggcacaga tgttcctttc tacaaaatcc caaggaaaaa gattccccca tcttcttccg   5340
tagattgcac cgaaattcag ccaacaatgt aagctttcct ttagaagcag cctgggcatg   5400
ccctcttctg tgaagcctgc cttgattttt cagcacagtg agaggcatcc tctttggtgt   5460
tcctcaaatt ccctctacca aatggtcttc ataattctct gcttctctgc ttccccttct   5520
ctctcctcag tggcaaggaa ttttttattt tttatagatt taggggatac aagtgcagct   5580
atcttatgca agcaatttca tgttgttggg tttttggttt ttgtttcctt tttgtggcct   5640
ctcgctcatt tcttatttct ttttgaggca gggtctcact ctgttgccca ggctgaagtg   5700
cagtggcatg atcatggttc actgcagcct tgacctccta gtctcaagca atcttcccac   5760
ctcagcctcc caagaagctg ggaccacagg agggcaccac catgcctggc taattttttt   5820
tttttttttt tttggtagag atgtgggtct ccctgtgttt cccagactgg tctcaaactc   5880
ctggacacaa gcgatcctcc agcctcagtc tcccaaagtg ctggaattac aggcgtgaag   5940
cactgtgccc agctctcttg ctcatatcta tactagtttt cttttggaag cttcagcctg   6000
ttgctacccc ccaccccac  ccccaccgac cccagctttc ttctcactta ggggctggga   6060
agtctgcatg ctgtctataa atccagaacc agaaggtatg gctgaagggg agggtaggat   6120
gatggttatt ttatattcag ctaaaaatat tcccagactg tgatgagaca actgtaaata   6180
agacagatgt ccacaatggt gtgactttgc ttttttaaaa atattgaaat gagtttcagg   6240
catctcagtg ggctgatagg ttgttgataa tagacagggc ctccttgaag aatgtccctg   6300
agacaaagtt gaagcttgag cctggttgag tccttgcttg ttcctaggtt gatatgaacg   6360
gctagttaac tggaagcaaa gagaagtcat cctgggggcc atggcagtga caagtaggac   6420
ttagggaggg aagcccttat accatttaag gtgctggccc agagaggagc cttcagtgac   6480
agacaaacaa gagctggcac aattttaatt cacttcaatt tactctaatt catttcaatc   6540
caatacaatt caatgcattc cattcattca accatgtatg acatccaatg tgggatccag   6600
actcatgatg attagagctg atatttatga gcacttacta tgtaccaggc actattctac   6660
atgctttaca ttgaaccctc acaataaccc aatgaggtgg gtactattat gatcttcgtt   6720
```

-continued

```
tttcatatga ggaaactagg catatggatg ttgagtaatt tgcccacggt cgctcagcta   6780
gcaatagcac agcgtattta aatttagcca ccctggattt agtttcctta cacttaacca   6840
ttatgcatca tggccccatt ttacagtggg cttgagtctt tgtcatataa cccagtaggt   6900
tagcagccac tattccaacc ctgtagattg actctagggt ccatgttctt taccccctgca   6960
ccgtgctact aacgtaggta caaaatgtcc tcagaaactc actttatacg gaagctcaga   7020
ggagggtcca caacccaggc aggggagacg atggtgtcag gggagggagg tgactgccca   7080
gccaggtctt gaaggctcag taggaattac ctgtgggaca aaggagggtc atccaagtga   7140
gggcacagtg ggtgccatgg cgtgcacaca caatagagca gactgagcct gggcttaaca   7200
ttgcattgcc ctggagccta aaaggggaaa caaagggccg ggcgacgtgg ctcacgcctg   7260
taatcccggc acattgggag gccaaggctg gagaatcacc tgaggttagg agttcgagac   7320
cagcctggcc aacatggcaa aaccgcatct ctactaaaat tataaaaact ggctgggtgt   7380
ggtggcacac gtctataatc cgagctactt gggaggccat tacactccag cctgggcgcc   7440
agagtgagac ttcatctcaa aaaaccaaac aacaaaaaca acaacaagaa caacaaaaaa   7500
acaaagagga gagcagggac tgggtgtggt gactcatgcc tgtaatccca aacactttgg   7560
gagaccaagg caggcagatc acctgaggtc aggagttcga gaccagcctg gccaacatgg   7620
taaaaccctg tctctactaa aaatacaaaa attagccgga tgtggtggca cgtgcctgta   7680
gtcccagctg cttgggaagc tgagggagga gaattgcttg aacccaggag gcagaggttg   7740
ctgagctgag aacatgccac tgcactccac cctgggtgac agagtgggac tctgtctgaa   7800
aaaaataata gtaataaata aaaataaaga gggaagcagc gggtggcaga ctcactgggc   7860
tgcatacgaa gtttggcttc agtctgaggt ccgaatagta aacagcagcg agacaagttt   7920
gggtttgggt catggaggaa gccatgccag ggctggtgtt gggcacaggg aaaggggcat   7980
ggcttgagac accagaccag cgtggaggct gtagtgtagt attgacctga ggacttcaac   8040
attctgatgg tgtacacacg attttttgag catgtaccat ggttatatat tacactttaa   8100
gtattacttt aagtattact acattaatat attttgtatg ttacaataaa tacatacaaa   8160
ttaggaaaat tgaaagagat caaaatgaaa tatataatat tttcaaatta ctaatcataa   8220
tggtgtcaat ctccaggcag ggtccattgc tacagttgac gatagtggat gaaaattcac   8280
tcctcagagt cttcttgata atttgaaatt gtcttgattg acttgtcaga tctgattaga   8340
tcaacatgtt ttaaatctcg aatgtgactg acagcttgta cgaggagaag tttcactctg   8400
ccttttccct tttgttcact tgactgccat tatttctatg cttccaatct gtgtttttct   8460
gcacgagttg gttaagccat tacttcattt tgtgaaagtt tgttgagtta aacttaggta   8520
acttaatctg tcaatccact taattgaatt cagtcctggt aaactataat agattattca   8580
aacctgccaa ttctaaaaag acattttgag acaatcagga aatctgaata tagcatgaat   8640
atcttacgat atacaaggat tattgttaat tttgttaggt atgataaaag catggtgggt   8700
tgtttttgtt tttgtttttt aagtctccat ctgttagaga ggcacattga aatggcatga   8760
tatctggggt ttgcttttat gccagaaaaa agaaaaagta cagaaggatt atagaaacaa   8820
gattggtctc atgtgacaat catcagagtt tggagatggg cacgtagggt catcgtgctg   8880
ttctctctgt tttcgtatat gctttaaaag ttctgtaata gttaattaaa aaaaaaaaaa   8940
aacaccctgg ctgagcattt agggaggcca agtggggagg atcgcttaaa ccaaggagtt   9000
caagacgagc ctaggaaaca tagggagacc cccccccatc tctaaaaaaa aaaaaaaaaa   9060
aaaaaacttt aaaatttaac ccagtgtggt ggcacatgcc tatagtccca gctactcagt   9120
```

-continued

```
aggctgaggt gagaggcttg cttgagcctg ggagcttgag gctgcagtgg gacgggattg   9180
taccacttca ctccagcatg ggcgacagag caagaccctg tctcaaaaaa aataaaaata   9240
tttgaggtga agcgaggctg taataacaaa tttaaaaata taaataaaac ataaaggctg   9300
ggtgtagtgg ctcacgcctg taatcccagc actttgggag gccaaagcag gcagatcacg   9360
aggtctggag atggagacca tcctggctaa cacgatgaaa ccccatctct accaaaaata   9420
caaaaaaatt agccgggtgt ggtggcgggt gcctgtagtc ccagctactt gggaggctga   9480
ggcaggagaa tggcgtgaac ccaggaggcg gagctttcag tgagctgaga ttacgccact   9540
gcactccagc ctgggcaaca gagcgagact ccgtctaaaa aaaaatgaaa ataaaaataa   9600
atgaaacata aaaccctgcc attagttgca atatgaagaa tatagagaaa tgcatatcaa   9660
atccttctca ttggaccaat attcccttag ggcaccttcc aaagctagga gactcaaggc   9720
tgtatgacat cctgagcaag tgaggggtgg cttctgggtg aatctgaata ttaaatattt   9780
gcagaattga aaacttcaca aagtaccttt agagatagaa tagcctagat ccatgtttct   9840
caaagtgtgg tccccagacc tgctgcctca gcatctcctg gaaatttagt agaaatgcag   9900
attctcaggc cctaggccag acctactgat cagaagctct gggcctgggg cccagcagtc   9960
tgtgttttca caagccctct tggtgattct tctgtgcatg aaagttcgag aattcctgga  10020
gctagactga ttcaaatctt gcctctgtat cttagagacc ttgggcagat tagtcaacct  10080
ctttctgcct ctgtttctac ttctgtcaga ggatgatagt acttgtttca ttaagttgtt  10140
gaaaggataa atgaattgac acacataaag agtattagct tttattatca aaagcttttt  10200
ttttgagaca gagttttgct cttattgccc aggggagtgc agtggtgcga tcttggctca  10260
ccgcaacctc cacctcccag gttcaagtaa ttctcctgcc tcagcctccc gagtagctgg  10320
gattacaggc atgcgccacc acgcccggct aattttgtat ttttagtaga gatggggttt  10380
ctccatgttg gtgaggctgg tctcgaactc ccaacctcag gtgatgcacc cgccttggcc  10440
tcccaaagtg ctgggattac aggcgtgagc caccgcgcct ggcccaaaag ctttaatttc  10500
ttaatttttt aaataaaata aataaaacta gaattgcttg ttttcttcca gctaccctgg  10560
tgattgtatt gagcattttc tggggtgtgt gttctttgct gtaatgacta ctggtctgga  10620
tgacctgtga tgagaccaga tgggcagggg cagtggagga gattctagag atatttagga  10680
gataagtcag ctgtacttga tgaaaagagt ggggagttaa ggctggctgc agatgtatga  10740
tttggcatag agaggtgcca gttcctgaga tgagagacag aaggggaggg acaggttgtg  10800
aggatgaatg aacaatgata tgttcattct gggcttggag ttaaggggcc tatgatatgc  10860
ttaggggaag cagagagtat caattaccta ttgctgcata acagccaccc caaacttagt  10920
ggcttaaaat agtaaccttt taatttactc atgatcatga ttctgtggtg caacaactgg  10980
gctgggttca gctgggcagt tcttctgtta gtttcaccca gggtcattca tgcatctgca  11040
gtttggggtg ggatggcctc agatgacctc attcacgtgt ttggcagttg gtgattcact  11100
gggggccatt actgtaacaa tcgcctacca ggcagagctt ccctaaggct tccaaactag  11160
gagactatcc tgggtcctgt gctgtggata ccactcagtc ccccatcccc accccatatt  11220
cctcaaaggc agagagaggg gctactagaa gacagaggag ttttcccagt gacatgtaaa  11280
cactccaaac cctggcacct tccacactgc agctttggtc tgcccctttg ggaaatctct  11340
gtttttcttc ccaggctgct ggaggggtga gagtcgccgg tagagtagag gctgtgggcg  11400
aggaggtggc ggcctcctga ggctgcagtg gtctttccag gcagcagtgg gagcacaggg  11460
```

-continued

```
tggaggtcaa ccctagagcc tgggagagtg aagctgggtg tgacttcaga gctgttggtg  11520
ctgaagtttc tgcaggccag aaggaggggc aagagtggga gggggcgcag atccagaatc  11580
acggaggcag ctgaccggag gaggcagctg cccaagggga tggactcaga aggccaaagt  11640
gctgttatcc aaacgaactc tttgcaagtg gtctctttgc aacaggcctg gggagagca  11700
gtcttgccta aagtcacacc gctaatcagc ggccggcacg gggtaacagt tactaacact  11760
cactacgtac ccaatgctgg gcgaagtgac ttgcatgagc cagcgagctc aatgctcatg  11820
gcaatcctct gagcagctgg cattgtttca tctcaatttt acagctcagg aagctgggac  11880
acagaggaag agccaggctc tgaacactga caacctgatt gagagaccca cactgttcat  11940
caccgttacg ctatatatgc tgtatagaaa ggcaggatgg cataatggtt aaacctaggt  12000
aggtagggtt tgaatcctcc tgctaccatt tactagctct gtgacttgga ctagttatag  12060
cacctctctg tgcctccctt tccccatctc taaaatgggg ataataaatc gtacctccta  12120
cctgaggctg ttgtgggcta agtctgtaag gcacgtagaa cagtgcctgg aacgtggggt  12180
actgtctatc tgtgtgcctg ctgttacaac aatggtgagt attgccttat ctctcgctgc  12240
tgaactacca ggttagactt ctttctgcaa gtcatgaggc tttcataaac ttttcctgaa  12300
ggctttccgt agaatgtaca attcccctct gggtccaggc atgggcgccc gggtagcaca  12360
tccacttctt atcacccctg aacaccttag agcccatcag cttatcaaac cagcagctga  12420
tgtgagtgca gagcagactg tgagaggtgg aggctgatac cagtgaggat gctccaagct  12480
gggacccagc cctgaagcgg gagcccagat aatggatggg tggaaatggg cctggagccc  12540
aggagaagtg ggaggatgag ggggcagggg gaggagaagc ctgaaatcaa atgttatttc  12600
ctgaccagtt tggggtgcat gagctctgtc aacagctcat ggaaactgct gccctaattt  12660
catcttgttg gctgaggcac aattcctctc tcagggacag tgtagagcct tggggaggaa  12720
ggccctgagc gcgtatacct ggaatcaggg aatcgggatc aggggcagca gctgtgccca  12780
ataaagcccc cacccaggat cctctgactt cctcatctct tttttttttt ttttgagctg  12840
cagtctcact ctgtcatcca ggctggagta cagtggtgcg atctcggctc actgcaacct  12900
cagccttctg ggttcaagcg attctcctgc ctcagcctcc tgagtagctg ggattacagg  12960
catgcgccac catgccaggc taatttttgt atttttagta gagacggggt ttcaccatgt  13020
tggccaggct ggtctcaaac tcctgacttc aagtgatctg cccacctcag cctcccaaag  13080
tgctaggatt acagacataa gccactgtgc ctggcctttt tttttttttt tttttgtaa  13140
acagggtctc cctctgtcac ccaggctgct ggagtgtagt ggtgtgaccg cagctcactg  13200
cagccttaac cttctaggca caagccatcc tcctacctca ccctcctgag tagctgggac  13260
tacaggcact cgccaccacg cccaagtaat tttgtatttt ttgtagagac aaggtcttgc  13320
tatgttgcct aggctggtct tgaactcctc agctcaagca atcctccctc cttggcctcc  13380
caaagtgctg ggattgtgct gggattacag gtgtgagcca ccatacctgg tctgacttcc  13440
taatctttag ggccccaact ctgcccttat ccaggcaact ctcctctccc catcttccac  13500
taacttcttt ggaatattcc agagctgtaa aagccttaga gagtatcaag tccaactcct  13560
atgtgttaca gacagggaaa ctgaggccta aagagggtaa tggacttgcc taagatcact  13620
tagtgaggtg agagaagaaa gagctagaga cagcctagcc tgtgcaagga catagttcca  13680
ggcattcaga gctgggctct gctgccggca tgtttggggc ctggtagtta gttcactgct  13740
gaactaccag gttagatttt ctttctccaa gttgtggagc tttcataaac ttttcctgaa  13800
ggtcttcctt acaatgtaca attctcctct gggcccggtc atgagcgccc ctcacaggct  13860
```

-continued

```
ctctctggtc cccttctgta aaatgagagg aaaatggaag aattgctcta ctcatggaat  13920
cttcaataag tctgggccct atgcatatag cattgctaca aaatggcaga tgcactttaa  13980
caatcgtgtt taataaaagg ttggatttgc atatctgaag tggggcatgc agtctccaac  14040
tgaacacaag cctcactgct cccgcatgtg cactgcacct tcatatacat atttcctgct  14100
tggctcctga gggaatttga gtaatcccaa gaggaacccc tgtagaaaat gtcccctggc  14160
cacacacccc cattcctaag gatgcaagca ggagatagaa acattccctg cacctccctc  14220
cttgttgtca gaagaagtgc aaagagttga atccttccta atgcccactt ctcacccacg  14280
ccccaaatcc ccaggtccca tggaggtcct tgggggcctc ctatatcctg gtggtgtcag  14340
gttgatttgg aaatgtcagt gtcctccctt gtcctctctg gcagaccctg ggtatgtgta  14400
tgtttcaatg gaagtgaatt taaatgtact ttataaatca aagacttttt ctgagacttt  14460
ggagagttcc agtaatgaga gcttctcatt gttatcaagg ccagggctgg agaccagtgg  14520
caggtgagtt cctattgctg tgattgtcat gatgatgttg atgaacagtc actatttatt  14580
gagcgttctc catgtgccag tcactgtact aaacattatt tcctttggat ttcccagaaa  14640
cctctcaggt gggtctaatt acccttattc agctgataag gaaagtaagc aacttacaag  14700
accacagggc tatgaagtgg aaacacataa attgatattt cattttattt atttatttat  14760
tttgagacag agtctcactg tgtcgcccag gctggagtgc agtggtgcgg tctcagctca  14820
ctgcaacctc tgcctcccgg gttcaagcga ttctcctgcc tgcctcccga gtagctggga  14880
ttacaggtgc ccaccaccac atccagctaa ttttttgta attttagtag agacggggtt  14940
tcaccatgtt ggccaggcta gtctcgaact gctgacttca tgatctgccc acctcatcct  15000
cctaaattgg tatctttata tgtccaaaag agtcaactgg tggcaattta gtgaggttta  15060
atctaatagg aaatgataga gctgggatcg aacagagcca tgtgaactca aaacctatgc  15120
ttccccttcc accttttga aaaacattgt ctaggctggg cacgatggct catgcctgta  15180
atcccagcac tttgggagac ggaggtgggt ggattacatg aggtcaggag ttcgagacca  15240
gcttggccaa aaattagcca ggcgtggtgg cgcgcgcctg tggttcccac tgaagcacag  15300
gaggctgaag cacaagaatc acttgaaccc gggaggtgga ggttgcagcg agccgagatc  15360
gcaccactgc actccaacct gggcaacaga gagactctgt ctcgaaaaaa aaaaattgtc  15420
tacatgctgg ttgcagaaaa tttaaacact aaaactaaaa aagtaaaaca cctcccaaac  15480
ttagagacaa tattaatgac ggaaaaaaaa ttcttcaaga tctctctctc tccagtcatt  15540
tattcatgtg cgaaaacagt tggtgattat tgataaaata gcttttagag tttggagcaa  15600
ttatgtgcat tacatatacc atttgattct ggcaacctaa tgaaggagta tgatcatttc  15660
ccctatttaa cagacaagaa caagaagagg gagggcagat ggtgtggtag tctaaggcac  15720
aggctccagc agattatcta ggtgtaaatc ttggctgtag gccaggccct gtggctcatg  15780
tctgtaatcc catcactttg ggaaaccgag gtgggcagat cacttgaggt caggagttcg  15840
agaccagctt ggccaacata gcgaaacccc ttctctatta aaaatacaaa aattagccgg  15900
gcacggtggc aggcacctgt aatcccagct acttgggagg ctgaggcagg agaatcactt  15960
gaacccagga ggcagaggtt gcagtgagcc aagatcttgc cactgtactc cagcctgggt  16020
gacgagtgaa actctatctc gatattaaaa aaaaaaatct tagctctacc caccggggca  16080
agttacgtaa cgcctctgtg ccttggtttt catatctgta aaatggtgac agtaacagca  16140
cccacgtcaa agtgtggttg tgagaacgaa acaagatagt ctatgtaaag tgattaaaac  16200
```

-continued agcgtaggca catggtaaac gcttaggaaa tgtaggctgt tataaagctc agagatgtta 16260
agtaactaga tcaagatcac acagttagag ggtgccagag tcctgatttg aacccaagtt 16320
tgtctcgttc tggagctcaa gctgctaacc ctttttcaaa actggaatta aaccaaagtg 16380
ctcaccctcc gctttgctgg gcccctccct gccctcaggt gcgtctcttc cactcacctg 16440
ccacagcagc ctctgctcag ggtctgagac cgggaaaggt gagggctacc caggtggccc 16500
tgatgttttc tgccagccag ctcaccaggt ccctcgcagc aggcggcaaa gggagggagg 16560
tttgctgtga agattatgtg gttcccaaca acaagagcgc tgggcctatc tctgccctct 16620
cttttctgtg tgtcctggga caagtcactt ggcttctgtg gcttcatttt ctcatgtgcc 16680
cagccagggg gttggccctc atatgcaata acagcagcaa tgacctttac tgagtgtcca 16740
tgtgcgtcaa gcacgtgtgc tttacacttg ttcttattat taggtttaat aatagaataa 16800
ttgccacatt tactgagcac tcattatggg ccaggccctg ccctaagtgc ttaattagct 16860
ttagctcctc taatccttat cttatcccca cacggcatgt tatgttatcc ccattattca 16920
gttgagaaca ttgaggctca aagaggcaaa gtaacttgac caaatacttg taaacgatct 16980
tgcatgcccc ttccagctgc catttagtaa gactctaatt tcataccacc ctaaatctcg 17040
tctgcttccc cctcgtcctt ctcgccatct ccccaccgag cagttggcca agatctgacc 17100
gtgatggcgg ccattggctt gggcttcctc acctcgagtt tccggagaca cagctggagc 17160
agtgtggcct tcaacctctt catgctggcg cttggtgtgc agtgggcaat cctgctggac 17220
ggcttcctga gccagttccc ttctgggaag gtggtcatca cactgttcag gtattgggat 17280
ggtggctgga tcacttctgg gtcatagagg gaatggaccc cgaaaggaca ggttccagaa 17340
gatctgggat attgccccct ctctgtctag caccagtgct gtgcaatatt taggacatcc 17400
ttatactaaa agattattca ttgtttaaaa ttcaaattaa ctgggcatcc tgtattttac 17460
tggacagccc tactccgtgt atcacaagga atccaggcct acattcctcc tgcatccttt 17520
ctttcctgtt attgtcgatt atgattttgt aaagttacat aatcaatata agtttatgga 17580
aaacgtaaga aggaaacacg ttagacagag agaaatagac atgccacacc tagagagaca 17640
ttctattttt tttttttttt ttgagacgga gtttcacttt tgttgcccag gctggagtgc 17700
aatggcgcta tctcggcaca ccacaacctc agccttctgg gttcaagcga ttctcctgcc 17760
tcagccgcct gagtagctgg gattacaggc atgtgccacc gcgcctggct gattttgtat 17820
ttttagtaga gatagggttt ctccgtgttg gtcaggctag tctcaaactc ctgacctcag 17880
gtgatccgcc cgcctcggcc tcccaaagtg ctgggattac agacatgagc caccgcgtcc 17940
agcctgagag acattctctt gaaaagaaag gactttcagc cccctaatgc tgctagacaa 18000
taaatagcca tgcctttatt ttcattaaat tacctgtgct ttgtttacat gcatttgtgt 18060
gaaatgctaa gaaccatcac aactaatgta tggtgccaga agtcagaata gttgttacct 18120
gggcaggagg tggatattga ttaggaagga acacaaaata accgcatggg gtgcagaaaa 18180
tgttctctat gttcacctgg gtgatgatta cacatcaagc tatacacgtt ttaaaagggc 18240
attggcactt aataggagga agtaggctaa attttttcct gaaacattgt tttgttttgt 18300
tcaaacctct gaatccctgt gctgcccaga tgatggtaaa cgtcatccta ggcatcttag 18360
ggacctctca aggccattcc agcctcccct tctaagaccc tgctaaacct ctgggcactg 18420
ctgttaaaca tttctctatg agccaggaac tgtgctgagc actccacaaa tattattttg 18480
tttaactctt ccgggtaggg atctaacctg gtatacaggt aaggaagtgg aagctcagag 18540
agggcaaggc acttgcctag ggccacacag ctaagtggtg gagatggctc caacttttta 18600

-continued

```
ttataacctt ttccacatgc tccagagtgc tcagaacatg aaacacagtc tagccagctc  18660
ccgattggcc ctggagggaa aaaactttat atatttttct tttttaaaag gtttagaggc  18720
tgggcatggt ggttcacacc tgtaatccca gtacttttgg gaaccgaggt gggcagatca  18780
cttgagccca gaagtttaag accagcctga ctaacacagt gagatcctgt ctctgcagaa  18840
aatagaaaaa tcagctaggc gtggtggtgt gcacccacag tcccagctac ttgggaggct  18900
gaggcaggag gatcacctga acccagtgag gttgaggctg agtgagccat gatcgtgcca  18960
cttcactcca gcctggacaa cagagtgaga ccctgtctca aaaaacagtt ttaggggccg  19020
ggcgcagtgg ttcatgcctg taatcccagc actttgggag gccaaggcgg ggggatcatg  19080
aggtcaggag atcgagacca tcctggctaa ctcggagaaa ccctgtctct actaaaaata  19140
caaaaaatta gccgggcgtg gtggtgggcg cctgtagtcc cagccactcg ggaggctgag  19200
gcaggagaat ggcgtgaacc cgggaggcgg agtttgcagt gaaccgagat ggtgccactg  19260
cactccagcc tgggtgacag agcgagactc cgtctcaaaa aaaaaaaaca aaaacagttt  19320
taggccaggc gcggtggttc atgcctgtaa tcctagtact ttaggaggcc tagcaggtgg  19380
attacctgag gtcaggagtc cgagaccaac ctgagcaaca tggtgaaatc ctgtctctac  19440
taaaaacaca aaaattagct gggtgtggcg gcaggcacct gtaatcccag ctacttggga  19500
ggctgaggca ggcgaatcac ttgaacccgg gaggcggagg ctatagtgag ccgagatcgc  19560
accattgcac tgtagcctgg gcgacagagt gaggctctgt ctcaaaaaca aaacaaaaca  19620
aaaacagtct atgagttaat tcccaccaga attcaataca cacacgcaca catgcacgca  19680
tacacacact gtgtccacct gggaagtgac aaagggcacc ctggggggatt tcaaatggtg  19740
gtggccctgg tttggtgttg ctgccttagc ttaaggtcac accagccttc agcctcctgc  19800
cccacagtct agggctgctc ccctcatctg atgtccacag ggacctgttt gttcttgact  19860
caatctagaa agacgagaag ggagagaagt cactcgcagc ctgagtgaac tcccctgccc  19920
cacccctgac tgcttggatc cccctagggg tgacccctgc tgaaactggc tccttcctga  19980
ccggttcccg tcagggctgt gctgatgggt ggtgcccagg cctgcccctg gggacggggt  20040
actctccctt ggcaacactc cagcttgtgc cacttgactt gggactgatt tggttctgtt  20100
ttgagtccct tcaggggagg ggcctatctt attcaacgtt gttgtttgtt ttcctcacat  20160
actgataact tagcaaatgg ctattggagc aaaaatgaaa ataaacggaa ctctgaagtg  20220
ggatgtttta aaattttatt tattttttta gagacagggt cttgctctgt tgcccagtct  20280
ggagtgcagt ggtacaatca tagctcattg cagcctgtgc ctcctgggct caagtgatcc  20340
tcccacctca gcctcctgag ttaaattttt ttacaggcgc ctgctaccat gccctgctaa  20400
tttttgtatt tttagtagac aaggggtttc accaggtggg tcaggttggt ctggaactcc  20460
cgacctcaag tgatccacct gcctaggcct cccaaagtac tgggattaca ggcgtgagcc  20520
actgtgtcca gcctaaaact gtttttgaga cagggtctca ctctgttgtc caggctggag  20580
tgaagtggca tgttcatggc tcactcagcc tcaacctcac tgggttcagg tgatcctcct  20640
gcctcagcct cccaagtagc tgggactgtg ggtgcacacc accacgccta gctgattttt  20700
ctattttctg cagagacagg acctcactgt gttgctcagg ctggtctcaa actcctgggc  20760
tcaagtgatc tgcccacctc ggctctgaaa agtactggaa ttacagcctc ctgagtagct  20820
gagaccacag gcacacacca ccacacctag cttttttttt ttttgctttt tgtagagatg  20880
gagtctcact atgttgccca ggctggtctc aaactccagg ccttaagcaa tcctcccacc  20940
```

-continued

```
tcagcctccc aaagtgcgaa gattacaggt gtgagccacc attcctggcc ttaaaagtgt  21000
gatattttta atgtattttg aaatctgcag gactctccct agaagataat agcaataacc  21060
aactccttta ttgtgcttga cgtatatcaa ctcactttgc ccttaccgtg gctccagagg  21120
cattgggtcc accttataaa tggaggcacc aaggcacaga gtgattaaat aaattgccca  21180
ggatcacaca gccagaaagt gtctgagtca agattccagc ccaggcagcc tagacctgag  21240
agcacgctcc taaccactgc acatcactgt cttagcacct cctcagcaca aactggccct  21300
tgaggaatga aataccgccg ccggcacaca cgctcctgag ttaagccttt gtcaatgaaa  21360
tgaacaccca cttaaaagga ataacctgtc caggcacgat ggaacattga gtaacccctt  21420
attctaaatt cctggtccct gtaagactcc ttccccatgc ccttgccctt ttctgacctt  21480
cccctaaagt ccttgaggct taagcgggca tagtctgcag caaacactgg ggaagctgag  21540
tccagacttc agagcacagg ctttggatct aggccagctg gatttgaacc tcacatttgt  21600
gatcagctgg catgactgtt tccaaaaagt ccattttaat cctctacgtg accctctgta  21660
aaatgggata ctgaatggtg agctagcacg attttacaga gagtgaattt tttttgtgtg  21720
tgtgtgaggc agtcttactc tgttgcccag gctggagtgc agtggtgcag tctcggccca  21780
ctgaaacctc tgcctcccgg gttcaagcga ctgccatgcc tcagcctcga gagtggctgg  21840
gattacaagc atgcaccacc atgcccgggt aatttttgta tttttagttg agacagagtt  21900
tcaccatgtt ggccaggcca ctcttgaacc cctggcctca agtgatccac ctgccttggc  21960
ctcccaaagt gctgggagta caggcatgag ccactgcacc cagccttata gggttaaaat  22020
ttaaaagagg tgatgctgtt acaagcctgt tttacaaaat gctcttataa taaatcatta  22080
tcatcactgt tgctgtggtt gtagcatcat catcattaac tcccagaggg aggagggagt  22140
ctcagagcaa gctgctcagg ggagactgga tgtccatgga ttgtccagct cagtaccact  22200
tcctccagga agtcctccct gataagtcca gtcagcatca ccctctcctt ccaatgaacc  22260
ccactagcct tgtgatatca cagatattct tagttgacag gctcatggtg tagcctgtct  22320
agatcataag tacatttttt ttttttttgg atcataagta tcttcaagac caaaataatt  22380
ttctactcct gagcatgctc attggtcaaa ggaaggaagg aatcataata gcgttaataa  22440
ggctagcgtc ttttcagaag ttggttcttt gtgccagtct tggtgctaga cacaccgata  22500
ggaagaatac tccttcacat ccccaggaca ccaacatggg atacgtttga tcatcattct  22560
taatttgcag aaggagaaat aggctcagtg agatgaaata gccactccag tggcaaggct  22620
gggactggaa gccgggcttg tcctgattcc aaatccagtt tctttccact gccacggaga  22680
cggagagaag ggacagtggc cccagatggg gatggggtga ctggatgtgg gcaggcctgc  22740
gggggaagag tgccctctgt tgagcatccg aatgatggca gcagaaaaga agactgggca  22800
gaatcccagt tatcagatcc cctgagggaa cagtcacccc gatcaccctc agtcagatga  22860
gtgtgtgtag atcaatgcct catagatgaa ggcactgagg cacagagtgg ttaagtcatc  22920
tgccagacca catggctcag ggtgcagagg ccaccttaac gggagaagag atggtcactc  22980
cactctgcag catcagcgcc caggtgggta gaaatcttgt cttctattcc cacagaaagt  23040
aggtgcccaa cagtgtttgt tgaaagaatg aatgaatgaa tgaatgaatg aatgaatgag  23100
tgagaggcat ccttccttct cagtcgtcct ggctctccct ctctccccca gtattcggct  23160
ggccaccatg agtgctttgt cggtgctgat ctcagtggat gctgtcttgg ggaaggtcaa  23220
cttggcgcag ttggtggtga tggtgctggt ggaggtgaca gctttaggca acctgaggat  23280
ggtcatcagt aatatcttca acgtgagtca tggtgctggg aggagggacc tgggagaaaa  23340
```

gggccaaaag ctccatttgg tggggtttcc agggttttga aaaataaaga caacctgtaa 23400
tcccagctac ttgggaggtt gaggagggaa gatcacttga ggccaggagt ttgagaccag 23460
cctgggcatc atagcaagat cctcatctct aaaaagtaat tttttctaaa ttatccagtt 23520
gtggtggcat gcacctgtag tctcagttac tcaggaggct gaggtgtgag ttggaaggat 23580
tgtttgagcc caggagttag ggaccgagct gggcaacata gcaagacctc atctctaaat 23640
aaataggtag gtggatagac agatagatag atagacagac agacagacag acagacaggc 23700
tgggtacagt ggctcacacc tgtaatccca gcactttggg aggccaagga gggcagatca 23760
cctgaggtca ggagttcaag accagcctgg tcaacatggg ggaacctcat ctctactaaa 23820
aatacaaaat ttagctgggc atggtggcag gcgcctgtaa tcccagctac tcaggaggct 23880
gaggcaagag aatcgcttga acccgagagg tggaggttgc agtgaaccga gatcgcgcca 23940
ttgcactgca gcctggggga caagagcaag acttcatctc aaatttaaaa taaagaaaaa 24000
agaaaagaaa agattgatag atagatagat atccaaatga gtttacaaaa atgtggtctg 24060
tgcaaatgtt taaacacaac aaaccaatgc ctttaactac tacagtataa tcctgtagga 24120
ttgtgctatt catgatataa ttatggttat ataaaagtaa ttaattctca gagcctcacc 24180
agcagtgggt ccagcaagtt tgtacagcca gcatcttctt tcagtcagtg cgtgtcagta 24240
actgcatatg tcctctcatt gggagagcct gtcgaaagtc taaatttgaa ggcagctgtg 24300
aaggtaaggc caatccaaat ggctctccca gatcctctgc tgtaaccctg accctgagtg 24360
aggacatagc caaccttccc atctcatagg tgagaaagct gatgcctgga gaggggaagg 24420
gactgcccaa gatcacatag caagatagtg gcagaaccca agcgagaacc cacagttcca 24480
gcctggctta gaagaaagtg cactggactt ggagtcaaag gctggggttt gcatcccagc 24540
tctgccataa atccctgtgt gactctgggc aatttaacct cttagagctt tagtttcttc 24600
atctgtaata tgagggtagc agtactacca catagggttt tgagggagta attgaattaa 24660
tcacatgaga tgatgcatgt ttacaaaaaa aagcatgaag cccctttact gtgcctcagt 24720
gtcccaaagg actttggatt ttactctgag aaatacaggg agaactaggg agtgttgggc 24780
agaggagagc catgatctga cttatgtttt aagatactct ggcttctggg ttcagaaaag 24840
actgaagggg caagagagga agcaggtgga gaccagagcg gcagtgattg ccatcatcca 24900
gactcagact aggacaatag ctgtgagagt gatgggaagt ggttggatcc tgactgtatt 24960
ttaatagcag aattgacagg atttgctgat agactgcacg tggggtggga gagggtcaag 25020
atgacttcaa ggttctcatc tggcacaact cagcggctgc tggtgccatt tactgagatg 25080
gggaatgttg gggtgggata gatctgggag ggaaaaccca gagttcagtg tcgaatgtgg 25140
tagcgttagg gttaaggttg ggggaggggg ggtagagatg tgtatgaaac atcccagtgg 25200
agacactgaa tggagatgta caagtctgaa gcttagtgga aaggttaggg ctagggatat 25260
aaatttggga gttgttacaa tacagatggt gtttaaagcc atgagaccca aggagatcac 25320
tcaggagtga ggataaagag agatgggaag aagtctgagg actgagtcct agaacaccct 25380
gcattttaga ggggggacat gtgtaagagc cagcaaagga gacagaattg tgcttggaga 25440
ggcaggagga agcccaggag agcgtgaggt cctggaaggc aaggaaagag agggccccag 25500
gtgggctgaa tgctgctgag aggtcaagtc ggatgagggc tgggaagtag ccattggatt 25560
tggccaggag accttggcat gcatggttgt agaggaggat gaaggcaaca gcctggcttg 25620
actgattcaa gagcaggaga tgagaaagtg gagacagcat gcaggggcag ctctgccaag 25680

-continued

```
gactttgcta taaaggggaa cagagaaatg gaggagaagc aggagggcaa taatccgata  25740
gagaggaaaa atctgatgat acagaagaga gatgaactgc aagagtcaag cctttgagtt  25800
ggaaagcagg agtgggattt tgagcactga tacctttagg ccgatgcagg gacagttcat  25860
cttttttttt tttttataca acattttatt taaaaaaatt attttcatag aatacatttt  25920
cacattagag attcccattg tgcggaaata acaatttatt acttatagtt ttatatttgt  25980
ggacagattg ttttagaaca agtagaatac atttgagaat taaatctcag tttacaatgg  26040
ataatatttt gatatgtctc tggggaaact tgcccttaaa tggaacttct gtatcttcag  26100
aagcactcca agcgtttctt cctaggattt agaaatttat aatatgagat agcagcattt  26160
cctaatttta aaatttccct agtatatgta accatcagta ggtggtatct actgactaga  26220
gagggaagtt tttgaaaatt aaacactgtc taattttctg caaagttttt attcatgaat  26280
taagagtatt tccctttgtc cattattccc aaggcaaata tggaaatttg atcatgtact  26340
aatcataata aagctggatt ctctttaaga gattgagaaa ttaaaaggca aaagctgata  26400
tatcatgttt agttatattg tgagtcttat aagaagctgg gaggcaaccc cattaactca  26460
ccagaataca gaactcagtc tcacaactta gatataattc ctctcaaacc ttttcctcaa  26520
agattaaatt ctgaaaataa tcttgtgatt aagagaagaa ggctgtccac caatgggctt  26580
atctgttatt tcttccttat tgtgagctta atggcatgac aaagcagagg caaagaggca  26640
tacatcaatt cttcaaagta ggaagtcaaa aaggtcagag cttccacagc atggcaacag  26700
ctttgcagat gcccacatcg tgatagttga aatagcaaag cccagcaaag gttaaagctg  26760
aaaatgccaa aagccctgcc ttggcagctt tctgcgaggc atccccatga acataatcag  26820
taacaacttg tccaaggccc cagtgaccat gaagagtgag ggctgcagcc agggaatagt  26880
ccgtcgcaga gcaaggattc aaataagcag ccggaagcag acccgggagc aaaacactga  26940
caaccctctc gctagtccag tggagagatg cagccttgga gccagaatgg tggctcggtg  27000
acaagtgtat gtgctgcact ccacaccatt ctgggatagg tcggtcctga agaaatgctg  27060
agatatgagc aggtctgacc actggagttc gcagcaacag agctcggcct ccttgggcac  27120
cgcaaacggc actcagcctc cagggaaccg ccatctcgtt cctgaggcgg agagttcatc  27180
ttaacgagag aaatggcagg gactgtgaat aggccggcag atttggtggc gggtgccaca  27240
ggttcagtct cctgcaggga gaggagaaaa tgccttacta attccttgta ttttctcaga  27300
gaaacaagag gcaccgtcat cagcctcatg tgagggtggg aaggagggat ggggtttgcg  27360
gagagggaaa gtgtggtatg gtcatctgtg ggagtggaag agagtgagag ggctgcaggg  27420
gtgcagcggg actgcaggct ggcaccaggg tccctagggc ttgtagttgg tggaaagtgc  27480
atcagtgacc agggctgtgt gcagctgctc caggcaggtg tggaagaagc agagttgaac  27540
ttgcccagcc tggagtgctg cccagagtga gcccaaagcc caggggagac cagagatggg  27600
gctgtttgca aaggaggaag tataacagta gcccacaaaa tctgagctgg ttaagaaagg  27660
agagagagtg aaaatgggga gcccagcctg gcagcctggg tacacatctc agctcaaccc  27720
acactagctg aatccatttg ggccccttcg ttgacctctc tgtgcctcag tttccctatc  27780
tatagaatgg ggataagaat aaggctactt cctagggctg ttgtgaggat tgaacaagtg  27840
accgaacact tgttcaattt tgaacactgt tctaaagcat ttaggacagt gcctggcatg  27900
gggtaagtgt tgcggcagtg ctgttatttt catcatcacc attgttctca ggctgcgttg  27960
attggagctg ctgaagggag gcaatttaag gaagtgagcc ggacagatag gaggtggtgg  28020
tggttatcag gtgcgatgct tgaaactgag gcttcggagg caacagttac tggtaatgac  28080
```

aaggtctaag gcttgacagt gggtggcaga agtgtaacgc agggaaagag acgagcggtc 28140
aaggagccga gagggaagga gttgggtgga ctaagatcat ttgtggaaga atgatggaga 28200
gaaaggctga agggcagggg ctgacatcat cagtgaccaa gaggcggccg ggaggctgag 28260
accacagcaa gaaagggaga gtgtgatggc atcttcttca agggagctgg ggatgtttgg 28320
ggtggaaaaa agaacaatgg tctgggaggg aatatgggaa attttttttt tttttttttt 28380
tttttttttt gagatggagt ttcgctgttg tcatccaggc tggattgcaa tgttgcaatc 28440
ttggctcact gcaacttctg ccttccaggt tcaagtgatt ctcctgtctc agcttcccga 28500
gtagctgaga ttacaggcac acaccaccac gcctggctta cttttgtatt tttagtagag 28560
acggagtttt gccatgttgg ccaggctggt ctcaaactcc tgacctcagg tgatccaccc 28620
gccttggcct cccaaagtgc tgggattaga ggtgtgagcc accgcgccca gcctggaagt 28680
ttgtatttat taatttttgg ttgtcttcat ctgtgtatgt gactttaacc cctaaatact 28740
tcagtgtaca tttctttttt tttttttctt tgagacagag tcttgctcca tcaatcaccc 28800
aggctggagt gcggtggtgt gatctcggct cactgcaacc tccgcctcct ggattcaagc 28860
aattcttgtg cctcaccctc ccgagtagct gggattaggg gcatgccacc atgcccagtt 28920
aatttttgta tttttagtag agatggagtt tcaccatatt ggccaggctg gtcttgagct 28980
cctggcctca gttgatccac ctgtctcagc ctcccaaatt gctgagatta caggcgtggg 29040
ccaccataac cggcctcagt gtatatttct gatgcagttg ggttctgtat ccccctccaa 29100
tctcatctcg aattgtaatc cccacgtgtt gagggcatga cctcgtggga ggtgattgga 29160
tcacaggggt ggtttccccc atgctgttct tgtgacagtg agtgggtttt caggagagct 29220
gatggtttga aagtgtggca cttcctctct ctctttctct ctctctctca cctgacacca 29280
cgtaagatgt gccttgcttc cctttcacct tccaccatga ttgtaagttt cctgaggcct 29340
ccccggccat gccaaactgt gagtcaattc agcctctttt gtttataaat tacgcagtct 29400
caggaagtat ctttatagca gtgtgaaaac agactaacac aatttcctaa aacaagggga 29460
cattctctta cataaccttt tttcagttaa caaaaatgag aaattgacat tgatatatta 29520
tgattacctt attctcattt caccaatttt ctcaataata tcttttctag aaaaaaatat 29580
atattttttg tggtcgagga ttacatcttg catttagttc tcatgtctta ttaaattcca 29640
tcaatctgga gcagtttctt catctttctt tatctttcat gaccttgaca tgttttgaag 29700
tttcgagcca gttcttttgt agaatgtggg tttgtctgct gttcctcatg attagattgt 29760
gggtatgcat ttttggtagg aattctccaa gagccgtgtg tgcccttctt agtatatcat 29820
atcagaagac atgctatcaa tttgccccat tactgggtgt gttaactgtg atcattgggt 29880
taagatggta cctgccagga tcttccactg caaagttact attttcccct ttgtaattaa 29940
taaacatctt gtgaggagat aatttcctat agaaatcctg ttgatcatcc aactttcacc 30000
cactgatttt agtgttcatt gattcttccc tgaataaatt agtactataa taattgccaa 30060
tggtggtttt ctaattccat ctttccttca gtagttggca ttcttctgta aggaaaagct 30120
ttcgcttctc tgttcatcca ctcatctatg tacttattta tatcaccatg ggctcctgga 30180
ttccggttta cacacttcca ttttctgcct tttctctctg cttaatataa ggattaatga 30240
gaactccctg attcccagga agaaaatgtc agcagagctt tcttaggcgg aatgaagaga 30300
attcagtgta agaaccataa aggtgtatct gtgtagtatg gacagtttta aaaaacaaac 30360
aaacacaaag aacctccaag ggcaggaggt gctgccagac tcaggagggc actagaactg 30420

-continued gctatgagaa gccactgaga tcccaggtag tctgtgctct ccatcttttg gctcttattc 30480
tctccgtaca tctaacatct ctgtacacca gctttctctt tagcgaaaaa cgtgtcccct 30540
ccacccaccc atccacctcc acttgttcct gcatttctat gtcccagatc ctgcagaaaa 30600
caactctttt ctctcagtta gtctcaattc tgtagtccag ggagagagaa tctgatcagt 30660
cccctgggtc atttttccac tctggtccaa gcagctacag ctggcatggg aaatagttca 30720
cacagtaaaa acatggctgt caagaagagg agtaaatttc agaggcagaa cactccctgt 30780
gagcccgaac ctcttcctgc tttgttgcag tcttcataac gattgcttta aaagactgca 30840
ttgatataac atcatctctc ttctctgcat ctttgacttg ctagcttaac tggtctagag 30900
gagggcttag cactgatttt gagtattcat tttcctcaaa acttcaattc agcctgggtt 30960
tcttcagcag gagggcccgg gggaaccaga gccagggacc agagtcattt cagtgcacca 31020
gctcaagaaa tgaatattcc aggccaagaa tccccaagtg ttcttcctga actccttcct 31080
ggtggagttc aaagagatga aaaacacaag cccgcttttc agttcttatc aggaaactgc 31140
atagactttc ctctttatgt atgactgagg gctttttacc atcatttgtt cccttcacaa 31200
atatttattt ggtatttact atataccagg gactcttgtg gcagtggaaa atacaactct 31260
catggaacgt ctgttccaga aggaaagact gccaataaac aataaaatag gcaaaagata 31320
tagcatgtta gagagtggta agtaccacag ataaaaatga aatggagaaa agaaacacga 31380
aaagttgggg agagaggata actgtttgag agggtggcca ggggcagctt catcttatca 31440
agagggtgat tttttgagta cagacctgaa ggtaacgagt gcacaagcca tatgggtacc 31500
tgagaacagc ggcagaacaa tggcagggtg ctgggagggc tgtttaccag ccacgctgtt 31560
tagaattgtc agcacatggt gataaaaaaa aaaaaaaaaa aaaaaaaaca ggctgggagc 31620
agtggctcat gcctgtaatc ccagcgcttt gggaggccaa ggcggatgga tcacttgagg 31680
tcaggagttc gagaccaggc tggggaacat ggtgaaaccc cgtctctact aaaaatacaa 31740
aaattagccg ggcacggtgg tgggtgcctg taatcccagc tacttgggag gctgaagcag 31800
gagaatcgct tgaacccaac gggtggaggt tgcagtgagc caagatggca ccagtgcact 31860
ctagcctggc gacagagtga gactccgtct caaaaataaa taaataaata aatacaaata 31920
aaaagcagac agacttttta gttggcttta gaattcttag acaccctcta cagacaaggc 31980
accccgattg cttgcaccca gggtggacta ctccctccac cctgcccttg ttacaccctg 32040
gctgggggtc agcatttcag gcagctgaat gacccaaagt gggaacacgc tagtgggttt 32100
gaggatgagc aagtggagga gggcaatagg aggtgacgcc cgagaggtca ggtgagagtg 32160
gatcctgcag ggtcgtggca agaacctgga ccttgacttt gagtgacatg ggagccgctg 32220
gaggcttctg agcagaggag taacatgatc tgacttgcat tttattttat ttatttattt 32280
gacgcagtgt cactctgtcg ctgaagctgg agtgcagtgg cgacatctca gctcactata 32340
gcctccgcct cccaggttcc agtgaatctc ctgcatcagc ctcccaggta gataggatta 32400
caagcaagca tcaccacgcc tggctaattt ttgtattttt agtagagaca gggttttgcc 32460
atgttggcca ggctggtatc gaactcctga cctcaggtga tccacccacc tcagcctccc 32520
aaagtgctgg gattacaggc aaaattagaa tatatctaga atttcctgaa gaccttagtt 32580
tggtattata agaagtctgg ttgcttcatg ttgcaaaatt tatatcactc atcactcccg 32640
cagagttaaa attccgctga gaagtaggaa tcagtgaggt gcgtgtccat gtgggttttt 32700
gccacaccta agtgaacctt ggtcaaaagc atataagagc tactgatagg ccgggtgtgg 32760
tggctcatgc ctgtaatctc agcactttgg gagggaagga tctcttgagc ccaggagttc 32820
aagaccagcc tgagcaacat agcaagattc catctttaca caaaatttaa aaattggcca 32880
ggcatggttg tacattcctg taatcccagc tactcaggag gctgaggtgg gaggattgct 32940
tgagcctggg agttggagac tacagtgagc tgtggccaca ccactgcact ccagcttgag 33000
caatggagca agactctgtc tcaaaaaaaa aaaaaaaagg ccaggcgcag tggctcatgc 33060
ctgtaatccc agcactttgg gaggccgagg cgggtggatc gcctgaggtc aggagtttga 33120
gaccagcctg gcaaacacgg tgaaacccca tctctactaa aaatacaaaa ttagcccagc 33180
gtagtggcgc atgcctgtaa tcccagctac tagggaagct gaggcaggag aatcgcgtga 33240
acctgggagg caaatgttcc agtgagccga gatcgtgcca ttgcactcca gcctgggcag 33300
agcctgctgg gttgggctgg gtaagctctg aacaccagtc tcatggcttc aagtcacacc 33360
tcctaagtga agctctgaac tttctccaag gactatcagg gcttgccccg ggcagaggat 33420
gccgacactc actgctctta ctgggtttta ttgcagacag actaccacat gaacatgatg 33480
cacatctacg tgttcgcagc ctattttggg ctgtctgtgg cctggtgcct gccaaagcct 33540
ctacccgagg gaacggagga taaagatcag acagcaacga tacccagttt gtctgccatg 33600
ctgggtaagg acaaggtggg gtgagtggtc tcctacttgg gctgagcaga atggctcaga 33660
aaaggctctg gctgaaaaaa tctccctcct ttaccaagtt cccctgggtg tctgaagccc 33720
ttccatcatg attcatttct ttgagtagtg tttgctaaat tcataccttt gaattaagca 33780
cttcacagag caggttcagg aggcctgggg tatgcagatt tcaaccctct tggcctttgt 33840
ttccttgtct gtaaaatgtg gttagctggt atcagcttga gagctcggag gggagacgtg 33900
acttccccat ctaactctaa gtgacaaggc tgagactctc cagccctagg attctcatcc 33960
aaaacccctc gaggctcaga cctttggagc aggagtgtga ttctggccaa ccaccctctc 34020
tggcccccag gcgccctctt cttgtggatg ttctggccaa gtttcaactc tgctctgctg 34080
agaagtccaa tcgaaaggaa gaatgccgtg ttcaacacct actatgctgt agcagtcagc 34140
gtggtgacag ccatctcagg gtcatccttg gctcaccccc aagggaagat cagcaaggtg 34200
agcagggcgc tgcccttggg cagcacttgg gtctaacagg actagcacac atatttatgc 34260
ccctccccac cccagggcca gcgtgggttg ggagagggca tgccgggtgg tggagctgtg 34320
cctgcctcta cagtggagct ctaggtagaa tgctgggtgg tcacagtggg cctgggactc 34380
aggagactgt ccagtgatca aaggctttct gggggtagtg attaaatcca tccatgctaa 34440
catgaaacag acctcagttt gaaccccatt tctgctagtt gctaaagtca gtcaccatga 34500
gcgagagtca gcagcaacag actagactag aattagccag cctctctctt ccccccaaca 34560
aatttcaaga atggaaccat cagaatcaga agtagagaag tatgtgacac tagccatgtg 34620
gctctggtca agccacttca acgttttgag tctcagtggc ctcatctgta aagtgggaat 34680
taagagatgg tgcatgtaaa gtgcttaacg gggagtaaat ggtaggcaaa cattagctgc 34740
tgctattagt aaagagagac gatggtgtgt gtgagtcttg tgggcagaga tgggtgagag 34800
gggagacaaa acaagttctc atgatgatgg gggaaggggc tccagctggt ggtgtcggag 34860
ggaagtctgg acagaccagt ggtggggctc gggtgggagg cactgggggg gctggagtgg 34920
aaagaatgtg gccacagatg acagcttcac agcagaattc agtgctaaga ggaagtgagt 34980
ggccatgagt tccatggtga cagaaagtct aagacaccca gcaaggcagg agtgggtgtc 35040
aactcaggga agcccagagg ctaatcctag gtgagagctg agggtgtcag ataagagcaa 35100
ggcaaggctc cggttctgga gcagtgaagg acatagcaga gctatgaccc aggaacaagg 35160

-continued

```
cccagcttat tgaaactggg cccagtcaca cagggtggca caggcaccaa gtagccaata  35220
ataataataa aaacaataac aatgatttgt gtctactggg catttattca tgttctatgc  35280
cagacactgg gctaagagct ttatatgtgg aaactcattt aatccttaca ataaccttat  35340
gaagaaggta catccaaaac cccattcttc taggccaggt gcagtggctc acacctgtaa  35400
tcccaatatt ttgggaggct gaggcaagag gattggttga ggccaggagt tcaagaccag  35460
cccaggcaac atagcaagac cctgtctcta aaaaataaaa caaaaaccca ttcttcccgc  35520
tgcccaggga cacaccacta atgagtgtga tgggtgccta ggatgctgag cacctggact  35580
tcccagctca ttccctaaat gctgcacaat cagggtaact gtgccctgag cctaagaggc  35640
agtagtgagc tggcccatca tgtccactga tgaaggacac gtagccccaa cacaggggag  35700
aagtggtttc aggatcagca aagcagggag gatgttacag ggttgccttg ttcccagcgt  35760
gctggtcact tgcagcaaga tggtgttctc tctctacctt gcttccttta cccacacgct  35820
atttctttgc agacttatgt gcacagtgcg gtgttggcag gaggcgtggc tgtgggtacc  35880
tcgtgtcacc tgatcccttc tccgtggctt gccatggtgc tgggtcttgt ggctgggctg  35940
atctccgtcg gggagccaa gtacctgccg gtaagaaact agacaactaa cctcctctgc  36000
tttggctgaa ggccagcagg acgctgggac ctgatgggcc actgtgcagt gcacagctgc  36060
attaggcagg tgtcggcgca ttctcttatt ggcttcaacg cctagtgagg gatccatcct  36120
ggctcggtgg cgcatttgtt aagatgctcg ggagcaggtg gcagaaccca tttgagcttg  36180
cttgggcatt ggggagaatt tgttatcagg ctactggggt gtcacagaac tcaaggacag  36240
ggactggagt gttgtgggga gccccgaagc ccctgtttta cttctttctt tgcttttcct  36300
gaatatctgc tttattctta ctctatagac atgcttcctc ctctttcacc ccacattgtg  36360
gggtgtagtc ttttgcttca agaaagcagc ctggtggatg gaatctcttg gccccaatcc  36420
caaattctct ggagaagggg ctctttggtt taacttggat aatgttgtct tcagctgggg  36480
gtgggcacat cgtgcatatg tggctgctgc cggggaacca cgtggatgat gtgagaggag  36540
cagcacccag aagagggagt gctgggctga tggtccaggt cgtgtccact tctgattgtt  36600
taattcttct tctaagtgga tggatctttc tccaatactc agcaaatcct gatcgttcca  36660
gaatacttca ttatagccaa ttggttataa tgtgcttctc taagagaaat atttagggac  36720
aacaaatctt catgggtttg aagacttgat ggaggaaaaa ggagtagatt ttcgaaggct  36780
ggatttggat gaacaggggc tattcaggga gtgcattcca acctaaaatt aggaaaaact  36840
ggctgggcgc agtggctcac gcgctttggg aggccgaggc gggcagatgg cctgaggtca  36900
ggagttcaag accagcctgg ccaacatggt gaaacccatc tctactaaaa gtacaaaaat  36960
tagccaggca tggtggcggg cacctgtcat cttagcgact caggaggctg agacacgaga  37020
atcacttgaa cctgggagac agagcttgca gtgagctgaa atcgtgccat ggcactccag  37080
cctgggcgac agaacaagac tctgtcttaa aaaaaaaaaa agtggtttat atacagagtg  37140
gaatattatt tagccataaa aagaatgaaa tcctgtcatt tgcagcaaca tggatggaac  37200
tggaggtaat taaaaaataa aattaaataa ggaaaaacgt atcaatactt cgattaacca  37260
aaaccagggc aaatctgatt ttcatctttg caaggggaac aaatttcttt tatctcctct  37320
ggctttgaaa ccctgaaatg aaaggaggaa gggcagaaaa aagaacacat agcaagttat  37380
catcagtctc agcgcccatc gcattccctg agcttgtttc cttgacttca tcactggcag  37440
gactattcaa aaatgattcg ctcattcatt catatattca ttcattcatc attccttcat  37500
tcaacacata cgttttaaca ctcatcttgc ttttcaagct atagtttagt gagcgaaatg  37560
```

gatacacaca atacagtgtg agaacagcaa gagggcacat ctgagctagc ctgggatggg 37620
tctggaaatg cttcctggag cagaggaaac ggttgacagc caagtgttga cagagaagta 37680
gtattagcca ggcagagaca tggggaatgt attccaggca gaaggcacag tgtgtatgaa 37740
agcttattgt taagaagagt gtgtggccca accaggaaac agacattcta aaggcatagg 37800
gtccacccag gagcatggtg gacccagatc cctgaaagat gggaggtgct caggcacact 37860
tcctgggcta gttgaggagt ctggatattt atttatttat ttatttattt atttatttat 37920
ttattgagac agagtctcat tctgtcaccc aggctggagt gcagtggtgc aatctcagct 37980
cactgcaacc tccacctcct gggttcaagt gattctccta cctcagcctc ctgagtagct 38040
gggattacag gtgcccacca ccatgcctgg ctaattttcg tgtgtgtatg tattttgttg 38100
ttgttgttgt tgttgttgtt gttgttgttg agacggtgtc tcgctctttt gcccaggctg 38160
gagtgcagtg gcgccatctc agcttactgc aagctccgcc tcccgggttc acaccattct 38220
cctgcctcag cctcctgagt agctgggtct acaggcgccc accaccacgc ccagctaatt 38280
ttttgtgttt ttagtagaga cggggtttca ccatgttggc cctgctggtc ttgaactccc 38340
gacttcaggt gatccaccca tgtcggcctc ccaaagtgct gggattacag gcatgagcca 38400
ccgtgcccaa cctggatttt tattctgaag actaataggg attctaagga aggaaccagc 38460
ctgattgaat ttgcatatgt gtccacatct gctggctcac ggctgtgtgg gaggctgagt 38520
gatggggagg aaggattact gagtagggat ctgaaggtgt ggcctcatgc tttctttcta 38580
accagctgtg ttgtctttgg gatggtgctt aaatttgggc tagaccagtg ggtcttggtc 38640
accccccagg ggacatctta caatgtctgg aggcgttctt ggttgacaca gtggggtgag 38700
ggctgctact ggcagctcgt ggggagagac cagggatgct gcttaacatc ctacagtaca 38760
cagggcagcc cccaccacaa ggaattatca gctgaaattg tgaacagtgt ctacactaga 38820
cccttgctac tcatagtgtg gtccgtagac cagcagcatt ggcatcacct gggaccttgt 38880
tagaaatgct gttagacccc accccacatc cactaaagcc agctcttcat ttcaacaaac 38940
tccccgatga tgtgagtgca cattcaagtc tgagaagggc ttctttgagg tgagccttag 39000
tgcccatccc cctttggtgg ccccggatac caagggtgtg tgaaaggggt gggtagggaa 39060
tatgggtctc acctgccaat ctgcttataa taacacttgt ccacaggggt gttgtaaccg 39120
agtgctgggg attccccaca gctccatcat gggctacaac ttcagcttgc tgggtctgct 39180
tggagagatc atctacattg tgctgctggt gcttgatacc gtcggagccg gcaatggcat 39240
gtgggtcact gggcttaccc cccatcccct taacactccc ctccaactca ggaagaaatg 39300
tgtgcagagt ccttagctgg ggcgtgtgca ctcggggcca ggtgctcagt aggcttcggt 39360
gaatatttgt tggctgattt attcagaaat tctgtccagc ccctaccttg gatggattta 39420
tcacctctcc aggccacctc ttctttccaa atagggccac ctaggtatag accaaagaca 39480
cgaaatcttt tgtgatccca caaacacaga gcaggtcaaa taggcccaag ccaattgaga 39540
ctgtggttca ggtcgtgatg cagagctttg ctgtggacgt gctcccactg cgtactagct 39600
gggcatgtgg cttaaccttt ctcagcctca gtcgccccat tgtaaatgga gataatgata 39660
ctatctcccc tcacaggact gttgggatgc tactggattt aataagctaa tgcagggaca 39720
tgctaagcac aacccatccc tgaggcccag agaggggtgg gccttggctg aggtctcact 39780
gcgaggtggg aatgtgggcc tccagaccag aggtaggtcc tgtggcccct agacagtgga 39840
cagcaatggt cagtttgaca caccagagcc ctagccatta cttcctggat gttgtgtgaa 39900

-continued

```
tattttctgg acatggctta tataaaatga aaaagtgaat tgggcacgat acagggatag  39960
atttttagag atgaactggt agcatgatga taatcatatt cactgataac atttactact  40020
gttattgact gctttaaaag tgttgggcat tgtgctagaa accattatat gcattatctc  40080
cttgaattct cacaaccgcc tactgaggta ttctcagact ctaagaaatg agatttaaga  40140
gaagttatct gcccaaggtc actcggctgg aacctggctg taaaaatggc tgaagcaggt  40200
gatgaggagc tgatgcgttt ggacgtgtct cagagaaatc atggaggcgc tgcggttcct  40260
accggttctt ggatgccttc tacagagaca accatagccc caaattatag ggatcacata  40320
tcagtgggtg agacatcctt gcttgggatg aggaggggat gagctgtgtg aagcaaggcg  40380
cctctgtgat gggttccagt gatgtgtctg ccactgtctt aataactgtg caattctaag  40440
cagaaccttt cctgtctctg ggcctgagag ttcccctctg aaagatgagg acttgaccta  40500
gcaaggtcct actcacatgc ctgtagagaa caggcagggg aagttagaaa aaaaaaaaag  40560
ccagtgaagg aagggagctc ttcagcttgc acccatcatc acagtgcagg gacccaggct  40620
cagtgttgcc agatccaatg acttctcaag agctcaaaat ctagagtttt gcatgtgctc  40680
tcccaagtac tggcagaaaa ttcaagattg ttagtaacac tgtgtggcta aattctgctt  40740
gtgggctgcc tagattccca attctgtgat tctgtggttc tctggaagca ttggttctcc  40800
acagcacctg catcacttgg aaacttgtta gaaatgcaag ccctacctac ggccccaccc  40860
cagacctacc cagttagaaa tctgggggtg ggacctatca gtccatgttt gaacaagccc  40920
cacaagtgtt ctcttgcaag ctcaagtttt agaaccactg acctatagcc aaaaaagaaa  40980
aagccaatca gtggttttct ggtaaaggat taacttaaca aactggcttt ccaagaaaat  41040
aaagccttga ttggtagcac ttgcaatttc tatggtacaa acgcttcccg catgactgag  41100
ttcaagctgt caaggagaca tcactataca tggacttggg aagagatgag aacaatcagc  41160
ccactgagcc tatgggaact ggctccagca catccctgca agtcaactct catcagggtg  41220
agtgagttga ggaccaagaa gcagttatcc tcttgccttt gcaggaccca ggcaaaggga  41280
agggcatagt gacagtgatg atctctcttc cggaagtctt tggtttgctg agagtaaaag  41340
gcgtgggctt caccagtggt gaagccagtc atgcagcctt agtcctggta ctgaaactct  41400
ctaaatctca gttttctatc tgtaaaatgg gaaaataaga cctatgtcac agggttgctg  41460
tgcagattta gcaacagaac atagccccgt tctttatgat gactgatgct gcatccgtat  41520
gaggacatct ctatgtaatg gaaagatgga gagaggatta agcgcaaagt cacaacactt  41580
aatgggaact gtggattagc tacttggtgg cattgggcaa gtcagttgac tttgcattaa  41640
ttccacaaac aatatttccc aatttcctat tcagatgagc atatgtgatt gagtcagatg  41700
ctgtgatcag aaccaggatg gagcatttcc cacaaactgt gggattttta agtaatggga  41760
aggcacactg aaatggcact gaatcatgca gttgcagata ctctttttca attctcagtc  41820
ctttgattac gtcagggaga aaagaaagtc cccacttggc ctgagaatct ctgcaccctt  41880
ctagctcttg ttaaccactc ttttgaatag cagagaaaac ctcagactgc catatctggg  41940
agagatttta gcaacatttt gttttcattg tatctctttt tacagctacc tcccatttcc  42000
cttctatttc aagctagtaa ctcagttttc ttttaaattc aattatttaa atgtaaaaat  42060
aagtctattt ggagaaaaaa aattttaata gcatctctgg aatgccagta tggctaaatt  42120
catgaatgtt gtcctcaaat gctgaaatct gggaagcatc tggccaagct ttgtggacag  42180
gcctgcctag tttgaatccc aagagccacc cagtccaagc cacaaaacat tggaattctt  42240
ggttcacttc cctaacctga acttgccctc tgtgaaatag ggacactaat agctcactca  42300
```

-continued

```
cagggctgct gtgaggacat gtgttgagct gagggtctcg ccaggggaga ccctgtgcag  42360
ggagactgtt atcatggtga tggatttctg cttcattcat ttctttttcc agacagcatc  42420
atatagaatg agttgtgggg tggcagtcag caggtttggg tttatcctct attctgccac  42480
ttattactta aaaaaacccc aaaaaaccca acttatatag tataagctat atccagaaaa  42540
gtgcaaatat catacaagta ccatttgatg aatcttctga tatccccaca taaccaacac  42600
ccagaacctc ttcttgtctc attccaggat aaccactaac ctgacttcta acagcatcag  42660
tcagttttgt ctgtttttgt acattatata tgtgatggtt tgaatgtgtc cccaaattt  42720
catgtgctgg aaacttaatc cttcaattca tatgttgatg gtttttggag gaagggcctt  42780
tgggaagtaa ttaggattag ataaggtcat ggggtgaggt atgatggcac tggtgactta  42840
taagaagaga aagagaaatc tgagctggca tgctcttgcc ctctcactgt gtgatgactt  42900
ctccatgtca tgatgcagca agaaggccct caccagatgg tggcaccatg cttttggact  42960
tcccagcctc tagaactgtg agctaaatca atttattttc tttataatca cccagtttga  43020
tattttgtca tagcaacaga atatggacaa agaaagaaaa ttaatgcaag aagtagagtt  43080
tttactgtaa cagattcctg aaaatgtgga agtggctttg gaactgggtg atgggaatag  43140
gttggaagag ttttgaggag caggctagaa aaagcctgta ttgtcaagaa tggagcatta  43200
tgccaggcac ggtgtctcag gcttataatc ccagcacttt gggaggccaa agcaggtgga  43260
tcacctgagg tcaggagttc gagaccagcc tagctaacat ggtgaaacgc tgtttctacc  43320
aaaaatacaa aaaattagct gggcgtggtg gcgcacacct gtaatctcag ctactcagga  43380
ggctgaagca ggagaatcac ttgaacccag gaggcagagg ttgcagtgag ctgagatcgt  43440
gctattgcac tccagcttgg gcaacaagag caaaactcca tctcaaaaaa aaaaaaaaag  43500
aaagaaaaag aatggagcat taaagacagt tctgcagttc tggtgagggc ttaaaggaag  43560
accccagaac tagggaaagt ctggaacttc ttaatggtta ctgaagtcgt tgagatcaga  43620
gtgctgatag aaatatggct ggtaaaggcc attctgatga ggtctcagat agaactgaag  43680
aaccacgtgt tggaaactgg agcaaaggtc atccttttta taaagaagca aagatcttag  43740
ctgaactttt tctgtgccag agtcatttat ggaaggcaga aaatctgtag gtcagccatg  43800
ttgtagggaa tgaaagaaca ttttcagctg agaacactga gagtgtgaca caactaccga  43860
ctgataagaa aactagtaca cataaattag ccaggcgtgg tggtgggcgc ctgtattccc  43920
agctacctgg gaggctgagg caggagaatg gcatgaaccc gggaggcaga gcttgcagtg  43980
agccaagatc gcgccactgc actccagcct gggcgacaga gcaaaactcc gtctcaaaaa  44040
gaaaaaaaaa aggaagaaag aaaattagta cacatagaac aaagccagag gctgttcatc  44100
aggacaaggg agaaaaactc caaagccatt tcagagatct tcaagactgc ccctcccatt  44160
actggcccag agctctaaga gggcagaatg gtttggaatg accagctgct gcccagggct  44220
gccttgggtc tctgctcccc acatttctgg tgcagcattc ctcagccatc ccagctgtgg  44280
ttcaggtggc cacaggtgtg atgtggaagg taaaagtcat aaaccttggc agcatacaca  44340
tggcactaat tttgcaggtg tgcagaatgc aaaagctgag gggcatgcc ttcttccacc  44400
tacatttcaa agggtgctgt gaacagccac cccagagagc ccctagtaga gcagggtcta  44460
gtggagctac aagggtgggg ccaccgccaa gaccccagaa tggtagagct atcatagtgc  44520
aatgccagct tgggagaact gcaggcatga gactccaacc tgtgcgaagt gcaacatggg  44580
cagaacccag caaaaccaca ggggcagagc tccccgaagc ttcgggggtc caaattccat  44640
```

agtgtgtcca ggaggtggca cacagagtaa aagatcattc tgaaggttta aggtttaatg 44700
ttgttttcta tgttgggttt tgtactttcc tggaaccagt taccctttt cccttgcctc 44760
tttttccttt tagaatggga atgtctgtcc tatgcctgtt ccactgttgt attttggaag 44820
tcaataactt gttttgactt tacaggctta cagccagagg gaatctccca tagaatgaat 44880
tgtaccttaa gtctcaccca catctgattt agatgagacc atggactttg gaattttgag 44940
ttggtgctgg aacaagttaa gactttgggg gttgtctaag tgtggtgttt catgcctgta 45000
atcccagtga tttgggaggt tgaggtggga ggattgcttg agcccaggag ctcaagacca 45060
gcctgggcaa catagtgaga cctgtctcta caaaaaataa aaataaaaaa attagccagg 45120
tattgtggca tatacctgta attctagcta ctcaggaggc tgaggtgaga ggatcacttg 45180
agcccaggag tttgaggctg cagtgagcta tggtcgtgcc actgcattcc agccagggca 45240
acagagtgag actctgtctc tacaaataaa attaaataaa cttagctgga tatggtggca 45300
cacatctgta gtcctagcta ctcaggaggc tgagacagga ggattacttg agccaaggag 45360
tttgaggctg cagtgagcta tgatcatgcc actgcattcc agcctggatg atagagcaaa 45420
atcccatctc taaaaaaaaa aaaaaaaaaa aaaaaaaaaa aaaaaacttt agtgctattg 45480
gaatgaattt tgcatgtaag aaggacatgc attttggggg ctggggcagg atgctgtggt 45540
ttgaatgcat ccctcaaatt tcatgtgttg gaaacttaat ctccaaattc atatgttgat 45600
gaaattggag gtgaagcctt tgggaggtaa ctaggattag ataaagtcat cagggtgggg 45660
cccctatgat gagactggtg gcttacaaga ggaagagaga actgagctga catgctcttg 45720
ccctcttgcc atgtgatacc ctctgccatg taatggcagg cacagcaaga aggtcctcaa 45780
cagatgccag cagcatgttc ttggacttcc cagcctccag aaccatgagc tatatatact 45840
tattttacaa attacccatt ctgtggtatt ctgttatagc aatagaaaat gaactgagat 45900
aatatacatg gaatcataca gtaagtctgt gcttttgtat gcttctttta ctcaacattg 45960
tagttgtgag attcatccag gttgttaagc attgctgtac cctttttcca ctgggatata 46020
gtgttctgtc atgcttgggt cttaatttat aaaggtgact gagtggcatt ttcttccagt 46080
attattggaa ggaaagtttt gttgttcaca gttcccctgt aaacaagagg cagaacacgt 46140
catgcagggc cacacaaaac tgtatcatcc agggaccagg cagcagaaag agaggggaa 46200
ctgggactat gcctttatga aaaagagtgg tgggagagta actgggtgag ggcatccact 46260
aatgggcagg aagtgaaaac acatatgtta gaatttgtag ctgaggggtt tataatatga 46320
gtttcctatg cctgagaaag ctgacttgca agaaaatgag ataaacaact ttggccatta 46380
gtgtggccct gtcataaatg aatgccagat aggcaaatag agaatctaag aaaagatagt 46440
tggaacaagt gttccattgt gtgaatgcag cagaatttat ttatccatta ttgaggagga 46500
tttgggtagt ttccagtttg gagctattat gaatattcta gtattgctcc tatgaacatt 46560
ctagcacttt tatttttgga gcacacgaat gcacttctgt tgattatatg cctagaagtg 46620
aaattgttga attatacagt attcacacag tcagctttag tggctactgc taaacaattt 46680
tctctagtag tttgcgccaa tctaatcacc agtagtgtat agaagctcct tttactccac 46740
attttgccaa cacttggtgt tttccttctt tttgattagt catttagcaa tcaaacctat 46800
tgtttacatt ttgatatctc caataactaa ctaaatggag cacttttaat atgcttttttg 46860
gacagttgaa tatcttttct tgtgaaatgt ctattcaagt tagtttgccc attttctatt 46920
gtggtgttct gtctttttct tattgatttg taggaattcc ttacgtatcc tggatatgaa 46980
tcccactttg tgcgttacct tttccttct ttctttcttt ttgaaacaga gtctccttct 47040

-continued gtcacccagg ctggaatgca gtggcgctat ctcagcccac tacaacctct gcctcccagc 47100
ttcaagcaat tctcatactt catcctcctg agtagcttag attacaggcg catgccacca 47160
tgcccagcta acttctgtat agacaaaata atttttggta gagacagggt tttgccatgt 47220
tggacaggct gatcttggac tcctggcctc aactttggcc caccttggcc tcccaaagtg 47280
ccaggattac aggtgtgagc caccatgccc agcccacctt ttactttctt aatggtgtct 47340
tttgaacaag agaggttctt aattttaata tagcccaatt tatcattgtt ccctttatgt 47400
ttagttcttt tatgtccttt ttaagaattt ttgcagccag cgcggtggct cacacctgta 47460
atcccagcac tttgggaggc tgaggctggc ggatcacaag gtcaagagat cgagatcatc 47520
ctggccaaca tggtgaagcc ctgtgcctac taaaaataca aaaaattagc tgggcgttgt 47580
ggctcttgcc tgtagtctca gctactcggg aggctgagat cacgccactg cactccagcc 47640
tggtgacaca gcaagactcc atctcaaaaa aaaatttttt ttgcaaggtc atgcatatgt 47700
cccccctgatt tttttcctaa aaatcactta ttattagatc aatgaattga gtaattgact 47760
acatttttca gtcattcaac aaatatttcc ctgaggtttt gataacctga actgtgtttg 47820
gagctgggga ggaagcaaac tattgaagat atacaaagat ggcaaagatg agggcctgga 47880
gcttgccaca cggaaggggg gatggctgcc tgaatggttg ggcaggtagt tgttgacatc 47940
tgcactccct acatgagcag cagggtggca actcttttta tctttttaat ttatttttct 48000
tttctttctt tcttttttt tttttgagat ggagtctcgc tgtgttgccc aggctggagt 48060
gcagtggcgt gatctcagct cactgcaaac tccacctccc aggttcacgc cgttctcctg 48120
cctcagcctc ctgagtagct gggactacag gcgcctgcca ccactcccgg ctaatgtttt 48180
gtatttttag tagagaaggg gtttcactgt gttagccagg atggtctcca tctcctgacc 48240
tcatgatctg cccgcctcgg cctcccaaag tgtggggatt acaggtgtga gccaccacac 48300
ccggccttaa tttattttc tagtctgcag gtaattcttt ttaattctct ccactctcct 48360
atgatcttat gaggtaggga ctgtcattat ttctcccact ttataatgaa caatcagtaa 48420
agacagggaa gataaccaaa tgacatacaa ggtggggtcc accccatgag gctgcaggct 48480
tggagctttg ctttgtctta aaaatgagaa catgagctgc ccacctgttg agacaagaaa 48540
caggaaaggc ttaaaaaact ggcttgttat gtacaactat ccgtggggct gcagtgaacg 48600
ggctggcagt gcccaggtgc aggctgaacc ctgggacaat cacattcagc atccaagggc 48660
ccccgtaata gcttaatgtt tgaattgaac ccctggggtt gccttgaagg agagaggtcg 48720
tggaagtatg ttcaaggggt agggatgggc aggggagatg ggtctgaaag ccaagctcta 48780
ccccacccac cttgccccaa gagaaataga accttcatct ttaattgcct aacgagaaaa 48840
ctggggctgg ccagatgtgg tggctcatgt ctgtaatccc agcactttgg gaggccgagg 48900
cgggcagatc acttgaggtc aggagttcga gatcaccctg gtcaacatgg tgaaaccccg 48960
tctctattaa taatacaaaa attatccagg tatggtggcg catgcctgta gtcccagcta 49020
cttgaggcac aagaatcgct tgaacctggg ggacagaggt tgcagtgagc cgaccactgc 49080
actccagtct ggacgacaga gtgagactcc atctcacaaa caaaaacaga aaaaaaaaaa 49140
aaaaaaagag agagagagaa aactggaggc tctgagaggt tgagggactt gcccagggtc 49200
ttgcagctag taagtgacag agctgggact tgagcttggg ttttctgact cctggtctgg 49260
ttcattatcc atgaggtgct gggaactaaa ataagccaca atcttggaat ctccgtcgcc 49320
tccctccctc ccacatgtct gcgtggcttt ttgggaaaat gccaggggaa tgtaccagcc 49380

-continued

```
agggagagga cccttgtttt cctcatggcc cttcctggca atggcactac tgacaccgac  49440
agtccttttt gtccctgatg acctctgctg cctgatgccc aagtgaccac ctctgctttg  49500
tcatttctag gattggcttc caggtcctcc tcagcattgg ggaactcagc ttggccatcg  49560
tgatagctct cacgtctggt ctcctgacag gtcagtgtga ggccaccttt cttccaccat  49620
tgccaggaca cagcacccac gtccagagcg caccctgccg tgtggctgga tgtctatgtg  49680
ccccatctcc ttccctgagg atcacataat ttcagaattg gaaaggttct tagaggtcac  49740
ctgctgctaa tgtggactgt gaggccaggg cagggaaggg acatccctga ggttataagt  49800
agggtgagtg gcaacgttgc agacttttga acccagggct ggtgatcaca ctcagttttg  49860
cacagaagcc cgagaaaatc cttacaccca aaagcctacc ttttatttct gaggacaccc  49920
ataatactat tttattcaac agatatttat tcaatatcca ctatgagcca ggcactgggg  49980
acacagcagt gagcaaaaca aattccctga ccccatggaa ttgaccttct agtgggggaa  50040
ggtattagca ataaatagac aaataagtgt ctactacgcc agatgggaag aagtggctgt  50100
gaagacagag caaactagag aaacatagag tcaatgtggg atggggtgtt cttttagggg  50160
ggtggtcagg gaaagcttat ctgagtagtt agcttttaag cagagacccc aatgaagagg  50220
agggagatat gcgatgcatt tagttagggg aagaacattc catgaaaata ggatagcaag  50280
tgcaaaggcc ctgagacagc agcatgcttt gtgtgttgag ggaacagtaa ggagaccagt  50340
gtggttggtg tgaatggagt gagaaggagc agcaggggtt gagggcagaa tggtagtgag  50400
gagcaggccc ttataaaaga tgggaagcca ctggagatct ttcaacaaag gggaaaagta  50460
tgtttctgtt cttgcaataa aatagaacag caaaaaatct aggggagttg ctaattagcc  50520
agttttactt atatgccagg tgaaaatatg tggctaggtg cagtggctca tacctgtaat  50580
tgcagcagtt tgggagaccg aagtgggcag atcatctgag atcaggattc aagaccagca  50640
tggccaacat ggtgaaaccc catctctact aaaaattaaa aaataagcca ggcgtggtgt  50700
tggatcccag ctacttggga ggctgaggca gtagaattgc ttgaacccgg gaggcagagg  50760
ttgcagtgag ccgagactct gtctaaaaaa aaagaaaaaa agaaaataca cattcaggcc  50820
aggtgcagtg gctcacgcct gtaatcccag cactttggga ggctgagaca ggtagatcac  50880
ttgaggtcag gagttcgaga ccagcctgac caacatggca aaaccctgtc tctaccagaa  50940
atacaaaaat tagccaggcg tggtggcgtg tgcctgtagt cccagctact ggggaggctg  51000
aagtagggga atggcttgac cccaggaggt ggaggttata gtgagtcgag gttgcaccac  51060
tgccctccag cctaggtgac agagtgagac tgtctcaaaa aaaaaagaaa gaaaatatac  51120
attccatcca gaactgttca cctttattct acaagcaaac atcttttatt ggttagacac  51180
ccatatatgt gtccctaagc aggaggtgaa tgccaaataa gagacaaatg gcgtaagaca  51240
ctatgagttg tgtgacgttg ggcatgtcac tttactccct ctgagccttg gttagcttct  51300
ctgtaaaatg aaaggattat ggtaactaag ctggcttcct tccagcttta acaaactgta  51360
tggaggtact ttttggagtt acctgggtaa tttttgagtg tgagattggc tagaattgct  51420
ttaatatacc atgtctggcc ttagcttttt gcagagtctt tgtgaagaag cagaggcgga  51480
gtagcgttaa ttccgtaagt taacgttcag ttcgtggcag ctggcaatcc aaccctggga  51540
aaggctgccg gatttagcaa aaatgcaagg tgtctgtttt taaatttgaa atgaattggg  51600
tatcctgcat tttatttggc aaccctgtcc tgggactcac actattcact gttatcactg  51660
gtatgttcaa agtggtgctg acttgccctc tgtcttgcaa agtaccagga ggtcttttct  51720
tattcttcac tggagtcaaa aaagagaata gaggaaaaga caatcatatt gttcctttaa  51780
```

-continued gagttaagac caacaagttt tcttctttac atgttgtttt tgacatgagc aaactggtga 51840
ttaaaaacaa cttgggtggc tcatacttgt aatcccagca ccttgggaag ctgaggtggg 51900
agaatagctt gaggccagga gttcaagcca gggcaacata gtgagacccc atctctacaa 51960
aagatacaaa aattagccag gcgtggtggt acacctgtag tcccagctgc tctggaggct 52020
gagatgggag gatcagttga gcttgggagg cagaagttgc agtgagctga gatcatgcca 52080
ctgcactcca gcctggacaa cagagcaaga ccctgtctca aaaaaggaaa caaaacaact 52140
tggacaatgg aagggggaaa aagttcctca agcagccaaa attgcaccaa atggactccc 52200
agaagacaag catttaattt gttaattgag ccctctatgg gcctgtctgt atttatttaa 52260
gaaacaatcc tatcaagcat agttattggg tttctcagcc caggtagatt agaaatagca 52320
gattagaggt gggctaggtt tctagaggta aagtacacca gcagaagtta gaagtgaaag 52380
caaagagcct aacagaggaa gagaaattct tttttttttc ttttttaga cgcagttttg 52440
ctcttgttgc ccaggctgga gtgcaatggc gctatctcgg ctcactacaa cctcagcctc 52500
ctgggttcaa gtgattctcc tgcctcagcc tcccgagtag ctgggattac aggcatgcac 52560
caccacaccc ggctaatttt gtatttttag tagagacagg gtttctccat gttggtcatg 52620
ctggtctcga actcctgacc tcaggtgatc cgcccacctt ggcctcccaa agtgctggga 52680
ttacagggat aagccactgc gaccggccga caaattctta aaactggaca caagaacaca 52740
aaacgcttgg gctgctgaga gattagaaca acaaccctcc acagctacac accttttcca 52800
cgttatatgg cacgttataa gtgggtgttc ctagtgatgg ttctgatttt ttttaaaaaa 52860
agtctaaata tgtttaatgt tgtctcagaa gacaaaatat attttagaca gatattcctc 52920
agtgatgagt aagcctcagc tatctggaaa attcatgcag gcgccagaga tcgttactga 52980
gtaattcaag ctaactgcgt catgctggtt gtaccctgca tgccaatatc agctaaaagc 53040
agcaccacga aagggaaata cgaatctcac taagcactcg cccattcttg ttaacgacac 53100
tggaactgat catccttaat aatacacaga taaatctatc aggagcattt ccttgcttcc 53160
tgtgaaagga agcactcatt ccatgtgtcc tgtgaaattc atccaacttc aggaagctgg 53220
aggaatacat atggccaagc tatctgggca gagagtagac agggaatgga ggttgggcac 53280
agtggctcac acctgtaatc gcagccattt agaaggcaaa ggcgggcaga tcacttgagc 53340
tcaggtgttc aagaccagcc tgggcaacat ggctaagtcc tgtctctgca aaaaatacca 53400
aaaactgagc tggatatggt agcacacacc tgtggtccca gctacttggg aggctgaggt 53460
gggagggttg cttgaccccg ggagtttgag gctgcaatga gctgtgattg tgccactgca 53520
ctccagcctg gataacagaa tgagactctg tcccaaaaat aaaaaataaa atcaaagaca 53580
cttaaaaaga tggggaaaag gaaggacagg cacttaagca agttataagc tactttccta 53640
actacacaag tggaatctta agctgaggtt cccaggagtt gactggagcc agagaagaca 53700
gacctatagg agcacccaat tggagtcacc ctccatagta gcccatatgt cttacatgga 53760
tcagctttcg tggggccctt ttactccatc tggggaaggg cgtcagatct gtggctctca 53820
tgtactgctc agtacactgc cattcccagt tctttttttc aaaaaaaaaa aaaaaatgtc 53880
tacagaatcg gccaggtgtg gtggctcatg cctgtaatac tagcactttg gaaggctgag 53940
gtgggtggat cacctgaggt cgggagttcg agaccagcct ggccaacatg gtgaaactcc 54000
atctctacta aaaaaaaaaa aaaaaaaaaa attagctgga tgtggtggca ggcgcctata 54060
atctcagcta cttgggaggc tgaggcagga taatcgcttg aacctgggag gcagaggctg 54120

-continued

```
cagtgagccg agatcacgcc attgtactcc agcctgggcg atagagtgag actctgtctc  54180
aaaataaata aaataaaata aaataaaata aaataaaata ggctacagaa ttaagctggt  54240
ccaggaatga cagggcttcc atttatttgt ctttcaattg tgggagaaaa aggatttctg  54300
ttgagatact gtcgttttga cacacaatat ttcgattaat cttgagatta aaaatcctgt  54360
gctccaaatc ttttaacatt aaattatgca tttaaacagg tttgctccta aatcttaaaa  54420
tatggaaagc acctcatgag gctaaatatt ttgatgacca agttttctgg aaggtaagat  54480
ttttcaccta ttaacgtgat agattttgag tgcatgaact taaaaacata cctgagtata  54540
tatgttgact tgctgtttat gagtaaaaca aaaacaaaaa tggagtaagg agcattgcag  54600
gaggaactag aggagaaaca aatccatgat atgcatgtgt gtgggggagg gtggcgggga  54660
ggtggtaaag gtcaccattt ccctgatacc tcaaattcat tcagagtcag ggatgagaca  54720
gctttcactg gccacacttc cctccccct atctgcagtc ctcagcgtag ccaaatagtc  54780
tgacatgcgg gtgacagaac cccacaatgc aaaagctgga agaaacctca agccttggag  54840
tccaacccct tttttgacag atgctaagag tggagacatg acttatcaag atcttacaac  54900
tggctgggca cggtggctca cgcctgtgat cccagcactt tgggaggctg aggtggggcg  54960
atcacctgag gccaggagtt cgagaccagc ctggccaacg tgtcgaaacc ccatctctac  55020
taaaaataca aaagttagct gggtgtggtg gcacatgcct gtaatcccag ttactcagga  55080
ggctgaggca ggagaatcac ttgaacctgg gaagcgaagt ttgcagtgat ctgagatcat  55140
gccactgcac tccagcctgg gtgacagagc gagactttgc ctcaaaaaca aaacaaaaca  55200
attgtacata tttaaagtgt tgtaaccaag tgagttacag agaaacacca cactttgagc  55260
ctaattcagg agtcctttat tagccggcga cctagagacg actagtgctc aaaattctct  55320
cggccccaaa gaaggggcta gattttcttt tataccttgg tttagaaagg ggagcgggaa  55380
ttgagctgaa gcaatcttac agaagtaaaa caggcaaaaa agttaaaaag acaaatggtt  55440
acaggaaaac aaacagttcc aggtgcagga gctttaaagc catcacaagg tgacaggtgc  55500
gggggctctg ggtgctatct gccggacaca aacgcagggg cactagagta ctatcacccg  55560
ggcaaattcc tgggaactgc ggacacagct tgccacagta ccttatcagc taattgcact  55620
ctttgatgtg ctgggagtca gcttgcacaa gttaagtcct tgaggaaggg ggtgggtaag  55680
gagcccttaa cgtcttgcaa atgaaggagc cgaatggaat ccctccggct ttcttagcta  55740
agagagagtc aatcaagtta atacaagtta gggtatcaca aaagtatata atttgataca  55800
ttttaacgta tttatacact gaagagacca tcaccaccat caagacaagg agcacaccca  55860
tcacttccac acacttcctc ctgctccttt gaaattcctc cctccctacc cacctggtcc  55920
cacccaaagg caaccactga actactttct gtcactaagg tttgcatttt ctgtaatttt  55980
tttgtttgag acagggtctc actccgccac ccacaccgta atgcagtggc accatcatgg  56040
ctcactgtag cctcaacctc cccaggctca ggagatcctc cccctcagc ctcctgagta  56100
gctaggacca caggtgtagg ccaccatggc aggctaattt ttgtattttt ttgtagagat  56160
ggggtttcac cgtattacct aggctggtct cgaactcatg ggttcaagca atcctcctgc  56220
cttggcctct caaagtgctg ggattatagg catgagccac tgtgcccagc cctctgtaat  56280
gttacacaaa gggaatcatg cagcacgtac tgcccttggt ctggcttctt ttgctcagca  56340
tgattattct gagaatcatc cgtgttgttg cgtgtaactg acttcatcag cttctctctg  56400
cagctgtcag ctcttggctt ctcccaacag ccaatctctc tttatcccct gcaagtgttc  56460
ttgcctattt agcagaatca aggtactcta tcgaaaagac tcggaaaatt ggtttaatct  56520
```

-continued

```
attcattcat tcctcaggta tttatcgaat aactattcta taccaagtac tatgctaatc  56580
aaccaaggac agcacaaaca ggagaaatct ccagctcagt cacttgagtt gcaataaata  56640
tttgctggat aggtcaggtg cagtggctca cacttgtaat cccagcactt tggggattac  56700
tgagacggga ggatctcttg agcccaggag gccaaggctg cagagaacca tgatcatgcc  56760
actgcactcc agcctgggtg acagagtgag atcctgtctc tgaaaaaaaa tatttgctgg  56820
ataaattaag gaaatctgac gaaccccatc agtagccatt gcagcaacag gtaaactaga  56880
acgagtgtga atttggaatg aggaaacccg atgttggcca tcattctgta atgtcatgta  56940
ttatgtaatg tattatatat taatgtatgt attatgtagg caagttcctt gacctctctc  57000
actggtaaca taagagtagt aatctttgtg ctacttcact gggttatttt aaagatcaag  57060
tgaggtaata atgtctgtaa caacattctg taaaatgcaa accgccacat gaatgtgaaa  57120
gtttattact agggatttag ccaaccacaa gggaatgtgt gagcataaga gctatcatat  57180
tgcaagccta cagtttctga ttttgtgcta ggtgcttttc cacattacct gattttatcc  57240
tcacaacagc cctgcataaa agtaagtatg tcgcccaggt gcggtggctc atgcctataa  57300
tcccagcact ttgggagccc gaggtgggca aatcacttga gatcaggagt ttgaaaccag  57360
cctggtcaac gtggtgcaac cctgtctcta ctaaaaatac aaaaaaaaat tagacaggcg  57420
tggtggtgga tgcctgtaat cccagctact tgggaagctg aggcaggaga atggcttgag  57480
cccgggagat ggagattgca gtgagatgag attgcgccac tgcactccag cctgggtgac  57540
agagcaaggc tatgtctcaa aagagaaaaa aaaagtaagt atctcagtct tgaagatgat  57600
gaaatggagg cctagagaga ttaagtaact tgcccaaaat gacagaacta atgcatagaa  57660
aagaagaaat gtgatgtctt ttggctccaa agacacccca catatgcgtt ggttacagtt  57720
actagagaaa agttattcca cccccacccc acccccagaa atcttctgac ttgttttctc  57780
gcagttgagt aggaccattt attcggcagt gtaccattct cagcttgcag ttgaaagcca  57840
aatatccatt aaagaggcaa ggatgcaaac ttgctaagct gataaatcca ggggtgattt  57900
tttttttttt tgcaaaccat ccaacaagac attttaaata ctcattgaat ttcatagaac  57960
tgactgccag gattggaaag acattaaagc cagctcagcc actgcctcgc tggttggcca  58020
gaccacgcct ggcacttctg ggagggagca ctcaccaccc cccaagggca cccatctcat  58080
cctccgaagg tttatgaaaa tgcactcatc atttgctaat tcattccact acgtgtatta  58140
cctaatttgt gacacgatgt gaagtaccag agagataatt ctaaataaaa tatagttatg  58200
ggtctcaagg agccagatat gctaatctcc tatcctcctg cagtttacag tggtcctcac  58260
cagatactta tttacaaaaa ttcagtttat tatttatttt tttgagacag agtcttgctc  58320
tatagctcag gctagagtgt aatggtgtga tctcggctca cttcaacctc tgcctcccag  58380
gttcaagtga ttctcctgcc tcaacctccc aagtagctgg gactacaggc acctgccacc  58440
acggctaatt tttggagttt tagtagagac agggtttcac cacgttggcc aggctggcct  58500
cgaactcctg acctcaggtg atctgcccac atcagcctcc caaaatgttg ggattacagg  58560
cgtgagccac catgcccggc caaaacttca gtttataaca caatctttca cgtgtcttct  58620
gctttcatta aaagaataga cagttccctt ctttatttca gtttaataaa ccatggattt  58680
tatttcatgc tttgcaaaac acaagggctc actgacatgc acttcttaaa ctaattctgg  58740
ctggtcgcct gtaattccag cactttggga ggctgaggcc gacagatcac ttcaagtcag  58800
gagttcaaga ccagcctggc caatatggtg aaaccacgtc tctaccaaaa atataaaaaa  58860
```

-continued

```
ttagccaggt gtggtggtgc gtgactataa tcccagctac tcaggggcct gaggcagaaa  58920
aatcacttga acccgggagg cggaggttac agtgagctga gatcgcgcca ctgcactcca  58980
gcctgggcga cagagtgaga ctctgtctca aaaaataaat aaatacaaat aatgtaaaat  59040
acgaaacaag caatcctggc agtagctgct ggaatgagag gagggagagg tcatagggag  59100
gtcggggaca atggagcatg gagttgtgtt ggatttggct aagcagcagg aagtgcaagg  59160
cattccaagc aagaggaggg gggcaggtgg ggagcatctg caagaacaga agcagcatga  59220
gcaacctggc tcggcagtgt gtgaaaaggc tgaaaggtgg ctagagccac ttcaatttca  59280
tccttcaggc aaatgggaaa ttcccaaagg tttgagtggg gaagcaatgc ctacaatgaa  59340
agtttgagag tgaagcagag tgatcgaatt aagcatgtag gccgagttct gaaataactg  59400
caatgtgctg aagatcatcc attggcttct gaatgagtat ttgcagttta tttttaaaa  59460
tgattttatt gccaagaaag ataaacacta ctgttttggt acaaaaacat aacaaaatgt  59520
gttgagtccc tcttgctgtt ttacgcgaag ttttaaaaat ctactcttgt cacagtggta  59580
tcacccctac ttctgatttc aaataaatgt tctagagaca cagtaagggc ccaacaaacg  59640
cttgttcaac aacacaagga gagccagctt ttaaagtagg aaaacaggcc gggcgccgtg  59700
gctcacacct gtaatcccaa cactttggga ggctgaggtg ggcagatcac ttgaggtcag  59760
gagttcaaga acagcttggc caacatggtg aaaccctgtc tctactaaaa acacaaacat  59820
tagccaggcg tggtggtgca caccagtagt cccagctatt caggaggctg aggcaggaaa  59880
atggcttgaa ctggggaggc agtggttgca gtgagccgag atcgtgccac tgcactccag  59940
cctgggggac agagggagac tccatctcaa aataaaacaa aacaaaacca aatcatacaa  60000
aaacattagc tgggtgtggt ggtgcatacc tgtaatccca gctacttggg aagctgaggc  60060
agaattactt gaacccctgg ggggaggttg cagtgagctg agatcttgcc actacactcc  60120
agcctgggca acagagtgag gagactctgt ctcaaaaaat atatatatta aaaaaaagaa  60180
aaaaaaaagt aaactaggaa aacacatcag cagcctgcca acagactccc ctagcctcgg  60240
tgagggccag tgttctggga ggcagatctg aattctagtc ctagttcacc cactggcagg  60300
ctggtgccct tgggcaggtc gcttctctgg ggctcagttt cttcctctat aaaatgagat  60360
caaatcccat gttctaagag tttgtgctct ggagtcagac agatctgggt tctaccactg  60420
ccagctctgt gatcttgtag cttcagtctc gtcatctgac atggagataa cagtaactgt  60480
ctcactgtgt tgttagggtt taaaggagat aatgtatgtg aaatgttagc aaacaagtgt  60540
tagctaccct gatttccggt ttcagagttc tgtggtccca gtttatgcca catgcagtga  60600
cgttgtatgg taggctgtgg tgtggcacca cttcagaact cagcgcatgc acagcttgca  60660
gaagagaagg ccagaggaga cctaagaagg ctcttcgaac acttgaaaga ccggcatgta  60720
ggccgggcgc agtgactcac gcctgtaatc ccagcagttt tggaggtcga ggcgggtgga  60780
tcacctgagt ttgggagttt gataccagcc tgaccaacaa ggtgaaaccc cgtctctact  60840
aaaaaataca aacattagct gggcatggtg gcgggtgcct gtaatcccag ctactccggt  60900
ggttgaggca gaattgcttg aacccgggag gcagaggttg cagtgagctg agattgcatc  60960
actgcactcc agcctgagac aagagcgaaa ctccatctca aacaaaacaa acaaccaacc  61020
aaacaaaacc aaaaaaaaaa ctggcatgta gaagaaaaat actttttctc tacacttctc  61080
caaagaattt aactaggccc aggggaggtg cagtataaat ttctaacaat ctcaactgtc  61140
tgccaaatgg aatgagctac ttcatatggc agtagtgagt cctctgtctt tggaggcatt  61200
caaataaaag ccagatggcc atttatcaac aatccatgta aaacgttaga tgaaataaaa  61260
```

```
cctatatatc caagatctct tccaattcag attttatgaa agaatttcta aggtctttgt  61320
aatgagacat ttaggctgtt tcaagagatc aagccaaaat cagtatgtgg gttcatctgc  61380
aataaaaatg tttgttttgc ttttacagtt tcctcatttg gctgttggat tttaagcaaa  61440
agcatccaag aaaaacaagg cctgttcaaa aacaagacaa cttcctctca ctgttgcctg  61500
catttgtacg tgagaaacgc tcatgacagc aaagtctcca atgttcgcgc aggcactgga  61560
gtcagagaaa atggagttga atcctttctc tgccactctt tgaggagaat ctcaccattt  61620
attatgcact gtagaataca acaataaaat acagccatgt accacataac aacatcttgg  61680
taaacaacag actgcatata tgatggtggt catccagtaa gctaaggtta atttattatt  61740
attccttgtt tttttttttt tttttttttt tttgagatgt agtcttactc tgtcacccag  61800
gctagagtgc aatggcacca tcttggctca ctgcaacctc tacctcctgg gttcaagcaa  61860
atctcctgcc tcagcctcca aagtagctgg gattacaggc acccaccaca tctggctaat  61920
tttttgtatt tttagtaaag atggggtttc accatgttgg ccaggctgat ctcaaactcc  61980
tgacctcaag tgatctgccc gcctcggcct cccaaagtgc tggaaccaca ggcctgagcc  62040
actgtgccca gccttgtttg ctttttttaac agataacagt gtgctcatag aaactgcttt  62100
gacatgactg caatcatgtg cttcatagaa acttaattag attataccac tagagtcttc  62160
agatttttat acttttttttt tttgaaacgg agtctcactc tgtcaccagg ctggagtgca  62220
gtgccgcaat ctcggctcac tgcaacctcc gcctcccagg ttcaagcaat tctcctgcct  62280
cagcctcccg agtagctgga attacaagtg cgcactacca cacccagcta atttttgcat  62340
ttttacttga cagggtttca ccatgttggc taggatagtt tcaccaggat ctcttggcct  62400
catgatcagc ctgcctcggc ctcccaaagt gctgggatta caggtgtgag ccaccgtgcc  62460
cagcctatac ttccctttt gaataccatt tggtgttttg aagaattaac agctttgtga  62520
acgtggcagt gcttgtgatt caggcttcca ttgagaccaa ggggagaacc tggttgcagg  62580
acaaacagac ggacagcgtg tggcagtgtt taaatgctct tctgaaggct gatacgacag  62640
ctctctgtgc actgattgca tatgcatccc aagattatat tattgttttc tactgctatg  62700
tgtcacactt tgccaaacag gatgtggaaa atgaataagc ggttttctta ggcacttctt  62760
aacagacaat tggtcaaaat gaactccatt gcttaagaaa cacataaaca ccatttagtc  62820
actgaacata gctatatgta tggttgttac tatgggaaat cttgttttgc caattttctt  62880
tgaaaattct ggcagaccaa ggttcttttt gtttacataa tacttgaaaa ataaaaatga  62940
acaagctaac aaactaccaa gttttcactt acataaatgt agttgcatac agaaaatgtg  63000
actgtgaatt aatttttcta ggacttttaa actataagca ctatttgcac aaaagagaac  63060
caatctatca attacaaact cacataattt tacagatttt tttttcccta cacagcacat  63120
aaaacagaag gaatttgaag ccaccctcca aacacagggg aaggaggctg tgtgtatatc  63180
ctcattgtct ttcacattct aaggtggttc cactcagtga ctgaaatcct taagcgttgt  63240
attagtctgc ttgggctacc ataacagcag cttaaactgt tgtttagcca ctcagactta  63300
aacaacagaa atttatttcc ttatagttct ggaggctgga agttcaaggt gccggcaagg  63360
ttggtttctg gtgagacctc tctccctgtc ttgcagatgg ctgcctcctc cctgtgtcct  63420
catagagcct gtcttctgct tttacacttc tggtgtcatc ttcctttttt tttttttttt  63480
tttttttttt ttgagacaga gtctcgctct atcgcccagg ctggagtgca gtggcccgat  63540
ggatctcggc tcactgcaac ctctgcctcc caggttcaag caattctcct gcctcagcct  63600
```

-continued

```
cccaagtagc tgggactaca ggtgcccacc atcatgcctg gctaattttt gtatttttag  63660
tagagacagg gtttcaccat attggccagg ctggtctcga actcctgacc ttgtcatctg  63720
cctgcctcgg cctcccaaag tgctaggatt acaggcgtga gccaccgcac ccggcctctt  63780
cctcttctta taaggacacc agtcctatta gattagggct ccaccctcat aacctcattt  63840
gaccttaact attatttctt taaagcacct atttccaaat atagtcactt taggggttag  63900
ggcttcaaaa gatgaatctg agggagctca attcagtaaa tagcagtagt cattaatgga  63960
caatgtatac aaagataatt tcgtgattac tgtccttatg cataaacgtc ctcagtgttc  64020
cactgcgttt atccagattt agtatcacaa agactttgct ctgagaaaaa tgtgattttt  64080
tttttttttt tttttgaga cagagtcttg ctctgtcacc caggatggag tgcagtggtg  64140
caatctcggc tcactgaaac ctccgcctcc caggttcacg ccattctcct gcctcaatct  64200
cccgagtagc tgggactaca ggcgtccgcc aagatgccca gctaattttt tttttttttt  64260
ttttttttga gacggagtct cgctctgtta cccaggctgg agtgcagtgg cgcgatctcg  64320
gctcactgca agctccgcct cccgggttca cgccattctc ctgcctcagc ctccggagta  64380
gctgggacta caggcgcccg ccactacgcc cggctaactt ttttgtattt ttagtagaga  64440
cggggtttca ccatgttagc caggatggtc tcaatctcct gacctcgtga tccacctgcc  64500
tcagcctccc aaagtgctgg gattacaggc atgagccacc gcgcccagca gatttttttt  64560
tttttttttg agatggagtc ttgctctgtt gcccaacctg gagtgcagtg ttatgatttt  64620
ggctcactgc aacctctacc atgttcaagc gattctccca cctctgcctc ccgtgtagct  64680
gggatcacag gcacacgcca ccacacctag ctactttttg tatttttagt agaaatgggg  64740
tttcaccatg ttggccagga tggtcccgaa ctcctgacct caagtgatcc tcctgcctcg  64800
gccttccaaa gtgctgggat tacaggtgtg agccactgtg cctggccaaa aatgtgattt  64860
cttatttccc acattgccaa ttccatttca attaactata atagctatgt ctattgagca  64920
ctcaagcgta ttctagaaac tgttcctgat tctggg                            64956
```

<210> SEQ ID NO 26
<211> LENGTH: 65624
<212> TYPE: DNA
<213> ORGANISM: Homo sapiens

<400> SEQUENCE: 26

```
acccttggcg tggacacatt tccagggagg gaccggagga cctcctacct cattggtcac     60
tgccagtgac tgagcttgac tcaggtagga gggcatggca ggtattctca gggagtctgg    120
tgtttacaga aaagtcatga ttacacgtga aagctgtggg ctccctggct tgattcacca    180
cacctgcagg aagcctggct gctcagacca gcacgccgtg gacatagcac cacttgctca    240
gcttcatttc cgtaactcag gctgccaggc ctgctgacaa attttcacgt ttgtaataac    300
cctgtgagga gaccagagta catcttactt gactcataag gaaattgaga ctgggtgatt    360
tagtaacttg ggaggcagaa ttgcaaagtg attagcaaca caagccatgg tgtcagatgg    420
atctgggtta ggtcccacct ctgccgttta ttagctgtgt ggctttgggt actcacgcca    480
cctctctgag cagcagtttc ctcttttgta agcgtaatga tgcctacact cacaggcttg    540
agaggaagat ccgatgaaat agcatatgca aaatgattgg ttccgtgctt ggcattccag    600
aaatggtagc tgttattcag ccaacaaata tttattgagc acctactatg gacttccctg    660
gtgctgagga tacaacagca accacagcag tcaaaagtcc ctgtctttat gttgctcaga    720
ttctcatagg ggaaagcaga taatgaacaa atacacggcc agacgcagtg gctcacgcct    780
```

-continued

```
gtaatcccag tactttgcga ggccaaggtg ggcaagtcac ctgaggtcag gagttcgaga    840
ccagcctagc caacatggtg aaaccctgtc actactaaaa atacaaaaat tagcgcagtg    900
tggtggctca tgcctgtagt cccagctact tgggaggctg aggaaggaga atcgcttgaa    960
cctaaaaggc agaagttgca atgagccaag atcgtgccac tgcattccag cctgggtgac   1020
agagtactcc atctaaaaaa aaaacctaaa tacacaagta aaaatataga cttcgtcaga   1080
tgctagtaag tgctgtgaag gaaactaaaa ggggaacaca aggaaccctt gtcaagggga   1140
gcagaaaggg gagttgatgc tgtcctttta aatagggcaa tcagaggcca ggcacagtgg   1200
ctcacactta taatcccagc actttgggag ttcgaggcag gtggatcact tgaggtcagg   1260
agttcaagac cagccaggcc aatgtggtga aaccctgtct ctactaaaac tacaaaaact   1320
agccaggtgt ggtatcgcgt gcctataatc ccagctactc gggaggctga ggcgggagaa   1380
tcgcttgaac ctgggaggcg gaggttgcag tgagccgaga ttgtgccatt gcagtccagc   1440
ctgggcaaca agagcaaaac ttcatctaaa aaaaaaacac agcaaaaaag ggcagtcagg   1500
gaaaacttcc ctgagaaggg gatggtggag tacagatcca gggaggtgag gtggggagca   1560
agccagtaca gttgttcctt gactttcgat gaggttatgt cctgataaag ccatggtaag   1620
taggaaatat tgtaagtcaa aaatgcattt aatacaccta acctacggaa catcatagct   1680
tagtgtcacc taccttaaac atgcttagaa cgcttacatt agcctacggt tgggcaaaat   1740
catctaacac aaagcctatt ttatgataaa gtattgaata tctcatgtaa tgtactgagt   1800
actgtacgga aagtgaaaga cggagtggtg ggatgggaac tctaagcacg gcttccactg   1860
catgtgtgtt gctttcgcgc catcataaag ttgaaaagcg ttaagtcaaa ccaccgtacg   1920
tcggaggcca tctgtatctg gtaggaggag tgtttcagac agagagaaca gcaggtgcaa   1980
tagagtgctt ttttcccagc attttattat gaaaaatttc aaacatctac caaaaaaagt   2040
tgaaagactt gtacggtgaa aagccataca tctcacagct agaatcaaca attaacattt   2100
tactgtattt ggtttttgac ttatctatcc tagatccctt gtgctttctg tagcaggtga   2160
cctgccttga agatttaaag acagaatatc gggaaatgta gtcagaaaat ggggcctttt   2220
ataagagtca gaggggaaga gcaaaaactc tgctttcgag aaatctgtcg ggagaggcca   2280
actgcaggga tacctccctt ttttaatgaa agcatttctg ttctgcgagg agcgggatcc   2340
tcttgtcaag cagtcagtcc ctgctgcttc cttactgggg caggatcagg acgcacaggg   2400
atttggagtg ccttggaacc aaccaccacc cacgctgttt gccagctggt aaacatgcct   2460
gtcaggtcta ggggttggca ttgcctggaa atctttagtg ttcatcttgc tgacatctgg   2520
tgccctcggg taggtaggtg cagttggctg cctggtttac agagcttgta ctgggcccag   2580
gttagcaggg gtcacatccc tttatcccac tgtgcagggg agttccttct caggaaaccc   2640
agtttataag aagtactgac tgccagaaat agagcagaga tcagaaccag gaggcaattg   2700
tgagaggaat ggagacttct gacctctggg gattggggta ccctccccct taattgctgt   2760
tggggtagca gagggcttag aagcccatgt tcctagactt ttagaattgg aagaagactt   2820
agaagtaatc taggctgggg gtccccaacc cccaggctgt ggcccgttag gaacctgacc   2880
gcacagcatg aggggtaggc cagcgagcac taccgcctga gctccgcctc ctgtcagatc   2940
agcagcggca ttagattctc acaggggcac aaaccctatt gggaaccgcg catgagaggg   3000
atctaggttg cgtgctcctt aggagaatct aactaatgcc tgatgatctg aggtggaaca   3060
gtttcatccc cacaccatcc ctccaacctc accccggtcc atggaaaaat tgtcttctac   3120
```

-continued

```
aaaacccgtc cctggtgcca aataggttgg ggacccctga tctaggctac agttaagtgg   3180
tcaaacaccc aggtcctgaa gttaggctgc ctgggtttaa atcccagctc tactgcttac   3240
tagccctgtg accttgagca agtcacttag tttttctgtg cctcagttta ctcatttgta   3300
ataaaagctt aatagtaccc atcccagtgt catgaactaa gttcatatat gtaaagtgct   3360
tagaatggtg cctagcaagt acttagtaac agttagctct gaaaatgtat aaagcaaaat   3420
taaccaatgt tttagtggtt tgcagccaac ttttttctat gcgtgtgcta acatattatt   3480
ttataagagt gggaatatat tgtacatgct gttatataac ttgcttttttc actaaacagt   3540
ctatcctctg tgtcagtttt gataaaagcg ttttcctctt gcttttcctg catatgttca   3600
gaaccatcat attggtagca agtttcatgt cctgcagttt tcttaaccaa ccccctgcta   3660
gcggacattt aggttagtct cagttttttc cttctgtaaa taaagctgca ctgagcaaga   3720
agtgaccgat gccaagtgac tagatgacct taggtatgac ctctctgggt cttggtttct   3780
tggtctaaaa acaaaatgac aggattcgac tgggtgatta aaatctcctc tgatctacat   3840
aggaattgtt ttcaagacat ttctgcattc ctctagtgac agggtgctca ctacctcatg   3900
agtatttcag tggacaactg taatggtcaa taaagtatcc actttccacc ttccacttcc   3960
ctgtagctcc tggccctggc tttattctct ggggctccac acattcagtt tacactcagt   4020
ggccagtggc tggggccatt gtagaaaatg aggaaactcc aattccttcc ttcttttctt   4080
cctctttcat cccttcctcc ctccctacat ccctctctct cttccttcct tccttgacac   4140
ttaccatgta ccagaccttc tgccaggcac atggatggga gcacagttcc gggaagttgg   4200
ctgcagggtt agaactaagt cccaagcccc gtaaagctca tgccagggga ctggactgtc   4260
cagtactgag ggatggggat gctgaggctg gtggccttcc tcagatgcac tgtagtgccc   4320
caggcagagt cctgggctgc cctgtgagga ggtgaccaga ggtagagcaa cttcacccta   4380
aggctggatc aggatcccct ccaggttttt actagagcca aacccacatc tcctttctct   4440
tctgccaccc cccctaaaa tgcttagaaa cacatagatt taaatacaag ttcaaatgta   4500
agtaatttca actgtgtaac tatgaggagt caattctacg tgggtcctat ctgtatcctc   4560
cccagggctc agctccattc tttgctttca ttcattctca ttcaatacat tgttgttaag   4620
agctcactgg gtgccctctc tgtcatgtag taaggtttta aaaagaaagc ctcttctgag   4680
cttcagtttc cttatttata aaataggagt attgatccgt tccttgcttt tcttacaagg   4740
atatgctgaa gatgactgaa gtacagagta aagaaggatt atgtttgggt gtcaaaggaa   4800
tagaatgccc tctttcaaac tgagcacagc aggaacctgt aacaggaaca cagcaacttg   4860
ttgaatgaat gacaatattg gaaaacatac atttcctccc ctccccatca tagtccctct   4920
gcttccgtgt taactccata gacaggccag cacagccagc cttgcagcct gagataaggc   4980
ctttggcggg tgtctcccct atcgctccct caagccctca agtaggtgtt ggagagaggg   5040
gtgatgcctg gtgctggtgg aacccctgca cagagacgga cacaggatga gctctaagta   5100
cccgcggtct gtccggcgct gcctgcccct ctgggcccta acactggaag cagctctcat   5160
tctcctcttc tattttttta cccactatga cgcttcctta gaggatcaaa aggggctcgt   5220
ggcatcctat caaggtgaga gttcattgga acagtggtca caggagcaaa tagcaggggc   5280
aggggcgggg gaggcctatg gttctccagg ggcacagatg ttcctttcta caaaatcccg   5340
aggaaaagat tcccccatct tcttccgtag attgcaccga aattcagtca acaatgtaag   5400
ctttccttta gaagcagcct gggcatgccc tcttctgtga agcctgcctt gatttttcag   5460
cacagtgaga ggcatcctct ttggtgttcc tcaaattccc tctaccaaat ggtcttcata   5520
```

```
attctctgct tctctgcttc cccttctctc tccttagtgg caaggatttt ttttattttt   5580
atagatttag ggatacaag tgcagctagc ttatgcaagc aatttcatgt tgttgggttt   5640
tcgggttttg tttcctttt gtggcctctc gctcatttct tatttctttt tgagacaggg   5700
tctcactctg ttgcccaggc tgaagtgcag tggcatgatc atggttcact gcagccttga   5760
cctcctagtc tcaagcaatc ttcccacctc agcctcccaa gaagctggga ccacaggagg   5820
gcaccaccat gcctggctaa atttttttt tttttggta gagatgtggg tctccctgtg   5880
tttcccagac tggtctcaaa ctcctggaca caagcgatcc tccagcctca gtctcccaaa   5940
gtgctggaat tacaggcgtg aagcactgtg cccagctctc ttgctcatat ctatactagt   6000
tttcttttgg aagcttcagc ctgttgctac cccccacccc cacccccacc gaccccagct   6060
ttcttctcac ttaggggctg ggaagtctgc atgctgtcta taaatccaga accagaaggt   6120
atggctgaag gggagggtag gatgatggtt attttatatt cagctaaaaa tattcccaga   6180
ctgtgatgag acaactgtaa ataagacaga tgtccacaat ggtgtgactt tgcttttta   6240
aaaatattga aatgagtttc aggcatctca gtgggctgat aggttgttga taatggacag   6300
ggcctccttg aagaatgtcc ctgagacaaa gttgaagctt gagcctggtt gagtgcttgc   6360
ttgttcctag gttgatatga acggctagtt aactggaagc aaagagaagt catcctgggg   6420
gccatggcag tgacaagtag gacttaggga gggaagccct tataccattt aaggtgctgg   6480
cccagagagg agccttcagt gacagacaaa caagagctgg cacaatttta attcatttca   6540
atttacttta attcatttca atccaataca attcaatgca ttccattcat tcaaccatgt   6600
atgacatcca atgtgggatc cagacacatg atgattagaa ctgatattta tgagcactta   6660
ctatgtacca ggcactattc tacatgcttt acattgaacc ctcacaataa cccaatgagg   6720
tgggtactat tatgatcttc gtttttcata tgaggaaact aggcatatgg atgttgagta   6780
atttgcccaa ggtcgctcag ctagcaatag cacagcgtat ttaaatttag ccaccctgga   6840
tttagtttcc ttacacttaa ccattatgca tcatggcccc attttacagt ggcgttgagt   6900
catttgtcat ataacccagt aggtgtagca gccactattc caaccctgta gattgactct   6960
agggtccatg ttctttaccc ctgcaccgtg ctactaacgt aggtacaaaa tgtcctcaga   7020
aactcacttt atatggaagc tcagaggagg gtccacaacc caggcagggg agacgatggt   7080
gtcaggggag gcttctggag ggaggtgcct gcccagccag ctcttgaagg ctcagtagga   7140
attacctgtg ggacaaaggc gggtcatcca agtgagggca cagtgggtgc cattgcgtgt   7200
gcacacacta gagcagactg agcttgggct taacattgca ttgccctgta gcctaaaaag   7260
agaagcaagg ggctgggcga ggtagctgac acctgtaatc ccagcacttt gggaggccaa   7320
ggctggagaa tcacctgagg ttaggagttc aagaccagcc tggccaacat ggcaaaaccc   7380
catctctact aaaattataa aaactagccg ggtgtggtgg cacacgtctg taatcccagc   7440
tacttgggag gccattacac tccagcctgg gcgacagagc aagacttcat ctcaaaaaac   7500
caaacaaaaa caacaacaac aacaaaaaac aaagaggaga gcagggactg ggtgtggtgg   7560
ctcatgcctg taatcccaaa cactttggga ggccaaggcg ggcagatcac ctgaggtcag   7620
gagttcgaga ccagcctggc ccatatggtg aaaccctgtc tctactaaaa atacaaaaat   7680
tagccggatg tggtggcacg tgcctgtagt cccagctgct tgggaagctg agggaggaga   7740
attgcttgaa cccaggaggt agaggtagct gagctgagaa tacgccactg cactccagcc   7800
tgggtgacag agtgggactc tgtctgaaaa aaataatagt aataaataaa aataaacagg   7860
```

-continued

```
gaagcagtgg gtggtagact cactgggctg catacggagt ttggcttcag tctgaggtcc   7920
gaatagtaaa caggagcgcg acaagtttgg gtttgggtca tggcggatgc catgccaggg   7980
ctggtgttgg gcacagggga aggggcatgg cttgagacac aagaccagcg tggaggctgt   8040
agtgtagtat tgacccgagg gcttcaacct tctgatggtg tacacaccat tttttgagca   8100
tgtaccatgg ttatatgtta cactttaagt attactacat taatatattt tgtatgttat   8160
aataaataca tacaaattag gaaaattgaa agagatcaga atgaaatata taatattttc   8220
aaattactaa tcataatggt gtcaatctcc aggcagggtc cattgctaca gttgacgata   8280
gtggatgaaa attcactcct cagagtcttc ttgataattt gaaattgtct tgattgactt   8340
gtcagatctg attagatcga catttttttaa atctcgaatg tgactgacag cttgtacaag   8400
gagaagtttc actctgcctt tcctttttgt tcacttgact gccattattt ctctgcttcc   8460
aatctgtgtt tttctgcacg agttggttaa gccattactt cattttgtga aagtttgttg   8520
agttaaactt aggtaactta atctgtcaat ccacttaatt gaattcagtc ctggtaaact   8580
ataatagatt attcaaacct gccaattcta aaaagacatt ttgagacaat caggaaatct   8640
gaatatagca tgaatatctt acgatataca aggattattg ttaattttgt taggtatgat   8700
aaaagcatgg tgggtttttt ttttgttttt gtttttaag gctctatctg ttagagaggc   8760
acattgaaat ggcatgatat ctggggtttg ctttcatacc agaaaaaaga aaaagtagag   8820
aaggattata gaaacaagat tggtctcatg tgacaatcat cagagtttgg agatgggcac   8880
gtagggtcat cgtgctgttc tctctgtttt catatatgct ttgaaagttc tgtaatagtt   8940
aattaaaaaa aaaaaaaaca ccctggctga gcacttaggg aggccaagtg gggaggattg   9000
cttaaaccaa gaagttcaag accagcctag gaaacatagg gagacccccc cccgccatct   9060
ctaaaaaaaa aaaaaaaaaa ctgtaaaatt taacccagtg tggtggcaca tgcctgtagt   9120
cccagctact cagtaggctg aggtgagagg cttgcttgag cctgggagct tgaggctgca   9180
gtgggacggg attgtaccac ttcactccag catgggcgac agagcaagac cctgtctcaa   9240
aaaaaaatga aaatatttga ggtgaagcga gactgtaata acaaatttaa aaatataaat   9300
aaaacataaa ggctgggtgc ggtggctcac gcctgtaatc ccagcacttt gggaggccaa   9360
ggcaggcaga tcacgaggtc tggagatgga gaccatcctg gctaacatga tgaaacccca   9420
tctctactaa aaatacaaaa aattagctgg gtatggtggc gggtgcctgt agtcccagct   9480
acttgggagg ctgaggcagg agaatggcgt gaacccagga ggcggagctt tcagtgagct   9540
gagattacac cactgcactc cagcctgggc aacagggcga gactccatct caaaaaaaaa   9600
atgaaaataa aaataaataa aacataaaac cctgccatta gttgcaacat gaagaatata   9660
gagaaatgcg tatcaaatcc ttctcattgg accaatattc ccttagggca ccttccaaag   9720
ctaggagact caaggctgta tgacatcctg agcaagtgag ggtggcttc tgggtgaatc   9780
tgaatattaa atatttgcag aattgaaaac ttcacaaagt acctttagag atagaatagc   9840
ctagatccat gtttctcaaa gtgtggtccc cagacctgct gcctcagcat ctcctggaaa   9900
tttagtagaa atgcagattc tcaggcccta ggccagacct actgatcaga agctctgggc   9960
ctggggccca gcaatctgtg ttttcacaag ccctctgggt gattcttctg tgcgtgaaag  10020
ttcgagaatt cctggagcta gactgattca aatcttgcct ctgtatctta gagaccttgg  10080
gcagattagt caacctcttt ctgcctctgt ttctacttct gtcagaggat gatagtactt  10140
gtttcattaa gttgttgaaa ggataaatga attgacacac ataaagagta ttagctttta  10200
ttatcaaaag cttttttttt ttgagacaga gttttgctct tattgcccag gggagtgcag  10260
```

tggtgcgatc ttggctcacc gcaacctccg cctcccaggt tcaagtaatt ctcctgcctc 10320
agcctcccga gtagctggga ttacaggcat gcgccaccac gcccggctaa ttttgtattt 10380
ttagtagaga cggggtttct ccatgttggt caggctggtc tcgaactccc aacctcaggt 10440
gatccacccg cctcggcctc ccaaagtgct gggattacag gcgtgagcca ccatgcctgg 10500
cccaaaagct ttaatttctt aattttttaa ataaaataaa taaaactaga attgcttgtt 10560
ttcttccagc taccctggtg attgtattga gcattttctg ggtgtgtgt tctttgctgt 10620 aatgactact ggtctggatg acctgtgatg agaccagatg ggcaggggca gtggaggaga 10680
ttctagagat atttaggaga taaagtcagc tgtacttgat gaaaagagtg gggagttaag 10740
actggctgca gatgtatgat ttggcataga gaggtgccag ttcctgaggt gagagacaga 10800
aggggaggga caggttgtga ggatgaatga acaatgatat gttcattctg ggcttggagt 10860
taaggggcct atgatatgct taggggaagc agagagtatc aattacctat tgctgcataa 10920
cagccacccc aaacttagtg gcttaaaata gcaacctttt aatttactca tgatcatgat 10980
tctgtggtgc aacaactggg ctgggttcag ctgggcagtt cttctgttag tttcacccag 11040
ggtcattcat gcatctgcag tttggggtgg gatggcctca gatgacctca ttcacatgtt 11100
tggcaattgg tgattcactg ggggccatta ctgtaacaat cgcctaccag gcagagcttc 11160
cctaaggcta ccaaactggg agactatcct gggtcctgtg ctgtggatac cactcagtcc 11220
cccatcccca ccccatactc ctcaaaggca gagagagggg ctactagaag acagaggagt 11280
tttcccagtg acatgtaaac actccaaacc ctggcacctt ccacactgca gctttggtct 11340
gcccctttgg gaaatctctg tttttcttcc caggctgctg gaggggtgag agtcgccggt 11400
agagtagagg ctgtgggcga ggaggtggcg gcctcctgag gctgcagtgg tctttccagg 11460
cagcagtggg agcacagggt ggaggtcaac cctagagcct gggggagtga agctggttct 11520
gccttcagag ctcttggtgc tgaagtttct gcaggccaga gggaggggca agagtgggag 11580
ggggtgcaga tccagaatca cagaggcagc tgaccggagg aggcagctgc ccaaggggat 11640
ggactcagaa ggccaaagtg ctgttatcca aacgaactct ttgcaagtgg tctctttgca 11700
acaggcctgg gggagagcag tcttgcctaa agtcacaccg ctaatcagcg gccggcacgg 11760
ggtaacagtt actaacactc actacgtacc caatgctggg caaagtgact tgcatgagcc 11820
agcgagctca atgctcatgg caatcctctg agcagctggc attgtttcat ctcaatttta 11880
cagctcagga agctgggaca cagaggaaga gccaggctct gaacactgac aacctgattg 11940
agagacccac actgttcatc accgttacgc tatatatgct gtatagaaag gcaggatggc 12000
ataatggtta aacctaggta ggtagggttt gaatcctcct gctaccattt actagctctg 12060
tgacttggac tagttatagc acctctctgt gcctcccttt ccccctctct aaaatgggga 12120
taataaatcg tacctcctac ctgaggctgt tgtgggctaa gtctgtaagg cacgtagaac 12180
agtgcctgga acgtggggta ctgtctatct gtgtgcctgc tgttacaaca atggtgagta 12240
ttgccttatc tctcgctgct gaactaccag gttagacttc tttctgcaag tcatgaggct 12300
ttcataaact tttcctgaag gctttccgta gaatgtacaa ttcccctctg ggcccaggca 12360
tgggcgcccg ggtaggacat ccacttctta tcacccctga acaccttaga gcccatcagc 12420
ttatcaaacc agcagctgat gtgagtgcag agcagactgt gagaggtgga ggctgatacc 12480
agtgaggatg ctccaagctg ggacccagcc ctgaagcggg agcccagata atggacgggt 12540
ggaaatgggc ctggagccca agagaggtgg gaggatgagg gggcaggggg aggagaagcc 12600

```
tgaaatcaaa tgttatttcc tgaccagttt ggggtgcatg agctctgtca acagctcatg  12660
gaaactgctg ccctaatttc atcttgttgg ctgaggcaca attcctctct cagggacagt  12720
gtagagcctt ggggaggaag gccctgagcg catatacctg gaatcaggga atcgggatca  12780
ggggcagcag ctgtgcccga taaagccccc acccaggatc ctctgacttc ctcatctctc  12840
ttttttttg agccggagtc tcactctgtc atccaggctg gagtacagtg gtgcgatctc  12900
ggctcactgc aacctcagcc ttctgggttc aagcgattct cctgcctcag cctcctgagt  12960
agctgggatt acaggcatgc gccaccatgc caggctaatt ttgtattttt agtagagacg  13020
ggatttcacc atgttggcca ggctggtctc aaactcctga cttcaagtga tctgcccacc  13080
tcagcctccc aaagtgctag gattacaggc ataagccact gtgcccggcc tttttttttt  13140
tttttttttt tttttttaaa aaaagggtct ccctctgtcg cctaggctgc tggagtatag  13200
tgatgtgatc gtggctcact gcagccttaa ccttctaggc acaagccatc ctcccacctc  13260
accctcctga gtagctggga ctacaggcac ttgccaccac gcccaagtaa ttttgtattt  13320
tttgtagaga caaggtcttg ctatgttgcc taggctggtc ttgaactcct cagctcaagc  13380
aatcctcctt ccttggcctc ccaaagtgct gggattacag gtgtgagcca ccacacctgg  13440
tctgacttcc taatctttag ggccccaact ctgcccttat ccaggcaact ctcctctccc  13500
catcttccac taacttcttt ggaatattcc agagctgtaa aagccttaga gagtatcaag  13560
tccaactcct atgtgttaca gacagggaaa ctgaggccta aagagggtaa tggacttgcc  13620
taagatcgct tagtgaggtg agagaagaaa gagctagaga cagcctagcc tgtgcaagga  13680
catagttcca ggcattcaga gctgcgctct gctgccggca tgtttggggc ctggtagtta  13740
gttcactgct gaactaccag gttagatttt ctttctccaa gttgtggggc tttcataaac  13800
ttttcctgaa ggtcttcctt acaatgtaca attctcctct gggcccggtc atgagcgccc  13860
ctcacaggct ctctctggtc cccttctgta aaatgagagg aaaatggaag aattgctcta  13920
ctcatggaat cttcaataag tctggaccct atgcatatag cattgctaca aaatggcaga  13980
tgcactttaa caatcgtgtt taataaaagg ttggatttgc atatctgaag tggggcatgc  14040
agtctccaac tgaacacaag cctcactgct cccacatgtg cactgcacct tcatatacat  14100
atttcctgct tggctcctga gggaatttga gtaatcccaa gaggaacccc tgtagaaaat  14160
gtcccctggt cacacacccc cattcctaag gatgcaagca ggagatagaa acattccctg  14220
cacctccctc cttgctgtca gaagaagtgc aaagagttga atccttccta atgcccactt  14280
ctcacccacg ccccaaatcc ccaggtcccg tggaggtcct tgggggtctc ctatatcctg  14340
gtggtgtcag gttgatttgg aaatgtcagt gtcctccctt gtcctctctg gcagaccctg  14400
ggtgtgtgta cgtttcaatg gaagtgaatt taaatgtact ttataaatca aagacttttt  14460
ctgagacttt ggagagttcc agtaatgaga gcttctcatt gttatcaaag ccagggctgg  14520
agaccagtgg caggtgagtt cctattgctg tgattgtcat gatgatgttg atgaacagcc  14580
actatttatt gagtgttctc catgtgctag gcactgtact aaacattatt tccttcggat  14640
gtcccagaaa cctctcaggt ggctctaatt acccttattc tgttgataag gaaagtaagc  14700
aacttagaag accacagggc tatgaagttg aaacacgtaa attgatattt tattttattt  14760
atttatttat ttatttattt tgagacagag tctcactgtg tcgcccaggc tggagtgcag  14820
tggtgcggtc tcagctcact gcaacctccg cctcctgggt tcaagcgatt ctcctgcctc  14880
agcctcccga gtagctggga ttacaggtgc ccgccaccac atccagctaa ttttttttgta  14940
attttagtag agacggggtt tcaccatgtt ggccaggcta gtctcgaact gctgacctca  15000
```

tgatctgccc acctcatcct cctaaattgg tatttttata tgtccaaaag agtcaactgg 15060
tggcaattta gtgaggttta atctaatagg aaatgataga gctgggatcg aacagagcta 15120
tgtgaactca aaacctatgc ttccccttcc accttttcga aaaacattgt ctaggctggg 15180
cacggtggct catgcctgta atcccagcac tttgggagac ggaggtgggt ggattacatg 15240
aggtcaggag ttcgagacca gcttggccaa aaattagcca ggcgtggtgg tgcgcgcctg 15300
tggttcccac tgaagcacag gaggctgaag cacaagaatc acttgaaccc gggaggcaga 15360
ggttgcagca aaccgagatc gcaccactgc actccaacct gggtaacaga gagactctgt 15420
ctcgaaaaaa aaaaaattgt ctacatgctg gttgcagaaa atttaaacac taaaactaaa 15480
aaagtaaaac atctcccaaa gttagagaca atattcatga tgggaaaaaa aaaattcttc 15540
aagatttctc tctctccagt catttattca tgtgcgaaaa cagttggtga ttattgataa 15600
gaagagggag ggcagatggt gtggtagtcc aaggcacagg ctccagcaga ttatctaggt 15660
ttaaatcttg gctgtaggcc aggccctgtg gctcatgtct gtaatcccat cactttggga 15720
aaccgaggtg ggcagatcac ttgaggtcag gagtttgaga ccagcttggc caacatagtg 15780
aaaccccttc tctattaaaa atacaaaaat tagccgggca cggtggtggg cacctgtaat 15840
cccagctact tgggaggctg atgcaggaga atcacttgaa cccaggaggc agaggttgca 15900
gtgagccaag atctcgccac tgtactccag cctgggtgac aagagtgaaa ctctatctca 15960
aaattaaaaa aaaaaaatct tagctctacc caccggggca agttacataa cgcctctgtg 16020
ccttggtttt catatctgta aaatggtgac agtaacagca cccatgtcaa agtgtggttg 16080
tgagaacgaa acaagatagt ctatgtaaag tgattaaaac agcgtaggca catggtaaac 16140
gcttaggaaa tgtaggctgt tataaagctc agagatgtta agtaactaga tcaagaccac 16200
acagttagag agtgccacag tcttgatttg aacccaaatt tgtctcgttc tggagctcaa 16260
gctgctaacc ctttttcaaa actggaatta aaccaaagtg ctcaccctcc gctttgctgg 16320
gcccctccct gccctcaggt gcatctcttc cactcacctg ccacagcagc ctctgctcag 16380
ggtctgagac tgggaaaggt gagggctacc caggtggccc tgatgttttc tgccagccag 16440
ctcaccaggt ccctcgcagc aggcggcaaa gggagggagg tttgctgtga agattatgtg 16500
gttcccaaca acaagagcac tgggcctatc tctgccctct cttttctgtg tgtcctggga 16560
caagtcactt ggcttctgtg gctttatttt ctcatgtgcc cagccagggg gttggccctc 16620
atatgcaata acagcagcaa tgacctttac tgagtgtcca tgtgcatcaa gcacgtgtac 16680
tttacacttg ttcttattat taggtttaat aatagaataa ttgccacatt tactgagcac 16740
tcattatggg ccaggccctg ccctaagtgc ttaattagct ttagctcctc taatccttac 16800
cttatcccca cacggcatgt tatgttatcc ccattattca gttgagaaca ttgaggctca 16860
aagaggcaaa gtaacttgac caaatacttg taaacgatct tgcatgcccc ttccagctgc 16920
catttagtaa gactctaatt tcataccacc ctaaatctcg tctgcttccc cctcctcctt 16980
ctcaccatct ccccaccgag cagtcggcca agatctgacc gtgatggcgg cccttggctt 17040
gggcttcctc acctcaaatt tccggagaca cagctggagc agtgtggcct tcaacctctt 17100
catgctggcg cttggtgtgc agtgggcaat cctgctggac ggcttcctga gccagttccc 17160
tcctgggaag gtggtcatca cactgttcag gtattgggat ggtggctgga tcacttctgg 17220
gtcatagagg gaatggaccc cgaaaggaca ggttccagaa gatctgggat attgccccct 17280
ctctgtctag caccagtgct gtgcaatatt taggacatcc ttatgctaaa agattattca 17340
ttgtttaaaa ttcaaattta actgggcatc ctgtatttta ctggacagcc ctactctgtg 17400
tatcacaagg aatccaggcc tacattcctc ctgcatcctt tctttcctgt tattgtcgat 17460
tatgattttg taaagttaca taatcagtat aagtttatgg aaaacgtaag aaggaaacac 17520
gttagacaga gagaaataga catgccacac ctagagagac attctatttt tttttttct 17580 tttttgagac ggagtttcgc ttttgttgcc caggctggag tgcaatggcg ctatctcggc 17640
acaccacaac ctcagccttc tgggttcaag cgattctcct gcctcagcct cctgagtagc 17700
tgggattata ggcatgtgcc accacacctg gctgattttg tatttttagt agagataggg 17760
tttctctgtg ttggtcaggc tagtctcaaa ctcctgacct caggtgaccg gcctgcctcg 17820
gcctcccaaa gtgctgggat tacaggcatg agccaccgcg tccagcctga gagacattct 17880
cttgaaaaga aaggactttc agccccctaa agctactaga caagaaatag ccatgccttt 17940
attttcatta aattacctgt gctttgttta gatgcctttg tgtgaaatgc taagaaccat 18000
cacaactaat gtatggtgcc agaagtcaga atagtggtta cctgggcagg aggtggatat 18060
tgattaggaa ggaacacaaa atagccccat ggggtgcaga aaatgttctc tgtgttcacc 18120
tgggtgatga ttacacatca agctatacac attttaaaag ggcattggca cttaatagaa 18180
ggaactaggc taaatttttt cctgaaacat tgttttgttt tgttcaaacc tctgaatctc 18240
tcagctcccc agatgatggt aaacgtcatc ctaggcatct tagggacctc tcaaggcctc 18300
tcaaggccat tccagcctcc ccttctaaga ccctgctaaa cctctgggca ctgctgttaa 18360
acatttctct atgagccagg aactgtgctg agcactccac aaatattatt ttgtttaact 18420
cttccaggta gggatctaac ctggtataca ggtaaggaag tggaagctca gagagggcaa 18480
ggcacttgcc tagggccaca cagctaagtg gtggagatgg ctctaacttt tttttataac 18540
cttttccaca tgctccagag tggtcagaac atgaaacaca gtctagccag ctcctgactg 18600
gccctagagg aaaaaaactg tatgtatttt tcttttttaa aaggtttaga ggctgggcat 18660
ggtggttcac gcctgtaatc ccagtacttt tgggagctga ggtgggcaga tcacttgagc 18720
ccaggagttt gagaccagcc tgagcaacgc agtgagaccc tgtctctgca gaaaatagaa 18780
aaatcagcta ggcgtggtgg tgtgcaccca cagtcccagc tacttgggag gctgaggcag 18840
gaggatcacc tgaacccagt gaggctgagg ctgagtgagc catgatcgtg ccactttact 18900
ccagcctgga caacagagtg agaccctgtc tcaaaaaaca gttttagggg ccgggcgcgg 18960
tggctcatgc ctgtaatccc agcactttgg gaggtggggg tgggcagatc atgaggtcag 19020
gagatggaga ccatcctggc taactcggag aaaccctgtc tcgactaaac atacaaaaaa 19080
ttagctgggc gtggtggcgg gcgcctgtag tcccagccac tcgggaggct gaggcaggag 19140
aatggcgtga accttggagg cggagtttgc agtgagccga gatcgtgcca ctgcactcta 19200
gcctgggcga cagagcgaga ctctgtctca aaaaaaaaaa aaccaaaaac aacagtttta 19260
ggccaggcgc ggtggttcat gcctgtaatc ctagtacttt aggaggccta gacagatgga 19320
ttacctgagg tcaggagttc gagaccgacc tgagcaacat ggtgaaatcc tgtctctact 19380
aaaaacacaa aaattagctg ggcattgtgg caggcacctg taatcccagc tacttgggag 19440
gctgaggcag gcgaatcact tgaacccggg aggcggaggc tatagtgagc cgagatcgcg 19500
ccattgcact gtagcctggg cgacagagtg aggctccgtc tcaaaaacaa aacaaaacaa 19560
aaaccatctt agagttaatt cccaccggga ttcaatacac acacacacac acacacacac 19620
acgcacgcac gcacgcacgc ccgcatacac acactgcatc cacctggaaa gtgacaaagg 19680
gcaccctggg gggaattcaa atggtggtgg ccctggtttg gtgttgctgc cttagcttaa 19740
ggtcacacca gccttcagcc tcctgcccca cagtctaggg ctgctccctt catctgatgt 19800
ccacagggac ctgttcattc ttgactcaat ccaggaagat gagaagggag agaagtcact 19860
cgcagcctga gtgaactccc ttgctccacc cctgactgct tggatccccc taggggtgac 19920
ccctgctgaa actggctcct tcctgaccgg ttcccgtcag ggctgtgctg atgggtggtg 19980
cccaggcctg cccctgggga cggggtactc tcccttggca acactccagc ttgtgccact 20040
tgacttggga ctgatttggt tctgttttga gtcccttcag gggaggggcc tatcttattc 20100
aacgttgttg tttgttttcc tcacatactg ataacttagc aaatggctat tggaacaaaa 20160
atgaaaataa atggaaccct gaagtgggat gttttaaatt tttatttatt atttttttag 20220
agacagggtc ttgctctgtt gcccagtctg gagtgcagtg gtacaatcat agctcactgc 20280
agcctctgcc tcctgggctc aagtgatcct cccacctcag cctcctgagt taaatttttt 20340
tacagacgcc tgctaccatg cccggctaat ttttgtgttt ttagtagaga cggggtttca 20400
ccaggtgggt caggttggtc tcgaactcct gacctcaagt gatccacccg cctaggcctc 20460
ccaaagtact gggattacag gcgtgagcca ctgtgcccgg cctaaaactg tgtttgagac 20520
agggtctcac tctgttgtcc aggctggagt gaagtggcat gttcatggct cactcagcct 20580
cagcctcact gggttcaggt gatcctcctg cctcagcctc ctaagtagct gggactatgg 20640
gtgcacacca ccacgcctag ctgatttttc tgtcttctgc agagacagga cctcactgtg 20700
ttgctcaggc tggtctcaaa ctcctgggct caagtgatct gcccacctcg gctccgaaaa 20760
gtactggaat tacagcctcc tgagtagctg agaccacagg cacacaccac cacgcctagc 20820
ttttttttt tttttttgc tttttgtaga gatggagtct cactatgttg cccaggctgg 20880
tctcaaactc caggccttaa gcaatcctcc cacctcagcc tcccaaagtg ctaagattac 20940
aggtgtgagc caccattcct ggccttaaaa gtgtgatatt tttaatgtat tttgaaatct 21000
gcaggactct ccctagaaga taatagcaat aaccaactcc tttattgtgc ttgacgtata 21060
tcaactcact ttgcccttac cgtggctcca gaggcattgg gtccacctta taaatggagg 21120
caccaaggca cagagtgatt aaataagttg cccaggatca cacagccaga aagtgtctga 21180
gtcaagattc cagcccaggc agcctagacc tgagagcacg ctcctaacca ctgcacatca 21240
ctgtcttagc acctcctcag cacaaactgg cccttgagga atgaaatacc gccgccggca 21300
cacacgctcc tgagttaagc ctttgtcaat gaaatgaaca cccacttaaa aggaataacc 21360
tgtccaggca cgatggaaca ttgaataacc ccttattcta aattcctggt ccctgtaaga 21420
ctccttcccc atgcccttgc ccttttatga ccttccccta aagtccttga ggcttaagcg 21480
ggcatagtct gcagcaaaca ctggggaagc tgagtccaga cttcagagca caggctttgg 21540
atctaggcca gctggatttg aacctcacat ttgtgatcag ctggcatgac tgtttccaaa 21600
aagtccattt taatcctcta cgtgaccctc tgtaaaatgg ggatactgaa cggtgagcta 21660
gcacgatttt acagagagtg aatttttttt tttttttttt tttgtgagac agagtcttac 21720
tctgtcgccc aggctggagt gcagtggtgc aatctcggct gactgcaacc tctgcctccc 21780
gggttcaagc gactgccatg cctcagcctc gagagtggct gggattacaa gcatgcacca 21840
ccatgcccgg gtaatttttg tatttttagt tgagacagag tttcaccatg ttggccaggc 21900
cactcttgaa cccctggcct caagtgatcc acctgccttg gcctcccaaa gtgctgggag 21960
tacaggcatg agccactgcg cccagcctta tagggttaaa atttaaaaga ggtgatgctg 22020
ttacaagcct gttttacaaa atgctcttat aataaatcat tatcatcact gttgctgtgg 22080

-continued

```
ttgtagcatc atcatcatta actcccagag ggaggaggga gtctcagagc aagctgctca  22140
ggggagactg gatgtccatg gattgtccag ctcagtacca cttcctccag gaagtcctcc  22200
ctgataagtc cagtcagcat caccctctcc ttccaatgaa ccccactagc cttgtgatat  22260
cacagatatt cttagttgac aggctcatgg tgtatgtagc ctgtctagat cataagtaca  22320
tttttttttt ttttggatca taagaacctt caagaccaaa ataattttct cctcctgagc  22380
atgctcattg gtcaagggaa ggaaggaatc gtaatagtgt taataaggct agtgtctttt  22440
caggagttgg ttctttgtgc cagtcttggt gctagacaca ccgataggaa gaatactcct  22500
tcacatcccc aggacaccaa catgggatac gtttgatcat cattcttaat ttgcagaagg  22560
agaaataggc tcagtgagat gaaatagcca ctccagtggc aaggctggga ctggaagccg  22620
ggcttgtcct gattccaaat ccagtttctt tccactgcca cggagaggga gagaagggac  22680
agtggcccca gatgaggatg gggtgactgg atgtgggcag gcctgcgggg gaagagtgcc  22740
ctctgttgag catccgaatg atggcagcag aaaagaagac tgggcagaat cccagttatc  22800
agatcccctg agggaacagt caccccgatc accctcagtc agatgagtgt gtgtagatca  22860
atgcctcata gatgaaggca ctgaggcaca gagtggttaa gtcatctgcc agaccacatg  22920
gctcagggtg cagaggccac cttaacggga gaagagatgg tcactccact ctgcagcatc  22980
agcgcccagg tgggtagaaa tcttgtcttc tatttccaca gaaagtaagg tgcccaacag  23040
tgtttgttga atgaatgaat gaatgaatga atgagtgaga ggcatccttc cttctcagtc  23100
atcctggctc tccttctcac ccccagtatt cggctggcca ccatgagtgc tatgtcggtg  23160
ctgatctcag cgggtgctgt cttggggaag gtcaacttgg cgcagttggt ggtgatggtg  23220
ctggtggagg tgacagcttt aggcaccctg aggatggtca tcagtaatat cttcaacgtg  23280
agtcatggtg ctgggaggag ggacctggga gaaaagggcc aaaagctcca tttggtgggg  23340
cttccggggt tttgaaaaat aaagacaacc tgtaatccca gctacttggg aggttgagga  23400
gggaagatca cttgaggcca ggagtttgag acccgcctgg gcatcatagc aagatcctca  23460
tctctaaaaa gtaatttttt ctaaattatc cagttgtggt ggcatgcacc tgtagtgtca  23520
gttactcagg aggctgaggt gtgagttgga aggattgctt gagcccagga gttagagatg  23580
aacctgggca atatagcaag acctcatctc taaataaata ggtaggtgga tagatagata  23640
gatagataga tagatagata gatagacaga cagacagaca gacagacaga cagacaggct  23700
gggtacagtg gctcacacct gtaatcccag cactttggga ggccaaggag ggcagatcac  23760
ctgaggtcag gagttcaaga ccagcctggt caacatgggg gaacctcatc tctactaaaa  23820
atacaaaatt tagctgcgca tggtggcagg tgcctgtaat cccagctact caggaggctg  23880
aggcaagaga atcgcttgaa cccggagggt ggaggttgca gtgaactgag atcgcgccat  23940
tgcactgcag cctgggggac aagagcaaga cttcatctcc aataaaaaaa aaagaaaaaa  24000
gaaaagaaaa gattgataga tagatagata cccaaatgag gttacaaaag tgtggtctgt  24060
gcaaatgttt aaacacaaca aaccagtgcc tttaactact acagtataat cctgtaggat  24120
tgtgctattc atgatgtaat tatggttgta taaaagtaat taattctcag agcctcacca  24180
gcagtgggtc cagcaagttt gtacagccag catcttcttt cagtcagtgc gtgtcagtaa  24240
ctgcacatgt cctctcattg ggagagcctg tcgaaagtct aagtttgaag gcagctgtga  24300
aggtaaggcc aatccaaatg gctctcccag ctcctctgct gtaaccctga ccctgagtga  24360
ggacatagcc aaccttccca tctcataggt gagaaggctg atgcctggag aggggaaggg  24420
actgcccaag atcacatagc aagatagtgg cagaacccaa gcgagaaccc acagttccag  24480
```

-continued cctggcttag aagaaagtgc actggacttg gagtcaaagg ctggggtgtg catcccagct 24540
ctgccataaa tccctgtgtg actctgggca atttaacctc ttagagcttt agtttcttcg 24600
tctgtaatat gagggtagca gtactaccac atagggtttt gagggagtaa ttgaattaat 24660
cacatgaaat gatgcacgtt tacaaaaaaa agcatgaagc ccctttactg tgcctcagta 24720
tcccaaagga ctttggattt actctgagaa atacagggag aactagggag tgttgggcag 24780
aggagagcta tgatctgact tatgttttaa gatactctgg cttctgggtt cagaaaagac 24840
tgaaggggca agagaggaag caggtggaga ccagagcagc agtgatggcc atcatccaga 24900
ctcagactag gacaatagct gtgagggtgg tgggaagtga ttggatcctg actatatttt 24960
aatagcagaa ttgacaggat ttgctgatag actgcacgtg gggtgggaga gggtcaagat 25020
gacttcaagg ttctcatctg gcacaactca gcagctgctg gtgccattta ctgagatggg 25080
gaacattggg gtgggataga tctgggaggg aaaacccaga gttcagtgtc gaatgtggta 25140
gcgttagggt taaggttggg gcgggtagag atgtgtatga aacatcccag tggagacact 25200
gaatggagat gtacaagtct gaagcttagt ggaaaggtta gggctaggga tataaatttg 25260
ggagttgtta caatacagat ggtgtttaaa gccatgagac ccaaggagat cactcaggag 25320
tgaggataaa gagagatggg aagaagtctg aggactgagt cctagaacac cctgcatttt 25380
agagggggga catgtgtaag agccagcaaa ggagacagaa ttgtgcttgg agaggcagga 25440
ggaagcccag gagagcgtga ggtcctggaa ggcaaggaaa gagagggccc caggtgggct 25500
gaatgctgct gagaggtcaa gtcggatgag ggctgggaag tagccattgg atttgacaag 25560
gagaccttgg catgcatggt tgtagaggag gatgaaggca aaagcctggc ttgactgatt 25620
caagagcagg agatgagaaa gtggagacag catgcagggg cagccctgcc aaggactttg 25680
ctctaaaggg gaacagagaa atggaggaga agcaggaggg caataatccg atagagagga 25740
aaaatctgat gatacagaag agagatgaac tgcaagagtc aagcctttga gttggaaagc 25800
aggagtggga ttttgagcac tgataccttt aggccgatgc agggacagtt catctttttt 25860
aaaattatta ttattataca acattttatt taaaaattta ttttcacaga atacattttc 25920
acattagaga ttcccattgt gcgaaaataa caatttatta cttatagttt tatatttgtg 25980
gacagattgt tttagaacaa gtagaataca tttgagaatt aaatctcagt ttacaatggg 26040
taatattttg atacgtctat ggggaaactt gcccttaaat ggaacttctg tatcttcaga 26100
agcactccaa gcgtttcttc ctaggattta gaaatttata atatgagata tcagcatttc 26160
ctaattttaa aatttcccta gtatatgtaa ccatcggtag gtggtatcta ccgactagag 26220
agggaagttt ttgaaaatta aacactgtct aattttctgc aaagttttta ttcatgaatt 26280
aagagtattt cccttagtcc attattccca aggcaaatat ggaagtttga tcatatgcta 26340
atcatactaa agctggattc tctttaagag attgagaaat taaaaggcaa aagctgatat 26400
atcatgttta gttatactgt gagtcttata agaagctggg aggcaacccc attaactcac 26460
cagaatacag aactcagtct cacaacttaa atataattcc tctcaaacct tttcctcaaa 26520
gttaaattct gaaaataatc ttgtgattaa gagaagaagg ctgtccacca atggacttat 26580
ctgttatttc ttccttattg tgagcttaat ggcatgacaa agcagaggca aagaggcata 26640
catcaattct tcaaagtagg aagtcaaaaa ggtcagagct tccacagcat ggcaacagct 26700
ttgcagatgc ccacatcgtg atagttgaaa tagcaaagcc cagcaaaggt taaagctgaa 26760
aatgccaaaa gccctgcctt ggcagctttc tgcgaggcat ccccatgaac atagtcagta 26820
acaacttgtc caaggcccca gtgaccatga agagtgaggg ctgcagccag ggaatagtcc 26880
gtcgcagagc aaggattcaa ataagcagcc ggaagcagac ccgggagcaa aacactgaca 26940
accctctcgc tagtccagtg gagagatgca gccttggagc cagaatggtg gctcggtgac 27000
aagtgtatgt gctgcactcc acaccattct gggataggtc ggtcctgaag aaatgctgag 27060
atatgagcag gtctgaccac tggagttcgc agcaacagag ctcggcctcc ttgggcaccg 27120
caaacggcac tcagcctcca gagaaccgcc atctcgttcc tgaggcggag agttcatctt 27180
aacgagagaa atggcaggga ctgtgaatag gccggcagat ttggtggcgg gtgccacagg 27240
ttcagtctcc tgcagggaga ggagaaaatg ccttactaat tccttgtatt ttctcagaga 27300
aacaagaggc accgtcatca gcctcatgtg agggtgggaa ggagggatgg ggtttgcgga 27360
gagggaaagt gtggtatggt catctgtggg agtggaagag agtgagaggg ctgcaggggt 27420
gcagcgggac tgcaggctgg caccagggtc cctagggctt gtagttggtg gaaagtgcat 27480
cagtgaccag ggctgtgtgc agctgctcca ggcaggtgtg gaagaagcag agttgaactt 27540
gcccagcctg gagtgctgcc cagagtgagc ccaaagccca agggagacca gagatggggc 27600
tgtttgcaaa ggaggaagta taacagtagc ccacaaaatc tgagctggtt aagaaaggag 27660
agagagtgaa aatggggagc ccagcctggc agcctgggta cacatctcag ctcaacccac 27720
actagctgaa tccatttggg ccccttcgtt gacctctctg tgcctcagtt tccctatcta 27780
tagaatgggg ataagaataa ggctacttcc tagggctgtt gtgaggattg aacaagtgac 27840
cgaacacttg ttcaattttg aatactgttc taaagcattt aggacagtgc ctggcatggg 27900
gtaagtgttg cggcagtgct gttattttca tcatcaccat tgttctcagg ctgcgttgat 27960
tggagctgct gaagggaggc aatttaagga agtgagccgg acagatagga ggtggtggtg 28020
gttatcaggt gcgatgcttg aaactgaggc ttcggaggca acagttactg gtaatgacaa 28080
ggtctaaggc ttgacagtgg gtggcagaag tgtaacgcag ggaaagagac gagcggtcaa 28140
ggagccgaga gggaaggagt tgggtggact aagatcattt gtggaagaat gatggagaga 28200
aaggctgaag ggcaggaact gacatcatca gtgaccaagg ggcggccagg aggctgagac 28260
cgcagcaaga aagggagagt gtgatggcat cttcttcaag ggagctgggg atgtttgggg 28320
tggaaaaaag aacaatggtc tgggagggaa tatgggaagt ttttttttt tttttcagat 28380 ggagtttcgc tgttgtcacc caggctggat ggcaatgttg caatctcggc tcactgcaac 28440
ctctgccttc caggttcaag tgattctcct gtctcagctt cccgagtagc tgagattaca 28500
ggcacacacc accacgcctg gcttactttt gtatttttag tagagacgga gttttgccat 28560
gttggccagg ctggtctcaa actcctgacc tcaggtgatc cacccgcctt ggcctcccaa 28620
agtgctggga ttagaggtgt gagccaccgc gcccagcctg gaagtttgta tttattaatt 28680
tttggttgtc ttcatctgtg tatgtgactt taacccctaa atacttcagt gtacatttct 28740 ttttttttt ttttttttt tgagacagag tcttgctcca tcacccaggc tggagtgcag 28800
tggtgtgatc tcggctcact gcaacctccg cctcctggat tcaagcaatt cttgtgcctc 28860
accctcccga gtagctggga ttaggggcat gccaccatgc ccagttaatt tttgtatttt 28920
tagtagagat ggagtttcac catattggcc aggctggtct tgagctcctg gcctcagttg 28980
atccacctgt ctcagcctcc caaattgctg agattacagg cgtgggccac cataaccggc 29040
ctcagtgtat atttctgatg cagttgggtt ctgtatcccc ctccaatctc atctcgaatt 29100
gtaatctcca cgtgttgagg gcaggacctt gtgggaggtg atgggatcac aggggtggtt 29160
tcccccatgc tgttcttgtg acagtgagtg ggttttcagg agagctgatg gtttgaaagt 29220
gtggcacttc ctctctctct ttctctctct ctctcacctg ccaccacgta agatgtgcct 29280
tgcttccctt tcaccttcca ccatgattgt aagtttcctg aggcctctcc ggccatgcca 29340
aactgtgagt caattcagcc tcttttgttt ataaattacg cagtctcagg aagtatcttt 29400
atagcagtgt gaaaacagac taacacaatt tcctaaaaca aggggacatt ctcttacata 29460
accattgttc agttaacaaa aatgagaaat tgacattgat atattatgat taccttattc 29520
tcatttcacc aatttttca ataatatcct ttctagaaaa aaatacatat tttttgtggt 29580
cgaggattac atcttgcatt tagttctcat gtcttattaa attccatcaa tctggaacag 29640
tttcttcatc tttctttatc tttcatgacc ttgacatgtt ttgaagtttc gagccagttc 29700
ttttgtagaa tgtgggtttg tctgctgttc ctcatgatta gattgtgggt atgcattttt 29760
ggtaggaatt ctccaagagc cgtgtgtgcc cttcttagta tatcatatca gaagacatgc 29820
tatcaatttg ccccattact gggtgtgtta actgtgatca ttgggttaag atggtacctg 29880
ccaggatctt ccactgcaaa gttactattt tcccctttgt aattaataaa catcttgtga 29940
ggagataatt tcctatagaa atcctgttga tcatccaact ttcacccact gattttagtg 30000
ttcattgatt cttccctgaa taaattagta ctataataat tgccaatggt ggttttctaa 30060
ttccatcttt ccttcaatag ttggcattct cctgtaagga aaagctttcg cttctctgtt 30120
catccactca tctatgtatt tgtttatatt accatggact cctggattcc ggtttacaca 30180
cttccatttt ctgccttttc tctctgctta atataaggat taatgagaac tccctgattc 30240
ccaggaagaa aatgtcacca gagctttctt aggtggaatg aagagaattc agtgtaagaa 30300
ccataaaggt gtatctgtgt agtatggaca gttttaaaaa acaaacaaac aaaaagaacc 30360
tccaagggca ggaagtgctg ccagactcag gagggcacta gaactgacta tgagaagcca 30420
ctgagatccc aggtagtctg tgctctccat cttttggctc tgattctctc tgtacatcta 30480
acatctctgt acaccagctt tctctttagc gaaaaacgtg tcccctccac ccacccatcc 30540
acctccactt gttcctgcat ttctatgtcc cagatcctgc agaaaacaac tcttttctct 30600
cagttagtct caattctgta gtccagggag agagaatctg atcagtcccc tgggtcattt 30660
ttccactctg gtccaagcag ctacagctgg catgggaaat agttcacaca gtaaaaacat 30720
ggctgtcaag aagaggagta aatttcagag gcagaacact ccctgtgagc ccgaacctct 30780
tcctgctttg ttgcagtctt cataacgatt gctttaaaag actgcattga tataacatca 30840
tctctcttct ctgcatcttt gacttgctag cttaactggt ctagaggagg gcttagcact 30900
gattttcagt attcattttc ctcaaaactt caattcagcc tgggtttctt cagcaggagg 30960
gctcggggga accagagcca gggaccagag tcatttcagt gcaccagctc aagaaatgaa 31020
tattccaggc caagaatccc caagtgttct ttctgaagtc cttcctggtg gagctcaaag 31080
agatgaaaaa cgcaagcccg cttttcagtt cttatcagga aactgcatag actttcctct 31140
ttatgtatga ctgagggctt tttaccatca tttgttcact tcacagatat ttatttggta 31200
tttactatat accaggcact cttgtggcag tggaaaatac aactctcgtg gaacatctgt 31260
tccagaagga aagactgcca ataagcaata aaataggcaa aagatatagc atgttagaga 31320
gtggtaagta ccacagagaa aaataaaatg gagaaaagaa acacgaaaag ttggggagag 31380
aggacaactg tttgaggggg tggccagggg cagcttcatc tcatcaaggg ggtgattttt 31440
tttgagtaca gacctgaagg taacgagtgc acaagccaca tgggtacctg agaacagcgg 31500
cagaacaatg gcagggtgct gggagggcta tttaccaccc atgctgttta gaattgtcag 31560

-continued

```
cacatggtga taaaaaaaaa aataggctgg gtgcggtggc tcatgcctgt aatcccagcg  31620
ctttgggagg ccaaggcgga tggatcactt gaggtcagga gttcgagacc aggctgggga  31680
acatggtgaa accccgtctc tactaaaaat acaaaaatta gccgggcaca gtggtgggcg  31740
cctgtaatcc cagctacatg ggaggctgaa gcaggagaat cgcttgaacc cagtgggtga  31800
agtttgcagt gagccaagat ggcaccactg cactccagcc tggcgacaga gcgagactcc  31860
gtctcaaaaa taaataaata aataaataaa aataaaaagc agacagactt tttagttggc  31920
tttagaattg ttagacaccc tctgcagaca aggcaccccg attgcttgca cccagggtgg  31980
actactccct ccatcctgcc cttgttacac cctggctggg ggtcagcatt tcaggcagct  32040
gaatgaccca aagtgggaac acgctagtgg gtttgaggat gagcaagtgg aggagtgcaa  32100
taggaggtga cgcccgagag gtcaggtgag agtggatcct gcagggtcgt ggcaagaacc  32160
tggaccttga ctttgagtga catgggagcc gctggaggct tctgagcaga ggagtaacat  32220
gatctgactt gcattttatt ttatttattt atttgacgca gtctcactct gtcgccgaag  32280
ctggagtgca gtggcgccat ctcagctcac tacagcctct gcctcccagg ttccagtgaa  32340
tctcctgcct cagcctccca ggtagatggg attacaagca agcatcacca cgcctggcta  32400
atttttgtat ttttagtaga gacagggttt tgccatgttg gccaggctgg tatcgaactc  32460
ctgacctcag gtgatccacc cacctcagcc tcccaaagtg ctgagattac aggcttgagc  32520
caccacgccc ggcctgactt gcattttaac agggtcactc tgtctgctgt gtggagaaca  32580
gtccgcagga agacaagggt ggaaatgggg agaccagtta ggaggttact gtaacaattt  32640
ggggtagcgg tgatggtggc ttaaaccaag atggggtcag tgggaaatgg tgctaaaaat  32700
cctgccaatt ctgggtattt ttagaaagca cagctgacag ctttctccag tagcccacta  32760
aataagttat gaagcattac taaaatgtga tagtcatgat gcaaaattag aatatatcta  32820
gaatctcccg aagaccttag tttggtatta caagaagtct ggttgcttca tgttgcaaaa  32880
tttatatcac tcatcactcc tgcagagtta aaattccgct gagaagtagg aatcagtgaa  32940
gtgcgtgtcc atgtgggttt ttgccacacc taagtgaacc ttggtcaaaa gcatataaga  33000
gctactgata ggccgggcgt ggtggctcat gcctgtaatc tcagcacttt gggagggaag  33060
gatctcttga gcccaggagt tcgagaccag cctgagcaac atagtgagat tccatcttta  33120
cacaaaattt aaaaattggc caggcatggt tgtgcactcc tgtaatccca gctacttagg  33180
aggctgaggt gggaggattg cttgagcctg ggagttggag actacagtga gctgtggcca  33240
caccactgca ctccagcttg agcaatggag caagactctg tctcaaaaaa aaaaaaaaaa  33300
aaaaaaaaaa gaggccgggc acagtggctc atgcctgtaa tcccagcact ttgggaggcc  33360
gaggcgggtg gatcgcctga ggtcaggagt ttgagaccag cctggcaaac acggtgaaac  33420
cccatctcta ctaaaaatac aaaattagcc cagcgtagtg gcgcatgcct gtaatcccag  33480
ctactaggga agctgaggca ggagaatcgc gtgaacctgg gaggcaaatg ttccagtgag  33540
ccgagatcgt gccattgcac tccagcctgg gcaaagcctg ctgggttggg ctgggtaagc  33600
tctgaacacc agtctcgtgg cttcaagtca cacctcctaa gtgaagctct gaactttctc  33660
caaggaccat cagggctttc ccctgggcag aggatgccga cactcactgc tcttactggg  33720
ttttattgca gacagactac cacatgaacc tgaggcactt ctacgtgttc gcagcctatt  33780
ttgggctgac tgtggcctgg tgcctgccaa agcctctacc caagggaacg gaggataatg  33840
atcagagagc aacgataccc agtttgtctg ccatgctggg taaggacaag gtggggtgag  33900
tggtctcata cttgggctga gcagaatggc tcagaaaagg ctctggctga aaaaatctcc  33960
```

-continued

```
ctcctttacc aacttcccct gggtgtctga agcccttcca tcatgattca cttctttgag  34020
tagtgtttgc taaattcata cctttgaatt aagcacttcc ttttagggac ctctcttcat  34080
taatatccac tagaaaggag agactcatta tgtgtgagtt tcaataagtt tatccaatcc  34140
ctttgttttc aactgaaagg agggaaacgg acaagtgaag aaggtagggc ccaggagtga  34200
aggaacaagg gtgggaatag taataatgtt gtactttgaa aatctactgg gaaaatgatg  34260
aacttagact gctgggagag gctaatagaa aatcgggcag tgagcttgat agtaggcaaa  34320
ggactatcag gccacggggt caagttaaag cagcacattc attaaaaaaa aaaaaataag  34380
cgtttgggcc aggcgtggtg gctcaagcct gtaatcccag cactttggga ggccaaggtg  34440
ggtggatcac ctgaggtcag gagttcgaga ccagcctggc caacagggcg aaaccccatc  34500
tctactaaaa atacaaacaa atcagctggg catggtggtg cacgcctgta atcccagcta  34560
cttgggaggc tgaggcagga gaatcttttg aatccaggtg gtggaggttg cagtgagcca  34620
agatcgcgcc actgcactcc agcctgggca acagagcaag agtccatctc aattaaaaag  34680
aaaaaaaaat taaaataagc atttgaccat cacagagcag gttcaggagg cctggggtat  34740
gcagatttca accctcttgg cctttgtttc cttgtctgta aaatgtggtt agctggtatc  34800
agcttgagag ctcggagggg agacgtgact tccccatcta actctaagtg acaaggctga  34860
gactctccag ccctaggatt ctcatccaaa acccctcgag gctcagacct ttggagcagg  34920
agtgtgattc tggccaacca ccctctctgg cccccaggcg ccctcttctt gtggatgttc  34980
tggccaagtg tcaactctgc tctgctgaga agtccaatcc aaaggaagaa tgccatgttc  35040
aacacctact atgctctagc agtcagtgtg gtgacagcca tctcagggtc atccttggct  35100
cacccccaaa ggaagatcag catggtgagc agggcgctgc ccttgggcag cacttgggtc  35160
taacaggact agcacacata tttatgcccc tccccacccc agggccagcg tgggttggga  35220
gagggcatgc cgggtggtgg agctgtgcct gcctctacag tggagctcta ggaagaatgc  35280
tgggtggtca cagggggcct gggactcagg agactgtcca gtgatcaaag gctttctggg  35340
gggagtgatt aaatccatcc atgctaacat gaaacagacc tgagtttgaa ccccgtttct  35400
gctagttgct caagtcagtc accatgagcg agagtcagca gcaacagact agactagaat  35460
tagccagcct ctctcttccc cccaacaaat ttcaagaatg gaaccatcag aatcagaagt  35520
agagaagtat gtgacactag ccatgtggct ctggtcaagc cacttcaacg ttttgagtct  35580
cagtggcctc atctgtaaag tgagaattaa gagatggtgc atgtaaagtg cttaacgggg  35640
agtaaatggt aggcaaacat tagctgctgc tattagtaca gagagacaat ggtgtgtgtg  35700
agtcttgtgg gcagagatgg gtgagagggg agacaaaaca agttctcatg atgatggggg  35760
caggggtcc agctggtggt gtcggaggga agtctggaca gaccagtggt ggggctcggg  35820
tgggaggcac tggggggct ggagtggaaa gaatgtggcc acagatgaca gcttcacagc  35880
agaattcagt gctaagagga agtgagtggc catgagttcc atggtgacag aaagtctaag  35940
acacctagca aggcaggagt gggtgtcagc tcagggaagc tcagaggcta aacctaggtg  36000
agagctgagg gtgtcagata agagcaaggc aaggctccgg ttctggagta gtgaaggaca  36060
tagcagagct ataacccagg aacaaggccc agcttattgg aactgggacc agtcacacag  36120
ggtggcacag gcaccaagta gccaataata ataataaaaa caataacaat gatttatgtc  36180
tattgggcat ttattcatgt tctatgccag acactggact aagagcttta tatgtggaaa  36240
ctcatttaat ccttacaata accttatgaa gaaggtacat ccaaaacccc attcttctag  36300
```

gccaggtgca gtggctcaca cctgtaatcc caatattttg gaaagctgag gcaagaggat 36360
tggttgaggc caggagttca agaccagccc aggcaacata gcaagaccct gtctctaaaa 36420
aataaaacaa aaacccattc ttcccgctgt ccagggacac accactaatg agtgtgatgg 36480
gtgcctagga tgctgagcac ctggacttcc cagctcattc cctaaatgct gcacaatcag 36540
ggtaactgtg ccctgagcct aagaggcagt agtgagctgg cccaccgtgt ccactgatga 36600
aggacacgta gccccaacac aggggagagg tggtttcagg atcagcaaag cagggaggat 36660
gttacagggt tgccttgttc ccagcgtgct ggtcacttgc agcaagatgg tgttctctct 36720
ctaccttgct tcctttaccc acacgctatt tctttgcaga cttatgtgca cagtgcggtg 36780
ttggcaggag gcgtggctgt gggtacctcg tgtcacctga tcccttctcc gtggcttgcc 36840
atggtgctgg gtcttgtggc tgggctgatc tccatcgggg gagccaagtg cctgccggta 36900
agaaactaga caactaatgc tctctgcttt ggctgaaggc cagcaggacg ctgggacctg 36960
atgggccact gtgcagtgca cagctgcatt aggcaggtgt tggtgcattc tcttattggc 37020
ttcaacgcct agcgagggat ccatcctggc tcggtggcac atttgttaag atgctgggga 37080
gcaggtggca gaacccattt gagcttgctt gggcactggg gagaatttgt taccaggcta 37140
caggggtgtc acagaactca aggacaggga ctggagtgtt gtggggagcc cagaagcccc 37200
tgttttactt ctttctttgc ttttcctgaa tatctgcttt attcttactc tatagacctg 37260
cttcctcctc tttcacccca cattgtgggg tgtagtcttt tgcttcaaga aagcagcctg 37320
gtggatggaa tctcttggcc ccaatcccaa attctctgga gaaggggctc tttggtttaa 37380
cttggataat gttgtcttca gctgggggtg ggcacatcgt gcatatgtgg ctgctgccgg 37440
ggaaccacgt ggatgatgtg agaggagcag cacccagaag agggagtgct gggctgatgg 37500
tccaggtcgt gtccacttct gattgtttaa ttcttcttct aagtggatgg atctttctcc 37560
aatactcagc aaatcctgat cgttccagaa tacttcatta tagccaattg gttataatgt 37620
gcttctctaa gagaaatatt tagggacaac aaatcttcat gggtttgaag acttgatgga 37680
ggaaaaagga gtagattttc gaaggctgga tttggatgaa caggggctat tcagggagtg 37740
cattccaacc taaaattagg aaaaactggc tgggcgcagt ggctcacgcg ctttgggagg 37800
ccgaggcggg cagatggcct gaggtcagga gttcaagacc agcctggcca acatggtgaa 37860
accatctcta ctaaaagtac aaaaattagc caggcgtggt ggcgggcacc tgtcatctta 37920
gctactcagg aggctgagat gcgagaatca cttgaacctg ggagacagag cttgcagtga 37980
gccgaaattg cgccactgca ctccagcctg ggcgacagaa caagactctg tcttaaaaaa 38040
aaaaaagtgt tttatataca gagtggaata ttatttagcc ataaaaagaa tgaaatcctg 38100
tcatttgcag caacatggat ggaactggag gtcattaaaa aataaaataa aataaataag 38160
gaaaaacgta tcaatacttc gattgaccaa aaccagggca aatctgattt tcatctttgc 38220
aaggggaaca aatttctttt atctcctctg gctttgaaac cctgaaatga aaggaggaag 38280
ggcagaaaaa agaacacata gcaagttacc atcaggctca gcgcccatcg cattccctga 38340
gcttgtttcc ttgacttcat cactggcagg actattcaaa aatgattccc tcattcattc 38400
atatattcat tcattcatca ttccttcatt caacacatac gttttaacac tcatcttgct 38460
tttcaagcta tagtttagtg agcgaaatgg atacacagaa tacagtgtga gaacagctac 38520
agggcacatc tgagctagcc tgggatgggt ccggaaatgc ttcctggagc agaggaaacg 38580
gttgacagcc aagtgttgac agagaagtag tattagccag gcagagacat ggggaatgta 38640
ttccaggcag aaggcacagt gtgtatgaaa gcttattggt aagaagagtg tgtggcccaa 38700

-continued ccaggaaaca gacattctga aggcataggg tccacccagg agcatggtga acccagatcc 38760
ctgaaagatg ggaggtgctc aggcacactt cctgggctag ttgaggggtc tggattttta 38820
tttacttatt tttttattta ttgagacaga gtctcgttct gtcacccagg ctggagtgca 38880
gtggtgcaat ctcagctcac tgcaacctcc acctcctggg ttcaagtgat tctcctacct 38940
cagcctcctg agtagctggg attacaggtg cccaccacca tgcctggcta atttgtgtgt 39000
gtgtgtgtgt gtgtgtgtgt gtgtgtgtgt tttgttgttg ttgttgttgt tgagacggtg 39060
tctcgctctt ttgcccaggc tggagtgcag tggcgccatc ttggcttact gcaagctctg 39120
cctcccgggt tcacaccatt ctcctgcctc agcctcctga gtagctggga ctacaggcgc 39180
cctccaccac gcccagctaa tttttttgtgt ttttagtaga gacggggttt cgccatgttg 39240
gccatgctgg tcttgaactc ttgacttcag gtgatccacc cacgttggcc tcccaaagtg 39300
ctgggattac aggcatgagc caccgtgccc gacctggatt tttattctga agactaatgg 39360
ggatcctaag gaaggaacca gcctgactga atttgcatat gtgtccacat ctgctggctc 39420
atggctgtgt gggaggctga gtgatgggga ggaaggatta ctgagtaggg atctagaggt 39480
gtggcctcat gctttctttc taaccagctg tgttgtcttt gggatggtgc ttaaatttgg 39540
gctagaccag tgggtcttgg tcacccccca ggggacatct gacaatgtct ggaggcgttc 39600
ttggttgaca cagtggggtg agggctgcta ctggcagctc gtggggagag accaggaatg 39660
atgcttaaca tcctacagtg cacagggcag cccccatcac aaggaattat cagctgaaat 39720
tgtgaatagt gcctacacta gacccttgct actcatagtg tggtccgtag atgagcagca 39780
ttggcatcac ctgggacctt gttagaaatg ctcttagacc ccaccccaca tccactaaag 39840
ccagctcttc atttcaacaa actccccatt gatgtgagta cacattcaag tctgagaagg 39900
gcttctttga ggtgagcctt agtgcccatc cccatttggt ggcgccggat accaagggtg 39960
tgtgaaaggg gtgggtaggg aatatgggtc tcacctgcca atctgcttat aataacactt 40020
gtccacaggt gtgttgtaac cgagtgctgg ggattcacca catctccgtc atgcactcca 40080
tcttcagctt gctgggtctg cttggagaga tcacctacat tgtgctgctg gtgcttcata 40140
ctgtctggaa cggcaatggc atgtgggtca ctgggcttac cccccatccc cttaacactc 40200
ccctccaact caggaagaaa tgtgtgcaga gtccttagct ggggcgtgtg cactcggggc 40260
caggtgctca gtaggcttcg gtgaatattt gttggctgat ttattcagaa attatgtcca 40320
gcccctacct tggatggatt tatcacctct ccaggccacc tcttctttcc aaataggacc 40380
acctaggtat agaccaaaga cacgaaatct tctgtgaccc cacaaacaca gagcaggtca 40440
aataggccca agccaattga gactgtggtt caggtcgtga tgcagagctt tgctgtggac 40500
gtgctcccac tgcgtactag ctgggcatgc ggcttaacct ttctcagcct cagtcgcccc 40560
cttgtaaatg gagataagga tactatctcc cctcacaggg ctgttgggat gctactggat 40620
ttaataagct aatgcaggga catgctaagc acaacccatc cctgaggccc agagaagggt 40680
gggcctcggc tgaggtctca ctgtgaggtg ggaatgtggg cctccagacc agaggtaggt 40740
cctgtggccc ctagacagtg gacagcaatg gtcagtttga cacaccagag ccctagccat 40800
tacttcctgg atgttgtgtg aatattttct ggacatggct tatataaaat gaaaaagtga 40860
attgggcacg atatagggat agatttttag agatgaactg atagcatgat gataatcata 40920
ttcactgata acatttacta ctgttattga ctgctttaaa agtgttgggc attgtgctag 40980
aaaccattat atgcattatc tccttgaatt ctcacaaccg cctactgagg tattctcaga 41040

-continued ctctaagaaa tgagatttaa gagaagttat ctgcccaagg tcacccggct ggaacctggc 41100
tgtaaaaatg gctgaagcag gtgatgagga gctgatgtgt ttggacgtgt ctcagagaaa 41160
tcatggaggc gctggggttc cttccggttc ttggatgcct tctacagaga caaccatagc 41220
cccaaattat agggatcaca tatcagtggg tgagacatcc ttgcttggga tgaggagggg 41280
atgagctgtg tgaagcaagg tgcctctgta atgggttcca gtgatgtgtc tgccactgtc 41340
ttaataactg tgcaattcta agcagaacct ttcctgtctc tgggcctgag agttcccctc 41400
tgtaagatga ggacttgacc tagcaaggtc ctactcagat gcctgtagag aacaggcagg 41460
ggaagttaga aaaaaaaaaa gccagtgaag gaagggagct cttcagcttg cacccaccat 41520
cacagtgcag ggacccaggc tcagtgttgc cagatccaat gacttctcaa gagctcaaaa 41580
tctagagttt tgcatgtgct ctcccaagta ctggcagaaa attcaagatt gttagtaaca 41640
ctgtgtggct aaattctgct tgtgggctgc ctagattccc aattctgtga ttctgtggtt 41700
ctctggaagc attggttctc cacagcacct gcatcacttg gaaacttgtt agaaatgcaa 41760
gccctaccta cggccccacc ccagacctac ccagttagaa atctgggggt gggacctatc 41820
agtccatgtt tgaacaagcc ccacaagtgt tctcttgcaa gctcaagttt tagaaccact 41880
gacctatagc caaaaaagaa aaagccaatc agtggtttgc tggtagagga ttaacttaac 41940
aactggcttt ccatgaaaat aaagccttga ttggtagcac ttgcaatttc tatggtacaa 42000
acgcttccca catgactgag ttcaagctat caaggagacg tcactgcaca tggacttggg 42060
aagagatgag aacaatcagc ccactgagcc tatgggaact ggctccagca catccctgca 42120
agtcaactct catcagggtg agtgagttga ggaccaagaa gcagttatcc tcttgccttt 42180
gcaggaccca ggcaaaggga agggcatagt gacagtgatg atctctcttc cggaagtctt 42240
tggtttgctg agagtaaaag gcgtgggctt caccagtggt gaagccagtc atgcagcctt 42300
agtcctggta ctcaaactcc ctaaatctca gttttctatc tgtaaaatgg gaaaataagt 42360
cctatgtcac agggttgctg tgcagattta gcaatagaac atagccccgt tctttatgat 42420
gactgatgct gcatcagtat ggggacatct ctatgtaatg gaaagatgga gagaggatta 42480
agtgcaaagt cacagcactt aatgggaact gtggattagc tacttggtgg cattgggcaa 42540
gtcagttgac tttgcattaa ttccacaaac aatatttccc aatttcctat tcagatgagc 42600
atatgtgact gagtcagatg ctgtgatcag agccaggatg gagcatttcc cacaaactgt 42660
gggattttta agtgatggga aggcacactg aaatggcatt gaatcatgca gttgcagata 42720
ctctttttca attctcagtc ctttgattac atcagggaga aaagaaagtc cccacttggg 42780
ctgagaatct ctgcaccctt ctagctcttg ttaaccactc ttttgaatag cagagaaaac 42840
ctcagactgc catatctggg agagatttta gcaacatttt gttttcattg tatctctttt 42900
tacagctacc tcccatttcc cttctatttc aagctagtaa cacagttttc ttttaaattc 42960
atttatttaa atgtaaaaat aagtctattt ggagaaaaaa aatttttaat agcatctctg 43020
gaatgccagt atggctaaat tcatgaatgt tgtcctcaaa tgctgaaatc tgggaagcat 43080
ctggccaagc tttgtggaca ggccttccta gtttgaatcc caagagccac tcattccgag 43140
ccacaaaaca ttggaattct tggttcactt ccctaacctg aacttgtcct ctgtgaaata 43200
gggacattaa tagctcactc acagggctgc tgtgaggaca tgtgttgagc tgagggtctg 43260
gccaggggag accctgtgca gggagactgt tatcatggtg atggatttct gcttcattca 43320
tttctttttc cagacagcat catatagaat gagttgtggg gtggcagtca gcaggtttgg 43380
gtttatcctc tattctgcca cttattactt aaaaaaaaaa acccaactta tatagtataa 43440

-continued

```
gctatatcca gaaaagtgca aatatcatac aagtaccatt tgatgaatct tctgatatcc  43500
ccacataacc aacacccaga acctcttctt gtctcattcc aggataacca ctaacctgac  43560
ttctaacagc atcagtcagt tttgtctgtt tttgtacatt atatatgtga tggtttgaat  43620
gtgtccccca aatttcatgt gctagaaact taatccttca attcatatgt tgatgctatt  43680
tggaggaagg gcctttggga agtaattagg attagataag gtcatggggt gaggtatgat  43740
ggcactggtg acttataaga agagaaagag aaatctgagc tggcatgctc ttgccctctc  43800
accgtgtgat gacttctcca tgtcatgatg cagcaagaag gccctcacca gatggtggca  43860
ccatgctttt ggacttccca gcctctagaa ctgtgagcta aatcaattta ttttctttat  43920
aatcacccag tttgatattt tgtcatagca acagaatatg gacaaagaaa gaaaattaat  43980
gcaagaagta gagtttttac tgtaacagat tcctgaaaat gtggaagtgg ctttggaact  44040
gggtgatggg aataggttgg aagagttttg aggagcaggc tagaaaaagc ctgtattgtc  44100
aagaatggag cattaggcca ggcacggtgg ctcagactta taatcccagc actttgggag  44160
gccaaagcag gtggatcacc tgaggtcagg agttcgagac cagcctggct aacatggtga  44220
aacgctgttt ctaccaaaaa tacaaaaaat tagctgggca ctctggcgca cacctgtaat  44280
cccagctact caggaggctg aagcaggaga atcacttgaa cccaggaggc agaggttgca  44340
gtgagctgag atcgtgctat tgcactccag cttgggcaac aagagcaaaa ctccaactca  44400
aaaaaaaaaa aaaaagaaaa agaaaaagaa tggagcatta aagacagttc tacagttctg  44460
gtgagggctt aaaagaagac cccagaacta gggaaagtct ggaacttctt aatggttact  44520
gaagtcgttg agatcagaat gctgatagaa atgtggctgg tgaaggccat tctgatgagg  44580
tctcagatgg aactgaagaa ccacgtgttg gaaactggag caaaggtcat cctttttata  44640
aagaagcaaa gatcttagct gaactttgtc tgtgccagag tcatttatgg aaagcagaaa  44700
atccgtaggt cacccatgtt gtagagaatg aaagaacatt ttcagctgag aaaactgaga  44760
gtgtgaccaa gctaccgatt gataagaaaa ctagtacaca taaattagcc aggcgtggtg  44820
gtgggcgcct gtagtcccag ctacatggga ggctgaggca ggagaatggc atgaacccgg  44880
gaggcagagc ttgcagtgag ccgagatcgc gccactgcac tccagcctgg gcgacaaagc  44940
gagactccat ctcaaaaaaa aaaaaaaaaa aaaggaagaa agaaaattag tacacataga  45000
acaaagccag aggctgttca tcaggacaag ggagaaaaac tccaaagcca tttcagagat  45060
cttcaagact gcccctccca ttactggccc agagctctaa gagggcagaa tggtttggaa  45120
tgaccagctg ctgcccaggg ctgccttggg tctctgctcc ccacatttct ggtgcagcat  45180
tcctcagcca tcccagctgt ggttcaagtg gccacaggtg tgatgtggaa ggtaaaagtc  45240
ataaaccttg gcagcataca catggcacta attttgcagg tgtgcagaat gcaaaagctg  45300
agggggcatg ccttctccca cctacatttc aaagggtgct gtgaacggcc accccagaga  45360
gcccctagta gagcaaggtc tagtggagct acaagggtgg ggccaccgcc aagaccccag  45420
aatggtagag ctatcatagt gcaatgccag cttgggagaa ctgcaggcat gagactccaa  45480
cctgtgcgaa gtgcaacatg ggcagaaccc agcaaaacca caggggcaga gctccccgaa  45540
gcttcggggg tccaaattcc atagtgtgtc caggaggtgg cacacagagt aaaagatcat  45600
tctgaaggtt taaggtttaa tgttgttttc tatgttgggt tttgtacttt cctggaacca  45660
gttacccttt ttcccttgcc tctttttcct tttagaatgg gaatgtctgt cctatgcctg  45720
ttccactgtt gtattttgga agtcaataac ttgttttgac tttacaggct tacagccaga  45780
```

-continued

```
gggaatctcc catagaatga attgtacctt aagtctcacc cacatctgat ttagatgaga  45840
ccatggactt tggaattttg agttggtgct ggaacaagtt aagactttgg gggttgtcta  45900
agtgtggtgt ttcatgcctg taatcccagt gatttgggag gctgaggtgg gaggattgct  45960
tgagcccagg agttcaagac cagcctaggc aacatagtga gacctgtctc tacaaaaata  46020
aaaataaaaa gttagccagg tattgtggca tgtgcctgta attctagcta ctcaggaggc  46080
tgaggtgaga ggatcacttg agcccaggag tttgaggctg cagtgagcta tggtcgtgcc  46140
actgcattcc agccagggca acagagtgag actctgtctc tacaaataag attaaataaa  46200
cgtagctgga gatggtggca cacgtctgta gtcctagcta ctcaggaggc tgagacagga  46260
ggattacttg agccaaggag tttgaggctg cagtgagcta tgatcatgcc actgcattcc  46320
agcctggatg atagagcaaa atcccatctt taaaaaaaaa aaaaaaaaaa aaaaaaatat  46380
atatatatat atatatatat atatatatat atatatatat actttggtgc tattgggatg  46440
aattttgcat gtacgaagga catgcatttt gggggctggg gcagaatgct atggtttgaa  46500
tgcatccctc aaatttcatg tgttggagac ttaatctcca aattcatatg ttgatgaaat  46560
tggaggtgaa gcctttggga ggtaactagg attagataaa gtcatcaggg tggggcccct  46620
atgatgagac tggtggctta caagaggaag agagacctga gctgacatgc tcttgccctc  46680
ttgccatgtg ataccctctg ccatgttatg gcacagcaag aaggtcctca acagatgcca  46740
gcagcatgct cttagacttc ccagcctcca gaaccatgag ctatatataa ttattttata  46800
aattacccat tctgtggtat tctgttatag caacagaaag tgaactgaga taatatacat  46860
ggaatcatac agtaagtctg tgcttttgta tgcttctttt actcaacatt gtagttgtga  46920
gattcatcca ggttgttaag cattgctgta cttttttcc actgggatat agtgttctgt  46980
catgcttggg tcttaattta taaaggtgac tgagtggcat tttcttccag tattattgga  47040
aggaaagttt tgttgttcac agttcccctg taaaaaagag gcagaacacg tcttgcaggg  47100
ccacacaaaa ctgtgtcatc cagggaccag gcagcagaaa gagaggggga actgggccta  47160
tgcctttatg aaaaagagtg gtgggagagt aactgggtga gggcatccac taatgggcag  47220
gaagtgaaaa cacatatgtt ggaatttgta gctgaggggt ttataatatg agtttcccat  47280
gcctgagaaa gctgacttgc aagaaaacga gataaacaac tttggccatt agtgtggccc  47340
tgtcataaat gaatgccgga tagacaaatc gagaatctaa gaaaagatag ttggaacaag  47400
tgttccattg tgtgaatgca gcagaattta tttatccatt attgaggagg atttgggtag  47460
tttccagttt ggagctatta tgaatattct agtattgctc ctctgaacat tctagcactt  47520
ttgtttttgg agcacacgaa tgcacttctg ttgattatat gcctagaagt gaaattgttg  47580
agttatacag tattcacaca gtcagcctta gtggctactg ctaaacagtt ttctctagta  47640
gtttgcgcca atctaatcac cagtagtgta tagaagctcc ttttactcca cattttgtta  47700
acacttggtg ttttccttct ttttgattag tcatttagca gtgaaaccta ttttttacat  47760
tttgatatct ccaataacta actaaatgga gcacttttaa tatgcttttt ggacagttga  47820
atatcttttc ttgtgaaatg tctattcaag ttagtttgcc cattttctat tgtggtgttc  47880
tgtctttttc ttattgattt taggaattcc ttacatatcc tggatatgaa tcccactatg  47940
tggcttacct ttttccttct ttctttttga aacagagtct ccttctgtca cccaggctgg  48000
aatgcagtgg cgctatctca gctcactaca acctctgcct cccaggttca agcaattctc  48060
atacttcagc ctcctgagta gcttagatta caggtgcatg ccaccatgcc caccgaattt  48120
ttgtatagac aaaataattt ttggtagaga cagggttttg ccatgttggc caggctgatc  48180
```

ttgaatccta gcctcaactt tggcccacct tggcctccca aagtgccagg attacaggtg 48240
tgagccacca tgcccagccc accttttact ttcttaatgg tgtcttttga acaaggaggt 48300
tcttaatttt aatatagccc aatttatcat tgttcccttt atgcttagtt cttttatgtc 48360
ctgtttaaga atttttgcag ccagctcggt ggctcacacc tgtaatccca gcactttggg 48420
aggctgaggc tggcagatca caaggtcaag agatcgagat catcctggcc aacatggtga 48480
aaccctgtcc ttactaaaaa tacaaaaaat tagctgggcg ttgtggctct tgcctgtagt 48540
ctcagctact cgggaggctg agatcacgcc actgcactcc agcctggtga cacagcaaga 48600
ctccatctaa aaaaaaaaga aatttgcaag gtcatgcata tgtccccctg aatttttttc 48660
taaaaatcac ttaattttag atcaatgaat tgagtaattg actccatttt tcagtcattc 48720
aacaaacatt tccctgaggt tttgataacc tgaactgtgt ttggagctgg ggaggaagca 48780
aactattgaa tatatacaaa gatggcaaag atgagggcct ggagcttgcc acacggaagg 48840
ggggatggct gcctgaatgg ttgggcaggt agttgttgac atctgcactc cctacaagag 48900
cagcagggtg gcaactcttt ttatcttttt aatttatttt tcttttctct tttttttttg 48960
agatggagtc ttgctctgtt gcccaggctg gagtgcagtg gcgtgatctc agctcactgc 49020
aaactccacc tcctgggttc acaccgttct cctgcctcag cctcctgagt agctgggact 49080
gcaggcacct gccaccactc ccggctaatg ttttgtattt ttagtagaga aggggtttca 49140
ctgtgttagc caggatggtc tccatctcct gacctcatga tccacccgcc tcggcctccc 49200
aaagtgcggg gattacaggt gtgagccacc acacccggcc ttaatttatt tttctagtct 49260
gcaggtaatt ctttttaatt ctctccactc tcctatgatc ttatgaggta gggactgtga 49320
ttatttctcc cactttataa tgaacaatca gtaaagacag ggaagataac caaatgacat 49380
acaaggtggg gtccacccca tgaggctgca ggcttggagc tttcctttgt cttaaaaatg 49440
agaacatgag ctgcccacct gttgagacaa gaaataggaa aggcttaaaa aactggcttg 49500
ttgtgtacaa ctatccgtgg ggctgcagtg aacgggctgg cagtgcccag gtgcatgctg 49560
aaccctggga caatcacatt cagcatccag gggcccccgt aatagcttaa tgtttgaatt 49620
gaacccctgg ggttgccttg aaggagagag atcctggaag tatgttcaag gggtagggat 49680
gggcagggga gatgggtctg aaagccaagc tctaccccac ccaccttgcc ccaagagaaa 49740
tagaaccttc atctttaatt gcctaacgag aaaactgggg ctggccagat gtggtggctc 49800
atgtctgtaa tcccagcaat ttgggaggcc aaggcgggca gatcacttga ggtcaggagt 49860
tcgagttcag cctggtcaac atggtgaaac cccgtctcta ttaataatac aaaaattatc 49920
caggtatggt ggcgcatgcc tgtagtccca gctacttgag gcacaagaat cgcttgaacc 49980
tgggggacag aggttgcagt gagccgacca ctgcactcca gtctggacga cagagtgaga 50040
ctccatctca caaacaaaaa cagaaaaaaa aaaaaaaaaa agagagagag agaaaactgg 50100
aggctctgag aggttaaagg acttgcccag ggtcttgcag ctagtaagtg acagagctgg 50160
gacttgagct tgggttttct gactcctggt ctggttcatt atccatgagg tgctgggaac 50220
taaaataagc cacaatcttg gaatctccgt cgcctccctc cctcccacat gtctgcgtgg 50280
ctttttggga aaatgccagg ggaatgtacc agccagggag aggacccttg ttttcctcat 50340
ggcccttcct ggcaatggca ctactgacac cgacagtcct ttttgtccct gatgacctct 50400
gctgcctgat gcccaagtga ccacctctgc tttgtcattt ctaggattgg cttccaggtc 50460
ctcctcagca ttggggaact cagcttggcc atcgtgatag ctctcacgtc tggtctcctg 50520

-continued acaggtcagt gtgaggccac ctttcttcca ccattgccag gacacagcac ccacgtccag 50580
agcgcaccct gccgtgtggc tggatgtcta tgtgccccat ctccttccct gaggatcaca 50640
taatttcaga attggaaagg ttcttagagg tcacctgctg ctaatgtgga ctgtgaggcc 50700
agggcaggga agggacatcc ctgaggttat aagtagggtg agtggcaacg ttgcagactt 50760
ttgaacccag ggctggtgat cacactcagt tttgcacaga agcccgagaa aatccttaca 50820
cccaaaagcc taccttttat ttctgaggac acccataata ctattttatt caacagatat 50880
ttattcaata tccactatga gccaggcact ggggacacag cagtgagcaa aacaaattcc 50940
ctgaccccat ggaattgacc ttctagtggg ggaaggtatt agcaataaat agacaaataa 51000
gtgtctacta cgccagatgg gaagaagtgg ctgtgaagac agagcaaact agagaaacat 51060
agagtcaatg tgggatgggg tgttctttta ggggggtggt cagggaaagc ttatctgagt 51120
agttagcttt taagcagaga ccccaatgaa gaggagggag atatgcgatg catttagtta 51180
ggggaagaac attccatgaa aataggatag caagtgcaaa ggccctgaga cagcagcatg 51240
ctttgtgtgt tgagggaaca gtaaggagac cagtgtggtt ggtgtgaatg gagtgagaag 51300
gagcagcagg ggttgagggc agaatggtag tgaggagcag gcccttataa aagatgggaa 51360
gccactggag atctttcaac aaaggggaaa agtatgtttc tgttcttgca atacaataga 51420
aaagcaaaaa atctagggga gttgctaatt agccagtttt acttatatgc caggtgaaaa 51480
tatgtggcta ggtgcagtgg ctcatacctg taattgcagc agtttgggag accgaagtgg 51540
gcagatcatc tgaggtcagg attcaagacc agcctggcca acatggtgaa accctgtctc 51600
tactaaaaat taaaaaatta gccaggcgtg gtggtgggca cctgtaatcc cagctacttg 51660
ggaggctgag gcaggagaat tgcttaaacc cgggaggcag aggttgcagt gggccgagac 51720
tctgtctaaa aaaaaaagaa aatacacatt caggccaggc acagtggctc acgcctgtaa 51780
tcccagcact ttgggaggct gaggcaggta gatcacctga ggtcaggagt tcgagaccag 51840
cctgaccaac atgggaaaac cctgtctctg ccagaaatac aaaaattagc caggcgtggt 51900
ggtgtgtgcc tgtagtccca gctactcggg aggctgaagt aggggaatgg cttgacccca 51960
ggaggtggag gttatagtga gccaaggttg caccagccta ggtgacagag tgagactgtc 52020
tcaaaaaaaa aaaaaagaaa gaaaatatac attccatcca gaacttgtta ttctacaagc 52080
aaacatcttt tattggttag acacccatat atgtgtccct aagcaggagg tggatgccaa 52140
ataagagaca aatggcgtaa gacactatga gttgtgtggt gacattgggc atgtcacttc 52200
actccctctg agccttggtt agcttctctg taaaatgaaa ggattatggt aactaagctg 52260
gcttccttcc agctttaaca aactgtatgg aggtacattt tggagttact tgggtaattt 52320
ttgagtgtga gattggctag aattgcttta atataccaat gtctggcctt agcttttggc 52380
agagtctgtg tgaagaagca gaggcggagt agagttaatt ccgtaagtta acgttcagtt 52440
cgtggcagct ggcaatccaa ccctgggaaa ggctgccgga tttagcaaaa atgcaaggtg 52500
tctgttttta aattcgcaat gaattgggta tcctgcattt tatttggcaa ccctgtcctg 52560
ggactcacac tattcactgt tatcactggt atattcgaag tggtgctgac ttgccctctg 52620
tcttgcaaag tacccggggg tcttttctta tgcttcactg gagtcaaaaa agagaataga 52680
ggaaaagaca atcatattgt tcctttaaga gttaagacca acaagctttc ttctttacat 52740
gttgtttttg acatgagcaa actggtgatt aaaaacaact tgggtggctc atacttgtaa 52800
tcccagcact ttggaaagct gaggtgggag aatagcttga ggccaggagt tcaagccagg 52860
gcaatcctat agtgagaccc catctctaca aaagatacaa aaattagcca ggtgtggtgg 52920

```
tacacctgta gtcccagctg ctccggaggc tgagatggga ggatcagttg agcttgggag  52980
gcagaagttg cagtgagctg agatcgtgcc actgcactcc agcctggaca acagagcaag  53040
accctgtctc aaaaaaggaa acaaaacaac ttggacaatg gaagggggag aaagttcctc  53100
aagaagccaa aattgcacca aatggactcc cagaagccaa gcatttaact tgttaattga  53160
gccctctgtg ggcctgtcta tacttattta aggaacaatc ctatcaagca tagttattgg  53220
gtttctcagc ccaggtagat tagaaatagc agattagagg tgggctaggt ttctagaggt  53280
aaagtacacc agcagaagtt agaagtgaaa gcaaagagcc taacagagga agagaaattc  53340
ttttttttt ttttagacgg agttttgctc ttgttgccca ggctggagtg caatggcgct  53400
atctcggctc aacgcaacct ccgcctcctg ggttcaagtg attctcctgc ctcagcctcc  53460
tgagtagctg ggattacagg catgcaccac cacgcccggc taattttgta tttttagtag  53520
agacagggtt tctccatgtt ggtcatgctg gtctcgaact cctgacctca ggtgatccgc  53580
ccaccttggc ctcccaaagt gctgggatta caggcataag ccactgtgcc cggccaacaa  53640
attcttaaaa ctggacacaa gaacacaaaa cgcttgggct gctgagagat tagaccaaca  53700
accctccacg gctacaaacc ttttccacgt tatatggcac gttataagtg ggtgttccta  53760
gtgatggttc tgattttttt tttaaaaagt ctaaatatgt ttaatgttgt ctcagaagac  53820
aaaatatatt ttagacagat attcctcagt gatgagtaag cctcagctat ctggaaaatt  53880
catgcaggcg ccagagatca ttactgagta attcaagcta ataactgcgt catgctggtt  53940
gtaccctgca tgccaatatc tgctaaaagc agcaccacga aagggaaata cgaatctcac  54000
taagcactca cccattcttg ttaacgacac tggaactgat catccttaat aatacacaga  54060
taaatctatc aggagcattt ccttgcttcc tgtgaaagga agtactcatt ccatgtgtcc  54120
tgtgaaattc agccagcttc gggaagctgg aggaatacat atggccaagc tacctgggca  54180
gagagtagac agggaatgga ggttgggcac agtggctcac acctgtaatt gcagcccttt  54240
agaaggcaaa ggcgggcaga tcacttgagc tcaggtgttc aagaccagcc tgggcaacat  54300
ggctaaaccc cgtctctgca aaaaatacaa aaaaatgagc tgggtatggt agcacacact  54360
tgtggtccca gctacttggg aggctgaggt ggggggggttg cttgtgcctg ggagtttgag  54420
gctgcaatga gctgtgattg tgccactgca ctccagcctg gataacagaa tgagaccctg  54480
ttccaaaaat aaaaaataaa atcaaagaca cttaaaaaga tggggaaaag gaaggacagg  54540
cacttaagca agttataagc tactttccta actacacaag tggaatctta agctgaggtt  54600
cccaggagtt gactggagcc agagaagaca gacctatagg agcacccaac tggagtcgcc  54660
ctccatagta gcccatatgt cttacatgga tcagctttcg tggggccctt ctactccgtc  54720
tggggaaggg cgtcagatct gtggctctca tgtactgctc agtacactgc cattcccagt  54780
tctttttttc aaaaaaaaaa aaattgttta cagaatcggc cgggtgtggt ggcttatgcc  54840
tataatacta gcaatttgga aggctgaggt gggtggatca cctgaggtca ggagttcgag  54900
accagcctgg ccaacatggt gaaaccccat cctactaaaa aaaaaaaaaa aaaaaaatta  54960
gctggatgtg gtggcaggcg cctataatct tagctacttg ggaggctgag gcaggagaat  55020
cgcttgaacc tgggaggcag aggctgcagt gagccgagat catgccacgg tactccagcc  55080
tgggtgatag agtgagactc tgtctcaaaa taaataaaat aaaataaaat aaaataaaat  55140
aaaataaaat agtctacaga attaagctgg tccaggaatg acagggcgtc catttatttg  55200
tctttcaatt gtgggagaaa aaggatttct gttgagacac tgtcgttttg acacacacaa  55260
```

```
tattttgatt aatcttgaga ttaaaaatcc tgtgctccaa atcttttaac attaaattat  55320
gcatttaaac aggtttgctc ctaaatctca aaatatggaa agcacctcat gtggctaaat  55380
attttgatga ccaagttttc tggaaggtaa gatttttcac ctattaacgt gatagatttt  55440
gagtgcatga acttaaaaac atacctgggt atatatgttg acttgctgtt tatgagtaaa  55500
acaaaaacaa aaatggagta aggagcattg caggaggaac tagaggagaa acaaatccat  55560
gatatgcatg tgtgtggggg agggtggcgg ggaggtggta aaggtcacca tttccctgat  55620
acctcaaatt cattcagagt cagggatgag acagctttca ctggccacac ttcccctccc  55680
gctatctgca gtcctcagcg tagccaaata gtttgacatg cgggtgacag aaccccgcaa  55740
tgcaaaagct ggaagaaacc tcaagccttg gagtccaacc cctttttga cagatgctaa  55800
gagtggagac atgacttatc aagatcttac aactggctgg gcacggtggc tgacgcctgt  55860
aatcccagca ctttgggagg ctgaggtggg gcgatcacct gaggccagga gttcgagacc  55920
agcctggcca acgtgtcaaa accccatctc tactaaaaat acaaaagtta gctgggcgtg  55980
gtagcacatg cctgtaatcc cagttactca ggaggctgag gcaagagaat cgcttgaaat  56040
caggaggcag aggttgcagt gagctgagat tgcgccactg cactccagcc tgggtgacaa  56100
gagctgacac tctgtctcaa aaaaaaaaaa aaaaaaaaaa aattcttaca gtgtgtgagt  56160
atccaggctg agtcctgaac acagctcttg ataaatgata acaagcaggc acaaaaaaat  56220
tgtagtacag gagtctgagg tcacttagca aagggacata aagttcaaac agctcagcag  56280
ctgctgaggg tcccgtgtta cattgtagca tttgttgttg tgactgggct agaaagaagg  56340
tgaagaaggt tggagctcac tccctgcctc ccctcccact ctcctccctt tgacctacac  56400
tcatagttca cgcagcactc tgatgtgtcc ccttaggcca tcctctagtc aatgctgtgg  56460
gtaggctgga ccagcaggga ccagtattgt cacagcaagt ccaggccaac agtggtcagg  56520
ctgctgcccg gtgttgtgcc tttgtgagtg gcagatccaa gaccggaacc caggccttct  56580
gagtcccagg ccaatgcttg ccccacccag catccaagat gttgctcact aaagagacag  56640
agaagcagcc ttattatggg cctggacacc tgtgcatgag gggtcaagca gagaggacct  56700
ggggagagac cctgcccctt cttttccttc tccttcctct cctttctctt cttcttcctc  56760
ttcaaatagc tttttgaggt gtaactggca tacaatcaat tgtacatatt taggctgggt  56820
atggtggctc acgcctgtaa tcccagcact ttgggaggcc aaggcgggtg gatcacttga  56880
ggtcaggagt ttgagaccag cctgggcaac ccggtgaaac cccgtctcca ctaaaactac  56940
aaaaattagc caggcgtggt ggcagctgcc tgtaatcccg gctactcggg aggctgaggc  57000
aggagaatca cttgaacctg ggaagcgaag tttgcagtga tctgagatca tgccactgca  57060
ctccagcctg ggtgacagag cgagactttg cctcaaaaac aaaacaaaac aattgtacat  57120
atttaaagtg ttgtaaccaa gtgagttaca gagaaacacc acactttgag cctaattcag  57180
gagtccttta ttagccggcg acctagagac gactagtgct caaaattctc tcggccccaa  57240
agaaggggct agattttctt ttataccttg gtttagaaag gggaggggga attgagctga  57300
agcaatctta cagaagtaaa acaggcaaaa aagttaaaaa gacaaatggt tacaggaaaa  57360
caaacagttc caggtgcagg agctttaaag ccatcacaag gtgacaggtg cgggggctct  57420
gggtgctatc tgccggacac aaacgcaggg gcactagagt actatcaccc gggcaaattc  57480
ctgggaactg cggacacagc ttgccacagt accttatcag ctaattgcac tctttgatgt  57540
gctgggagtc agcttgcaca agttaagtcc ttgaggaagg gggtgggtaa ggagccctta  57600
acgtcttgca aatgaaggag ccgaatggaa tccctccggc tttcttagct aagagagagt  57660
```

caatcaagtt aatacaagtt agggtatcac aaaagtatat aatttgatac attttaacgt 57720
atttatacac tgaagagacc atcaccacca tcaagacaag gagcacaccc atcacttcca 57780
cacacttcct cctgctcctt tgaaattcct cccttcctac ccacctggtc ccacccaaag 57840
gcaaccactg aactactttc tgtcactaag gtttgcgttt tctgtaattt ttttgtttga 57900
gacagggtct cactccgcca cccacaccgt aatgcagtgg caccatcatg actcactgta 57960
gcctcaacct ccccaggctc aggagatcct ccccccctcag cctcctgagt agctaggacc 58020
acaggtgtag gccaccatgg caggctaatt tttgtatttt tttgtagaga tggggtttca 58080
ccgtattacc taggctggtc tcgaactcat gggttcaagc aatcctcctg ccttggcctc 58140
tcaaagtgct gggattatag gcatgagcca ctgtgcccag ccctctgtaa tgttacacaa 58200
agggaatcat gcagcacgta ctgcccttgg tctggcctct tttgctcagc atgattattc 58260
tgagaatcat ccgtgttgtt gcgtgtaact gacttcatca gcttctctct gcagctgtca 58320
gctcttggct tctcccaaca gccaatctct ctttatcccc tgcaagtgtt cttgcctatt 58380
tagcagaatc aaggtactct atcgaaaaga ctcggaaaat tggtttaatc tattcattca 58440
ttcctcaggt atttatcgaa taactattct ataccaagta ctatgctaat caaccaagga 58500
cagcacaaac aggagaaatc tccagctcag tcacttgagt tgcaataaat atttgctgga 58560
taggtcaggt gcagtggctc acacttgtaa tcccagcact ttggggatta ctgagacggg 58620
aggatctctt gagcccagga ggccaaggct gcagagaacc atgatcatgc cactgcactc 58680
cagcctgggt gacagagtga gatcctgtct ctgaaaaaaa atatttgctg gataaattaa 58740
ggaaatctga cgaaccccat cagtagccat tgcagcaaca ggtaaactag aacgagtgtg 58800
aatttggaat gaggaaaccc gatgttggcc atcattctgt aatgtcatgt attatgtaat 58860
gtattatata ttaatgtatg tattatgtag gcaagttcct tgacctctct cactggtaac 58920
ataagagtag taatctttgt gctacttcac tgggttattt caaagatcaa gtgaggtaat 58980
aatgtctgta acaacattct gtaaaatgca aaccgccaca tgaatgtgaa agtttattac 59040
tagggattta gccaaccaca agggaatgtg tgagcataag agctatcata ttgcaagcct 59100
acagtttctg attttgtgct aggtgctttt ccacattacc tgattttatc ctcacaacag 59160
tcctgcataa aagtaagtat gtcgcccagg tgcggtggct catgcctata atcccagcac 59220
tttgggagcc cgaggtgggc aaatcacttg agatcaggag tttgaaacca gcctggtcaa 59280
cgtggtgcaa ccctgtctct actaaaaata caaaaaaaaa ttagacaggc gtggtggtgg 59340
atgcctgtaa tcccagctac ttgggaagct gaggcaggag aatggcttga gcccgggaga 59400
tggagattgc agtgagatga gattgcgcca ctgcactcca gcctgggtga cagagcaagg 59460
ctatgtctca aaagagaaaa aaaaagtaag tatctcagtc ttgaagatga tgaaatggag 59520
gcctagagag attaagtaac ttgcccaaaa tgacagaact aatgcataga aaagaagaaa 59580
tgtgatgtct tttggctcca aagacacccc acatatgcgt tggttacagt tactagagaa 59640
aagttattcc accccccaccc caccccccaga aatcttctga cttgttttct cgcagttgag 59700
taggaccatt tattcggcag tgtaccattc tcagcttgca gttgaaagcc aaatatccat 59760
taaagaggca aggatgcaaa cttgctaagc tgataaatcc aggggtgatt tttttttttt 59820
ttgcaaacca tccaacaaga cattttaaat actcattgaa tttcatagaa ctgactgcca 59880
ggattggaaa gacattaaag ccagctcagc cactgcctcg ctggttggcc agaccacgcc 59940
tggcacttct gggagggagc actcaccacc ccccaagggc acccatctca tcctccgaag 60000

```
gtttatgaaa atgcactcat catttgctaa ttcattccac tacgtgtatt acctaatttg  60060
tgacacgatg tgaagtacca gagagataat tctaaataaa atatagttat gggtctcaag  60120
gagccagata tgctaatctc ctatcctcct gcagtttaca gtggtcctca ccagatactt  60180
atttacaaaa attcagttta ttatttattt ttttgagaca gagtcttgct ctatagctca  60240
ggctagagtg taatggtgtg atctcggctc acttcaacct ctgcctccca ggttcaagtg  60300
attctcctgc ctcaacctcc caagtagctg ggactacagg cacctgccac cacggctaat  60360
ttttggagtt ttagtagaga cagggtttca ccacgttggc caggctggcc tcgaactcct  60420
gacctcaggt gatctgccca catcagcctc ccaaaatgtt gggattacag gcgtgagcca  60480
ccatgcccgg ccaaaacttc agtttataac acaatctttc acgtgtcttc tgctttcatt  60540
aaaagaatag acagttccct tctttatttc agtttaataa accatggatt ttatttcatg  60600
ctttgcaaaa cacaagggct cactgacatg cacttcttaa actaattctg gctggtcgcc  60660
tgtaattcca gcactttggg aggctgaggc cgacagatca cttcaagtca ggagttcaag  60720
accagcctgg ccaatatggt gaaaccacgt ctctaccaaa aatataaaaa attagccagg  60780
tgtggtggtg cgtgactata atcccagcta ctcaggggcc tgaggcagaa aaatcacttg  60840
aacccgggag gcggaggtta cagtgagctg agatcgcgcc actgcactcc agcctgggcg  60900
acagagtgag actctgtctc aaaaaataaa taaatacaaa taatgtaaaa tacgaaacaa  60960
gcaatcctgg cagtagctgc tggaatgaga ggagggagag gtcataggga ggtcggggac  61020
aatggagcat ggagttgtgt tggatttggc taagcagcag gaagtgcaag gcattccaag  61080
caagaggagg ggggcaggtg gggagcatct gcaagaacag aagcagcatg agcaacctgg  61140
ctcggcagtg tgtgaaaagg ctgaaaggtg gctagagcca cttcaatttc atccttcagg  61200
caaatgggaa attcccaaag gtttgagtgg ggaagcaatg cctacaatga aagtttgaga  61260
gtgaagcaga gtgatcgaat taagcatgta ggccgagttc tgaaataact gcaatgtgct  61320
gaagatcatc cattggcttc tgaatgagta tttgcagttt attttttaaa atgattttat  61380
tgccaagaaa gataaacact actgttttgg tacaaaaaca taacaaaatg tgttgagtcc  61440
ctcttgctgt tttacgcgaa gttttaaaaa tctactcttg tcacagtggt atcacccccta  61500
cttctgattt caaataaatg ttctagagac acagtaaggg cccaacaaac gcttgttcaa  61560
caacacaagg agagccagct tttaaagtag gaaaacaggc cgggcgccgt ggctcacacc  61620
tgtaatccca acactttggg aggctgaggt gggcagatca cttgaggtca ggagttcaag  61680
aacagcttgg ccaacatggt gaaaccctgt ctctactaaa aacacaaaca ttagccaggc  61740
gtggtggtgc acaccagtag tcccagctat tcaggaggct gaggcaggaa aatggcttga  61800
actggggagg cagtggttgc agtgagccga gatcgtgcca ctgcactcca gcctggggga  61860
cagagggaga ctccatctca aaataaaaca aaacaaaacc aaatcataca aaaacattag  61920
ctgggtgtgg tggtgcatac ctgtaatccc agctacttgg gaagctgagg cagaattact  61980
tgaacccctg gggggaggtt gcagtgagct gagatcttgc cactacactc cagcctgggc  62040
aacagagtga ggagactctg tctcaaaaaa tatatatatt aaaaaaaaga aaaaaaaaag  62100
taaactagga aaacacatca gcagcctgcc aacagactcc cctagcctcg gtgagggcca  62160
gtgttctggg aggcagatct gaattctagt cctagttcac ccactggcag gctggtgccc  62220
ttgggcaggt cgcttctctg ggctcagtt tcttcctcta taaaatgaga tcaaatccca  62280
tgttctaaga gtttgtgctc tggagtcaga cagatctggg ttctaccact gccagctctg  62340
tgatcttgta gcttcagtct cgtcatctga catggagata acagtaactg tctcactgtg  62400
```

-continued

```
ttgttagggt ttaaaggaga taatgtatgt gaaatgttag caaacaagtg ttagctaccc  62460
tgatttccgg tttcagagtt ctgtggtccc agtttatgcc acatgcagtg acgttgtatg  62520
gtaggctgtg gtgtggcacc acttcagaac tcagcgcatg cacagcttgc agaagagaag  62580
gccagaggag acctaagaag gctcttcgaa cacttgaaag accggcatgt aggccgggcg  62640
cagtgactca cgcctgtaat cccagcagtt ttggaggtcg aggcgggtgg atcacctgag  62700
tttgggagtt tgataccagc ctgaccaaca aggtgaaacc ccgtctctac taaaaaatac  62760
aaacattagc tgggcatggt ggcgggtgcc tgtaatccca gctactccgg tggttgaggc  62820
agaattgctt gaacccggga ggcagaggtt gcagtgagct gagattgcat cactgcactc  62880
cagcctgaga caagagcgaa actccatctc aaacaaaaca aacaaccaac caaacaaaac  62940
caaaaaaaaa actggcatgt agaagaaaaa tactttttct ctacacttct ccaaagaatt  63000
taactaggcc caggggaggt gcagtataaa tttctaacaa tctcaactgt ctgccaaatg  63060
gaatgagcta cttcatatgg cagtagtgag tcctctgtct ttggaggcat tcaaataaaa  63120
gccagatggc catttatcaa caatccatgt aaaacgttag atgaaataaa acctatatat  63180
ccaagatctc ttccaattca gattttatga aagaatttct aaggtctttg taatgagaca  63240
tttaggctgt ttcaagagat caagccaaaa tcagtatgtg ggttcatctg caataaaaat  63300
gtttgttttg cttttacagt ttcctcattt ggctgttgga ttttaagcaa aagcatccaa  63360
gaaaaacaag gcctgttcaa aaacaagaca acttcctctc actgttgcct gcatttgtac  63420
gtgagaaacg ctcatgacag caaagtctcc ttatgtataa tgaaacaagg tcagagacag  63480
atttgatatt aaaaaattaa agactaaaaa cttagtttaa gagtcaattt aataagttta  63540
aaataaatgt ttagtttcat taggatgatg ctatcaatat tttcttggtt acagacacat  63600
tattaaagtt ttgggttaat tttattgaca attcttaaga ttctttctca tgcttaataa  63660
agcatgctac tcagttaact cttgtctaca tcagcaaagc agataataca aaacaggaaa  63720
attacaaatc actgatactt agtccttgtg ggaatcatgc ttttctccca gcagttttac  63780
aaggtggctg gcattccctg agcatattct gaattgcact gtggggaaag aggttgtgct  63840
cagttgtagg gtggggggat gcactgcctg aggattaaaa aactagttct gtgaccgtga  63900
ggaagtcgtt taaatttcca tggtctgttc cctcctatgt gaaaagagaa ggtgggcttc  63960
aacctctaag atcttctcca gttttcacat tttatggact tttgtagaaa aaacatcagg  64020
agttcatgtg ggatgacagc aagtcatttc tttgaggaga gtcttgatca ccaggcaata  64080
ttcacagtgt agagactgtc agatgaccat ggctagcatg gaaatgagac ccacacattt  64140
aaatcaccca gcaaatattc cgaaggctaa ttgtagcaca ttttatgaaa gacatttcaa  64200
actgtggtcc tgaagagtgt atcccatctt gcagaggtgg ggagcctggg gggacaagag  64260
ttctgaagag gaagagacaa caagagttcc cagtagctaa tgtttgtcat tctagttgac  64320
cgtgctggtc tattaggcta gtggttcagt acacagatga aatgcaacat ggaacccagt  64380
ttattatcag aacaactaca aagaaattgt cccctgtcta agactggagt gtcaagtctc  64440
tgcccttttt tcctttcctt caatggtgga tgtggagtga ctgtgcatcc caccagaacc  64500
acgtgtcatg gctgagtcac atcttcctgc ccttggaatg agaggcacag cggaagacct  64560
tcccatggaa gggacacagg gagcctggtg gctggaccat ggtgcttctc tcttccaaca  64620
cgtccactca cccccttggga gaccctcaaa agccagttac attacatgtt cacagaattt  64680
ttggtaaaag taaataccaa ttatagtgag gaagaatttt gaccacggaa tattttaaaa  64740
```

actaaaaaat gtttatattt catttaacat ttgacacaga agagaccaca tttgaataaa 64800
cacattaaat cttcagagca ctttcattgt ggttttggac ctcagatatg acaaatactt 64860
acattgacaa atccataatt tcttttgtaa tttcttttta tttttacaaa ttataccatg 64920
ataaaatttg acaaaaatta ttcatgtgaa agtttcctct aacattttat aagttaatca 64980
agtgcatacc acaatagatt tttggttgtt gtttaggtgt tctcgtgatt ttagtattac 65040
acaactttaa gctgagacta cactcagaaa taagtttaga aaatggcatt acaaaaggtt 65100
gggagtgagc agtaaaaaaa caaacaaacc catgcagggc tgttgtgctg tgggaaatca 65160
gatgtgttca ctgccataag tcttcagtgc ggccaaactt aaaaaccagc cctctgtgaa 65220
taaaacaaga aatatcacat gactccctga atttgagaaa agagtatgtg agatttcgag 65280
aatggtgtga aacaaacaac gaagaataat tgatgagttg tagaagaaat tttggtacga 65340
aatgtatcaa aacagaaact gatcattcta aggtagtgaa ttcttccatt atgttcaact 65400
gtgctattaa ccaccatatt cccaacaacc ttaactttca agtactgaat acacatgtga 65460
cttttaaaaa gttaccagtg tttactatgt aaccattata tgtctgattt tttttttttt 65520
ttttgagaca gagtcttgct ctgtcgccca ggctggagtg cagtggcgtg atctcggctc 65580
actgcaagct ctgcctcccg ggttcatgcc attctcctgc ctct 65624

<210> SEQ ID NO 27
<211> LENGTH: 332
<212> TYPE: DNA
<213> ORGANISM: Homo sapiens

<400> SEQUENCE: 27
ttggagagag gggtgatgcc tggtgctggt ggaacccctg cacagagacg gacacaggat 60
gagctctaag tacccgcggt ctgtccggcg ctgcctgccc ctctgggccc taacactgga 120
agcagctctc attctcctct tctatttttt tacccactat gacgcttcct tagaggatca 180
aaaggggctc gtggcatcct atcaaggtga gagttcattg gaaaagtggt cacaggagca 240
aatagcaggg gcaggggcgg gggaggcctg tggttctcca ggggcacaga tgttcctttc 300
tacaaaatcc caaggaaaaa gattccccca tc 332

<210> SEQ ID NO 28
<211> LENGTH: 384
<212> TYPE: DNA
<213> ORGANISM: Homo sapiens

<400> SEQUENCE: 28
caagccctca agtaggtgtt ggagagaggg gtgatgcctg gtgctggtgg aacccctgca 60
cagagacgga cacaggatga gctctaagta cccgcggtct gtccggcgct gcctgcccct 120
ctgggcccta acactggaag cagctctcat tctcctcttc tattttttta cccactatga 180
cgcttcctta gaggatcaaa aggggctcgt ggcatcctat caaggtgaga gttcattgga 240
acagtggtca caggagcaaa tagcaggggc aggggcgggg gaggcctatg gttctccagg 300
ggcacagatg ttcctttcta caaaatcccg aggaaaagat tcccccatct tcttccgtag 360
attgcaccga aattcagtca acaa 384

<210> SEQ ID NO 29
<211> LENGTH: 384
<212> TYPE: DNA
<213> ORGANISM: Homo sapiens

<400> SEQUENCE: 29
caagccctca agtaggtgtt ggagagaggg gtgatgcctg gtgctggtgg aacccctgca 60
cagagacgga cacaggatga gctctaagta cccgcggtct gtccggcgct gcctgcccct 120
ctgggcccta acactggaag cagctctcat tctcctcttc tattttttta cccactatga 180
cgcttcctta gaggatcaaa aggggctcgt ggcatcctat caaggtgaga gttcattgga 240
acagtggtca caggagcaaa tagcaggggc aggggcgggg gaggcctatg gttctccagg 300
ggcacagatg ttcctttcta caaaatcccg aggaaaagat tcccccatct tcttccgtag 360
attgcaccga aattcagtca acaa 384

<210> SEQ ID NO 30
<211> LENGTH: 384
<212> TYPE: DNA
<213> ORGANISM: Homo sapiens

<400> SEQUENCE: 30
caagccctca agtaggtgtt ggagagaggg gtgatgcctg gtgctggtgg aacccctgca 60
cagagacgga cacaggatga gctctaagta cccgcggtct gtccggcgct gcctgcccct 120
ctgcgcccta acactggaag cagctctcat tctcctcttc tattttttta cccactatga 180
cgcttcctta gaggatcaaa aggggctcgt ggcatcctat caaggtgaga gttcattgga 240
acagtggtca caggagcaaa tagcaggggc aggggcgggg gaggcctatg gttctccagg 300
ggcacagatg ttcctttcta caaaatcccg aggaaaagat tcccccatct tcttccgtag 360
attgcaccga aattcagtca acaa 384

<210> SEQ ID NO 31
<211> LENGTH: 384
<212> TYPE: DNA
<213> ORGANISM: Homo sapiens

<400> SEQUENCE: 31
caagccctca agtaggtgtt ggagagaggg gtgatgcctg gtgctggtgg aacccctgca 60
cagagacgga cacaggatga gctctaagta cccgcggtct gtccggcgct gcctgcccct 120
ctgcgcccta acactggaag cagctctcat tctcctcttc tattttttta cccactatga 180
cgcttcctta gaggatcaaa aggggctcgt ggcatcctat caaggtgaga gttcattgga 240
acagtggtca caggagcaaa tagcaggggc aggggcgggg gaggcctatg gttctccagg 300
ggcacagatg ttcctttcta caaaatcccg aggaaaagat tcccccatct tcttccgtag 360
attgcaccga aattcagtca acaa 384

<210> SEQ ID NO 32
<211> LENGTH: 384
<212> TYPE: DNA
<213> ORGANISM: Artificial sequence
<220> FEATURE:
<223> OTHER INFORMATION: RHCE_consensus_ex01

<400> SEQUENCE: 32
caagccctca agtaggtgtt ggagagaggg gtgatgcctg gtgctggtgg aacccctgca 60
cagagacgga cacaggatga gctctaagta cccgcggtct gtccggcgct gcctgcccct 120
ctgsgcccta acactggaag cagctctcat tctcctcttc tattttttta cccactatga 180
cgcttcctta gaggatcaaa aggggctcgt ggcatcctat caaggtgaga gttcattgga 240
acagtggtca caggagcaaa tagcaggggc aggggcgggg gaggcctatg gttctccagg 300
ggcacagatg ttcctttcta caaaatcccg aggaaaagat tcccccatct tcttccgtag 360
attgcaccga aattcagtca acaa 384

<210> SEQ ID NO 33
<211> LENGTH: 400
<212> TYPE: DNA
<213> ORGANISM: Homo sapiens

<400> SEQUENCE: 33
tcttgcatgc cccttccagc tgccatttag taagactcta atttcatacc accctaaatc 60
tcgtctgctt ccccctcgtc cttctcgcca tctccccacc gagcagttgg ccaagatctg 120
accgtgatgg cggccattgg cttgggcttc ctcacctcga gtttccggag acacagctgg 180
agcagtgtgg ccttcaacct cttcatgctg gcgcttggtg tgcagtgggc aatcctgctg 240
gacggcttcc tgagccagtt cccttctggg aaggtggtca tcacactgtt caggtattgg 300
gatggtggct ggatcacttc tgggtcatag agggaatgga ccccgaaagg acaggttcca 360
gaagatctgg gatattgccc cctctctgtc tagcaccagt 400

<210> SEQ ID NO 34
<211> LENGTH: 400
<212> TYPE: DNA
<213> ORGANISM: Homo sapiens

<400> SEQUENCE: 34
tcttgcatgc cccttccagc tgccatttag taagactcta atttcatacc accctaaatc 60
tcgtctgctt ccccctcctc cttctcacca tctccccacc gagcagtcgg ccaagatctg 120
accgtgatgg cggcccttgg cttgggcttc ctcacctcaa atttccggag acacagctgg 180
agcagtgtgg ccttcaacct cttcatgctg gcgcttggtg tgcagtgggc aatcctgctg 240
gacggcttcc tgagccagtt ccctcctggg aaggtggtca tcacactgtt caggtattgg 300
gatggtggct ggatcacttc tgggtcatag agggaatgga ccccgaaagg acaggttcca 360
gaagatctgg gatattgccc cctctctgtc tagcaccagt 400

<210> SEQ ID NO 35
<211> LENGTH: 400
<212> TYPE: DNA
<213> ORGANISM: Homo sapiens

<400> SEQUENCE: 35
tcttgcatgc cccttccagc tgccatttag taagactcta atttcatacc accctaaatc 60
tcgtctgctt ccccctcctc cttctcacca tctccccacc gagcagtcgg ccaagatctg 120
accgtgatgg cggcccttgg cttgggcttc ctcacctcaa atttccggag acacagctgg 180
agcagtgtgg ccttcaacct cttcatgctg gcgcttggtg tgcagtgggc aatcctgctg 240
gacggcttcc tgagccagtt ccctcctggg aaggtggtca tcacactgtt caggtattgg 300
gatggtggct ggatcacttc tgggtcatag agggaatgga ccccgaaagg acaggttcca 360
gaagatctgg gatattgccc cctctctgtc tagcaccagt 400

<210> SEQ ID NO 36
<211> LENGTH: 400
<212> TYPE: DNA
<213> ORGANISM: Homo sapiens

<400> SEQUENCE: 36
tcttgcatgc cccttccagc tgccatttag taagactcta atttcatacc accctaaatc 60

```
tcgtctgctt ccccctcctc cttctcgcca tctccccacc gagcagttgg ccaagatctg    120

accgtgatgg cggccattgg cttgggcttc ctcacctcga gtttccggag acacagctgg    180

agcagtgtgg ccttcaacct cttcatgctg gcgcttggtg tgcagtgggc aatcctgctg    240

gacggcttcc tgagccagtt cccttctggg aaggtggtca tcacactgtt caggtattgg    300

gatggtggct ggatcacttc tgggtcatag agggaatgga ccccgaaagg acaggttcca    360

gaagatctgg gatattgccc cctctctgtc tagcaccagt                          400
```

<210> SEQ ID NO 37
<211> LENGTH: 400
<212> TYPE: DNA
<213> ORGANISM: Homo sapiens

<400> SEQUENCE: 37

```
tcttgcatgc cccttccagc tgccatttag taagactcta atttcatacc accctaaatc    60

tcgtctgctt ccccctcctc cttctcgcca tctccccacc gagcagttgg ccaagatctg    120

accgtgatgg cggccattgg cttgggcttc ctcacctcga gtttccggag acacagctgg    180

agcagtgtgg ccttcaacct cttcatgctg gcgcttggtg tgcagtgggc aatcctgctg    240

gacggcttcc tgagccagtt cccttctggg aaggtggtca tcacactgtt caggtattgg    300

gatggtggct ggatcacttc tgggtcatag agggaatgga ccccgaaagg acaggttcca    360

gaagatctgg gatattgccc cctctctgtc tagcaccagt                          400
```

<210> SEQ ID NO 38
<211> LENGTH: 400
<212> TYPE: DNA
<213> ORGANISM: Artificial sequence
<220> FEATURE:
<223> OTHER INFORMATION: RHCE_consensus_ex02

<400> SEQUENCE: 38

```
tcttgcatgc cccttccagc tgccatttag taagactcta atttcatacc accctaaatc    60

tcgtctgctt ccccctcctc cttctcrcca tctccccacc gagcagtygg ccaagatctg    120

accgtgatgg cggccmttgg cttgggcttc ctcacctcra rtttccggag acacagctgg    180

agcagtgtgg ccttcaacct cttcatgctg gcgcttggtg tgcagtgggc aatcctgctg    240

gacggcttcc tgagccagtt ccctyctggg aaggtggtca tcacactgtt caggtattgg    300

gatggtggct ggatcacttc tgggtcatag agggaatgga ccccgaaagg acaggttcca    360

gaagatctgg gatattgccc cctctctgtc tagcaccagt                          400
```

<210> SEQ ID NO 39
<211> LENGTH: 400
<212> TYPE: DNA
<213> ORGANISM: Homo sapiens

<400> SEQUENCE: 39

```
tcccacagaa agtaggtgcc caacagtgtt tgttgaaaga atgaatgaat gaatgaatga    60

atgaatgaat gagtgagagg catccttcct tctcagtcgt cctggctctc cctctctccc    120

ccagtattcg gctggccacc atgagtgctt tgtcggtgct gatctcagtg gatgctgtct    180

tggggaaggt caacttggcg cagttggtgg tgatggtgct ggtggaggtg acagctttag    240

gcaacctgag gatggtcatc agtaatatct tcaacgtgag tcatggtgct gggaggaggg    300

acctgggaga aagggccaa aagctccatt tggtggggtt tccagggttt tgaaaaataa    360
```

-continued agacaacctg taatcccagc tacttgggag gttgaggagg 400

<210> SEQ ID NO 40
<211> LENGTH: 400
<212> TYPE: DNA
<213> ORGANISM: Homo sapiens

<400> SEQUENCE: 40
ttgtcttcta tttccacaga aagtaaggtg cccaacagtg tttgttgaat gaatgaatga 60
atgaatgaat gagtgagagg catccttcct tctcagtcat cctggctctc cttctcaccc 120
ccagtattcg gctggccacc atgagtgcta tgtcggtgct gatctcagcg ggtgctgtct 180
tggggaaggt caacttggcg cagttggtgg tgatggtgct ggtggaggtg acagctttag 240
gcaccctgag gatggtcatc agtaatatct tcaacgtgag tcatggtgct gggaggaggg 300
acctgggaga aaagggccaa aagctccatt tggtggggct tccggggttt tgaaaaataa 360
agacaacctg taatcccagc tacttgggag gttgaggagg 400

<210> SEQ ID NO 41
<211> LENGTH: 400
<212> TYPE: DNA
<213> ORGANISM: Homo sapiens

<400> SEQUENCE: 41
ttgtcttcta tttccacaga aagtaaggtg cccaacagtg tttgttgaat gaatgaatga 60
atgaatgaat gagtgagagg catccttcct tctcagtcat cctggctctc cttctcaccc 120
ccagtattcg gctggccacc atgagtgcta tgtcggtgct gatctcagcg ggtgctgtct 180
tggggaaggt caacttggcg cagttggtgg tgatggtgct ggtggaggtg acagctttag 240
gcaccctgag gatggtcatc agtaatatct tcaacgtgag tcatggtgct gggaggaggg 300
acctgggaga aaagggccaa aagctccatt tggtggggct tccggggttt tgaaaaataa 360
agacaacctg taatcccagc tacttgggag gttgaggagg 400

<210> SEQ ID NO 42
<211> LENGTH: 400
<212> TYPE: DNA
<213> ORGANISM: Homo sapiens

<400> SEQUENCE: 42
ttgtcttcta tttccacaga aagtaaggtg cccaacagtg tttgttgaat gaatgaatga 60
atgaatgaat gagtgagagg catccttcct tctcagtcat cctggctctc cttctcaccc 120
ccagtattcg gctggccacc atgagtgcta tgtcggtgct gatctcagcg ggtgctgtct 180
tggggaaggt caacttggcg cagttggtgg tgatggtgct ggtggaggtg acagctttag 240
gcaccctgag gatggtcatc agtaatatct tcaacgtgag tcatggtgct gggaggaggg 300
acctgggaga aaagggccaa aagctccatt tggtggggct tccggggttt tgaaaaataa 360
agacaacctg taatcccagc tacttgggag gttgaggagg 400

<210> SEQ ID NO 43
<211> LENGTH: 400
<212> TYPE: DNA
<213> ORGANISM: Homo sapiens

<400> SEQUENCE: 43
ttgtcttcta tttccacaga aagtaaggtg cccaacagtg tttgttgaat gaatgaatga 60
atgaatgaat gagtgagagg catccttcct tctcagtcat cctggctctc cttctcaccc 120
ccagtattcg gctggccacc atgagtgcta tgtcggtgct gatctcagcg ggtgctgtct 180
tggggaaggt caacttggcg cagttggtgg tgatggtgct ggtggaggtg acagctttag 240
gcaccctgag gatggtcatc agtaatatct tcaacgtgag tcatggtgct gggaggaggg 300
acctgggaga aaagggccaa aagctccatt tggtggggct tccggggttt tgaaaaataa 360
agacaacctg taatcccagc tacttgggag gttgaggagg 400

<210> SEQ ID NO 44
<211> LENGTH: 400
<212> TYPE: DNA
<213> ORGANISM: Artificial sequence
<220> FEATURE:
<223> OTHER INFORMATION: RHCE_consensus_ex03

<400> SEQUENCE: 44
ttgtcttcta tttccacaga aagtaaggtg cccaacagtg tttgttgaat gaatgaatga 60
atgaatgaat gagtgagagg catccttcct tctcagtcat cctggctctc cttctcaccc 120
ccagtattcg gctggccacc atgagtgcta tgtcggtgct gatctcagcg ggtgctgtct 180
tggggaaggt caacttggcg cagttggtgg tgatggtgct ggtggaggtg acagctttag 240
gcaccctgag gatggtcatc agtaatatct tcaacgtgag tcatggtgct gggaggaggg 300
acctgggaga aaagggccaa aagctccatt tggtggggct tccggggttt tgaaaaataa 360
agacaacctg taatcccagc tacttgggag gttgaggagg 400

<210> SEQ ID NO 45
<211> LENGTH: 400
<212> TYPE: DNA
<213> ORGANISM: Homo sapiens

<400> SEQUENCE: 45
aacaccagtc tcatggcttc aagtcacacc tcctaagtga agctctgaac tttctccaag 60
gactatcagg gcttgccccg ggcagaggat gccgacactc actgctctta ctgggtttta 120
ttgcagacag actaccacat gaacatgatg cacatctacg tgttcgcagc ctattttggg 180
ctgtctgtgg cctggtgcct gccaaagcct ctacccgagg gaacggagga taaagatcag 240
acagcaacga tacccagttt gtctgccatg ctgggtaagg acaaggtggg gtgagtggtc 300
tcctacttgg gctgagcaga atggctcaga aaaggctctg gctgaaaaaa tctccctcct 360
ttaccaagtt cccctgggtg tctgaagccc ttccatcatg 400

<210> SEQ ID NO 46
<211> LENGTH: 400
<212> TYPE: DNA
<213> ORGANISM: Homo sapiens

<400> SEQUENCE: 46
acaccagtct cgtggcttca agtcacacct cctaagtgaa gctctgaact ttctccaagg 60
accatcaggg ctttcccctg ggcagaggat gccgacactc actgctctta ctgggtttta 120
ttgcagacag actaccacat gaacctgagg cacttctacg tgttcgcagc ctattttggg 180
ctgactgtgg cctggtgcct gccaaagcct ctacccaagg gaacggagga taatgatcag 240
agagcaacga tacccagttt gtctgccatg ctgggtaagg acaaggtggg gtgagtggtc 300
tcatacttgg gctgagcaga atggctcaga aaaggctctg gctgaaaaaa tctccctcct 360
ttaccaactt cccctgggtg tctgaagccc ttccatcatg 400

<210> SEQ ID NO 47
<211> LENGTH: 400
<212> TYPE: DNA
<213> ORGANISM: Homo sapiens

<400> SEQUENCE: 47
acaccagtct cgtggcttca agtcacacct cctaagtgaa gctctgaact ttctccaagg 60
accatcaggg ctttcccctg ggcagaggat gccgacactc actgctctta ctgggtttta 120
ttgcagacag actaccacat gaacctgagg cacttctacg tgttcgcagc ctattttggg 180
ctgactgtgg cctggtgcct gccaaagcct ctacccaagg gaacggagga taatgatcag 240
agagcaacga tacccagttt gtctgccatg ctgggtaagg acaaggtggg gtgagtggtc 300
tcatacttgg gctgagcaga atggctcaga aaaggctctg gctgaaaaaa tctccctcct 360
ttaccaactt cccctgggtg tctgaagccc ttccatcatg 400

<210> SEQ ID NO 48
<211> LENGTH: 400
<212> TYPE: DNA
<213> ORGANISM: Homo sapiens

<400> SEQUENCE: 48
acaccagtct cgtggcttca agtcacacct cctaagtgaa gctctgaact ttctccaagg 60
accatcaggg ctttcccctg ggcagaggat gccgacactc actgctctta ctgggtttta 120
ttgcagacag actaccacat gaacctgagg cacttctacg tgttcgcagc ctattttggg 180
ctgactgtgg cctggtgcct gccaaagcct ctacccaagg gaacggagga taatgatcag 240
agagcaacga tacccagttt gtctgccatg ctgggtaagg acaaggtggg gtgagtggtc 300
tcatacttgg gctgagcaga atggctcaga aaaggctctg gctgaaaaaa tctccctcct 360
ttaccaactt cccctgggtg tctgaagccc ttccatcatg 400

<210> SEQ ID NO 49
<211> LENGTH: 400
<212> TYPE: DNA
<213> ORGANISM: Homo sapiens

<400> SEQUENCE: 49
acaccagtct cgtggcttca agtcacacct cctaagtgaa gctctgaact ttctccaagg 60
accatcaggg ctttcccctg ggcagaggat gccgacactc actgctctta ctgggtttta 120
ttgcagacag actaccacat gaacctgagg cacttctacg tgttcgcagc ctattttggg 180
ctgactgtgg cctggtgcct gccaaagcct ctacccaagg gaacggagga taatgatcag 240
agagcaacga tacccagttt gtctgccatg ctgggtaagg acaaggtggg gtgagtggtc 300
tcatacttgg gctgagcaga atggctcaga aaaggctctg gctgaaaaaa tctccctcct 360
ttaccaactt cccctgggtg tctgaagccc ttccatcatg 400

<210> SEQ ID NO 50
<211> LENGTH: 400
<212> TYPE: DNA
<213> ORGANISM: Artificial sequence
<220> FEATURE:
<223> OTHER INFORMATION: RHCE_consensus_ex04

<400> SEQUENCE: 50
acaccagtct cgtggcttca agtcacacct cctaagtgaa gctctgaact ttctccaagg 60
accatcaggg ctttcccctg ggcagaggat gccgacactc actgctctta ctgggtttta 120
ttgcagacag actaccacat gaacctgagg cacttctacg tgttcgcagc ctattttggg 180
ctgactgtgg cctggtgcct gccaaagcct ctacccaagg gaacggagga taatgatcag 240
agagcaacga tacccagttt gtctgccatg ctgggtaagg acaaggtggg gtgagtggtc 300
tcatacttgg gctgagcaga atggctcaga aaaggctctg gctgaaaaaa tctccctcct 360
ttaccaactt cccctgggtg tctgaagccc ttccatcatg 400

<210> SEQ ID NO 51
<211> LENGTH: 410
<212> TYPE: DNA
<213> ORGANISM: Homo sapiens

<400> SEQUENCE: 51
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagttt caactctgct ctgctgagaa gtccaatcga 180
aaggaagaat gccgtgttca acacctacta tgctgtagca gtcagcgtgg tgacagccat 240
ctcagggtca tccttggctc acccccaagg gaagatcagc aaggtgagca gggcgctgcc 300
cttgggcagc acttgggtct aacaggacta gcacacatat ttatgcccct ccccacccca 360
gggccagcgt gggttgggag agggcatgcc gggtggtgga gctgtgcctg 410

<210> SEQ ID NO 52
<211> LENGTH: 400
<212> TYPE: DNA
<213> ORGANISM: Homo sapiens

<400> SEQUENCE: 52
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagtgt caactctgct ctgctgagaa gtccaatcca 180
aaggaagaat gccatgttca acacctacta tgctctagca gtcagtgtgg tgacagccat 240
ctcagggtca tccttggctc acccccaaag gaagatcagc atggtgagca gggcgctgcc 300
cttgggcagc acttgggtct aacaggacta gcacacatat ttatgcccct ccccacccca 360
gggccagcgt gggttgggag agggcatgcc gggtggtgga 400

<210> SEQ ID NO 53
<211> LENGTH: 400
<212> TYPE: DNA
<213> ORGANISM: Homo sapiens

<400> SEQUENCE: 53
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagtgt caactctcct ctgctgagaa gtccaatcca 180
aaggaagaat gccatgttca acacctacta tgctctagca gtcagtgtgg tgacagccat 240
ctcagggtca tccttggctc acccccaaag gaagatcagc atggtgagca gggcgctgcc 300
cttgggcagc acttgggtct aacaggacta gcacacatat ttatgcccct ccccacccca 360
gggccagcgt gggttgggag agggcatgcc gggtggtgga 400

<210> SEQ ID NO 54

<211> LENGTH: 400
<212> TYPE: DNA
<213> ORGANISM: Homo sapiens

<400> SEQUENCE: 54
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagtgt caactctgct ctgctgagaa gtccaatcca 180
aaggaagaat gccatgttca acacctacta tgctctagca gtcagtgtgg tgacagccat 240
ctcagggtca tccttggctc acccccaaag gaagatcagc atggtgagca gggcgctgcc 300
cttgggcagc acttgggtct aacaggacta gcacacatat ttatgcccct ccccacccca 360
gggccagcgt gggttgggag agggcatgcc gggtggtgga 400

<210> SEQ ID NO 55
<211> LENGTH: 400
<212> TYPE: DNA
<213> ORGANISM: Homo sapiens

<400> SEQUENCE: 55
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagtgt caactctcct ctgctgagaa gtccaatcca 180
aaggaagaat gccatgttca acacctacta tgctctagca gtcagtgtgg tgacagccat 240
ctcagggtca tccttggctc acccccaaag gaagatcagc atggtgagca gggcgctgcc 300
cttgggcagc acttgggtct aacaggacta gcacacatat ttatgcccct ccccacccca 360
gggccagcgt gggttgggag agggcatgcc gggtggtgga 400

<210> SEQ ID NO 56
<211> LENGTH: 400
<212> TYPE: DNA
<213> ORGANISM: Artificial sequence
<220> FEATURE:
<223> OTHER INFORMATION: RHCE_consensus_ex5

<400> SEQUENCE: 56
ctctaagtga caaggctgag actctccagc cctaggattc tcatccaaaa cccctcgagg 60
ctcagacctt tggagcagga gtgtgattct ggccaaccac cctctctggc ccccaggcgc 120
cctcttcttg tggatgttct ggccaagtgt caactctsct ctgctgagaa gtccaatcca 180
aaggaagaat gccatgttca acacctacta tgctctagca gtcagtgtgg tgacagccat 240
ctcagggtca tccttggctc acccccaaag gaagatcagc atggtgagca gggcgctgcc 300
cttgggcagc acttgggtct aacaggacta gcacacatat ttatgcccct ccccacccca 360
gggccagcgt gggttgggag agggcatgcc gggtggtgga 400

<210> SEQ ID NO 57
<211> LENGTH: 34
<212> TYPE: DNA
<213> ORGANISM: Artificial sequence
<220> FEATURE:
<223> OTHER INFORMATION: Synthetic sequence: Next generation sequencing
      tag

<400> SEQUENCE: 57
acactctttc cctacctgta aaacgacggc cagt 34

-continued

<210> SEQ ID NO 58
<211> LENGTH: 28
<212> TYPE: DNA
<213> ORGANISM: Artificial sequence
<220> FEATURE:
<223> OTHER INFORMATION: Synthetic sequence: Next generation sequencing tag

<400> SEQUENCE: 58
ggttgctcgc caggaaacag ctatgacc 28

<210> SEQ ID NO 59
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 59
ggtcacttgc agcaagatgg 20

<210> SEQ ID NO 60
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 60
accttgcttc ctttacccac 20

<210> SEQ ID NO 61
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 61
tggccttcag ccaaagcaga 20

<210> SEQ ID NO 62
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 62
ctaatgcagc tgtgcactgc 20

<210> SEQ ID NO 63
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 63
tgtgtgaaag gggtgggtag 20

```
<210> SEQ ID NO 64
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 64

gtctcacctg ccaatctgct                                              20


<210> SEQ ID NO 65
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 65

gttggagggg agtgttaagg                                              20


<210> SEQ ID NO 66
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 66

ccagctaagg actctgcaca                                              20


<210> SEQ ID NO 67
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 67

atggcactac tgacaccgac                                              20


<210> SEQ ID NO 68
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 68

ttgtccctga tgacctctgc                                              20


<210> SEQ ID NO 69
<211> LENGTH: 20
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 69

tgtcctggca atggtggaag                                              20


<210> SEQ ID NO 70
```

<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 70
gcacatagac atccagccac 20

<210> SEQ ID NO 71
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 71
agctggtcca ggaatgacag 20

<210> SEQ ID NO 72
<211> LENGTH: 27
<212> TYPE: DNA
<213> ORGANISM: Artificial sequence
<220> FEATURE:
<223> OTHER INFORMATION: Synthetic sequence: Consensus sequence - specific primer

<400> SEQUENCE: 72
gtgggagaaa aaggatttct gttgaga 27

<210> SEQ ID NO 73
<211> LENGTH: 27
<212> TYPE: DNA
<213> ORGANISM: Artificial sequence
<220> FEATURE:
<223> OTHER INFORMATION: Synthetic sequence: Consensus sequence - specific primer

<400> SEQUENCE: 73
tcttgagatt aaaaatcctg tgctcca 27

<210> SEQ ID NO 74
<211> LENGTH: 27
<212> TYPE: DNA
<213> ORGANISM: Artificial sequence
<220> FEATURE:
<223> OTHER INFORMATION: Synthetic sequence: Consensus sequence - specific primer

<400> SEQUENCE: 74
agttcatgca ctcaaaatct atcacgt 27

<210> SEQ ID NO 75
<211> LENGTH: 20
<212> TYPE: DNA
<213> ORGANISM: Artificial sequence
<220> FEATURE:
<223> OTHER INFORMATION: Synthetic sequence: Consensus sequence - specific primer

<400> SEQUENCE: 75
cctgcaatgc tccttactcc 20

<210> SEQ ID NO 76
<211> LENGTH: 22

```
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 76

ggctgtttca agagatcaag cc                                              22


<210> SEQ ID NO 77
<211> LENGTH: 22
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 77

tcagtatgtg ggttcatctg ca                                              22


<210> SEQ ID NO 78
<211> LENGTH: 22
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 78

aggcaacagt gagaggaagt tg                                              22


<210> SEQ ID NO 79
<211> LENGTH: 22
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 79

tgctgtcatg agcgtttctc ac                                              22


<210> SEQ ID NO 80
<211> LENGTH: 24
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 80

cttgtgccac ttgacttggg actg                                            24


<210> SEQ ID NO 81
<211> LENGTH: 24
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 81

ctgttttgag tcccttcagg ggag                                            24


<210> SEQ ID NO 82
<211> LENGTH: 28
<212> TYPE: DNA
```

```
<213> ORGANISM: Artificial sequence
<220> FEATURE:
<223> OTHER INFORMATION: Synthetic sequence: Consensus sequence -
      specific primer

<400> SEQUENCE: 82

ctcacatact gataacttag caaatggc                                28


<210> SEQ ID NO 83
<211> LENGTH: 21
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 83

gatcacttga gcccaggagg c                                       21


<210> SEQ ID NO 84
<211> LENGTH: 22
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 84

ttaactcagg aggctgaggt gg                                      22


<210> SEQ ID NO 85
<211> LENGTH: 23
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 85

ctgaggtggg aggatcactt gag                                     23


<210> SEQ ID NO 86
<211> LENGTH: 23
<212> TYPE: DNA
<213> ORGANISM: Artificial sequence
<220> FEATURE:
<223> OTHER INFORMATION: Synthetic sequence: Consensus sequence -
      specific primer

<400> SEQUENCE: 86

aaattagccg ggcatggtag cag                                     23


<210> SEQ ID NO 87
<211> LENGTH: 400
<212> TYPE: DNA
<213> ORGANISM: Homo sapiens

<400> SEQUENCE: 87

agtggtttca ggatcagcaa agcagggagg atgttacagg gttgccttgt tcccagcgtg     60

ctggtcactt gcagcaagat ggtgttctct ctctaccttg cttcctttac ccacacgcta    120

tttctttgca gacttatgtg cacagtgcgg tgttggcagg aggcgtggct gtgggtacct    180

cgtgtcacct gatcccttct ccgtggcttg ccatggtgct gggtcttgtg gctgggctga    240

tctccgtcgg gggagccaag tacctgccgg taagaaacta gacaactaac ctcctctgct    300
```

-continued ttggctgaag gccagcagga cgctgggacc tgatgggcca ctgtgcagtg cacagctgca 360
ttaggcaggt gtcggcgcat tctcttattg gcttcaacgc 400

<210> SEQ ID NO 88
<211> LENGTH: 400
<212> TYPE: DNA
<213> ORGANISM: Homo sapiens

<400> SEQUENCE: 88
ggtggtttca ggatcagcaa agcagggagg atgttacagg gttgccttgt tcccagcgtg 60
ctggtcactt gcagcaagat ggtgttctct ctctaccttg cttcctttac ccacacgcta 120
tttctttgca gacttatgtg cacagtgcgg tgttggcagg aggcgtggct gtgggtacct 180
cgtgtcacct gatcccttct ccgtggcttg ccatggtgct gggtcttgtg gctgggctga 240
tctccatcgg gggagccaag tgcctgccgg taagaaacta gacaactaat gctctctgct 300
ttggctgaag gccagcagga cgctgggacc tgatgggcca ctgtgcagtg cacagctgca 360
ttaggcaggt gttggtgcat tctcttattg gcttcaacgc 400

<210> SEQ ID NO 89
<211> LENGTH: 400
<212> TYPE: DNA
<213> ORGANISM: Homo sapiens

<400> SEQUENCE: 89
ggtggtttca ggatcagcaa agcagggagg atgttacagg gttgccttgt tcccagcgtg 60
ctggtcactt gcagcaagat ggtgttctct ctctaccttg cttcctttac ccacacgcta 120
tttctttgca gacttatgtg cacagtgcgg tgttggcagg aggcgtggct gtgggtacct 180
cgtgtcacct gatcccttct ccgtggcttg ccatggtgct gggtcttgtg gctgggctga 240
tctccatcgg gggagccaag tgcctgccgg taagaaacta gacaactaat gctctctgct 300
ttggctgaag gccagcagga cgctgggacc tgatgggcca ctgtgcagtg cacagctgca 360
ttaggcaggt gttggtgcat tctcttattg gcttcaacgc 400

<210> SEQ ID NO 90
<211> LENGTH: 400
<212> TYPE: DNA
<213> ORGANISM: Homo sapiens

<400> SEQUENCE: 90
ggtggtttca ggatcagcaa agcagggagg atgttacagg gttgccttgt tcccagcgtg 60
ctggtcactt gcagcaagat ggtgttctct ctctaccttg cttcctttac ccacacgcta 120
tttctttgca gacttatgtg cacagtgcgg tgttggcagg aggcgtggct gtgggtacct 180
cgtgtcacct gatcccttct ccgtggcttg ccatggtgct gggtcttgtg gctgggctga 240
tctccatcgg gggagccaag tgcctgccgg taagaaacta gacaactaat gctctctgct 300
ttggctgaag gccagcagga cgctgggacc tgatgggcca ctgtgcagtg cacagctgca 360
ttaggcaggt gttggtgcat tctcttattg gcttcaacgc 400

<210> SEQ ID NO 91
<211> LENGTH: 400
<212> TYPE: DNA
<213> ORGANISM: Homo sapiens

<400> SEQUENCE: 91
ggtggtttca ggatcagcaa agcagggagg atgttacagg gttgccttgt tcccagcgtg 60
ctggtcactt gcagcaagat ggtgttctct ctctaccttg cttcctttac ccacacgcta 120
tttctttgca gacttatgtg cacagtgcgg tgttggcagg aggcgtggct gtgggtacct 180
cgtgtcacct gatcccttct ccgtggcttg ccatggtgct gggtcttgtg gctgggctga 240
tctccatcgg gggagccaag tgcctgccgg taagaaacta gacaactaat gctctctgct 300
ttggctgaag gccagcagga cgctgggacc tgatgggcca ctgtgcagtg cacagctgca 360
ttaggcaggt gttggtgcat tctcttattg gcttcaacgc 400

<210> SEQ ID NO 92
<211> LENGTH: 400
<212> TYPE: DNA
<213> ORGANISM: Artificial sequence
<220> FEATURE:
<223> OTHER INFORMATION: RHCE_consensus_ex06

<400> SEQUENCE: 92
ggtggtttca ggatcagcaa agcagggagg atgttacagg gttgccttgt tcccagcgtg 60
ctggtcactt gcagcaagat ggtgttctct ctctaccttg cttcctttac ccacacgcta 120
tttctttgca gacttatgtg cacagtgcgg tgttggcagg aggcgtggct gtgggtacct 180
cgtgtcacct gatcccttct ccgtggcttg ccatggtgct gggtcttgtg gctgggctga 240
tctccatcgg gggagccaag tgcctgccgg taagaaacta gacaactaat gctctctgct 300
ttggctgaag gccagcagga cgctgggacc tgatgggcca ctgtgcagtg cacagctgca 360
ttaggcaggt gttggtgcat tctcttattg gcttcaacgc 400

<210> SEQ ID NO 93
<211> LENGTH: 400
<212> TYPE: DNA
<213> ORGANISM: Homo sapiens

<400> SEQUENCE: 93
gaagggcttc tttgaggtga gccttagtgc ccatccccct ttggtggccc cggataccaa 60
gggtgtgtga aaggggtggg tagggaatat gggtctcacc tgccaatctg cttataataa 120
cacttgtcca caggggtgtt gtaaccgagt gctggggatt ccccacagct ccatcatggg 180
ctacaacttc agcttgctgg gtctgcttgg agagatcatc tacattgtgc tgctggtgct 240
tgataccgtc ggagccggca atggcatgtg ggtcactggg cttacccccc atccccttaa 300
cactcccctc caactcagga agaaatgtgt gcagagtcct tagctggggc gtgtgcactc 360
ggggccaggt gctcagtagg cttcggtgaa tatttgttgg 400

<210> SEQ ID NO 94
<211> LENGTH: 400
<212> TYPE: DNA
<213> ORGANISM: Homo sapiens

<400> SEQUENCE: 94
agaagggctt ctttgaggtg agccttagtg cccatcccca tttggtggcg cggataccaa 60
gggtgtgtga aaggggtggg tagggaatat gggtctcacc tgccaatctg cttataataa 120
cacttgtcca caggtgtgtt gtaaccgagt gctggggatt caccacatct ccgtcatgca 180
ctccatcttc agcttgctgg gtctgcttgg agagatcacc tacattgtgc tgctggtgct 240
tcatactgtc tggaacggca atggcatgtg ggtcactggg cttacccccc atccccttaa 300
cactcccctc caactcagga agaaatgtgt gcagagtcct tagctggggc gtgtgcactc 360

-continued ggggccaggt gctcagtagg cttcggtgaa tatttgttgg 400

<210> SEQ ID NO 95
<211> LENGTH: 400
<212> TYPE: DNA
<213> ORGANISM: Homo sapiens

<400> SEQUENCE: 95
agaagggctt ctttgaggtg agccttagtg cccatcccca tttggtggcg cggataccaa 60
gggtgtgtga aaggggtggg tagggaatat gggtctcacc tgccaatctg cttataataa 120
cacttgtcca caggtgtgtt gtaaccgagt gctggggatt caccacatct ccgtcatgca 180
ctccatcttc agcttgctgg gtctgcttgg agagatcacc tacattgtgc tgctggtgct 240
tcatactgtc tggaacggca atggcatgtg ggtcactggg cttacccccc atccccttaa 300
cactcccctc caactcagga agaaatgtgt gcagagtcct tagctggggc gtgtgcactc 360
ggggccaggt gctcagtagg cttcggtgaa tatttgttgg 400

<210> SEQ ID NO 96
<211> LENGTH: 400
<212> TYPE: DNA
<213> ORGANISM: Homo sapiens

<400> SEQUENCE: 96
agaagggctt ctttgaggtg agccttagtg cccatcccca tttggtggcg cggataccaa 60
gggtgtgtga aaggggtggg tagggaatat gggtctcacc tgccaatctg cttataataa 120
cacttgtcca caggtgtgtt gtaaccgagt gctggggatt caccacatct ccgtcatgca 180
ctccatcttc agcttgctgg gtctgcttgg agagatcacc tacattgtgc tgctggtgct 240
tcatactgtc tggaacggca atggcatgtg ggtcactggg cttacccccc atccccttaa 300
cactcccctc caactcagga agaaatgtgt gcagagtcct tagctggggc gtgtgcactc 360
ggggccaggt gctcagtagg cttcggtgaa tatttgttgg 400

<210> SEQ ID NO 97
<211> LENGTH: 400
<212> TYPE: DNA
<213> ORGANISM: Homo sapiens

<400> SEQUENCE: 97
agaagggctt ctttgaggtg agccttagtg cccatcccca tttggtggcg cggataccaa 60
gggtgtgtga aaggggtggg tagggaatat gggtctcacc tgccaatctg cttataataa 120
cacttgtcca caggtgtgtt gtaaccgagt gctggggatt caccacatct ccgtcatgca 180
ctccatcttc agcttgctgg gtctgcttgg agagatcacc tacattgtgc tgctggtgct 240
tcatactgtc tggaacggca atggcatgtg ggtcactggg cttacccccc atccccttaa 300
cactcccctc caactcagga agaaatgtgt gcagagtcct tagctggggc gtgtgcactc 360
ggggccaggt gctcagtagg cttcggtgaa tatttgttgg 400

<210> SEQ ID NO 98
<211> LENGTH: 400
<212> TYPE: DNA
<213> ORGANISM: Artificial sequence
<220> FEATURE:
<223> OTHER INFORMATION: RHCE_consensus_ex07

<400> SEQUENCE: 98
agaagggctt ctttgaggtg agccttagtg cccatcccca tttggtggcg cggataccaa 60

-continued gggtgtgtga aaggggtggg tagggaatat gggtctcacc tgccaatctg cttataataa 120
cacttgtcca caggtgtgtt gtaaccgagt gctggggatt caccacatct ccgtcatgca 180
ctccatcttc agcttgctgg gtctgcttgg agagatcacc tacattgtgc tgctggtgct 240
tcatactgtc tggaacggca atggcatgtg ggtcactggg cttacccccc atccccttaa 300
cactcccctc caactcagga agaaatgtgt gcagagtcct tagctggggc gtgtgcactc 360
ggggccaggt gctcagtagg cttcggtgaa tatttgttgg 400

<210> SEQ ID NO 99
<211> LENGTH: 400
<212> TYPE: DNA
<213> ORGANISM: Homo sapiens

<400> SEQUENCE: 99
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 100
<211> LENGTH: 400
<212> TYPE: DNA
<213> ORGANISM: Homo sapiens

<400> SEQUENCE: 100
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 101
<211> LENGTH: 400
<212> TYPE: DNA
<213> ORGANISM: Homo sapiens

<400> SEQUENCE: 101
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 102
<211> LENGTH: 400
<212> TYPE: DNA
<213> ORGANISM: Homo sapiens

<400> SEQUENCE: 102
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 103
<211> LENGTH: 400
<212> TYPE: DNA
<213> ORGANISM: Homo sapiens

<400> SEQUENCE: 103
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 104
<211> LENGTH: 400
<212> TYPE: DNA
<213> ORGANISM: Artificial sequence
<220> FEATURE:
<223> OTHER INFORMATION: RHCE_consensus_ex08

<400> SEQUENCE: 104
ttgggaaaat gccaggggaa tgtaccagcc agggagagga cccttgtttt cctcatggcc 60
cttcctggca atggcactac tgacaccgac agtccttttt gtccctgatg acctctgctg 120
cctgatgccc aagtgaccac ctctgctttg tcatttctag gattggcttc caggtcctcc 180
tcagcattgg ggaactcagc ttggccatcg tgatagctct cacgtctggt ctcctgacag 240
gtcagtgtga ggccaccttt cttccaccat tgccaggaca cagcacccac gtccagagcg 300
caccctgccg tgtggctgga tgtctatgtg ccccatctcc ttccctgagg atcacataat 360
ttcagaattg gaaaggttct tagaggtcac ctgctgctaa 400

<210> SEQ ID NO 105
<211> LENGTH: 400
<212> TYPE: DNA
<213> ORGANISM: Homo sapiens

<400> SEQUENCE: 105
tggtccagga atgacagggc ttccatttat ttgtctttca attgtgggag aaaaaggatt 60
tctgttgaga tactgtcgtt ttgacacaca atatttcgat taatcttgag attaaaaatc 120

-continued ctgtgctcca aatcttttaa cattaaatta tgcatttaaa caggtttgct cctaaatctt 180
aaaatatgga aagcacctca tgaggctaaa tattttgatg accaagtttt ctggaaggta 240
agatttttca cctattaacg tgatagattt tgagtgcatg aacttaaaaa catacctgag 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 106
<211> LENGTH: 400
<212> TYPE: DNA
<213> ORGANISM: Homo sapiens

<400> SEQUENCE: 106
gtccaggaat gacagggcgt ccatttattt gtctttcaat tgtgggagaa aaaggatttc 60
tgttgagaca ctgtcgtttt gacacacaca atattttgat taatcttgag attaaaaatc 120
ctgtgctcca aatcttttaa cattaaatta tgcatttaaa caggtttgct cctaaatctc 180
aaaatatgga aagcacctca tgtggctaaa tattttgatg accaagtttt ctggaaggta 240
agatttttca cctattaacg tgatagattt tgagtgcatg aacttaaaaa catacctggg 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 107
<211> LENGTH: 400
<212> TYPE: DNA
<213> ORGANISM: Homo sapiens

<400> SEQUENCE: 107
gtccaggaat gacagggcgt ccatttattt gtctttcaat tgtgggagaa aaaggatttc 60
tgttgagaca ctgtcgtttt gacacacaca atattttgat taatcttgag attaaaaatc 120
ctgtgctcca aatcttttaa cattaaatta tgcatttaaa caggtttgct cctaaatctc 180
aaaatatgga aagcacctca tgtggctaaa tattttgatg accaagtttt ctggaaggta 240
agatttttca cctattaacg tgatagattt tgagtgcatg aacttaaaaa catacctggg 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 108
<211> LENGTH: 400
<212> TYPE: DNA
<213> ORGANISM: Homo sapiens

<400> SEQUENCE: 108
gtccaggaat gacagggcgt ccatttattt gtctttcaat tgtgggagaa aaaggatttc 60
tgttgagaca ctgtcgtttt gacacacaca atattttgat taatcttgag attaaaaatc 120
ctgtgctcca aatcttttaa cattaaatta tgcatttaaa caggtttgct cctaaatctc 180
aaaatatgga aagcacctca tgtggctaaa tattttgatg accaagtttt ctggaaggta 240
agatttttca cctattaacg tgatagattt tgagtgcatg aacttaaaaa catacctggg 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 109

<211> LENGTH: 400
<212> TYPE: DNA
<213> ORGANISM: Homo sapiens

<400> SEQUENCE: 109
gtccaggaat gacagggcgt ccatttattt gtctttcaat tgtgggagaa aaaggatttc 60
tgttgagaca ctgtcgtttt gacacacaca atattttgat taatcttgag attaaaaatc 120
ctgtgctcca aatcttttaa cattaaatta tgcatttaaa caggtttgct cctaaatctc 180
aaaatatgga aagcacctca tgtggctaaa tattttgatg accaagtttt ctggaaggta 240
agatttttca cctattaacg tgatagattt tgagtgcatg aacttaaaaa catacctggg 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 110
<211> LENGTH: 400
<212> TYPE: DNA
<213> ORGANISM: Artificial sequence
<220> FEATURE:
<223> OTHER INFORMATION: RHCE_consensus_ex09

<400> SEQUENCE: 110
gtccaggaat gacagggcgt ccatttattt gtctttcaat tgtgggagaa aaaggatttc 60
tgttgagaca ctgtcgtttt gacacacaca atattttgat taatcttgag attaaaaatc 120
ctgtgctcca aatcttttaa cattaaatta tgcatttaaa caggtttgct cctaaatctc 180
aaaatatgga aagcacctca tgtggctaaa tattttgatg accaagtttt ctggaaggta 240
agatttttca cctattaacg tgatagattt tgagtgcatg aacttaaaaa catacctggg 300
tatatatgtt gacttgctgt ttatgagtaa aacaaaaaca aaaatggagt aaggagcatt 360
gcaggaggaa ctagaggaga aacaaatcca tgatatgcat 400

<210> SEQ ID NO 111
<211> LENGTH: 400
<212> TYPE: DNA
<213> ORGANISM: Homo sapiens

<400> SEQUENCE: 111
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctccaat gttcgcgcag gcactggagt cagagaaaat ggagttgaat 360
cctttctctg ccactctttg aggagaatct caccatttat 400

<210> SEQ ID NO 112
<211> LENGTH: 400
<212> TYPE: DNA
<213> ORGANISM: Homo sapiens

<400> SEQUENCE: 112
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctcctta tgtataatga aacaaggtca gagacagatt tgatattaaa 360
aaattaaaga ctaaaaactt agtttaagag tcaatttaat 400

<210> SEQ ID NO 113
<211> LENGTH: 400
<212> TYPE: DNA
<213> ORGANISM: Homo sapiens

<400> SEQUENCE: 113
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctcctta tgtataatga aacaaggtca gagacagatt tgatattaaa 360
aaattaaaga ctaaaaactt agtttaagag tcaatttaat 400

<210> SEQ ID NO 114
<211> LENGTH: 400
<212> TYPE: DNA
<213> ORGANISM: Homo sapiens

<400> SEQUENCE: 114
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctcctta tgtataatga aacaaggtca gagacagatt tgatattaaa 360
aaattaaaga ctaaaaactt agtttaagag tcaatttaat 400

<210> SEQ ID NO 115
<211> LENGTH: 400
<212> TYPE: DNA
<213> ORGANISM: Homo sapiens

<400> SEQUENCE: 115
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctcctta tgtataatga aacaaggtca gagacagatt tgatattaaa 360
aaattaaaga ctaaaaactt agtttaagag tcaatttaat 400

<210> SEQ ID NO 116
<211> LENGTH: 400
<212> TYPE: DNA

<213> ORGANISM: Artificial sequence
<220> FEATURE:
<223> OTHER INFORMATION: RHCE_consensus_ex10

<400> SEQUENCE: 116
ttatcaacaa tccatgtaaa acgttagatg aaataaaacc tatatatcca agatctcttc 60
caattcagat tttatgaaag aatttctaag gtctttgtaa tgagacattt aggctgtttc 120
aagagatcaa gccaaaatca gtatgtgggt tcatctgcaa taaaaatgtt tgttttgctt 180
ttacagtttc ctcatttggc tgttggattt taagcaaaag catccaagaa aaacaaggcc 240
tgttcaaaaa caagacaact tcctctcact gttgcctgca tttgtacgtg agaaacgctc 300
atgacagcaa agtctcctta tgtataatga aacaaggtca gagacagatt tgatattaaa 360
aaattaaaga ctaaaaactt agtttaagag tcaatttaat 400

<210> SEQ ID NO 117
<211> LENGTH: 305
<212> TYPE: DNA
<213> ORGANISM: Homo sapiens

<400> SEQUENCE: 117
ctgttttgag tcccttcagg ggaggggcct atcttattca acgttgttgt ttgttttcct 60
cacatactga taacttagca aatggctatt ggagcaaaaa tgaaaataaa cggaactctg 120
aagtgggatg ttttaaaatt ttattttttt tagagacagg gtcttgctct gttgcccagt 180
ctggagtgca gtggtacaat catagctcat tgcagcctgt gcctcctggg ctcaagtgat 240
cctcccacct cagcctcctg agttaaattt ttttacaggc gcctgctacc atgccctgct 300
aattt 305

<210> SEQ ID NO 118
<211> LENGTH: 308
<212> TYPE: DNA
<213> ORGANISM: Homo sapiens

<400> SEQUENCE: 118
ctgttttgag tcccttcagg ggaggggcct atcttattca acgttgttct ttgttttcct 60
cacatactga taacttagca aatggctatt ggaacaaaaa tgaaaataaa cggaaccctg 120
aagtgggatg ttttaaattt ttatttattt ttttagagac agggtcttgc tctgttgccc 180
agtctggagt gcagtggtac aatcatagct cattgcagcc tctgcctcct gggctcaagt 240
gatcctccca cctcagcctc ctgagttaaa tttttttaca gacgcctgct accatgcccg 300
gctaattt 308

<210> SEQ ID NO 119
<211> LENGTH: 308
<212> TYPE: DNA
<213> ORGANISM: Homo sapiens

<400> SEQUENCE: 119
ctgttttgag tcccttcagg ggaggggcct atcttattca acgttgttct ttgttttcct 60
cacatactga taacttagca aatggctatt ggaacaaaaa tgaaaataaa cggaaccctg 120
aagtgggatg ttttaaattt ttatttattt ttttagagac agggtcttgc tctgttgccc 180
agtctggagt gcagtggtac aatcatagct cactgcagcc tctgcctcct gggctcaagt 240
gatcctccca cctcagcctc ctgagttaaa tttttttaca gacgcctgct accatgcccg 300
gctaattt 308

<210> SEQ ID NO 120
<211> LENGTH: 417
<212> TYPE: DNA
<213> ORGANISM: Homo sapiens

<400> SEQUENCE: 120
ctgttttgag tcccttcagg ggaggggcct atcttattca acgttgttct ttgttttcct 60
cacatactga taacttagca aatggctatt ggaacaaaaa tgaaaataaa cggaaccctg 120
aagtgggatg ttttaaattt ttatttattt ttttagagac agggtcttgc tctgttgccc 180
agtctggagt gcagtggtac aatcatagct cattgctata gcttaaggac tcacctggca 240
gcaacaccaa accagggcca ccaccatttg aaatccccca gggtgccctt tgtcacttcc 300
cagtggtaca atcatagctc actgcagcct ctgcctcctg ggctcaagtg atcctcccac 360
ctcagcctcc tgagttaaat ttttttacag acgcctgcta ccatgcccgg ctaattt 417

<210> SEQ ID NO 121
<211> LENGTH: 417
<212> TYPE: DNA
<213> ORGANISM: Homo sapiens

<400> SEQUENCE: 121
ctgttttgag tcccttcagg ggaggggcct atcttattca acgttgttct ttgttttcct 60
cacatactga taacttagca aatggctatt ggaacaaaaa tgaaaataaa cggaaccctg 120
aagtgggatg ttttaaattt ttatttattt ttttagagac agggtcttgc tctgttgccc 180
agtctggagt gcagtggtac aatcatagct cattgctata gcttaaggac tcacctggca 240
gcaacaccaa accagggcca ccaccatttg aaatccccca gggtgccctt tgtcacttcc 300
cagtggtaca atcatagctc actgcagcct ctgcctcctg ggctcaagtg atcctcccac 360
ctcagcctcc tgagttaaat ttttttacag acgcctgcta ccatgcccgg ctaattt 417

<210> SEQ ID NO 122
<211> LENGTH: 58
<212> TYPE: DNA
<213> ORGANISM: Artificial sequence
<220> FEATURE:
<223> OTHER INFORMATION: Synthetic sequence: Forward primer sequence

<400> SEQUENCE: 122
aatgatacgg cgaccaccga gatctacact ctttccctac acgacgctct tccgatct 58

<210> SEQ ID NO 123
<211> LENGTH: 60
<212> TYPE: DNA
<213> ORGANISM: Artificial sequence
<220> FEATURE:
<223> OTHER INFORMATION: Synthetic sequence: Reverse primer sequence, which contains an 8-nucleotide barcode added for patient identification.
<220> FEATURE:
<221> NAME/KEY: misc_feature
<222> LOCATION: (25)..(32)
<223> OTHER INFORMATION: 8-nucleotide barcode added for patient identification.

<400> SEQUENCE: 123
caagcagaag acggcatacg agatnnnnnn nngtgactgg agttcagacg tgtgctcttc 60

<210> SEQ ID NO 124
<211> LENGTH: 33

-continued

<212> TYPE: DNA
<213> ORGANISM: Artificial sequence
<220> FEATURE:
<223> OTHER INFORMATION: Synthetic sequence: Forward sequencing primer

<400> SEQUENCE: 124
acactctttc cctacacgac gctcttccga tct 33

<210> SEQ ID NO 125
<211> LENGTH: 34
<212> TYPE: DNA
<213> ORGANISM: Artificial sequence
<220> FEATURE:
<223> OTHER INFORMATION: Synthetic sequence: Reverse sequencing primer

<400> SEQUENCE: 125
gtgactggag ttcagacgtg tgctcttccg atct 34

<210> SEQ ID NO 126
<211> LENGTH: 34
<212> TYPE: DNA
<213> ORGANISM: Artificial sequence
<220> FEATURE:
<223> OTHER INFORMATION: Synthetic sequence: Index sequencing primer

<400> SEQUENCE: 126
agatcggaag agcacacgtc tgaactccag tcac 34

<210> SEQ ID NO 127
<211> LENGTH: 59
<212> TYPE: DNA
<213> ORGANISM: Artificial sequence
<220> FEATURE:
<223> OTHER INFORMATION: Synthetic sequence: Forward primer sequence

<400> SEQUENCE: 127
aatgatacgg cgaccaccga gatctacact ctttccctac ctgtaaaacg acggccagt 59

<210> SEQ ID NO 128
<211> LENGTH: 60
<212> TYPE: DNA
<213> ORGANISM: Artificial sequence
<220> FEATURE:
<223> OTHER INFORMATION: Synthetic sequence: Reverse primer sequence,
which contains an 8-nucleotide barcode added for patient
identification.
<220> FEATURE:
<221> NAME/KEY: misc_feature
<222> LOCATION: (25)..(32)
<223> OTHER INFORMATION: 8-nucleotide barcode added for patient
identification.

<400> SEQUENCE: 128
caagcagaag acggcatacg agatnnnnnn nnggttgctc gccaggaaac agctatgacc 60

<210> SEQ ID NO 129
<211> LENGTH: 34
<212> TYPE: DNA
<213> ORGANISM: Artificial sequence
<220> FEATURE:
<223> OTHER INFORMATION: Synthetic sequence: Forward sequencing primer

<400> SEQUENCE: 129
acactctttc cctacctgta aaacgacggc cagt 34

<210> SEQ ID NO 130
<211> LENGTH: 28

<212> TYPE: DNA
<213> ORGANISM: Artificial sequence
<220> FEATURE:
<223> OTHER INFORMATION: Synthetic sequence: Reverse sequencing primer

<400> SEQUENCE: 130
ggttgctcgc caggaaacag ctatgacc 28

<210> SEQ ID NO 131
<211> LENGTH: 28
<212> TYPE: DNA
<213> ORGANISM: Artificial sequence
<220> FEATURE:
<223> OTHER INFORMATION: Synthetic sequence: Index sequencing primer

<400> SEQUENCE: 131
ggtcatagct gtttcctggc gagcaacc 28

<210> SEQ ID NO 132
<211> LENGTH: 43
<212> TYPE: DNA
<213> ORGANISM: Homo sapiens

<400> SEQUENCE: 132
tgtccggcgc tgcctgcccc tctgsgccct aacactggaa gca 43

<210> SEQ ID NO 133
<211> LENGTH: 38
<212> TYPE: DNA
<213> ORGANISM: Homo sapiens

<400> SEQUENCE: 133
ccggcgctgc ctgcccctct gggccctaac actggaag 38

<210> SEQ ID NO 134
<211> LENGTH: 41
<212> TYPE: DNA
<213> ORGANISM: Homo sapiens

<400> SEQUENCE: 134
gggcttcctc acctcrartt tccggagaca cagctggagc a 41

<210> SEQ ID NO 135
<211> LENGTH: 41
<212> TYPE: DNA
<213> ORGANISM: Homo sapiens

<400> SEQUENCE: 135
ggcttcctca cctcaaattt ccggagacac agctggagca g 41

<210> SEQ ID NO 136
<211> LENGTH: 38
<212> TYPE: DNA
<213> ORGANISM: Homo sapiens

<400> SEQUENCE: 136
cggtgctgat ctcagyggrt gctgtcttgg ggaaggtc 38

<210> SEQ ID NO 137
<211> LENGTH: 33
<212> TYPE: DNA
<213> ORGANISM: Homo sapiens

<400> SEQUENCE: 137

-continued

```
ggtgctgatc tcagcgggtg ctgtcttggg gaa                              33


<210> SEQ ID NO 138
<211> LENGTH: 43
<212> TYPE: DNA
<213> ORGANISM: Homo sapiens

<400> SEQUENCE: 138

gcctctaccc ragggaacgg aggataawga tcagasagca acg                   43


<210> SEQ ID NO 139
<211> LENGTH: 52
<212> TYPE: DNA
<213> ORGANISM: Homo sapiens

<400> SEQUENCE: 139

gcctgccaaa gcctctaccc aagggaacgg aggataatga tcagagagca ac         52


<210> SEQ ID NO 140
<211> LENGTH: 47
<212> TYPE: DNA
<213> ORGANISM: Homo sapiens

<400> SEQUENCE: 140

gaatgccrtg ttcaacacct actatgctst agcagtcagy gtggtga               47


<210> SEQ ID NO 141
<211> LENGTH: 52
<212> TYPE: DNA
<213> ORGANISM: Homo sapiens

<400> SEQUENCE: 141

gaagaatgcc atgttcaaca cctactatgc tctagcagtc agtgtggtga ca         52
```